US009044445B2

(12) United States Patent
Korber et al.

(10) Patent No.: US 9,044,445 B2

(45) Date of Patent: Jun. 2, 2015

(54) MOSAIC CLADE M HUMAN IMMUNODEFICIENCY VIRUS TYPE 1 (HIV-1) GAG IMMUNOGENS

(75) Inventors: Bette T. Korber, Los Alamos, NM (US); William Fischer, Sante Fe, NM (US); Norman Letvin, Boston, MA (US); Hua-Xin Liao, Durham, NC (US); Barton F. Haynes, Durham, NC (US); Beatrice H. Hahn, Birmingham, AL (US)

(73) Assignees: LOS ALAMOS NATIONAL SECURITY, LLC, Los Alamos, NM (US); BETH ISRAEL DEACONESS MEDICAL CENTER, Boston, MA (US); DUKE UNIERSITY, Durham, NC (US); THE UAB RESEARCH FOUNDATION, Birmingham, AL (US)

( * ) Notice: Subject to any disclaimer, the term of this patent is extended or adjusted under 35 U.S.C. 154(b) by 808 days.

(21) Appl. No.: 12/737,761

(22) PCT Filed: Aug. 14, 2009

(86) PCT No.: PCT/US2009/004664

§ 371 (c)(1), (2), (4) Date: Feb. 1, 2012

(87) PCT Pub. No.: WO2010/019262

PCT Pub. Date: Feb. 18, 2010

(65) Prior Publication Data

US 2012/0121631 A1 May 17, 2012

Related U.S. Application Data

(63) Continuation of application No. 12/192,015, filed on Aug. 14, 2008, now Pat. No. 7,951,377, which is a continuation-in-part of application No. 11/990,222, filed as application No. PCT/US2006/032907 on Aug. 23, 2006, now Pat. No. 8,119,140.

(60) Provisional application No. 60/710,154, filed on Aug. 23, 2005, provisional application No. 60/739,413, filed on Nov. 25, 2005.

(51) Int. Cl.

| | |
|---|---|
| ***A61K 39/21*** | (2006.01) |
| ***C07K 14/005*** | (2006.01) |
| *A61K 39/00* | (2006.01) |

(52) U.S. Cl.

CPC ............. *A61K 39/21* (2013.01); *A61K 2039/53* (2013.01); *C07K 14/005* (2013.01); *C12N 2710/24143* (2013.01); *C12N 2740/16122* (2013.01); *C12N 2740/16134* (2013.01)

(58) Field of Classification Search

CPC ................ A61K 39/21; C07K 14/005; C12N 2740/16211

See application file for complete search history.

(56) References Cited

U.S. PATENT DOCUMENTS

| | | | |
|---|---|---|---|
| 7,655,774 | B2 | 2/2010 | Mullins et al. |
| 7,951,377 | B2 | 5/2011 | Korber et al. |
| 8,119,140 | B2 | 2/2012 | Korber et al. |
| 2002/0198162 | A1 | 12/2002 | Punnonen et al. |
| 2003/0044421 | A1 | 3/2003 | Emini et al. |
| 2003/0104011 | A1 | 6/2003 | Rios |
| 2003/0147888 | A1 | 8/2003 | Haynes et al. |
| 2003/0180314 | A1 | 9/2003 | DeGroot |
| 2003/0194411 | A1 | 10/2003 | Rubinstein et al. |
| 2004/0001851 | A1 | 1/2004 | Haynes et al. |
| 2005/0137387 | A1 | 6/2005 | Mullins et al. |
| 2006/0216305 | A1 | 9/2006 | Lal et al. |
| 2006/0275897 | A1 | 12/2006 | Nabel et al. |
| 2007/0178562 | A1 | 8/2007 | Haynes et al. |
| 2009/0324631 | A1 | 12/2009 | Korber et al. |
| 2011/0150915 | A1 | 6/2011 | Korber et al. |
| 2011/0301328 | A1 | 12/2011 | Korber et al. |

FOREIGN PATENT DOCUMENTS

| | | |
|---|---|---|
| WO | WO 2005/028625 | 3/2005 |
| WO | 2007-024941 | 3/2007 |
| WO | WO 2007/024941 | 3/2007 |
| WO | 2007-047916 | 4/2007 |
| WO | WO 2007/047916 | 4/2007 |
| WO | WO 2010/019262 | 2/2010 |
| WO | WO 2012/047267 | 4/2012 |

OTHER PUBLICATIONS

International Search Report for PCT/US2009/004664, mailed Apr. 6, 2010.

Shinoda, K. et al., "Polygene DNA Vaccine Induces a High Level of Protective Effect Against HIV-Vaccinia Virus Challenge in Mice", IN: Vaccine, (Sep. 2004), vol. 22 (27-28), pp. 3523-3815.

Supplementary European Search Report dated Jul. 11, 2012 issued in connection with EP 09 80 6982.

Peng et al, "Replicating Ad-recombinants encoding non-myristoylated rather than wild-type HIV Nef elicit enhanced cellular immunity", AIDS 20:2149-2157 (2006).

International Search Report dated Jul. 3, 2008 in PCT/US06/32907 (Korber et al).

Shinoda et al, "Polygene DNA vaccine induces a high level of protective effect against HIV-vaccinia virus challenge in mice", Vaccine 22:3676-3690 (2004).

Korber et al, "Evolutionary and immunological implications of contemporary HIV-1 variation", British Medical Bulletin 58:19-42 (2001).

(Continued)

*Primary Examiner* — Jeffrey Parkin

(74) *Attorney, Agent, or Firm* — Nixon & Vanderhye P.C.

(57) ABSTRACT

The present invention relates, in general, to an immunogenic composition (e.g., a vaccine) and, in particular, to a polyvalent immunogenic composition, such as a polyvalent HIV vaccine containing nucleic acids encoding HIV-1 gag mosaic proteins, and to methods of using same. The invention further relates to methods that use a genetic algorithm to create sets of polyvalent antigens suitable for use, for example, in vaccination strategies.

18 Claims, 109 Drawing Sheets

(56) References Cited

OTHER PUBLICATIONS

Gaschen et al, "Diversity Considerations in HIV-1 Vaccine Selection", Science 296(5577):2354-2360 (2002).
Desrosiers, R., "Prospects for an AIDS Vaccine", Nature Medicine vol. 10, No. 3, 221-223 (2004).
Letvin, N., "Progress and obstacles in the development of an AIDS vaccine." (2006).
Gallo, R. C., "The end or the beginning of the drive to an HIV-preventive vaccine: a view from over 20 years," The Lancet 366:1894-1898.(2005).
McMichael, A. J., "HIV vaccines" Ann. Rev. Immunol. 24:227-255. (2006).
Haynes, B. F., and D. C. Montefiori, "Aiming to induce broadly reactive neutralizing antibody responses with HIV-1 vaccine candidates," Expert Rev. Vaccines 5(3):347-363. (2006).
Walker, B. D., and D. R. Burton, "Toward an AIDS vaccine" Science 320:760-765. (2008).
Supplementary European Patent Office (EPO) Search Report dated Nov. 9, 2012 in EP 06 80 2155 (Korber).
Nabel et al, "HIV vaccine strategies", Vaccine 20(15):1945-1947 (2002).
Altfeld et al, "HIV-1 superinfection despite broad CDS+ T-cell responses containing replication of the primary virus", Nature 420(6914):434-439 (2002).
Fischer et al, "Polyvalent vaccines for optimal coverage of potential T-cell epitopes in global HIV-1 variants", Nature Medicine 13(1):100-106 (2007).
Doria-Rose et al, "Human Immunodeficiency Virus Type 1 Subtype B Ancestral Envelope Protein Is Functional and Elicits Neutralizing Antibodies in Rabbits Similar to Those Elicited by a Circulating Subtype B Envelope", Journal of Virology 79(17):11214-11224 (2005).
Hanke et al, "DNA multi-CTL epitope vaccines for HIV and Plasmodium falciparum: immunogenicity in mice", Vaccine 16(4):426-435 (1998).
Gao et al, "Antigenicity and Immunogenicity of a Synthetic Human Immunodeficiency Virus Type 1 Group M Consensus Envelope Glycoprotein", Journal of Virology 79(2): 1154-1163 (2005).
International Search Report dated Apr. 18, 2012 in PCT/US2011/001664 (Liao).
International Search Authority Written Opinion dated Apr. 18, 2012 in PCT/US2011/001664 (Liao).
Tomaras et al. "Initial B-Cell Responses to Transmitted Human Immunodeficiency Virus Type 1: Virion-Binding Immunoglobulin M (IgM) and IgG Antibodies Followed by Plasma Anti-GP41 Antibodies with Ineffective Control of Initial Viremia", Journal of Virology, vol. 82, No. 24, pp. 14229-12463. (2008).
Weaver et al., "Cross-Subtype T-Cell Immune Responses Induced by a Human Immunodeficiency Virus Type 1 Group M Consensus Env. Immunogen", Journal of Virology, vol. 80, No. 14, pp. 6745-6756. (2006).
Liao et al., "A Group M Consensus Envelope Glycoprotein Induces Antibodies that Neutralize Subsets of Subtype Band C HIV-1 Primary Viruses", Virology, vol. 353, pp. 268-282 (Author Manuscript). (2006).
Go et al., "Giycosylation Site-Specific Analysis of Clade C HIV-1 Envelope Proteins", Journal of Proteome Research, vol. 8, No. 9, pp. 4231-4242 (Author Manuscript). (2009).
International Search Report dated Aug. 27, 2008 in WO 2007/024941 (Korber).
International Search Report dated Apr. 6, 2010 in PCT/US09/004664 (Korber).
International Search Authority Written Opinon dated Apr. 6, 2010 in PCT/US09/004664 (Korber).
Supplementary European Patent Office (EPO) Search Report dated Jul. 11, 2012 in EP 09 80 6982 (Korber).
Office Actions dated Apr. 2, 2013 and Nov. 21, 2013 in U.S. Appl. No. 13/399,963 (Korber et al.).
Office Actions dated Apr. 27, 2012, Dec. 13, 2012 and Oct. 9, 2013 in U.S. Appl. No. 12/960,287 (Korber et al.).
Office Actions dated Dec. 19, 2011, Jun. 22, 2012 and May 10, 2013 in U.S. Appl. No. 13/094,734 (Korber et al).
Office Actions dated Feb. 3, 2010, Jun. 4, 2010, Jan. 25, 2011 and May 27, 2011 in U.S. Appl. No. 11/990,222 (Korber et al.).
Office Actions dated Feb. 3, 2010 and Jun. 23, 2010 in U.S. Appl. No. 12/192,015 (Korber et al.).
Kong et al. "Expanded Breadth of the T-Cell Response to Mosaic Human Immunodeficiency Virus Type 1 Envelope DNA Vaccination" Journal of Virology, Mar. 2009, vol. 83, No. 5, p. 2201-2215.
Santra et al. "Mosaic Vaccines Elicit CD8+ T lymphocyte Responses in Monkeys that Confer Enhanced Immune Coverage of Diverse HIV Strains" Nat Med. Mar. 2010; 16(3):324-328. doi:10.1038/nm.2108.
Korber et al "T-Cell Vaccine Strategies for Human Immunodeficiency Virus, the Virus with a Thousand Faces" Journal of Virology, Sep. 2009, vol. 83, No. 17 p. 8300-8314.
Santra et al "A centralized gene-based HIV-1 vaccine elicits broad cross-clade cellular immune responses in rhesus monkeys" PNAS, Jul. 29, 2008, vol. 105,No. 30, 10489-10494.
Notice of Allowance dated Dec. 23, 2014 in U.S. Appl. No. 13/399,963 (Korber et al.).
Notice of Allowance dated Dec. 22, 2014 in U.S. Appl. No. 13/094,734 (Korber et al.).

gp120 Coverage

Nef Coverage

Gag Coverage
Position Number

Resorted by conservation
1.0
0.8
0.6
0.4
0.2
0

Gag coverage 9-mer Frequencies (0–60%)

9-mer Frequencies (0–10%)

Fig. 9

>nef_coreB.syn1.1
EVGFPVRPQVPLRPMTYKGALDLSHFLKEKGGLEGLIYSQKRQDILDLWVYHTQGYFPDW
QNYTPGPGIRYPLTFGWCFKLVPVE >nef_coreB.syn3.1
EVGFPVKPQVPLRPMTYKAAVDLSHFLKEKGGLEGLVYSQKRQDILDLWIYHTQGYFPDW
QNYTPGPGTRFPLTFGWCFKLVPVD
>nef_coreB.syn3.2
EVGFPVTPQVPLRPMTYKGALDLSHFLREKGGLEGLIYSQKRQEILDLWVYHTQGYFPDW
HNYTPGPGVRYPLTFGWCFKLVPVE
>nef_coreB.syn3.3
EVGFPVRPQVPLRPMTYKAALDLSHFLKEKGGLEGLIHSQRRQDILDLWVYHTQGFFPDW
QNYTPGPGIRYPLTFGWCYKLVPVE >nef_coreB.syn4.1
EVGFPVTPQVPLRPMTYKAAVDLSHFLREKGGLEGLIHSQKRQDILDLWIYHTQGYFPDW
QNYTPGPGIRYPLTFGWCYKLVPVE
>nef_coreB.syn4.2
DVGFPVRPQIPLRPMTYKAALDLSHFLREKGGLEGLVYSQKRQDILDLWVYHTQGFFPDW
QNYTPGPGTRFPLTFGWCFKLVPVD
>nef_coreB.syn4.3
EVGFPVRPQVPLRPMTYKGAVDLSHFLKEKGGLEGLIYSQKRQEILDLWVYHTQGYFPDW
GNYTPGPGTRYPLTFGWCLKLVPVE
>nef_coreB.syn4.4
EVGFPVKPQVPLRPMTYKGALDLSHFLKEKGGLDGLIYSQRRQDILDLWVYNTQGYFPDW
HNYTPGPGVRYPLTFGWCFKLVPVE >nef_coreB.syn6.1
EVGFPIRPQVPLRPMTFKGALDLSHFLKEKGGLDGLIYSQKRQEILDLWVYHTQGYFPDW
HNYTPGPGIRYPLCFGWCFKLVPVE
>nef_coreB.syn6.2
EVGFPVTPQVPLRPMTYKGAVDLSHFLKEQGGLEGLIYSQRRQDILDLWIYNTQGYFPDW
QCYTPGPGVRFPLTFGWCFKLEPVD
>nef_coreB.syn6.3
EVGFPVKPQVPLRPMTYKAAVDLSHFLKEKGGLEGLIYSQKRQDILDLWIYHTQGYFPDW
QNYTPGPGIRYPLTFGWCLKLVPVE
>nef_coreB.syn6.4
DVGFPVRPQVPLRPMTYKAALDLSHFLKEEGGLEGLIYSQQRQDILDLWVYHTQGFFPDW
QNYTPGPGTRYPLTFGWCYKLVPVE
>nef_coreB.syn6.5
EVGFPVRPQIPLRPMTYKGALDLSHFLREKGGLEGLVYSQKRQDILDLWVHHTQGYFPDW
GNYTPGPGTRFPLTFGWCFKLVPVD
>nef_coreB.syn6.6
EVGFPVRPQVPLRPMTYKGAFDLSHFLKDKGGLEGLIHSQKRQDILDLWVYNTQGYFPDW
QNYTPGPGVRYPLTFGWCFKLVPLE >nef_coreC.syn1.1
EVGFPVRPQVPLRPMTYKAAFDLSFFLKEKGGLEGLIYSKKRQEILDLWVYHTQGFFPDW
QNYTPGPGVRYPLTFGWCFKLVPVD

Fig. 9 cont'd-1

>nef_coreC.syn3.1
EVGFPVTPQVPLRPMTFKGAFDLGFFLKEKGGLDGLIYSKKRQDILDLWVYHTQGYFPDW
QNYTPGPGVRYPLTFGWCYKLVPVD
>nef_coreC.syn3.2
EVGFPVKPQVPLRPMTYKAAFDLSFFLKDKGGLEGLIWSKKRQEILDLWVYHTQGFFPDW
QNYTPGPGIRYPLTFGWPFKLVPVD
>nef_coreC.syn3.3
EVGFPVRPQVPLRPMTYKGAFDLSFFLKEKGGLEGLIYSKKRQEILDLWVYNTQGFFPDW
HNYTPGPGVRFPLTFGWCFKLVPVD >nef_coreC.syn4.1
EVGFPVRPQVPLRPMTYKGAFDLSFFLKEKGGLEGLIWSKKRQEILDLWVYNTQGYFPDW
QCYTPGPGVRFPLTFGWCFKLVPVD
>nef_coreC.syn4.2
DVGFPVRPQVPVRPMTYKAAFDLSFFLKDKGGLEGLIHSKRRQDILDLWVYNTQGFFPDW
HNYTPGPGIRYPLTFGWCFKLVPVD
>nef_coreC.syn4.3
EVGFPVKPQVPLRPMTYKAAVDLSFFLKEKGGLEGLIYSKKRQEILDLWVYHTQGFFPDW
QNYTPGPGTRYPLTFGWPFKLVPVD
>nef_coreC.syn4.4
EVGFPVTPQVPLRPMTFKGAFDLGFFLKEKGGLDGLIYSKKRQDILDLWVYHTQGYFPDW
QNYTPGPGVRYPLTFGWCYKLVPVD >nef_coreC.syn6.1
DVGFPVRPQVPLRPMTYKGAFDLSFFLKEKGGLDGLIYSKKRQEILDLWVYNTQGYFPDW
QCYTPGPGVRYPLTFGWCYKLVPVD
>nef_coreC.syn6.2
EVGFPVKPQVPVRPMTYKAAFDLSFFLKDKGGLEGLIWSKKRQEILDLWVYHTQGFFPDW
QNYTPGPGIRYPLTFGWCFKLVPVD
>nef_coreC.syn6.3
EVGFPVKPQVPLRPMTFKGAFDLGFFLKEKGGLEGLIYSKQRQDILDLWVYHTQGFFPDW
HNYTPGPGVRLPLTFGWCFKLVPVD
>nef_coreC.syn6.4
GVGFPVRPQVPVRPMTYKAAFDLGFFLKDKGGLEGLIYSKKRQDILDLWVYNTQGFFPDW
QNYTPGPGVRFPLTFGWCFKLVPVD
>nef_coreC.syn6.5
EVGFPVTPQVPLRPMTYKAAVDLSWFLKEKGGLDGLIYSRKRQEILDLWVHHTQGFFPDW
QNYTPGPGTRFPLTFGWCFKLVPVD
>nef_coreC.syn6.6
EVGFPVRPQVPVRPMTYKGAVDLSFFLKEKGGLEGLIHSKRRQDILDLWVYHTQGYFPDW
QNYTPGPGTRYPLTFGWPFKLVPVD >nef_coreM.syn1.1
EVGFPVRPQVPLRPMTYKGALDLSHFLKEKGGLEGLIYSKKRQEILDLWVYHTQGYFPDW
QNYTPGPGVRYPLTFGWCFKLVPVD

Fig. 9 cont'd-2

>nef_coreM.syn3.1
DVGFPVRPQVPLRPMTYKAAVDLSHFLKEKGGLEGLVYSQKRQDILDLWVYHTQGFFPDW
QNYTPGPGVRYPLTFGWCYKLVPVD
>nef_coreM.syn3.2
EVGFPVRPQVPVRPMTYKGAFDLSFFLKEKGGLEGLIYSKKRQEILDLWVYHTQGYFPDW
HNYTPGPGTRFPLTFGWCFKLVPVD
>nef_coreM.syn3.3
EVGFPVKPQVPLRPMTYKGALDLSHFLKEKGGLDGLIYSKKRQDILDLWVYNTQGYFPDW
QNYTPGPGIRYPLTFGWCFKLVPVE >nef_coreM.syn4.1
EVGFPVTPQVPLRPMTFKGAFDLGFFLKEKGGLEGLIYSKKRQEILDLWVYHTQGFFPDW
QNYTPGPGTRYPLCFGWCFKLVPVE
>nef_coreM.syn4.2
EVGFPVKPQVPLRPMTYKAAVDLSHFLKEKGGLEGLVYSQKRQDILDLWVYHTQGYFPDW
QNYTPGPGIRYPLTFGWCYKLVPVD
>nef_coreM.syn4.3

DVGFPVRPQVPLRPMTYKGALDLSHFLKEEGGLEGLIYSQKRQEILDLWVYNTQGYFPDW
QNYTPGPGVRYPLTFGWCFKLVPVD
>nef_coreM.syn4.4
EVGFPVRPQVPVRPMTYKGAFDLSFFLKEKGGLDGLIYSKKRQDILDLWVYNTQGFFPDW
HNYTPGPGTRFPLTFGWCFELVPVD >nef_coreM.syn6.1
EVGFPVRPQVPTRPMTYKGAVDLSHFLKEKGGLEGLVYSQKRQDILDLWVHHTQGFFPDW
QNYTPGPGTRYPLTFGWPFKLVPVD
>nef_coreM.syn6.2
DVGFPVRPQVPVRPMTYKAAFDLSFFLREKGGLDGLIYSKKRQDILDLWVYNTQGYFPDW
QNYTPGPGVRFPLTFGWCFELVPVD
>nef_coreM.syn6.3
NVGFPVRPQVPLRPMTFKGAFDLGFFLKEKGGLEGLIYSKKRQEILDLWVYHTQGYFPDW
HNYTPGPGTRFPLTFGWCFKLVPVE
>nef_coreM.syn6.4
EVGFPVTPQVPLRPMTYKGAFDLSFFLKEKGGLDGLIYSRKRQEILDLWVYNTQGFFPDW
QNYTPGPGIRYPLTFGWCFKLVPMD
>nef_coreM.syn6.5
EVGFPVKPQVPLRPMTYKAAVDLSHFLREKGGLEGLIHSQRRQDILDLWIYHTQGYFPDW
QCYTPGPGVRYPLTFGWCYKLVPVD
>nef_coreM.syn6.6
GVGFPVRPQIPLRPMTYKGALDLSHFLKEEGGLEGLIYSQKRQDILDLWVYHTQGFFPDW
HNYTPGPGIRYPLCFGWCFKLVPVD

Fig. 9 cont'd-3

>gagB.syn1.1
MGARASVLSGGELDRWEKIRLRPGGKKKYKLKHIVWASRELERFAVNPGLLETSEGCRQI
LGQLQPSLQTGSEELRSLYNTVATLYCVHQRIEVKDTKEALDKIEEEQNKSKKKAQQAAA
DTGNSSQVSQNYPIVQNLQGQMVHQAISPRTLNAWVKVVEEKAFSPEVIPMFSALSEGAT
PQDLNTMLNTVGGHQAAMQMLKETINEEAAEWDRLHPVHAGPIAPGQMREPRGSDIAGTT
STLQEQIGWMTNNPPIPVGEIYKRWIILGLNKIVRMYSPTSILDIRQGPKEPFRDYVDRF
YKTLRAEQASQEVKNWMTETLLVQNANPDCKTILKALGPAATLEEMMTACQGVGGPGHKA
RVLAEAMSQVTNSATIMMQRGNFRNQRKTVKCFNCGKEGHIAKNCRAPRKKGCWKCGKEG
HQMKDC-TERQANFLGKIWPSHKG-RPGNFLQSRP--------------------EPTAP
PEESFRFGEETTTPSQKQEPIDKELYPLASLRSLFGNDPSSQ >gagB.syn3.1
MGARASILSGGELDRWEKIRLRPGGKKQYRLKHIVWASRELERFAINPGLLETSDGCRQI
LGQLQPALQTGSEELKSLFNTVATLYCVHQRIDVKDTKEALDKIEEEQNKSKKKAQQAAA
DTGNSSQVSQNYPIVQNIQGQMVHQAISPRTLNAWVKVIEEKAFSPEVIPMFSALSEGAT
PQDLNTMLNTVGGHQAAMQMLKETINEEAADWDRLHPVHAGPIAPGQMREPRGSDIAGTT
STLQEQIGWMTNNPPIPVGEIYKRWIIMGLNKIVRMYSPSSILDIKQGPKEPFRDYVDRF
YKVLRAEQASQEVKNWMTETLLVQNSNPDCKTILKALGPGATLEEMMTACQGVGGPGHKA
RVLAEAMSQMTNSATIMMQKGNFRNQRKPVKCFNCGKEGHIAKNCRAPRKKGCWKCGREG
HQMKDC-TERQANFLGKIWPSYKG-RPGNFLQNRP--------------------EPTAP
PAESFRFGEETTTPSQKQETIDKELYPLASLRSLFGSDPSSQ
>gagB.syn3.2
MGARASVLSGGQLDRWEKIRLRPGGKKKYRLKHLVWASRELERFAVNPGLLETAEGCRQI
LEQLQPSLQTGSEELRSLFNTVAVLYCVHQRIEVKDTKEALDKVEEEQNKSKKKAQQTAA
DTGNNSQVSQNYPIVQNMQGQMVHQALSPRTLNAWVKVIEEKAFSPEVIPMFTALSEGAT
PQDLNTMLNTVGGHQAAMQMLKDTINEEAAEWDRLHPVQAGPVAPGQIREPRGSDIAGST
STLQEQIGWMTSNPPIPVGEIYKRWIILGLNKIVRMYSPVSILDIRQGPKEPFRDYVDRF
YKTLRAEQATQEVKNWMTETLLVQNANPDCKTILKALGPGATLEEMMTACQGVGGPSHKA
RVLAEAMSQVTNSATIMMQRGNFRNQRKIVKCFNCGKEGHIARNCRAPRKRGCWKCGKEG
HQMKDC-NERQANFLGKIWPSHKG-RPGNFLQSRP--------------------EPSAP
PEESFRFGEEKTTPSQKQEPIDKDLYPLASLKSLFGNDPSLQ
>gagB.syn3.3
MGARASVLSGGELDKWEKIRLRPGGKKKYKLKHIVWASRELERFAVNPGLLETSEGCRQI
LGQLQPSLQTGSEELRSLYNTVATLYCVHQKIEVKDTKEALEKIEEEQNKCKKKAQQAAA
GTGNSSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTHNPPIPVGDIYKRWIILGLNKIVRMYSPTSILDIRQGPKESFRDYVDRF
YKTLRAEQASQDVKNWMTETLLVQNANPDCRTILKALGPAATLEEMMTACQGVGGPSHKA
RILAEAMSQVTNPATIMMQRGNFRNQRKTVKCFNCGKEGHLARNCRAPRKKGCWKCGKEG
HQMKEC-TERQANFLGKIWPSHKG-RPGNFLQSRP--------------------EPTAP
PEESFRFGEETATPPQKQEPIDKELYPLTSLRSLFGNDPSSQ >gagB.syn4.1
MGARASVLSGGQLDRWEKIRLRPGGKKKYRLKHLVWASRELERFAVNPGLLETAEGCRQI
LEQLQPSLQTGSEELRSLFNTVATLYCVHQRIDVKDTKEALDKIEEEQNKCKKKAQQAAA
DTGNSSQVSQNYPIVQNIQGQMVHQALSPRTLNAWVKVVEEKAFSPEVIPMFTALSEGAT
PQDLNTMLNTVGGHQAAMQMLKETINEEAAEWDRLHPVQAGPVAPGQMREPRGSDIAGST
STLQEQIGWMTNNPPIPVGDIYKRWIILGLNKIVRMYSPVSILDIRQGPKESFRDYVDRF
YKVLRAEQASQEVKNWMTETLLVQNANPDCRTILKALGPAATLEEMMTACQGVGGPGHKA

Fig. 9 cont'd-4

RVLAEAMSQMTNSATIMMQRGNFRNQRKTVKCFNCGKEGHIAKNCRAPRKKGCWKCGKEG
HQMKEC-TERQANFLGKIWPSYKG-RPGNFLQSRP--------------------EPSAP
PAESFRFGEETTTPSQKQETIDKELYPLTSLRSLFGNDPSLQ
>gagB.syn4.2
MGARASVLSGGELDKWEKIRLRPGGKKKYKLKHIVWASRELERFAINPGLLETSEGCRQI
LGQLQPALQTGSEELRSLYNTVATLYCVHQKIEVKDTKEALEKVEEEQNKSKQKAQQAAA
DTGNNSQVSQNYPIVQNLQGQMVHQAISPRTLNAWVKVIEEKAFSPEVIPMFAALSEGAT
PQDLNTMLNTVGGHQAAMQMLKETINEEAADWDRLHPVHAGPIAPGQIREPRGSDIAGTT
SNLQEQIAWMTNNPPIPVGEIYKRWIIMGLNKIVRMYSPTSILDIKQGPKEPFRDYVDRF
YRTLRAEQASQDVKNWMTETLLVQNANPDCRTILKALGPGATLEEMMTACQGVGGPSHKA
RVLAEAMSQVTNPATIMMQRGNFRNQRKPVKCFNCGKEGHLAKNCRAPRKRGCWKCGKEG
HQMKDC-NERQANFLGKIWPSHKG-RPGNFLQNRP--------------------EPSAP
PEESFRFGEETATPSQKQEPIDKELYPLASLRSLFGSDPSSQ
>gagB.syn4.3
MGARASILSGGELDRWEKIRLRPGGKKQYRLKHIVWASRELERFAVNPGLLETSEGCKQI
LEQLQPALQTGSEELKSLYNTVAVLYCVHQRIEIKDTKEALEKIEEEQNKSKKKAQQTAA
DTGNNSQVSQNYPIVQNLQGQMVHQPISPRTLNAWVKVIEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTSNPPIPVGEIYKRWIILGLNKIVRMYSPTSILDIRQGPKEPFRDYVDRF
YKTLRAEQATQEVKNWMTETLLVQNANPDCKTILKALGPGATLEEMMTACQGVGGPSHKA
RILAEAMSQVTNSATVMMQRGNFRNQRKTIKCFNCGKEGHLARNCRAPRKKGCWKCGREG
HQMKDC-TERQANFLGKIWPSYKG-RPGNFLQNRP--------------------EPTAP
PAESFRFGEETTTPPQKQEPIDKELYPLASLKSLFGNDPSSQ
>gagB.syn4.4
MGARASVLSGGKLDKWEKIRLRPGGKKKYQLKHIVWASRELERFALNPGLLETSDGCRQI
LGQLQPSLQTGSEELKSLFNTVAVLYCVHQRIEVKDTKEALDKVEEEQNKSKKKAQQAAA
GTGNSSQVSQNYPIVQNMQGQMVHQALSPRTLNAWVKVIEEKAFSPEVIPMFSALSEGAT
PQDLNTMLNTVGGHQAAMQMLKDTINEEAAEWDRVHPVHAGPIAPGQMREPRGSDIAGTT
STLQEQIGWMTHNPPIPVGEIYKRWIILGLNKIVRMYSPSSILDIRQGPKEPFRDYVDRF
YKTLRAEQASQEVKNWMTETLLVQNSNPDCKTILKALGPAATLEEMMTACQGVGGPSHKA
RVLAEAMSQVTNSATIMMQKGNFRNQRKIVKCFNCGKEGHIARNCRAPRKKGCWRCGKEG
HQMKDC-TERQVNFLGKIWPSYKG-RPGNFLQSRP--------------------EPTAP
PEESFRFGEEKTTPSQKQEPIDKDLYPLASLKSLFGNDPLSQ >gagB.syn6.1
MGARASILSGGELDRWEKIRLRPGGSKKYRLKHIVWASRELERFAVNPGLLETAEGCRQI
LGQLQPSLQTGSEELRSLYNTIATLYCVHQRIEIKDTKEALEKIEEEQNKSKKKAQQTAA
DTGNNSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQIREPRGSDIAGTT
SNLQEQIGWMTSNPPIPVGEIYKRWIILGLNKIVRMYSPISILDIRQGPKEPFRDYVDRF
YRTLRAEQASQDVKNWMTETLLVQNANPDCKTILKALGPGATLEEMMTACQGVGGPGHKA
RVLAEAMSQVTNSATVMMQRGNFRNQRRTVKCFNCGKEGHIARNCRAPRKKGCWKCGQEG
HQMKDC-TERQANFLGKIWPSYKG-RPGNFLQSRP--------------------EPTAP
PAESFRFGEETTTPPQKQEPIDKELYPLTSLKSLFGNDPSSQ
>gagB.syn6.2
MGARASVLSGGKLDRWEKIRLRPGGKKKYRLKHVVWASRELERFAVNPGLLESSEGCRQI
LEQLQPSLQTGSEELRSLFNTVATLYCVHQRIDVKDTKEALDKIEEEQNKCKKKAQQAAA
DTGNNSQVSQNYPIVQNLQGQMVHQPISPRTLNAWVKVVEEKAFSPEVIPMFAALSEGAT
PQDLNTMLNTVGGHQAAMQMLKETINEEAAEWDRVHPVHAGPIAPGQMREPRGSDIAGST
STLQEQIGWMTNNPPIPVGDIYKRWIILGLNKIVRMYSPASILDIRQGPKEPFRDYVDRF
YKTLRAEQATQEVKNWMTETLLVQNANPDCRTILKALGPGATLEEMMTACQGVGGPGHKA
RVLAEAMSQMTNSATIMMQKGNFRNQRKTIKCFNCGKEGHIARNCKAPRKKGCWKCGREG
HQMKDC-IERQANFLGKIWPSHKG-RPGNFLQNRP--------------------EPTAP
PEESFRFGEETATPPQKQEPIDKELYPLASLKSLFGSDPSSQ

Fig. 9 cont'd-5

>gagB.syn6.3
MGARASVLSGGELDRWEKIRLRPGGKKKYRLKHLVWASRELERFAVNPGLLETSDGCRQI
LGQLQPALQTGSEELKSLYNTVATLYCVHQKIDVRDTKEALDKIEEEQNKSKQKAQQAAA
DTGNSSQVSQNYPIVQNIQGQMVHQAISPRTLNAWVKVVEEKAFSPEVIPMFTALSEGAT
PQDLNTMLNTVGGHQAAMQMLKETINEEAAEWDRLHPVQAGPVAPGQMREPRGSDIAGTT
STLQEQIGWMTHNPPIPVGEIYKRWIIMGLNKIVRMYSPSSILDIRQGPKESFRDYVDRF
YKVLRAEQASQEVKNWMTETLLVQNANPDCKTILKALGPGATLEEMMTACQGVGGPSHKA
RVLAEAMSQVTNSATIMMQRGNFRNQRKTVKCFNCGKEGHIAKNCRAPRKRGCWKCGKEG
HQMKEC-TERQANFLGKIWPSHKG-RPGNFLQSRP--------------------EPTAP
PEESFRFGEEKTTPSQKQETIDKELYPLASLRSLFGNDPSSQ
>gagB.syn6.4
MGARASVLSGGELDKWEKIRLRPGGKKKYQLKHIVWASRELERFAVNPGLLETSEGCKQI
LEQLQPALQTGSEELRSLYNTIAVLYCVHQKIEIKDTKEALDKVEEEQNKSKKKAQQAAA
GTGNSSQVSQNYPIVQNLQGQMVHQPLSPRTLNAWVKVVEEKAFSPEVIPMFTALSEGAT
PQDLNTMLNTVGGHQAAMQMLKETINEEAADWDRLHPVHAGPIAPGQMREPRGSDIAGST
STLQEQIGWMTHNPPIPVGDIYKRWIILGLNKIVRMYSPTSILDIKQGPKEPFRDYVDRF
YKTLRAEQATQEVKNWMTETLLVQNANPDCRTILKALGPAATLEEMMTACQGVGGPSHKA
RILAEAMSQVTNPATIMMQRGNFRNQRKPVKCFNCGKEGHIARNCRAPRKRGCWKCGKEG
HQMKDC-TERQVNFLGKIWPSHKG-RPGNFLQNRP--------------------EPSAP
PAESFRFGEETTTPSQKQEPIDKEMYPLASLRSLFGSDPSSQ
>gagB.syn6.5
MGARASVLSGGQLDRWEKIRLRPGGKKQYRLKHIVWASRELERFAINPGLLETSEGCRQI
LGQLQPSLQTGSEELKSLFNTVAVLYCVHQRIEVKDTKEALEKVEEEQNKSKKKAQQAAA
DTGNSSQVSQNYPIVQNLQGQMVHQALSPRTLNAWVKVIEEKAFSPEVIPMFSALSEGAT
PQDLNTMLNTVGGHQAAMQMLKDTINEEAAEWDRLHPVHAGPVAPGQMRDPRGSDIAGTT
STLQEQIAWMTNNPPIPVGEIYKRWIILGLNKIVRMYSPTSILDIRQGPKEPFRDYVDRF
YKVLRAEQASQDVKNWMTETLLVQNANPDCKTILKALGPAATLEEMMTACQGVGGPGHKA
RVLAEAMSQVTNSTTIMMQRGNFRNQRKIVKCFNCGKEGHLAKNCRAPRKKGCWKCGKEG
HQMKEC-TERQANFLGKIWPSHKG-RPGNFLQSRP--------------------EPSAP
PEESFRFGEETATPSQKQEPIDKDLYPLASLKSLFGNDPLSQ
>gagB.syn6.6
MGARASVLSGGKLDKWEKIRLRPGGKKKYKLKHIVWASRELERFALNPGLLETSEGCRQI
LRQLQPSLQTGSEELRSLYNTVATLYCVHQKIEVKDTKEALEKIEEEQNKSKKKAQQTAA
DTGNNSQVSQNYPIVQNMQGQMVHQALSPRTLNAWVKVVEEKAFSPEVIPMFSALSEGAT
PQDLNTMLNTVGGHQAAMQMLKDTINEEAAEWDRLHPAQAGPIAPGQIREPRGSDIAGTT
SNLQEQIAWMTHNPPIPVGDIYKRWIILGLNKIVRMYSPVSILDIRQGPKEPFRDYVDRF
YKTLRAEQASQEVKNWMTETLLVQNSNPDCKTILKALGPGATLEEMMTACQGVGGPGHKA
RVLAEAMSQVTNPATIMMQKGNFKNQRKTVKCFNCGKEGHLARNCRAPRKKGCWRCGKEG
HQMKDC-NERQANFLGKIWPSHKG-RPGNFLQSRP--------------------EPTAP
PEESFRFGEETTTPAQKQEPIDKELYPLTSLRSLFGNDPSLQ
>gagC.syn1.1
MGARASILRGGKLDKWEKIRLRPGGKKHYMLKHLVWASRELERFALNPGLLETSEGCKQI
IKQLQPALQTGTEELRSLYNTVATLYCVHEKIEVRDTKEALDKIEEEQNKSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGDIYKRWIILGLNKIVRMYSPVSILDIKQGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ
>gagC.syn3.1
MGARASVLRGEKLDKWERIRLRPGGKKHYMLKHLVWASRELERFALNPSLLETSEGCKQI
IQQLQPALKTGTEELRSLFNTVATLYCVHAGIEVRDTKEALDKIEEEQNKCQQKTQQAKE
ADG---KVSQNYPIVQNLQGQMVHQALSPRTLNAWVKVIEEKAFSPEVIPMFTALSEGAT

Fig. 9 cont'd-6

PSDLNTMLNTVGGHQAAMQMLKDTINEEAAEWDRLHPVQAGPVAPGQMREPRGSDIAGTT
SNLQEQIAWMTGNPPVPVGDIYKRWIILGLNKIVRMYSPVSILDIRQGPKEPFRDYVDRF
FKTLRAEQSTQEVKNWMTETLLVQNANPDCKTILRALGPAASLEEMMTACQGVGGPSHKA
RVLAEAMSQ-ANSTNIMMQRGNFKGPKRIIKCFNCGKEGHLARNCRAPRKKGCWKCGKEG
HQMKDC-IERQANFLGKIWPSNKG-RPGNFLQNRPE------PTAPPVEPTAPPAEPTAP
PAESFKFEE--TTPAPKQEPKDRE--PLTSLRSLFGSDPLSQ
>gagC.syn3.2
MGARASILRGEKLDTWEKIRLRPGGRKHYMLKHIVWASRELEKFALNPGLLETSEGCKQI
MKQLQPALQTGTEELKSLYNTVATLYCVHEKIEVRDTKEAVDKIEEEQNKSQQKTQQAKA
ADE---KVSQNYPIVQNIQGQMVHQPISPRTLNAWVKVIEEKGFNPEVIPMFTALSEGAT
PQDLNTMLNTVGGHQAAMQMLKDTINDEAAEWDRLHPVHAGPIAPGQMREPRGSDIAGST
STLQEQITWMTSNPPVPVGEIYKRWIILGLNKIVRMYSPVSILDIKQGPKEPFRDYVDRF
FKVLRAEQATQDVKNWMTDTLLIQNANPDCKTILKALGPGASLEEMMTACQGVGGPGHKA
RVLAEAMSQ-ANNTNIMMQRSNFKGPKRIVKCFNCGKEGHIAKNCRAPRKKGCWKCGQEG
HQMKDC-TERQANFLGKIWPSQKG-RPGNFLQNRP--------------------EPSAP
PAESFRFGE--TTPAPKQELKDRE--PLTSLKSLFGSDPLSQ
>gagC.syn3.3
MGARASILRGGKLDKWEKIRLRPGGKKRYMLKHLIWASRELERFALNPGLLETAEGCKQI
IKQLQPALQTGTEELRSLYNTVATLYCVHKRIDVRDTKEALDKIEEEQNKIQQKTQQAKA
ADG---KVSQNYPIVQNAQGQMVHQAISPRTLNAWVKVVEEKAFSPEIIPMFTALSEGAT
PQDLNSMLNAVGGHQAAMQMLKDTINEEAAEWDRVHPVHAGPVAPGQIREPRGSDIAGTT
STLQEQIAWMTSNPPIPVGDIYKRWIIMGLNKIVRMYSPVSILDIKQGPKESFRDYVDRF
FKTLRAEQATQEVKNWMTDTLLVQNANPDCKTILRALGPGATLEEMMTACQGVGGPSHKA
RVLAEAMSQ-TNSA-ILMQRSNFKGSKRIVKCFNCGKEGHIARNCRAPRKRGCWKCGKEG
HQMKEC-TERQANFLGKIWPSHKG-RPGNFLQSRP--------------------EPTAP
PAESFRFEE--TTPAPKQESKDRE--PLISLKSLFGNDPLSQ >gagC.syn4.1
MGARASVLRGEKLDTWERIKLRPGGKKHYMIKHLVWASRELEKFALNPGLLETSEGCKQI
IQQLQPALKTGTEELKSLYNTVATLYCVHERIDVRDTKEALDKIEEEQNKIQQKTQQAKE
ADG---KVSQNYPIVQNAQGQMVHQALSPRTLNAWVKVVEEKAFSPEIIPMFTALSEGAT
PSDLNTMLNTIGGHQAAMQMLKDTINDEAAEWDRLHPVHAGPIAPGQIREPRGSDIAGTT
STLQEQITWMTSNPPVPVGEIYKRWIILGLNKIVRMYSPVSILDIKQGPKESFRDYVDRF
FKTLRAEQSTQEVKNWMTETLLVQNANPDCKTILKALGPGATLEEMMTACQGVGGPGHKA
RVLAEAMSQ-TNSA-ILMQRSNFKGSKRIVKCFNCGREGHIARNCKAPRKKGCWKCGKEG
HQMKDC-IERQANFLGKIWPSHKG-RPGNFLQNRPE------PTAPP--------EPTAP
PAESFRFGE--TTPAPKQEQKDRE--PLISLKSLFGSDPLLQ
>gagC.syn4.2
MGARASILRGEKLDKWERIRLRPGGKKHYMLKHLVWASRELDRFALNPGLLETSDGCKQI
IKQLHPALQTGTEELRSLFNTVATLYCVHAGIEVRDTKEAVDKIEEEQNKSQQKTQQAKA
ADE---KVSQNYPIVQNIQGQMVHQPISPRTLNAWVKVIEEKAFSPEVIPMFTALSDGAT
PQDLNTMLNTVGGHQAAMQMLKDTINEEAAEWDRIHPVHAGPVAPGQMRDPRGSDIAGST
STLQEQIAWMTNNPPVPVGDIYKRWIIMGLNKIVRMYSPVSILDIRQGPKEPFRDYVDRF
FRTLRAEQATQDVKNWMTDTLLIQNANPDCKTILRALGPGASLEEMMTACQGVGGPGHKA
RVLAEAMSQ-ANNTNIMMQKSNFKGPKRTVKCFNCGKEGHIARNCRAPRKRGCWKCGKEG
HQMKEC-TERQANFLGKIWPSQKG-RPGNFLQSRP--------------------EPSAP
PAESFRFEE--TTPAPKQESKDRE--PLTSLKSLFGSDPSSQ
>gagC.syn4.3
MGARASILRGGKLDTWEKIRLRPGGKKRYMLKHLIWASRELERFALNPSLLETSEGCKQI
MKQLQPALQTGTEELRSLYNTVATLYCVHKGIKVQDTKEALDKIEEEQKKSQQKTQQAEA
ADK--GKVSQNYPIVQNLQGQMVHQPLSPRTLNAWVKVIERKAFSPEVIPMFSALSEGAT
PQDLNSMLNAVGGHQAAMQMLKDTINEEAAEWDRVHPVHAGPIAPGQMREPRGSDIAGTT
SNLQEQIAWMTSNPPIPVGDIYKRWIVLGLNKIVRMYSPVSILDIKQGPKEPFRDYVDRF
FKTLRAEQATQEVKNWMTDTLLVQNANPDCKTILRALGPAASLEEMMTACQGVGGPGHKA

Fig. 9 cont'd-7

RVLAEAMSQ-ANS-NIMMQRGNFKGPKRIIKCFNCGKEGHLARNCRAPRKKGCWKCGREG
HQMKDC-TERQANFLGKIWPSNKG-RPGNFLQSRP--------------------EPTAP
PAESFGFGE--TTPAPKQELKDRE--PLTSLKSLFGNDPLSQ
>gagC.syn4.4
MGARASILRGGKLDKWEKIRLRPGGRKHYMLKHIVWASRELERFALNPGLLETAEGCKQI
IKQLQPALQTGTEELKSLFNTVATLYCVHEKIEVRDTKEALDKIEEEQNKCQQKTQQAKA
ADG---KVSQNYPIVQNLQGQMVHQAISPRTLNAWVKVIEEKGFNPEVIPMFTALSEGAA
PQDLNTMLNTIGGHQAAMQMLKDTINEEAAEWDRLHPVQAGPVAPGQMREPRGSDIAGTT
SSLQEQIAWMTGNPPVPVGDIYKRWIILGLNKIVRMYSPVSILDIRQGPKEPFRDYVDRF
FKVLRAEQATQDVKNWMTETLLVQNANPDCKTILRALGPGATLEEMMTACQGVGGPSHKA
RVLAEAMSQ-ANNANIMMQRSNFKGPKRIVKCFNCGKEGHIAKNCRAPRKKGCWKCGQEG
HQMKDC-NERQANFLGRIWPSHKG-RPGNFIQSRPEPTAPLEPTAPPA-------EPTAP
PAESFKFEE--TTPAPKQEPKDRE--PLTSLRSLFGSDPLSQ >gagC.syn6.1
MGARASVLRGEKLDTWERIKLRPGGKKHYMIKHLVWASRELEKFALNPGLLETAEGCKQI
IRQLQPALQTGTEELRSLYNTVATLYCVHKRIDVRDTKEALDKIEEEQNKSQQKAQQAKA
ADG---KVSQNYPIVQNLQGQMVHQSLSPRTLNAWVKVIERKAFSPEVIPMFSALSEGAT
PQDLNTMLNTVGGHQAAMQMLKDTINEEAAEWDRIHPVHAGPIAPGQMREPRGSDIAGTT
STLQEQITWMTSNPPVPVGEIYKRWIILGLNKIVRMYSPVSILDIRQGPKEPFRDYVDRF
FKTLRAEQSTQEVKNWMTDTLLAQNANPDCKIILRGLGPGATLEEMMTACQGVGGPGHKA
RVLAEAMSQ-ANS-NILMQRSNFKGPRRTIKCFNCGKEGHLAKNCRAPRKKGCWKCGKEG
HQMKEC-TERQANFLGKIWPSQKG-RPGNFLQSRP--------------------EPSAP
PAESFRFEE--TTPALKQEPKDRE--PLTSLRSLFGSDPLSQ
>gagC.syn6.2
MGASASILRGEKLDRWEKIRLRPGGKKCYMLKHIIWASKELERFALNPGLLETSEGCKQI
MKQLQPALQTGTEELKSLYNTVATLYCVHEKIEVRDTKEALDKIEEEQKKSQQKTQQAEA
ADK--GKVSQNYPIVQNAQGQMVHQALSPRTLNAWVKVVEEKAFSPEIIPMFTALSEGAA
PQDLNTMLNTVGGHQAAMQMLKDTINEEAAEWDRVHPVHAGPIAPGQIREPRGSDIAGTT
STLQEQVAWMTSNPPVPVGDIYKRWIVLGLNKIVRMYSPVSILDIKQGPKEPFRDYVDRF
FKTLRAEQSSQEVKNWMTDTLLVQNANPDCKTILRALGPAASLEEMMTACQGVGGPSHKA
RVLAEAMSQ-ANSTNIMMQRGNFKGPKRIVKCFNCGREGHIARNCRAPRKKGCWKCGQEG
HQMKDC-IERQANFLGKIWPSHKG-RPGNFIQSRPE------PTAPP--------EPTAP
PAESFRFGE--TTPAPKQESKDRE--PLTSLKSLFGNDPLSQ
>gagC.syn6.3
MGARASVLKGEKLDKWERIRLRPGGKKQYRLKHLVWASRELERFALNPSLLETSEGCRQI
IKQLQPALKTGTEELRSLYNTIATLYCVHKGIKVQDTKEALDKVEEEQNKSQQKTQQAKA
ADE---KVSQNYPIVQNLQGQMVHQPLSPRTLNAWVKVIEEKGFNPEVIPMFTALSEGAT
PQDLNSMLNAVGGHQAAMQMLKDTINEEAAEWDRLHPVQAGPVAPGQIREPRGSDIAGTT
SSLQEQIAWMTGNPPVPVGDIYKRWIILGLNKIVRMYSPVSILDIKQGPKESFRDYVDRF
FKTLRAEQATQDVKNWMTETLLVQNANPDCKTILRALGPGATLEEMMTACQGVGGPSHKA
RVLAEAMSQ-ANNANIMMQRSNFKGPKRTVKCFNCGKEGHIAKNCRAPRKKGCWKCGREG
HQMKDC-IERQANFLGKIWPSNKG-RPGNFLQNRTE------PTAPPA-------EPTAP
PAESFRFEE--TTPAPKQELKDRE--PLTSLKSLFGSDPLLQ
>gagC.syn6.4
MGARASILRGEKLDKWEKIRLRPGGRKHYMLKHIVWASRELEGFALNPGLLETSEGCKQI
IKQLQPALQTGTEELRSLFNTVATLYCVHSGIEVRDTKEAVDKIEEEQNKIQQKTQQAKE
ADG---KVSQNYPIVQNSQGQMVHQAISPRTLNAWVKVIEEKAFSPEVIPMFTALSEGAT
PSDLNTMLNTIGGHQAAMQMLKDTINDEAAEWDRLHPVHAGPIAPGQMRDPRGSDIAGST
STLQEQIAWMTNNPPVPVGDIYKRWIIMGLNKIVRMYSPVSILDIKQGPKEPFRDYVDRF
FRTLRAEQATQEVKNWMTETLLVQNANPDCRTILKALGPGATLEEMMTACQGVGGPGHKA
RVLAEAMSQ-ANNINIMMQRNNFKGPKRIIKCFNCGKEGHIARNCKAPRKKGCWKCGKEG
HQMKDC-NERQANFLGKIWPSHKG-RPGNFLQNRP--------------------EPTAP
PAESFRFEE--TTPTPKQEPKDRE--PLTSLKSLFGSDPSSQ

Fig. 9 cont'd-8

>gagC.syn6.5
MGARASILRGGKLDKWEKIRLRPGGKKRYMLKHLIWASRELERFALNPGLLETSDGCKQI
IQQLQPALKTGTEELKSLFNTVAVLYCVHKGIEVRDTKEAVDKIEEEQNKIQQKMQQQKV
TDG---KVSQNYPIVQNIQGQMVHQPISPRTLNAWVKVIEEKGFSPEVIPMFTALSEGAT
PSDLNTMLNTVGGHQAAMQMLKDTINEEAAEWDRTHPVHAGPVAPGQMREPRGSDIAGTT
STLQEQIGWMTNNPPIPVGEIYKRWIILGLNKIVRMYSPVSILDIKQGPKEPFRDYVDRF
FKALRAEQATQEVKGWMTDTLLVQNANPDCKTILKALGSGATLEEMMTACQGVGGPGHKA
RVLAEAMSQ-ANNTNIMMQKSNFKGPRRIVKCFNCGREGHIAKNCRAPRKKGCWKCGQEG
HQMKDC-TERQANFLGRIWPSHKG-RPGNFLQSRPE------PTAPL--------QPTAP
PAESFKFEE--TTPAPKQEQKDRE--PLTSLRSLFGNDPLSQ
>gagC.syn6.6
MGARASILRGGKLDTWEKIRLRPGGKKHYMLKHLVWASRELDRFALNPGLLETADGCKQI
IKQLHPALQTGTEEIKSLFNTVATLYCVHAGIEVRDTKEALDKIEEEQNKCQQKTQQAKE
ADK---KVSQNYPIVQNLQGQMVHQAISPRTLNAWVKVIEEKAFNPEIIPMFTALSDGAT
PQDLNTMLNTVGGHQAAMQMLKDTINEEAADWDRLHPVHAGPVAPGQLREPRGSDIAGTT
SNLQEQIAWMTSNPPIPVGDIYKRWIILGLNKIVRMYSPVSILDIKQGPKEPFRDYVDRF
FKVLRAEQATQDVKNWMTDTLLIQNANPDCKTILRALGPGASLEEMMTACQGVGGPSHKA
RVLAEAMSQ-TNSA-ILMQRSNFKGSKRIVKCFNCGKEGHLARNCRAPRKRGCWKCGKEG
HQMKDCTTERQANFLGKIWPSHKGGRPGNFLQNRPE------PTAPL--------EPTAP
PAESFGFGE--TTPAPKQEPKDRE--PLISLKSLFGSDPLSQ >gagM.syn1.1
MGARASILRGGKLDKWEKIRLRPGGKKHYMLKHLVWASRELERFALNPGLLETSEGCKQI
IKQLQPALQTGTEELRSLFNTVATLYCVHEKIEVRDTKEALDKIEEEQNKSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGEIYKRWIILGLNKIVRMYSPVSILDIRQGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ >gagM.syn3.1
---RASVLSGGKLDAWEKIRLRPGGKKKYKLKHIVWASRELERFAVNPGLLETSEGCRQI
LGQLQPSLQTGSEELRSLYNTVAVLYCVHQRIEVKDTKEALEKIEEEQNKSKKKAQQAAA
DTGNSSQVSQNYPIVQNLQGQMVHQAISPRTLNAWVKVIEEKAFSPEVIPMFTALSEGAT
PSDLNTMLNTIGGHQAAMQILKDTINEEAAEWDRLHPVHAGPIAPGQMREPRGSDIAGTT
STLQEQIGWMTNNPPIPVGEIYKRWIILGLDKIVRMYSPTSILDIRQGPKESFRDYVDRF
YKTLRAEQASQEVKNWMTETLLVQNANPDCKTILKALGPAATLEEMMTACQGVGGPSHKA
RILAEAMSQVTNSATIMMQRGNFRNQRKTVKCFNCGKEGHIAKNCRAPRKKGCWKCGKEG
HQMKDC-NERQANFLGKIWPSHKG-RPGNFLQSRP--------------------EPTAP
PEESFRFGEETTTPSQKQEPIDKELYPLASLKSLFGNDPLSQ
>gagM.syn3.2
MGARASILRGGKLDKWEKIRLRPGGKKHYMLKHLVWASRELERFALNPGLLETAEGCKQI
IKQLQPALKTGTEELKSLYNTVATLYCVHEKIEVRDTKEALDKLEEEQNKSQQKTQQAAA
GTGSSSKVSQNYPIVQNAQGQMVHQALSPRTLNAWVKVVEEKAFSPEVIPMFSALAEGAT
PQDLNTMLNTVGGHQAAMQMLKDTINEEAADWDRLHPVHAGPVAPGQMREPRGSDIAGST
STLQEQIAWMTSNPPIPVGDIYKRWIILGLNKIVRMYSPVSILDIKQGPKEPFRDYVDRF
FKTLRAEQATQDVKNWMTDTLLVQNANPDCKTILRALGPGASLEEMMTACQGVGGPGHKA
RVLAEAMSQ-ANNANIMMQRGNFKGQKR-IKCFNCGKEGHLARNCRAPRKKGCWKCGREG
HQMKDC-TERQANFLGRIWPSSKG-RPGNFPQSRP--------------------EPSAP
PAESFGFGE--TTPAPKQELKDRE--PLTSLKSLFGSDPLSQ
>gagM.syn3.3
MGARASVLSGGELDRWEKIRLRPGGKKKYRLKHLVWASRELEKFALNPGLLETSEGCKQI
MKQLQPALQTGTEELRSLFNTVATLYCVHQRIDVKDTKEALDKIEEEQNKIQQKTQQAKA
ADG---KVSQNYPIVQNIQGQMVHQPISPRTLNAWVKVVEEKGFNPEVIPMFSALSEGAT

Fig. 9 cont'd-9

PQDLNMMLNIVGGHQAAMQMLKETINEEAAEWDRVHPVHAGPIPPGQMREPRGSDIAGTT
SNLQEQIGWMTSNPPVPVGDIYKRWIVLGLNKIVRMYSPVSILDIRQGPKEPFRDYVDRF
FKVLRAEQATQEVKNWMTDTLLIQNANPDCKSILRALGPGATLEEMMTACQGVGGPSHKA
RVLAEAMSQ-TNSA-ILMQRSNFKGSKRIVKCFNCGKEGHIARNCRAPRKRGCWKCGQEG
HQMKDC-TERQVNFLGKIWPSNKG-RPGNFLQNRPE------PTAPPA-------EPTAP
PAESFRFEE--TTPAPKQEPKDRE--PLTSLRSLFGNDPSSQ

>gagM.syn4.1
MGARASVLSGGELDRWEKIRLRPGGKKKYKLKHIVWASRELERFAVNPGLLETSEGCRQI
LGQLQPSLQTGSEELRSLYNTVAVLYCVHQRIDVKDTKEALEKIEEEQNKSQQKTQQAKA
ADG---KVSQNYPIVQNAQGQMVHQAISPRTLNAWVKVIEEKGFSPEVIPMFSALAEGAT
PQDLNTMLNTIGGHQAAMQMLKDTINDEAAEWDRLHPVQAGPVAPGQIREPRGSDIAGTT
SNLQEQIGWMTSNPPIPVGDIYKRWIIMGLNKIVRMYSPTSILDIRQGPKESFRDYVDRF
FRTLRAEQASQEVKNWMTETLLVQNSNPDCKTILKALGPAATLEEMMTACQGVGGPGHKA
RVLAEAMSQ-VQQPNIMMQRGNFKGQKR-IKCFNCGREGHLARNCRAPRKKGCWKCGREG
HQMKDC-TESKANFLGKIWPSNKG-RPGNFLQSRP--------------------EPSAP
PAESFGFGEE-ITPSQKQEQKDKELYPLASLKSLFGNDPLSQ
>gagM.syn4.2
MGARASVLSGGKLDAWEKIRLRPGGKKKYRLKHLVWASRELDRFALNPSLLETAEGCKQI
MKQLQPALKTGTEELKSLYNTVATLYCVHEKIDVRDTKEALDKIEEEQNKIQQKTQQAKE
ADG---KVSQNYPIVQNIQGQMVHQPISPRTLNAWVKVVEEKAFSPEVIPMFTALSDGAT
PQDLNSMLNAVGGHQAAMQILKDTINEEAADWDRLHPVHAGPVAPGQMREPRGSDIAGTT
STLQEQIGWMTNNPPIPVGEIYKRWIILGLNKIVRMYSPVSILDIKQGPKESFRDYVDRF
FKVLRAEQATQDVKNWMTDTLLIQNANPDCKSILRALGPGATLEEMMTACQGVGGPSHKA
RILAEAMSQVTNSATIMMQRGNFRNQRKTVKCFNCGKEGHLARNCKAPRKRGCWKCGKEG
HQMKEC-TERQANFLGKIWPSSKG-RPGNFPQSRP--------------------EPTAP
PEESFRFGEETTTPSQKQEPIDKELYPLASLRSLFGNDPSSQ
>gagM.syn4.3
MGARASILRGGKLDKWEKIRLRPGGKKRYMLKHLIWASRELERFALNPGLLETAEGCQQI
IEQLQSTLKTGSEELKSLFNTVATLYCVHQRIEVKDTKEALDKVEEEQNKSKKKAQQAAA
DTGNSSQVSQNYPIVQNLQGQMVHQALSPRTLNAWVKVIEEKAFSPEIIPMFTALSEGAT
PSDLNTMLNTVGGHQAAMQMLKDTINEEAAEWDRVHPVHAGPIPPGQMREPRGSDIAGTT
SSLQEQIAWMTSNPPVPVGEIYKRWIVLGLNKIVRMYSPVSILDIRQGPKEPFRDYVDRF
FKTLRAEQASQDVKNWMTETLLVQNANPDCKTILRALGPGASLEEMMTACQGVGGPSHKA
RVLAEAMSQ-TNSA-ILMQRSNFKGSKRIVKCFNCGKEGHIARNCRAPRKRGCWKCGQEG
HQMKDC-NERQANFLGKIWPSHKG-RPGNFLQNRPE------PTAPP--------EPTAP
PAESFRFEE--TTPAPKQELKDRE--PLTSLKSLFGSDPLSQ
>gagM.syn4.4
MGARASVLRGEKLDKWERIRLRPGGKKHYMLKHLVWASRELEKFALNPGLLETSEGCKQI
IKQLQPALQTGTEELRSLFNTVATLYCVHAGIEVRDTKEALDKIEEIQNKSKQKTQQAAA
GTGSSSKVSQNYPIVQNLQGQMVHQPLSPRTLNAWVKVVEEKGFNPEVIPMFSALSEGAT
PQDLNMMLNIVGGHQAAMQMLKETINEEAAEWDRLHPVHAGPIAPGQMREPRGSDIAGST
STLQEQIAWMTGNPPVPVGDIYKRWIILGLNKIVKMYSPTSILDIKQGPKEPFRDYVDRF
YKTLRAEQATQEVKNWMTDTLLVQNANPDCKSILKALGTGATLEEMMSACQGVGGPAHKA
RVLAEAMSQ-ANNTNIMMQRSNFKGPKRIIKCFNCGKEGHIAKNCRAPRKKGCWKCGKEG
HQMKDC-TERQANFLGRIWPSSKG-RPGNFLQSRPE------PTAPPA-------EPTAP
PAESFKFEE--TTPAPKQEPKDRE--PLTSLRSLFGSDPLLQ >gagM.syn6.1
MGARASILSGGKLDAWEKIRLRPGGRKHYMLKHIVWASRELERFALNPGLLETAEGCQQI
IEQLQSTLKTGSEELKSLFNTVATLWCVHQRIEVKDTKEALDKLEEEQNKSQQKTQQAKA
ADG---KVSQNYPIVQNLQGQMVHQSISPRTLNAWVKAIEEKAFSPEVIPMFSALAEGAT
PQDLNTMLNTIGGHQAAMQILKDTINEEAAEWDRIHPVHAGPVAPGQMRDPRGSDIAGTT
SNLQEQIAWMTSNPPVPVGEIYKRWIILGLDKIVRMYSPVSILDIRQGPKEPFRDYVDRF
FKTLRAEQATQEVKGWMTDTLLVQNANPDCKTILKALGPGATLEEMMSACQGVGGPGHKA

Fig. 9 cont'd-10

RVLAEAMSQ-ANNTNIMMQKSNFKGPKRIIKCFNCGKEGHLARNCRAPRKKGCWKCGQEG
HQMKDC-TERQANFLGRIWPSHKG-RPGNFPQSRL--------------------EPTAP
PAESFGFGEE-IAPSPKQEPKEKELYPLTSLKSLFGNDPLSQ
>gagM.syn6.2
MGARASILRGGKLDKWEKIRLRPGGKKKYKLKHIVWASRELEKFALNPGLLETSEGCRQI
LGQLQPSLQTGSEELKSLYNTVATLYCVHQRIDVKDTKEALEKIEEEQNKSQQKTQQAAA
DKG----VSQNYPIVQNLQGQMVHQAISPRTLNAWVKVIEEKAFSPEIIPMFTALSEGAT
PQDLTTMLNTVGGHQAAMQMLKETINDEAAEWDRLHPVHAGPVAPGQLREPRGSDIAGST
STLQEQIAWMTGNPPVPVGDIYKRWIVLGLNKIVRMYSPTSILDIRQGPKEPFRDYVDRF
YKTLRAEQASQDVKNWMTETLLVQNANPDCRTILKALGPAATLEEMMTACQGVGGPAHKA
RVLAEAMSQVTNPATIMMQRGNFRNQRKTVKCFNCGKEGHLAKNCRAPRKRGCWKCGKEG
HQMKDC-NERQANFLGKIWPSNKG-RPGNFLQNRT--------------------EPTAP
PAESFRFGEEKTTPSQKQEPIDKELYPLASLRSLFGNDPSLQ
>gagM.syn6.3
MGARASVLRGEKLDKWERIRLRPGGKKRYMLKHLIWASRELERFALNPSLLETSEGCKQI
IQQLQPALKTGTEELRSLYNTVATLYCVHEKIEVRDTKEAVDKIEEEQNKSKKKAQQAAA
DTGNSSQVSQNYPIVQNIQGQMVHQALSPRTLNAWVKVVEEKGFNPEVIPMFSALSEGAT
PQDLNMMLNIVGGHQAAMQMLKDTINEEAAEWDRLHPVQAGPVAPGQMREPRGSDIAGTT
STLQEQITWMTSNPPIPVGEIYKRWIIMGLNKIVRMYSPVSILDIKQGPKESFRDYVDRF
FRTLRAEQASQEVKNWMTETLLIQNANPDCKTILRALGPAASLEEMMTACQGVGGPGHKA
RVLAEAMSQ-TNSA-ILMQRSNFKGSKRIVKCFNCGKEGHIARNCRAPRKKGCWRCGKEG
HQMKDC-TESKANFLGKIWPSHKG-RPGNFLQNRPEPTAPPEPTAPPAEPTAPPAEPTAP
PAESFKFEE--TTPAPKQELKDRE--PLISLKSLFGSDPLLQ
>gagM.syn6.4
MGARASILRGEKLDTWEKIRLRPGGKKQYRLKHIVWASRELDRFALNPSLLETAEGCKQI
IKQLHPALQTGTEELRSLFNTVATLYCVHAGIEVRDTKEALDKIEEEQNKIQQKTQQAKA
ADE---KVSQNYPIVQNMQGQMVHQPLSPRTLNAWVKVVEEKAFSPEVIPMFAALSEGAT
PSDLNTMLNTVGGHQAAMQMLKDTINDEAAEWDRLHPAQAGPIPPGQIREPRGSDIAGTT
STPQEQIGWMTNNPPIPVGEIYKRWIVLGLNKIVRMYSPISILDIRQGPKEPFRDYVDRF
FKALRAEQATQEVKGWMTETLLVQNSNPDCKTILRALGPGASLEEMMTACQGVGGPSHKA
RILAEAMSQ-ANS-NIMMQRSNFKGPKRIVKCFNCGKEGHIAKNCRAPRKKGCWKCGREG
HQMKDC-IERQANFLGKIWPSQKG-RPGNFLQSRP--------------------EPSAP
PAESFRFGE--TTPAPKQEPKDRE--PLTSLRSLFGSDPLSQ
>gagM.syn6.5
MGARASVLSGGELDRWEKIRLRPGGKKKYRLKHLVWASRELERFAINPGLLETSDGCKQI
IKQLQPALQTGSEELRSLYNTIATLYCVHQKIEVKDTKEALDKIEEIQNKSKQKTQQAAA
GTGSSSKVSQNYPIVQNAQGQMVHQSLSPRTLNAWVKVIEEKGFNPEVIPMFTALSEGAT
PHDLNTMLNTVGGHQAAMQMLKETINEEAAEWDRVHPVHAGPIPPGQMREPRGSDIAGST
STLQEQIGWMTSNPPIPVGDIYKRWIILGLNKIVRMYSPSSILDIRQGPKESFRDYVDRF
FKCLRAEQATQEVKNWMTDTLLIQNANPDCKSILRALGPGATLEEMMTACQGVGGPGHKA
RILAEAMSQ-VQQPNIMMQRGNFKGQKR-IKCFNCGREGHIARNCKAPRKKGCWKCGKEG
HQMKDC-TERQVNFLGKIWPSYKG-RPGNFLQSRP--------------------EPTAP
PEESFRFGEETTTPSQKQETIDKELYPLASLKSLFGNDPSSQ
>gagM.syn6.6
MGARASVLSGGKLDAWERIRLRPGGKKHYMLKHLVWASRELERFAVNPGLLETSEGCKQI
MKQLQPALQTGTEELKSLYNTVAVLYCVHQRIEIKDTKEALDKIEEEQNKCQQKTQQAKE
ADG---KVSQNYPIVQNLQGQMVHQPISPRTLNAWVKVIEEKGFSPEVIPMFTALSDGAT
PQDLNSMLNAVGGHQAAMQMLKDTINEEAADWDRLHPVHAGPIAPGQMREPRGSDIAGTT
SSLQEQIAWMTNNPPVPVGEIYRRWIILGLNKIVKMYSPTSILDIKQGPKEPFRDYVDRF
FKVLRAEQATQDVKNWMTDTLLVQNANPDCKSILKALGTGATLEEMMTACQGVGGPSHKA
RVLAEAMSQVTNSATIMMQKGNFRNQRKIVKCFNCGREGHLARNCKAPRKRGCWKCGKEG
HQMKEC-TERQANFLGKIWPSSKG-RPGNFPQSRP--------------------EPTAP
PAESFRFEE--TTPAPKQESKDRE--PLTSLKSLFGSDPSSQ

Fig. 10

>ENV-B.syn1.1
MRVTGIRKNYQHLWRWGTMLLWRWGTMLLGMLMICSATEKLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEIVMHSFNCGGEFFYCNSTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASMTLTVQARQLLSGIVQQQNNLLRAIEA
QQHLLQLTVWGIKQLQARVLAVERYLRDQQLLGIWGCSGKLICTTAVPWNASWSNKSLNE
IWNNMTWMEWEKEIDNYTNLIYNLLEESQNQQEKNEQELLELDKWASLWNWFDISNWLWY
IKIFIMIVGGLVGLRIVFAVLSIVNRVRQGYSPLSFQTRLPAPRGPDRPEGIEEEGGERD
RDRSVRLVDGFLALIWDDLRSLCLFSYHRLRDLLLIVTRIVELLG-------RRGWEALK
YWWNLLQYWSQELKNSAVSLLNATAIAVAEGTDRVIEALQRACRAILHIPRRIRQGLERA
LL- >ENV-B.syn3.1
MRVKETRKNYQHLWKWGTML--------LGMLMICSATEKLWVTVYYGVPVWRDANATLF
CASDAKAYDTEAHNVWATHACVPTDPNPQEVELKNVTENFNMWKNDMVEQMHEDIINLWD
QSLKPCVELTPLCVTLNCTDYVKNIT-NNATSTNSSW-GKPMEKGEIKFCSFNITTSIRN
KVQKQYALFYKLDIVPI-DNDNTS----------YRLISCNTSTITQACPKVTFEPIPIH
YCAPAGFAILKCNNKTFNGTGPCTNVSTVQCTHGIRPVISTQLLLNGSLAEEEVVIRSEN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR
N-NGTWTRN---DTERSNSTE---EHITLPCRIKQIINMWQEVGKAMYAPPIKGQISCSS
NITGLLLTRDGGNDT-----SGTEIFRPGGGDMRDNWRSELYKYKVVRIEPLGVAPTEAK
RRVVQREKRAVG-IGAVFLGFLGAAGSTMGAASMTLTVQARLLLSGIVQQQSNLLRAIEA
QQHMLQLTVWGIKQLQARLLAVERYLGDQQLLGLWGCSGKLICTTTVPWNTSWSNKSLNE
IWDNMTWMQWEREIDNYTGLIYNLLEKSQNQQEKNEQELLELDKWASLWNWFDITNWLWY
IKIFIMIVGGLVGLRIVFTVLSIVNRVRKGYSPLSFQTRLPTPRGPDRPGGIEEEGGEQD
RDRSGPLVNGFLALIWVDLRSLFLFSYHRLRDLLLIVARIVELLG-------RRGWEILK
YWWNLLLYWSQELKNSAVSLLNATAIAVAEGTDRVIEVVQRAFRAILHIPRRIRQGFERA
LL- >ENV-B.syn3.2
MRVTGIRKNYQHLWRWGTMLLWRWGTMLLGILMICSAAGKLWVTVYYGVPVWKEANTTLF
CASDAKAYDTEVHNVWATHACVPIDPNPQEVVLGNVTENFNMWKNNMVEQMHEDIISLWD
ESLKPCVKLTPICVTLNCTDDVRNVT-NNATNTNSSW-GEPMEKGEIKNCSFNITTSIRD
KVQKQYALFYKLDVVPI-DNDSNNTN--------YRLISCNTSVITQACPKISFEPIPIH
FCAPAGFAILKCNDKKFNGTGPCKNVSTVQCTHGIKPVVSTQLLLNGSLAEEEIVIRSEN
FTDNAKTIIVQLNESVVINCTRPNNNTRKSIHIGPGRAFYATGEIIGDIRQAHCNLSRAK
WNDTLKQIVIKLREQFG-NKTIVFNQSSGGDPEIVMHSFNCGGEFFYCNTTQLFNSTWTW
N-NSTW--N---NTKRSNDTE---EIITLPCRIKQIVNMWQKVGKAMYAPPIRGQIRCSS
NITGILLTRDGGNNNET---NRTETFRPGGGNMKDNWRSELYKYKVVKIEPLGIAPTKAR
RRVVQREKRAVGTIGAMFLGFLGAAGSTMGAASLTLTVQARQLLPGIVQQQNNLLKAIEA
QQHLLRLTVWGIKQLQARVLAVERYLRDQQLLGIWGCSGKIICTTAVPWNASWSNKSLDK
IWDNMTWMEWEKEIDNYTNLIYNLLEESQNQQEKNELELLELDKWANLWNWFDISNWLWY
IKIFIMIIGGLVGLRIVFAVLSIVNRVRQGYSPLSFQTRLPAPRGPDRPEGIEEEGGERD
RDRSVRLVDGFLALIWDDLRSLCLFLYHRLRDLLLIAARIVELLG-------RRGWEALK
YWWNLLQYWSQELKNSAISLLNATAVAVAEGTDRVIEALQRACRAILHIPRRIRQGLERL
LL- >ENV-B.syn3.3
MRVKGIRKNCQHLWRWGIML--------LGMLMICSAAEQLWVTVYYGVPVWKEATTTLF
CASDAKAYDKEVHNVWATHASVPTDPNPQEVVLENVTENFNMWKNNMVDQMHEDIISLWD
QSLKPCVKLTPLCVTLNCTD-LRNATNGNDTNTTSSS-REMMGGGEMKNCSFNVTTSIRD
KVQKEYALFYKLDVIPI-DSRNNSNNSTE--YNSYRLINCNTSVITQACPKVSFEPIPIH

Fig. 10 cont'd-1

YCTPAGFAILKCKDKKFNGTGPCTKVSTVQCTHGIRPVVSTQLLLNGSLAEEEVIIRSEN
FTNNAKTIIVQLKEAVEINCTRPSNNTRKSIPIGPGRAFYTTGDIIGDIRKAHCNISRAN
WNNTLRQIVEKLGEQFGNNKTIIFKQSSGGDPEIVTHSFNCGGEFFYCNSTQLFNSTWNF
--NGTWNKN---FNNTWNNTEGTNDTITLPCRIKQIINRWQEVGKAMYAPPISGQIRCSS
NITGLILTRDGGNNGNET--NGTEIFRPGGGNMRDNWRSELYRYKVVKIEPLGVAPTKAK
RRVVQREKRAVG-IGALFLGFLGAAGSTMGAASITLTVQARQLLSGIVQQQNNLLRAIEA
QQHLLQLTVWGIKQLQARILAVERYLKDQQLLGIWGCSGKLICTTAVPWNTSWSNRSLNE
IWNNMTWMEWEREIDNYTSLIYTLIEESQNQQEKNEQELLALDKWASLWNWFSITNWLWY
IRIFIMIVGGLIGLRIVFAVLSVVNRVRQGYSPLSFQTHLPAQRGPDRPEGTEEEGGERD
RDRSGRLVDGFLAIIWVDLRSLCLFSYHRLRDLLLIVTRIVELLG-------RRGWEVLK
YWWNLLQYWIQELKNSAVSLFNAIAIAVAEGTDRIIEVVQRAYRAILHIPTRIRQGLERA
LL-

>ENV-B.syn4.1
MRVTGIRKNYQHLWRWGTMLLWRWGTMLLGILMICSAAGKLWVTVYYGVPVWKDATTTLF
CASDAKAYDTEVHNVWATHASVPTDPNPQEVVLENVTEDFNMWKNNMVDQMHEDIISLWD
QSLKPCVELTPLCVTLNCTDDVRNVT-NNATNTNSSW-GEPMEKGEIKFCSFNITTSIRN
KVQKQYALFYKLDVVPI-DNDSNNTN--------YRLISCNTSVITQACPKVTFEPIPIH
YCAPAGFAILKCNNKTFNGTGPCTKVSTVQCTHGIRPVVSTHLLLNGSLAEEEVIIRSEN
FTDNTKTIIVQLKEAVEINCTRPNNNTRKGIHIGPGRAFYTTGEIIGDIRQAHCNLSRAK
WNDTLKQIVIKLREQFG-NKTIIFNQSSGGDPEIVMHTFNCGGEFFYCNTTQLFNSTW--
-------QN---ETSGSINITDIGENITLPCRIKQIVNMWQKVGKAMYAPPIKGQISCSS
NITGLLLTRDGGNNGNET--NGTEIFRPGGGNMKDNWRSELYRYKVVKIEPLGVAPTRAK
RRVVQREKRAVT-LGAMFLGFLGAAGSTMGAASMTLTVQARLLLSGIVQQQSNLLRAIEA
QQHLLRLTVWGIKQLQARILAVERYLQDQQLLGIWGCSGKLICTTAVPWNASWSNKSQDE
IWNNMTWMQWEKEIDNYTGLIYTLLEESQIQQEKNEQELLELDKWASLWNWFDITNWLWY
IKIFIMIVGGLIGLRIVFTVLSIVNRVRKGYSPLSFQTHLPAPRGPDRPGGIEEEGGEQD
RDRSGPLVNGFLALIWVDLRSLFLFSYHRLRDLLLIVARIVELLG-------RRGWEVLK
YWWNLLQYWSQELKNSAISLLNATAVAVAEGTDRVIEALQRACRAILHIPRRIRQGLERL
LL-
>ENV-B.syn4.2
MRVKGIRKNCQHLWRWGILL--------LGMLMICSAAEQLWVTVYYGVPVWRDANATLF
CASDAKAYDTEAHNVWATHACVPTDPNPQEVELKNVTENFNMWKNNMVEQMQEDIISLWD
QSLKPCVKLTPICVTLNCTDYVKNIT-NNATSTNSSW-GKPMEKGEIKNCSFNVTTSIRD
KVQKEYALFYRLDVVPI-DNDSNNNDSTNTNYTNYRLISCNTSTITQACPKVSFQPIPIH
YCAPAGFALLKCNDKKFNGTGPCKNVSTVQCTHGIKPVVSTQLLLNGSLAEEEIVIRSEN
FTNNAKTIIVQLNESVVINCTRPNNNTRKSIHIGPGRAFYATGDIIGDIRKAHCNISRAN
WNNTLRQIVEKLGEQFG-NKTIVFNQSSGGDVEIVMHSFNCGGEFFYCNSTQLFNSTWNF
--NGTWNKN---FNNTWNNTEGTNDTITLPCRIKQIINMWQGVGKAMYAPPISGQIRCSS
NITGLILTRDGGNN-NET--NRTETFRPGGGDMRDNWRSELYKYKVVKIEPLGIAPTKAR
RRVVQREKRAVGTIGAMFLGFLGTAGSTMGAASLTLTVQARLLLSGIVQQQNNLLKAIEA
QQHLLQLTVWGIKQLQARLLAVERYLGDQQLLGLWGCSGKLICTTTVPWNASWSNKSLDK
IWDNMTWMEWEREIDNYTGLIYNLLEKSQNQQEKNELELLELDKWANLWNWFDITKWLWY
IKIFIMIIGGLIGLRIVFAVLSVVNRVRQGYSPLSLQTRLPTQRGPDRPEGIAEEGGERD
RDRSGPLVDGFLAIIWVDLRSLCLFSYHHLRDLLLIVTRIVELLG-------RRGWEALK
YWWNLLLYWSQELKNSAVNLLNTTAIAVAEGTDRIIEVLQRIYRAFLHIPRRIRQGFERA
LL-
>ENV-B.syn4.3
MRVKEIRKNYQHLWKWGTML--------LGMLMICSAAGNLWVTVYYGVPVWKEANTTLF
CASDAKAYETEVHNVWATHACVPIDPNPQEVVLGNVTENFNMGKNNMVEQMHEDIISLWD
ESLKPCVKLTPLCVTLNCTDELKNATFRSNTTTNSSW--EKMEKGEIKNCSFNITTNMRD
KMQKEYALFYKLDVIPI-DSRNNSNNSTE--YNSYRLINCNTSVITQACPKISFEPIPIH
YCTPAGFAILKCKDKKFNGKGPCTNVSTVQCTHGIRPVVSTQLLLNGSLAEKEVVIRSDN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR

Fig. 10 cont'd-2

N-NGTWTRN---DTERSNSTE---EHITLPCRIKQIINMWQEVGKAMYAPPIRGQIRCSS
NITGILLTRDGGNDT-----SGTEIFRPGGGDMKDNWRSELYKYKVVRIEPLGVAPTEAK
RRVVQREKRAVG-IGAVFLGFLGAAGSTMGAAAVTLTVQARLLLSGIVQQQNNLLRAIEA
QQRLLQLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IKIFIIIVGGLVGLRIVFAVLSIVNRVRQGYSPLSFQTRLPAPRGPDRPEGIEEEGGERD
RDRSVRLVDGFLALIWDDLRSLCLFSYHRLRDLLLI----VELLG-------RRGWEILK
YWWNLLQYWGQELKNSAVSLLNATAIAVAEGTDRVIEVVQRAYRAILHIPTRIRQGLERA
LL-
>ENV-B.syn4.4
MRVKETRKNYQHLWRWGIML--------LGMLMICSATEKLWVTVYYGVPVWKEATTTLF
CASDAKAYDKEVHNVWATHACVPTDPSPQEVVLENVTENFNMWKNDMVEQMHEDIINLWD
QSLKPCVRLTPLCVTLNCTN-VNVTNLKNETNTKSSSGGEKMEEGEMKNCSFNITTSIRD
KVQKQYALFYKLDVVPI-DNDNTS----------YRLISCNTSVIKQACPKVSFEPIPIH
FCAPAGFAILKCNDKKFNGTGPCTNVSTVQCTHGIRPVISTQLLLNGSLAEEEVVIRSEN
FTDNAKTIIVQLNETVEINCTRPSNNTRKSIPIGPGRAFYTTGDIIGDIRQAYCNISRAK
WNNTLKQIVTKLREQFGNNKTIIFKQSSGGDPEIVTHSFNCGGEFFYCNSTKLFNSTWTW
N-NSTW--N---NTKRSNDTE---EIITLPCRIKQIINRWQEVGKAMYAPPIEGQIRCLS
NITGLLLTRDGGTNNT----NTNETFRPGGGNMRDNWRSELYKYKVVQIEPLGVAPTKAK
RRVVQREKRAVG-IGALFLGFLGAAGSTMGAASITLTVQARQLLSGIVQQQRNLLRAIEA
QQHMLQLTVWGIKQLRARVLAVERYLKDQQLLGIWGCSGRLICTTNVPWNTSWSNKSLNE
IWDNMTWMQWEREIDNYTSLIYTLIEESQNQQEKNEQDLLALDKWASLWNWFSITNWLWY
IRIFIMIVGGLVGLRIVFTVISIVTRVRQGYSPLSFQTRLPTPRGPDRPEGTEEEGGERD
RDRSGRLVDGFLALFWDDLRSLCLFLYHRLRDLLLIAARIVELLG-------RRGWELLK
YWWNLLQYWIQELKNSAVSLFNAIAIAVAEGTDWVIEISQRAFRAVLHIPVRIRQGLERA
LQ-
>ENV-B.syn6.1
MRVTGIRKNYQHLWRWGTMLLWRWGTMLLGILMICSAAGKLWVTVYYGVPVWKDATTTLF
CASDAKAYDTEAHNVWATHACVPIDPNPQEVVLENVTENFNAWKNNMVEQMHEDMISLWD
QSLQPCVRLTPLCVTLNCTDDVRN-----ATSTNSSW-GKPMEKGEIKNCSFNITTSIRD
KVQKQYALFYKLDVVPI-DNDSNNTN--------YRLISCNTSIITQACPKITFEPIPIH
YCTPAGFALLKCNDKKFNGTGPCTKVSTVQCTHGIRPVVSTHLLLNGSLAEEEVIIRSEN
FTNNAKTIMVQLNVSVEINCTRPSNNTRKSIHIGPGRAFYTTGDIIGDIRKAHCNISRAN
WNNTLRQIVEKLGEQFGNNKTIVFNHSSGGDLEIVTHSFICGGEFFYCNSTKLFNSTWTW
N-NSTW--N---NTKRSNDTE---EIITLPCRIKQIINMWQEVGKAMYAPPIRGKIRCSS
NITGLLLTRDGGTNNT----NTNETFRPGGGDMRDNWRNELYKYKVVRIEPLGIAPTEAK
RRVVQREKRAVG-IGAMFLGFLGTAGSTMGAASVALTVQARQLLPGIVQQQNNLLRAIDA
QQHLLQLTVWGIKQLQARILAVERYLKDQQLLGFWGCSGKLICTTNVPWNTSWSNKSYSQ
IWENMTWMEWEREINNYTGLIYNLLEKSQNQQEKNEQELLELDKWASLWSWFDISNWLWY
IKIFIIIVGGLVGLRIVFAVLSIINRVRQGYSPLSFQTHLPAPRGPDRPEGIAEEGGERD
RDRSGRLVNGFLALIWVDLRSLCLFSYHHLRDLLLI----VELLG-------RRGWEVLK
YWWNLLLYWSQELKNSAISLLNATAVAVAEGTDRVIEALQRACRAILHIPRRIRQGLERL
LL-
>ENV-B.syn6.2
MRVKETRKNYQHLWKWGTML--------LGILMICSATENLWVTVYYGVPVWKEATTTLF
CASDAKAYDKEVHNVWATHACVPTDPNPQEVELKNVTENFNMWKNNMVEQMQEDIISLWD
QSLKPCVRLTPLCVTLNCTD-LRNATNGNDTNTTSSS-REMMGGGEMKNCSFNITTNIRD
KVQKEYALFYKLDIVPI-DNDNTN----------YRLISCNTSVVTQACPKVSFEPIPIH
FCAPAGFAILKCNDKKFNGKGPCTNVSTVQCTHGIRPVISTQLLLNGSLAEEEVVIRSEN

Fig. 10 cont'd-3

FTNNVKTIIVQLNETVEINCTRPNNNTRRSIPIGPGRVFYTTEDIIGDIRQAHCNLSRTQ
WNNTLKQIVTKLREQFG-NKTIIFNQSSGGDPEIVMHTFNCGGEFFYCNTTKLFNSTW--
--NDTTINR----TEGSNNTR----NITLPCRIKQIINLWQEVGKAMYAPPIQGQISCSS
NITGLLLTRDGGNN-NET--NRTETFRPGGGNMRDNWRSELYKYKVVKIEPLGVAPTKAK
RRVVQREKRAVG-IGALFLGFLGAAGSTMGAASVTLTVQARQLLSGIVQQRNNLLRAIEA
QQRMLQLTVWGIKQLRARVLAVERYLKDQQLMGIWGCSGKLICTTTVPWNASWSNKSLNE
IWDNMTWMEWEREIDNYTSLIYTLIEESQNQQEKNELELLELDKWASLWNWFSITNWLWY
IRLFIMIVGGLVGLRIVFTVISIVTRVRQGYSPLSFQTRLPTPRGPDRPGGIEEEGGEQD
RDRSIRLVDGFLALIWDDLRSLCLFSYHRLRDLLWI----VELLG-------RRGWEALK
YLWNLLQYWSQELKKSAVSLFNATAIAVAEGTDWVIEVIQRAFRAFIHIPTRVRQGLERA
LQ-
>ENV-B.syn6.3
MRVKGIRKNCQHLWRWGILL--------LGMLMICSATEKLWVTVYYGVPVWKETTTTLF
CASDAKAYVAEKHNVWATHACVPTDPNPREVVMGNVTEEFNIWNNSMVEQMHEDIISLWE
QSLKPCVKLTPLCVSLKCTDL------KNDTNTNSSSGRMIMEKGEIKNCSFNITTGIRG
KVQ-EYSLFYKLDVVQM-DEDNTS----------YRLINCNTSVITQACPKVSFQPIPIH
YCAPAGFAILKCKDKKFNGTGSCKNVSTVQCTHGIRPVISTQLLLNGSLAEGEVVIRSEN
FTDNAKTIIVQLKDPVKINCTRPNNNTRKSIPIGPGRAFYATGDIIGDIRQAHCNISTTK
WNKTLGQVVKKLREQFK-NKTIVFKQSSGGDPEVVMHSFNCGGEFFYCNTSQLFNSTW--
--------N---STSLFNSTN---GTITLQCRIKQIINRWQEVGKAMYAPPIEGQIRCLS
NITGLLLVRDGGINVTNN--TGTEVFRPGGGDMRDNWRSELYKYKVIKIEPLGVAPTRAK
RRVVQREKRAVG-LGAMFLGFLGAAGSTMGAASITLTVQARQLLSGIVQQQRNLLRAIEA
QQHMLQLTVWGIKQLQARVLAVERYLQDQQLLGIWGCSGKLICTTTVPWNTSWSNKSLNQ
IWDNMTWMQWEKEIDNYTGLIYTLLEESQNQQEKNEHELLELDKWASLWNWFNITNWLWY
IKIFIMIIGGLIGLRIVFAVLSIVNRVRQGYSPISFQTRLPAPRGPDRPDGIEEEGGDRD
RDRSGRLVDGFLTLIWVDLRSLCLFSYRRLRDLLLIAARIVELLG-------HRGWEALK
YWWNLLQYWIQELKNSAVNLLNTTAIAVAEGTDRVIEVVQRAYRAILNIPTRIRQGFERA
LL-
>ENV-B.syn6.4
MRVKEIRKNCQRLWRWGTML--------LGMLMICSAAEQLWVTVYYGVPVWRDANATLF
CASDAKAYDTEVHNVWATHASVPTDPNPQEVVLGNVTENFNMWKNDMVEQMHEDVISLWD
QSLKPCVKLTPICVTLNCTDYVKNIT-NNATSTNSSW-GEPMEKGEIKNCSFNITTSMKD
KVQKTYALFYKLDVVPI-DNDSNNNDSTNTNYTNYRLISCNTSVIKQACPKVSFDPIPIH
YCTPAGFAILKCRDKKFNGTGPCKNVSTVQCTHGIRPVVPTQLLLNGSLAEEEIVIRSEN
FSDNAKTIIVHLNESVEINCTRLNNNTRKSIHMGPGRAFYATGEIIGDIRQAHCNISRAK
WNNTLKQIAIKLREQFGNNKTIIFKQSSGGDPEIVTHSFNCGGEFFYCNSTQLFNSTWNF
--NGTWNKN---FNNTWNNTEGTNDTITLPCRIKQIINMWQKVGKAMYAPPISGQIRCTS
NITGLLLTRDGGN---DT--SGTEIFRPGGGNMKDNWRSELYKYKVVQIEPLGVAPTEAK
RRVVQREKRAVG-IGAVFLGFLGAAGSTMGAAAVTLTVQARLLLSGIVQQQNNLLKAIEA
QQHLLRLTVWGIKQLQARLLAVERYLGDQQLLGLWGCSGKLICTTAVPWNTSWSNRSLNE
IWNNMTWMEWEKEIDNYTNLIYNLLEESQNQQEKNEKELLELDKWANLWNWFDISNWLWY
IRIFIMIVGGLIGLRIVFIVLSVVNRVRQGYSPLSLQTRLPTQRGPDRPEGTEEEGGERD
RDTSGRLVDGFLAIIWVDLRSLFLFSYHRLRDLLLIVTRIVELLG-------RRGWEILK
YWWNLLQYWGQELKNSAVSLLNATAITVAEGTDRVIEVLQRAGRAILHIPTRIRQGLERI
LL-
>ENV-B.syn6.5
MRVKGIRRNYQHLWRWGIML--------LGMLMICSATEQLWVTVYYGVPVWKEANTTLF
CASDAKAYKTEAHNVWATHASVPTDPNPQEIVLENVTENFNMWKNNMAEQMHEDIINLWD
QSLKPCVELTPLCVTLNCTDELKNATFRSNTTTNSSW--EKMEKGEIKNCSFNVTTSIRD
KMQKEYALFYRLDVVPI-DNDNTS----------YRLISCNTSVITQACPKISFEPIPIH
YCVPAGFAILKCNNKTFNGTGPCTNVSTVQCTHGIKPVVSTQLLLNGSLAEEDVVIRSEN
FTDNTKTIIVQLKEAVEINCTRPNNNTRKGIHIGPGRAFYTTGEIIGNIRQAHCNLSRAK
WNDTLKQIVIKLREQFG-NKTIVFNQSSGGDVEIVMHSFNCGGEFFYCNTTQLFNSTW--
--NANDIRN---VTRGSNRTTGGNDTLILPCRIKQIVNMWQEVGKAMYAPPIKGQIKCSS

Fig. 10 cont'd-4

NITGLLLTRDGGNNGNET--NGTEIFRPGGGDMRNNWRSELYKYKVVRIEPLGVAPTKAR
RRVVQREKRAVT-LGAMFLGFLGAAGSTMGAASMTLTVQARLLLSGIVQQQSNLLRAIEA
QQRLLQLTVWGIKQLQARILAIERYLKDQQLLGIWGCSGKIICTTAVPWNASWSNKSQDE
IWNNMTWMQWEREIDNYTGLIYNLIEESQNQQEKNEQELLALDKWANLWNWFDITKWLWY
IKIFIMIVGGLIGLRIVFTVLSIVNRVRKGYSPLSFQTRLPAQRGPDRPEGIEEEGGERD
RDRSGPLVDGFLAIFWVDLRSLFLFSYRHLRDLLLIVARIVELLG-------RRGWELLK
YWWNLLQYWSQELKSSAVSLLNATAIAVAEGTDRILEVLQRAYRAILHIPVRIRQGLERA
LL-
>ENV-B.syn6.6
MRVKGIRKNYQHLWRWGMML--------FGMLMICSAAGNLWVTVYYGVPVWREATTTLF
CASDAKAYETEVHNVWATHACVPTDPSPQEVVLENVTEDFNMWKNNMVDQMHEDIISLWD
ESLKPCVKLTPLCVTLNCTDDVRNVT-NNATNTNSSW-GEPMEKGEIKFCSFNITTSIRN
KVQKQYALFYKLDVIPI-DSRNNSNNSTE--YNSYRLINCNSSTITQACPKVTFEPIPIH
YCAPAGFAILKCNNKKFNGTGPCNNVSTVQCTHGIRPVVSTQLLLNGSLAEKEVVIRSDN
FTNNAKTIIVQLNESVVINCTRPNNNTRKRISMGPGRVYYTTGEIIGDIRRAHCNISRAQ
WNNTLKHIVEKLGKQFGNNKTI-FNHSSGGDPEIVMHSFNCRGEFFYCKSTKLFNSTWTR
N-NGTWTRN---DTERSNSTE---EHITLPCRIKQIINMWQGVGKAMYAPPIRGQIRCSS
NITGLILTRDGGNNDT----RGTEIFRPGGGDMKDNWRSELYRYKVVKIEPLGIAPTKAK
RRVVQREKRAVGTIGAMFLGFLGTAGSTMGAASLTLTVQARLLLSGIVQQQNNLLRAIEA
QQHLLQLTVWGIKQLQAKVLAVERYLRDQQLLGIWGCSGRLICTTNVPWNASWSNKSLDK
IWNNMTWMEWDREINNYTSLIYSLIEESQNQQEKNEQDLLALDKWASLWNWFDITNWLWY
IKIFIMVVGGLVGLRIIFAVLSIVNKVRQGYSPLSLQTHLPARRGPDRPEGIEGEGGERD
RDRSVRLVDGFLALFWDDLRSLCLFLYHRLRDLLLIVTRTVELLG-------RRGWEALK
YCWNLLQYWSQELKNSAVSLFNAIAIAVAEGTDRIIEVVQRICRAIRHIPRRIRQGFERA
LL- >ENV-C.syn1.1
MRVRGIQRNWPQWWIWGILG--------FWMLMICNVVGNLWVTVYYGVPVWKEAKTTLF
CASDAKAYEKEVHNVWATHACVPTDPNPQEIVLENVTENFNMWKNDMVDQMHEDIISLWD
QSLKPCVKLTPLCVTLNCTDVKVNATSNGTTTYNNSI-DS--MNGEIKNCSFNTTTEIRD
KKQKVYALFYRLDIVPL-DNNSSE----------YRLINCNTSTITQACPKVSFDPIPIH
YCAPAGYAILKCNNKTFNGTGPCNNVSTVQCTHGIKPVVSTQLLLNGSLAEEEIIIRSEN
LTNNAKTIIVHLNESVEIVCTRPNNNTRKSIRIGPGQTFYATGDIIGDIRQAHCNISEKQ
WDQTLYRVSEKLKEHFP-NKTIKFAPSSGGDLEITTHSFNCRGEFFYCNTSKLFNSTY--
--NSTQMHN---DTGS--NST-----ITLPCRIKQIINMWQEVGRAMYAPPIAGNITCKS
NITGLLLTRDGGTNN-----NNTETFRPGGGDMRDNWRSELYKYKVVEIKPLGIAPTKAK
RRVVEREKRAVG-IGAVFLGFLGAAGSTMGAASITLTVQARQLLSGIVQQQSNLLRAIEA
QQHMLQLTVWGIKQLQTRVLAIERYLKDQQLLGIWGCSGKLICTTAVPWNSSWSNKSQTD
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRLGRIEEEGGEQD
RDRSIRLVSGFLALAWDDLRSLCLFSYHRLRDFILVTARAVELLGRSSLRGLQRGWEALK
YLGSLVQYWGLELKKSAISLLDTIAIAVAEGTDRIIELIQRICRAIRNIPRRIRQGFEAA
LL- >ENV-C.syn3.1
MRVMGIQRNCQQWWIWGSLG--------FWMLMIYNVMGNLWVTVYYGVPVWKEAKTTLF
CASDAKAYDTEVHNVWATYACVPTDPNPQEMVLENVTENFNMWKNNMVDQMHEDIISLWD
QSLKPCVKMTPLCVTLNCSNAKKD---------NTTI-DNE-MKGEIKNCSFNITTELRD
KKKQVYALFYKLDIVPL-NSNSSE----------YRLINCNTSAITQACPKVSFDPIPIH
YCAPAGYAILKCNNETFNGTGPCNNVSTVQCTHGIRPVVSTQLLLNGSLAEKEIIIRSEN
LTDNVKTIIVHLNESVEINCTRPNNNTRRSIRIGPGQAFYATGEIIGDIRQAYCNISGEK
WNETLQRVGKKLKEHFP-NKTIKFAPSSGGDLEITTHSFNCRREFFYCNTSGLFNGTY--
--NGNGTYN---GTGTDTNST-----ITIPCRIKQIINMWQEVGRAMYAPPIEGNITCKS
NITGLLLVRDGGTENNTET-NNTETFRPGGGDMRDNWRSELYRYRVVEIKPLGIAPTKAK
RRVVERGKRAVG-IGAVFLGFLGVAGSTMGAASITLTVQARQVLSGIVQQQSNLLRAIEA
QQHLLQLTVWGIKQLQTRVLAIERYLKDQQLLGIWGYSGKLICTTAVPWNSSWSNRSQED

Fig. 10 cont'd-5

IWNNMTWMQWDREINNYTNTIYRLLEDSQNQQEKNEQDLLALDSWKNLWNWFDITNWLWY
IRIFIMIVGGLIGLRIIFAVLSIVNRVRQGYSPLSLQTLTPNPRELDRLGRIEEGGGEQD
RDRSIRLVSGFLALAWDDLRSLCLFSYHRLRDFILIAARAAELLGRSSLKGLQRGWEILK
YLGSLIQYWGLELKKSAINLLDTIAIVVAEGTDRIIELIQRICRAICNIPRRIRQGFEAA
LQ-
>ENV-C.syn3.2
MRVRGILRNWQQWWIWGILG--------FWMLMICNVVGNLWVTVYYGVPVWREAKTTLF
CASDAKAYEREVHNVWATHACVPTDPNPQELVLENVTENFNMWKNDMVDQMHQDIISLWD
ESLKPCVKLTPLCVTLKCVNVTKNS--NATVNSNATV-NNNTMGEEIKNCSFNATTEIRD
KKQNVYALFYRLDIVPL-NENNDNSS--------YRLINCNTSTITQACPKVTFDPIPIH
YCTPAGYAILKCNDKTFNGTGPCHNVSTVQCTHGIKPVISTQLLLNGSLAEEEIIIRSEN
LTNNVKTIIVHLNKSVEIVCTRPGNNTRKSVRIGPGQTFYATGDIIGDIRQAHCNISRTA
WNKTLQEVGKKLAEHFP-NKTIEFKPSSGGDLEVTTHSFNCRGEFFYCNTSKLFNSTYNS
TYNSTYNSN---STNSNSNST-----ITLQCRIKQIINMWQKVGRAIYAPPIAGNITCRS
NITGLLLTRDGGNNNDTGNNNDTEIFRPGGGDMKDNWRNELYKYKVVEVKPLGIAPTGAK
RRVVEREKRAVG-LGAVFLGFLGAAGSTMGAASMTLTVQARQLLSGIVQQQNNLLRAIEA
QQHMWQVTVWGIKQLQARVLALERYLKDQQLLGLWGCSGKLICTTNVPWNSSWSNKSLTD
IWENMTWMQWDKEISNYTDTIYRLLEVSQNQQEKNEKDLLALDSWNNLWNWFSITKWLWY
IKIFIMIVGGLIGLRIIFGVLSIVKRVRQGYSPLSFQTLTPNPRGPDRLGRIEEEGGEQD
KDRSIRLVNGFLALAWDDLRNLCLFSYHQLRDFILIVARAVELLGHSSLRGLQRGWEALK
YLGSLVQYWGLELKRSAISLLDTTAIAVAEGTDRIIEVIQRICRAIRNIPTRIRQGFEAA
LLQ
>ENV-C.syn3.3
MRVRGIQRNWPQWWIWGILG--------FWMIIICRVVGNLWVTVYYGVPVWTEAKATLF
CASDAKAYEKEVHNVWATHSCVPTDPNPQEIVLGNVTENFNMWENDMVDQMHEDVISLWD
QSLKPCVKLTPLCVTLNCT--------NANVTVNATSDGS--IKEEIKNCSFNTTTEIRD
KKQKVYALFYRPDIVPLSGSNSSE----------YILINCNTSTVTQACPKVSFEPIPIH
YCAPASYAILKCNNKTFNGTGPCQNVSTVQCTHGIKPVVSTQLLLNGSLAEGEIIIRSEN
LTNNAKTIIVHLNESIEIVCTRPNNNTRKSIRIGPGQTFFATGDIIGNIRQAHCNISEEK
WNKTLQEVSRKLREHFP-NKTIIFNSSSGGDLEITTHSFNCGGEFFYCNTTKLFNDS---
------------ALSAFNKTS--NETITLPCRIKQIINMWQGVGRAMYAPPIAGNITCNS
SITGLLLTRDGGT-------NNTEIFRPGGGNMKDNWRSELYKYKVVEIKPLGVAPTEAK
RRVVEREKRAVG-IGAVLLGFLGAAGSTMGAASITLTAQARQLLSGIVQQQSNLLKAIEA
QQHMLQLTVWGIKQLQARVLAIERYLQDQQLLGIWGCSGKLICTTTVPWNSSWSNKSQTD
IWDNMTWMQWDREISNYTNTIYRLLEESQNQQEQNEKDLLALDKWQNLWSWFSITNWLWY
IKIFIIIVGGLIGLRIILGVLSIVRRVRQGYSPLSFQTLIPNPRGPDRLGGIEEEGGEQD
RDRSVRLVSGFLSLAWDDLRSLCLFCYHRLRDFILVTARAVELLGRSSLRGLQKGWEALK
YLGNLVQYWGLELKKSAISLLDTIAIAVAEGTDRIIEFIQRICRAIRNIPRRIRQGLEAA
LQ-
>ENV-C.syn4.1
MRVRGILRNYQQWWIWGSLG--------FWMLMIYNVGGNLWVTVYYGVPVWKEAKTTLF
CASDAKAYDTEVHNVWATHACVPTDPDPQEIVLENVTENFNMWENDMVDQMHEDIISLWD
ESLKPCVKLTPLCVTLKCTNVTST---GNTTRGNNTS-EN---REEMKNCSFNTTTEIRD
KKQKVYALFYKPDVVPL-KENSSE----------YILINCNTSTVTQACPKVSFDPIPIH
YCAPAGFAILKCNNKTFNGTGPCNNVSTVQCTHGIKPVVSTQLLLNGSLAEEEIIIRSEN
LTDNAKTIIVHLNESIEIVCTRPGNNTRKSIRIGPGQAFYATGDIIGDIRQAYCNISKAT
WNKTLQEVGKELAKHFP-NKTINFNSSSGGDLEITTHSFNCGGEFFYCNTTKLFNNSL--
------------LNNTADNST---STITLQCRIKQIINMWQGVGQAMYAPPIAGNITCKS
NITGLLLLRDGGDTST----NGTEIFRPGGGNMKDNWRSELYKYKVVEVKPLGIAPTGAK
RRVVEREKRAVG-IGAVLLGFLGAAGSTMGAASITLTAQARQVLSGTVQQQSNLLRAVEA
QQHMLQLTVWGIKQLQTRVLAIERYLKDQQLLGIWGCSGKLICTTNVPWNSSWSNKSQEE
IWENMTWMQWDREISNYTGTIYRLLEESQNQQEKNEQDLLALDSWKNLWNWFDISNWLWY
IKIFIIIVGGLIGLRIIFGVLSIVKRVRQGYSPLSFQTLIPNPRGPDRLERIEEEGGEQD
RGRSIRLVSGFLAIAWDDLRSLCLFSYHQLRDFILIAVRAVELLGHSSLRGLQRGWEALK
YLGSLVQYWGLELKRSAISLLDTIAIVVAEGTDRIIEFIQRICRAIRNIPTRIRQGFEAA
LQ-

Fig. 10 cont'd-6

```
>ENV-C.syn4.2
MRVMGIQRNCQQWWIWGILG--------FWILMICNVMGNLWVTVYYGVPVWKEAKATLF
CASDAKAYEKEVHNIWATHACVPTDPNPQELVLENVTENFNMWDNDMVDQMHQDIISLWD
QSLKPCVKLAPLCVTLNCTNATVTATRNGSDIMNTTS-ND----GEMKNCSFNVTTELRD
KKKKEYALFYRLDIVPL-NEGSGNANQNNSNYSDYRLINCNTSAITQACPKVTFDPIPIH
YCTPAGYAILKCNDKTFNGTGPCHNVSTVQCTHGIRPVVSTQLLLNGSLAEGEIMIRSEN
LTNNAKTIIVHLNKSVEIVCTRPNNNTRKSVRIGPGQTFYATNDIIGDIRQAHCNISEEK
WNKTLQQVGKKLAEHFP-NKTIEFKPSSGGDLEVTTHSFNCRGEFFYCNTSGLFNGTF--
--DGT-------ESNSTSNAT-----ITIPCRIKQIINMWQKVGRAIYAPPIAGNITCRS
NITGLLLVRDGGNDNKT---NDTETFRPGGGDMRDNWRSELYKYKVVEVKPLGVAPTKAK
RRVVQREKRAVG-IGAVFLGFLGVAGSTMGAASMTLTVQARQVLSGIVQQQSNLLRAIEA
QQHLLQLTVWGIKQLQARVLALERYLRDQQLLGMWGCSGKLICTTAVPWNSSWSNKSQED
IWGNMTWMQWDKEISNYTNTIYRLLEDSQNQQERNEKDLLALDSWKNLWSWFDITNWLWY
IKIFIMIIGGLIGLRIIFAVLSIVNRVRQGYSPLSLQTLTPNPRGPDRLGRIEEEGGEQD
KDRSIRLVNGFLALAWDDLRNLCLFSYHRLRDFILIVARAVELLGRNSLRGLQRGWETLK
YLGSLIQYWGLELKKSAISLLDTTAIAVAEGTDRIIELIQRICRAICNIPRRIRQGLEAA
LQ-
>ENV-C.syn4.3
MRVRGIQRNWPQWWIWGILG--------FWMIIICRVVGNLWVTVYYGVPVWREAKTTLF
CASNAKAYEKEVHNVWATHACVPTDPNPQEIVLGNVTENFNMWKNDMVDQMHEDVISLWD
QSLKPCVKMTPLCVTLNCTDVKVNATSNGTTTYNNSI-DS--MNGEIKNCSFNTTTELRD
KKQKAYALFYRPDIVPLPGKDNSKDNSSEYEE--YILINCNSSTITQACPKVSFEPIPIH
YCAPASYAILKCNNETFNGTGPCKNVSTVQCTHGIKPVISTQLLLNGSLAEKEIIIRSEN
LTNNVKTIIVHLKESVEINCTRPNNNTRKSIRIGPGQTFYATGDIIGNIRQAHCNISREK
WNTTLKRVKEKLKEHFP-NKTIKFAPSSGGDLEITTHTFNCRGEFFYCNTSKLFNSTYV-
--NRTDMND---D--TGNNST-----ITLPCRIKQIINMWQEVGRAMYAPPIAGNITCNS
SITGLLLTRDGGNNT-----ENTETFRPGGGNMKDNWRNELYKYKVVEIKPLGVAPTEAK
RRVVEREKRAVG-LGAVFLGFLGAAGSTMGAASITLTVQARQLLSGIVQQQNNLLRAIEA
QQHMLQLAVWGIKQLQARVLAIERYLQDQQLLGIWGCSGKLICTTSVPWNSSWSNRSQED
IWNNMTWMQWDREISNYTDTIYRLLEVSQNQQEQNEKDLLALDKWQNLWSWFSITNWLWY
IRIFIMIVGGLIGLRIVFAVLSLVNRVRQGYSPLSFQTLTPSPRGPDRLGGIEEEGGEQD
RDRSIRLVSGFLSLAWDDLRSLCLFSYHRLRDFILIAARAAELLGRSSLRGLQRGWEILK
YLGSLAQYWGLELKKSAINLLDTIAIAVAEGTDRIIEVIQRICRAIYNIPRRIRQGFEAS
LL-
>ENV-C.syn4.4
MRVRGIPRNWQQWWIWGILG--------FWMLMICNVVGNLWVTVYYGVPVWTEAKTTLF
CASDAKAYEREVHNVWATYACVPTDPNPQEMVLENVTENFNMWKNDMVEQMHEDIISLWD
QGLKPCVKLTPLCVTLNCSNAKKD---------NTTI-DNE-MKGEIKNCSFNITTELRD
KKQQVYALFYKLDIVPL-NSNSSE----------YRLINCNTSTITQACPKVNFDPIPIH
YCAPAGYAILKCNNKTFNGTGPCQNVSTVQCTHRIKPVVSTQLLINGSLAEGEIIIRSEN
LTDNVKTIIVHLNESVEIVCTRPNNNTRKSMRIGPGQTFYATGEIIGDIRQAHCNISKEK
WNNTLQEVREKLREHFP-NKTIKFAPHSGGDPEITTHSFNCRGEFFYCNTSQLFNSTY--
--NSTQMHN---DTGS--NST-----ITLPCKIKQIINMWQGVGRAMYAPPIEGNITCTS
NITGLLLTRDGGT-------NNTEIFRPGGGDMRNNWRSELYKYKVVEIKPLGIAPTKAK
RRVVERGKRAVG-IGAVLFGFLGAAGSTMGAASIALTAQARQLLSGIVQQQSNLLKAIEA
QQHMWQVTVWGIKQLQARVLAMERYLKDQQLLGLWGCSGKLICTTTVPWNSSWSNKSQTD
IWDNMTWMQWDREINNYTNTIYKLLEDSQNQQEKNEKDLLALDSWNNLWNWFSITKWLWY
IKIFIMIVGGLIGLRIILGVLSIVRRVRQGYSPLSFQTLTPNPRELDRLGRIEEGGGEQD
RDRSVRLVSGFLALAWDDLRSLCLFCYHRLRDFILVTARAVELLGRSSLKGLQRGWEALK
YLGNLVQYWGLELKKSAISLFDTIAITVAEGTDRIIELVQRICRAIRNIPRRIRQGFEAA
LL-
>ENV-C.syn6.1
MRVRGIQRNWPQWWIWGILG--------FWIIIMCRVMGNMWVTVYYGVPVWREAKTTLF
CASDAKGYEKEVHNAWATHACVPTGPNPQEMVLENVTENFNMWKNNMVDQMHEDIINLWD
QSLKPCVRLTPLCVTLKCVNVTKNS--NATVNSNATV-NNNTMGEEIKNCSFNATTEIRD
KKQKAYALFYRPDIVPL-NENSSSENNSSE----YILINCNTSTITQACPKVSFDPIPIH
YCAPASYAILKCNNETFNGTGPCQNVSTVQCTHGIKPVISTQLLLNGSLAEEDIIIRSEN
```

Fig. 10 cont'd-7

LTNNAKTIIVHLNQSVEIVCTRPGNNTRKSMRIGPGQTFYATNDIIGNIRQAHCNISEGK
WNETLLRVKKKLEEHFP-NKTIKFEPSSGGDLEITTHTFNCRGEFFYCDTSTLFNHTY--
--VSAYMNNTDVSADRKNDTQ-SNSTITLPCRIRQIINMWQEVGRAIYAPPIAGNITCRS
NITGLLLVRDGGNTT-----NSTETFRPEGGNMKDNWRSELYKYKVVEIRPLGIAPTGAK
RRVVEREKRAVG-IGAVFLGFLGVAGSTMGAASMTLTVQARQVLSGVVQQQSNLLQAIEA
QQHLLQLTVWGIKQLQTRVLALERYLRDQQLLGIWGCSGKIICTTAVPWNTSWSNKSQED
IWNNMTWMQWDREINNYTNTIYKLLEESQNQQEKNEQDLLALDSWNSLWNWFSITKWLWY
IRIFIIIVGSLIGLRIIFGVLSIVKRVRQGYSPLLSQTLTPNPREPDRLGRIEEGGGEQD
RDRSVRLVNGFLALVWDDLRSLCLFCYHRLRDFILVTARVVELLGRSSLRGLQKGWEALK
YLGSLVQYWGLELKKSAINLLDTIAIAVGEGTDRIIEVIQRICRAIYNIPRRIRQGFEAS
LL-
>ENV-C.syn6.2
MRVRGILRNYQQWWIWGSLG--------FWMLMIYNVGGNLWVTVYYGVPVWTDAKTTLF
CASDAKAYDKEVHNVWATHACVPTDPNPQELVLENVTENFNMWKNDMVNQMHEDIISLWD
ESLKPCVKLTPLCVTLNCTNATVTATRNGSDIMNTTS-ND----GEMKNCSFNITTELRD
KKRKEYALFYRLDIVPL-DENNSSEKSSENSSEYYRLINCNTSAITQACPKVTFDPIPLH
YCAPAGYAILKCKDKTFNGTGPCSNVSTVQCTHGIKPVVSTRLLLNGSLAEGEIIIRSEN
LTNNVKTIIVHLKEPVEINCTRPNNNTRESIRIGPGQTFYATGDIIGDIRQAHCNISREK
WNKTLQEVGKKLAEHFP-NKTIKFAPHSGGDLEITMHSFNCRGEFFYCNTSGLFNGTY--
--MPTYMPN---GTESNSNST-----ITIPCRIKQIINMWQEVGRAMYAPPIEGNITCNS
NITGLLLVRDGGINKT----NNTETFRPGGGDMRNNWRSELYKYKVVEIKPLGVAPTEAK
RRVVEREKRA-A-LGAMFLGFLGAAGSNMGAASITLTAQARQLLSGIVQQRSNLLRAIEA
QQHLLQLTVWGVKQLQARVLAMERYLKDQQLLGLWGCSGKLICTTSVPWNSSWSNRSQEE
IWNNMTWMEWDREISNYTNTIYRLLEDSQNQQEKNEKDLLALDSWKNLWSWFDITNWLWY
IKIFIMIIGGLIGLRIVFAVLSIVNRVRQGYSPLSFQTLTPSPRGPDRLGRIEEEGGEQD
KDRSVRLVSGFLSLAWDDLRSLCLFSYHRLRDLILIAARAVELLGHSSLRGLQRGWEILK
YLGSLAQYWGLELKRSAISLLDTIAITVAEGTDRIIEIIQRICRAICNIPRRIRQGFETA
LL-
>ENV-C.syn6.3
MRVMGILRNCQQWWIWGVLG--------FWMLMICNVVGNLWVTVYYGVPVWKEAKTTLF
CASNAKAYEREVHNIWATHACVPTDPNPQEMVLKNVTENFNMWKNDMVDQMHEDVISLWD
QSLKPCVKLAPLCVTLNCTNVTVNDTLHQNFT-------------DMKNCSFNVTTELRD
KKQKVYALFYRLDVVPL-GDNNSS----------YRLINCNTSTIAQACPKVNFDPIPIH
YCTPAGYAILKCNDKTFNGTGPCKNVSTVQCTHEIKPVVSTQLLLNGSLAEEGIIIRSEN
LTDNAKTIIVHLNESVEINCTRPGNNTRQSIRIGPGQAFYATGAIIGDIRQAHCNISKDE
WEKTLKRVSEKLKEHFP-NKTIEFKPSSGGDLEVTTHSFNCRREFFYCNTSKLFNSTY--
--NSTQMHN---DTGS--NST-----ITLPCKIKQIINMWQGVGQAMYAPPIKGNITCKS
NITGILLTRDGGNLT-----NGTETFRPGGGDMKDNWRSELYRYRVVEIKPLGIAPTKAK
RRVVQREKRAVG-IGALFLGFLGTAGSTMGAASLTLTVQARQLLSSIVQQQSNLLRAIEA
QQHMLQLTIWGIKQLQTRVLAVERYLKDQQLLGMWGCSGKLICTTAVPWNASWSNKSQEE
IWGNMTWMQWDREISNYTDIIYRLLEESQNQQERNEKDLLALDSWNNLWNWFNITNWLWY
IKIFIMIVGGVIGLRIIFAVLSLVNRVRQGYSPLSFQTLTPNPRELDRLGRIEEEGGEQG
RDRSIRLVNGFLAIAWDDLRSLCLFSYRRLRDFILIAARAAELLGRSSLRGLQRGWETLK
YLGSLIQYWGLELKKSAISLFDTIAIAVAEGTDRIIELIQRICRAIRNIPRRIRQGLEAA
LQ-
>ENV-C.syn6.4
MRVMGIQRNCQQWWIWGILG--------FWMLMIYNVVGNLWVTIYYGVPVWKEAKATLF
CASDAKAYDTEVHNVWATHACVPTDPDPQEMVLGNVTENFNMWKNDMADQMHEDIISLWD
QGLKPCVKLTPLCVTLHCTN-------TNITNENRTI-GDKLNE-EMKNCSFNTTTELRD
KKQQVYALFYKPDVVPL-NGGEHNETGE------YILINCNSSTITQACPKVSFEPIPIH
YCAPAGFAILKCNNKTFNGTGPCHNVSTVQCTHGIRPVVSTQLLLNGSLAEEEIIIRSEN
LTDNVKTIIVHLNKSVEIVCTRPNNNTRKSIRIGPGQTFFATNDIIGDIRQAYCNISAEK
WNKTLERVEEKLKEHFP-NKTIKFNSSSGGDLEITTHSFNCRGEFFYCNTSNLFNGTY--
--HGTQSTN---ST----NST-----ITLQCRIKQIINMWQKVGRAMYAPPIAGNITCKS
NITGLLLLRDGGTEN-----NDTETFRPGGGNMRDNWRSELYKYKVVEVKPLGIAPTTAK
RRVVERDKRAVG-IGAVLLGFLGAAGSTMGAASMALTVQARQLLSGIVQQQSNLLRAVEA

Fig. 10 cont'd-8

QQHMLQLTVWGIKQLQARVLALERYLKDQQLLGIWGCSGRLICTTAVPWNSSWSNKTQGE
IWENMTWMQWDKEINNYTNTIYRLLEESQTQQEQNEKDLLALDSWKNLWNWFDITKWLWY
IKIFIMVVGGLIGLRIIFAVLSIVNSVRQGYSPLSLQTLTPNPRGPDRLERIEEEGGEQD
RNRSIRLVNGFLALAWDDLRSLCLFSYHHLRDFILVTARAVELLGRSSLKGLQRGWEALK
YLGNLVQYWGLELKKSAISLLDTTAIAVAEGTDRIIELVQRICRAILNIPTRIRQGFEAA
LQ-
>ENV-C.syn6.5
MRVRGIPRNWPQWWTWGILG--------FWMIIICRVVGNLWVTVYYGVPVWTEAKTTLF
CASDAKAYEREVHNVWATHSCVPTDPNPQEIVLGNVTENFNMWENDMVDQMHQDIISLWD
QSLKPCVKMTPLCVTLNCSNAKKD---------NTTI-DNE-MKGEIKNCSFNITTEIRD
KKQKVHALFYRLDIVPL-NEGSGNANQNNSNYSDYRLINCNTSTVTQACPKVTFDPIPIH
YCAPARYAILKCNNNTFNGTGPCNNVSTVQCTHGIKPVVSTQLLLSGSLAEEEIVIRSEN
LTNNAKIIIVHLNESVEIVCTRPNNNTRRSIRIGPGQTFYATGEIIGDIRQAHCNISAKQ
WNTTLERVKEKLREHFP-NKTIKFEPHSGGDPEITTHSFNCGGEFFYCNTSQLFNSTY--
--NSTYMSN---NTGENSNET-----ITLPCRIKQIINMWQQVGRAMYAPPIAGNITCNS
SITGLLLTRDGGNNNDTGNNNDTEIFRPGGGDMRDNWRSELYKYKVVELKPLGIAPTEAK
RRVVKREKRAVG-IGAVLFGFLGAAGSTMGAASIALTAQARQVLSGIVQQQNNLLRAIEA
QQHVLQLTVWGIKQLQTRVLAIERYLKDQQLLSLWGCSGKLICTTTVPWNSSWSNKSLTD
IWDNMTWMQWDREISNYTGTIYRLLEDSQSQQEKNEKDLLELDKWNNLWNWFDISNWLWY
IKIFIIIVGGLIGLRIIFAVLSIINRVRQGYSPLLFQTLTPNPRGLDRLGRIEEEGGEQD
KDRSIRLVNGFLALAWEDLRSLCLFSYHQLRDFILIVARAVELLG-------RRGWEALK
YLGNLVLYWGLELKKSAVSLLDTIAIAVAGGTDRIIEVVQRICRAIRNIPTRIRQGLEAA
LL-
>ENV-C.syn6.6
MRVRGILRNWQQWWIWGILG--------FWMVMICNVMGNLWVTVYYGVPVWQEAKTTLF
CASDAKAYEKEVHNVWATHACVPTDPSPQEIVLENVTENFNMWKNDMVEQMHEDIISIWD
QSLKPCVTLTPLCVTLNCTDVKVNATSNGTTTYNNSI-DS--MNGEIKNCSFNTTTEIRD
KKKQVYALFYKLDIVPL-NSNSSE----------YRLINCNTSAVTQACPKVSWDPIPIH
YCAPAGYAILKCNNKTFNGTGPCTNVSTVQCTHRIKPVVTTQLLLNGSLAEKEIIIRSEN
LTNNIKTIIVHLNESIEIVCTRPNNNTRKSVRIGPGQTFFATGDIIGDIRKAHCNISEDK
WNETLQRVGKKLVEHFP-NKTIKFAPSSGGDLEVTTHSFNCKGEFFYCNTTKLFD-----
------------DSERINTTT---TTIILPCRIKQFINMWQGVGRAMYAPPIAGNITCTS
NITGLLLTRDGGT-------NNTEIFRPGGGNMKDNWRNELYKYKVVEVKPLGVAPTKAK
RRVVEREKRAVG-LGAVFLGFLGAAGSTMGAASITLTVQARQLLFGIVQQQSNLLKAIEA
QQHMWQVTVWGIKQLQARVLAIERYLQDQQLLGIWGCSGKLICTTNVPWNSSWSNKSQTD
IWDNMTWMQWDKEISNYTDTIYRLLEVSQNQQEENEKDLLALDKWQNLWNWFSITNWLWY
IRIFIMIVGGLIGLRIILGVLSIVRRVRQGYSPLSFQTLIPNPRGPDRLGGIEEEGGEQD
RDRSIRLVSGFLALAWDDLRNLCLFSYHRLRDFILIVVRAVELLGRNSLRGLQRGWEALK
YLGSLGQYWGLEIKKSAISLLDTIAIVVAEGTDRIIEFIQRFCRAIRNLPRRIRQGFEAA
LL-
>ENV-M.syn1.1
MRVTGIRKNYQHLWRWGTMLLWRWGTMLLGMLMICSAAGNLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIKPVVSTQLLLNGSLAEEEVVIRSEN
FTNNAKTIIVQLNESVEINCTRPNNNTRKSIRIGPGQTFYATGDIIGDIRQAHCNISRAQ
WNNTLKHIVEKLGKQFGNNKTIVFNHSSGGDPEIVMHSFNCGGEFFYCNTTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASITLTVQARQLLSGIVQQQNNLLRAIEA
QQHLLQLTVWGIKQLQARVLAVERYLKDQQLLGIWGCSGKLICTTAVPWNSSWSNKSLNE
IWNNMTWMEWEREIDNYTGLIYTLIEESQNQQEKNEQELLELDKWASLWNWFDISNWLWY
IKIFIMIVGGLIGLRIVFAVLSIVNRVRQGYSPLSFQTRLPAPRGPDRPEGIEEEGGERD
RDRSIRLVSGFLALAWDDLRSLCLFSYHRLRDLLLIVTRIVELLG-------RRGWEALK

Fig. 10 cont'd-9

YWWNLLQYWSQELKNSAVSLLNATAIAVAEGTDRVIEALQRACRAILHIPRRIRQGLERA
LL-

>ENV-M.syn3.1
MRVRGIQRNWPQWWIWGILG--------FWMLMICNVVGNLWVTVYYGVPVWKEAKTTLF
CASDAKAYEKEVHNVWATYACVPTDPNPQEIHLENVTEEFNMWKNDMVDQMHEDIISLWD
QSLKPCVQLTPLCVTLNCTN-VNVTNLKNETNTKSSSGGEKMEEGEMKNCSFNITTSIRD
KVQKEYALFYKLDVVPI-DNDSNNTN--------YRLISCNTSVITQACPKVTFEPIPIH
YCTPAGFAILKCKDKKFNGTGPCKNVSTVQCTHGIKPVISTQLLLNGSLAEEEIIIRSEN
ITNNAKTIIVQLNESVEINCTRPGNNTRKSVRIGPGQTFYATGEIIGDIRQAHCNLSRAK
WNDTLKQIVIKLREQFG-NKTIVFNQSSGGDPEIVMHSFNCGGEFFYCNTTQLFNSTW--
--------N---STSLFNSTN---GTITLQCRIKQIINMWQEVGKAMYAPPIEGNITCKS
NITGLLLVRDGGT---EP--NDTETFRPGGGNMKDNWRSELYKYKVVKIEPLGVAPTKAK
RRVVQREKRAVGTIGAMFLGFLGAAGSTMGAASMTLTVQARLLLSGIVQQQNNLLRAIEA
QQHLLQLTVWGIKQLQARILAVERYLKDQQLLGLWGCSGKLICTTAVPWNTSWSNKSQTD
IWDNMTWMEWEREIDNYTGLIYTLIEESQNQQEKNEQELLELDKWASLWNWFDITKWLWY
IKIFIMIVGGLVGLRIVFAVLSIVNRVRKGYSPLSFQTLTPNPRGPDRLGRIEEEGGEQD
RDRSIRLVSGFLALAWDDLRSLCLFSYHQLRDFILIVARAVELLGRSSLRGLQRGWEALK
YLGSLVQYWGLELKKSAISLLDTIAIAVAEGTDRIIEVIQRICRAIRNIPRRIRQGFERA
LL-
>ENV-M.syn3.2
MRVTGIRKNYQHLWRWGTMLLWRWGTMLLGILMICSAAGKLWVTVYYGVPVWRDAETTLF
CASDAKAHETEVHNIWATHACVPTDPNPQEVVLGNVTENFNMWKNNMVEQMHEDIISLWD
ESLKPCVKLTPICVTLNCTDDVRNVT-NNATNTNSSW-GEPMEKGEIKNCSFNMTTELRD
KKQKVHALFYKLDIVPL-NSNSSE----------YRLINCNTSAITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEITTHSFNCGGEFFYCNSTKLFNSTWTR
N-NGTWTRN---DTERSNSTE---EHITLPCRIKQIVNMWQRVGQAMYAPPIRGQIRCSS
NITGLLLTRDGGNDT-----SGTEIFRPGGGDMRNNWRNELYKYKVVRIEPLGVAPTRAK
RRVVEREKRAVG-LGAVFLGFLGAAGSTMGAASLTLTVQARQVLSGIVQQQSNLLKAIEA
QQHLLKLTVWGIKQLQARVLAVERYLRDQQLLGIWGCSGKLICTTTVPWNASWSNKSLNE
IWNNMTWMEWEKEIDNYTNLIYNLLEESQNQQEKNEQDLLALDKWANLWNWFDISNWLWY
IKIFIIIVGGLIGLRIVFAVLSIINRVRQGYSPLSLQTLIPNPRGPDRPGGIEEEGGEQG
RDRSIRLVNGFLALAWDDLRNLCLFSYHRLRDLLLIVTRIVELLG--------RRGWEALK
YWWNLLQYWSQELKNSAISLLNATAVAVAEGTDRVIEALQRACRAILHIPRRIRQGLERL
LL-
>ENV-M.syn3.3
MRVKETRKNYQHLWKWGTML--------LGMLMICSAAEQLWVTVYYGVPVWKEATTTLF
CASDAKAYDTEVHNVWATHACVPTDPSPQEVVLENVTENFNMWKNDMVEQMHTDIISLWD
QSLKPCVKLTPLCVTLNCTDYVKNIT-NNATSTNSSW-GKPMEKGEIKNCSFNITTSIRN
KVQKQYALFYKLDIVPI-DNDNTS----------YRLINCNTSTITQACPKVSFDPIPIH
YCAPAGYAILKCNNKTFNGTGPCNNVSTVQCTHGIKPVVSTQLLLNGSLAEGEIIIRSEN
LTNNAKTIIVHLNKSVEINCTRPSNNTRKSIRIGPGQAFYATGDIIGDIRKAHCNISGTK
WNHTLEQVMEELKKHFP-NKTIKFNSSSGGDLEITTHSFNCRGEFFYCNTSGLFNSTW--
--NDTTINR----TEGSNNTR----NITLPCRIKQIINMWQGVGRAMYAPPIAGNITCKS
NITGILLTRDGGNNN-----STNETFRPGGGDMRDNWRSELYKYKVVEIKPLGIAPTKAK
RRVVEREKRAVG-IGAVFLGFLGTAGSTMGAASITLTVQARQLLSGIVQQQSNLLRAIEA
QQHMLQLTVWGIKQLQTRVLAIERYLKDQQLLGIWGCSGKLICTTNVPWNSSWSNKSQSE
IWDNMTWMQWDREISNYTDTIYRLLEDSQNQQEKNEKDLLALDSWKNLWNWFDITNWLWY
IRIFIMIVGGLIGLRIIFAVLSIVNRVRQGYSPLSFQTRLPAPRGPDRPEGIEEEGGERD
RDRSVRLVDGFLALIWDDLRSLCLFSYHRLRDFILIAARTVELLGHSSLKGLRLGWEGLK
YLWNLLQYWIQELKNSAVSLLNATAIAVAEGTDRVIEVVQRAYRAILHIPTRIRQGLERA
LL-

Fig. 10 cont'd-10

>ENV-M.syn4.1
MRVKETRKNYQHLWKWGTML--------LGMLMICSAAEQLWVTVYYGVPVWKEATTTLF
CASDAKAHETEVHNIWATHACVPTDPNPQEVVLGNVTENFNMWKNDMVEQMHTDIISLWD
QSLKPCVELTPLCVTLHCTDL------GNATNT--------MEKGEIKNCSFNMTTELRD
KKQKVYALFYRLDIVPI-DNDNTS----------YRLINCNTSVIKQACPKVTFEPIPIH
YCTPAGFAILKCNDKNFNGTGPCKNVSTVQCTHGIRPVVSTQLLLNGSLAEKEIIIRSEN
LTDNAKTIIVHLNKSVEINCTRPSNNTRKSVRIGPGQTFYATGDIIGDIRQAHCNISRAK
WNNTLKQIVTKLREQFK-NKTIVFNQSSGGDLEITTHSFNCRGEFFYCNTTQLFNSTW--
-------KN---DTEVSNNTK-GNDTITLPCRIKQIVNMWQEVGRAMYAPPIEGNITCNS
NITGILLTRDGGNNGNET--NGTEIFRPGGGNMRDNWRNELYKYKVVEIKPLGVAPTEAK
RRVVEREKRAVG-IGAVFLGFLGAAGSTMGAASITLTVQARQLLTGIVQQQSNLLRAIEA
QQHMLQLTVWGIKQLQTRVLAIERYLKDQQLLGLWGCSGKLICTTAVPWNSSWSNKTYND
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRPGGIEEEGGEQG
RDRSIRLVNGFLALAWDDLRNLCLFSYHQLRDFILIVARAVELLGRSSLRGLQRGWEALK
YLGSLVQYWGLELKKSAISLLDTIAIAVAEGTDRVIEVVQRAYRAILHIPTRIRQGLERL
LL-
>ENV-M.syn4.2
MRVRGIQRNWPQWWIWGILG--------FWMLMICNVVGNLWVTVYYGVPVWKEAKTTLF
CASDAKAYEKEVHNVWATHACVPTDPSPQEVVLENVTENFDMWKNNMVEQMQEDVISLWD
QSLKPCVKLAPLCVTLNCTDYVKNIT-NNATSTNSSW-GKPMEKGEIKFCSFNITTSIRN
KVQKQYALFYKLDVVQM-DEDNTS----------YRLISCNTSTITQACPKVTFDPIPIH
YCAPAGFAILKCNNKTFNGTGPCTNVSTVQCTHGIKPVVSTQLLLNGSLAEEEIIIRSEN
LTNNAKTIIVHLNESVEIVCTRPNNNTRKSIHIGPGRAFYATGEIIGDIRQAHCNLSRAK
WNDTLKQIVIKLREQFG-NKTIIFNQSSGGDPEITTHSFNCGGEFFYCNSTQLFNSTWNF
--NGTWNKN---FNNTWNNTEGTNDTITLPCKIKQIINMWQRVGQAMYAPPISGQIRCSS
NITGLILTRDGGN---DT--SGTEIFRPGGGDMRDNWRSELYKYKVVKIEPLGVAPTKAK
RRVVQREKRAVG-IGALFLGFLGAAGSTMGAASMTLTVQARQLLSGIVQQQSNLLKAIEA
QQHLLQLTVWGIKQLQARILAVERYLKDQQLLGIWGCSGKLICTTTVPWNASWSNKSLNE
IWDNMTWMEWEREIDNYTGLIYNLIEESQTQQEKNEQELLELDKWASLWNWFDITKWLWY
IKIFIMIIGGLIGLRIVFTVLSIVNRVRKGYSPLSFQTLTHHQREPDRPERIEEGGGEQD
RDRSGRLVDGFLAIIWVDLRSLCLFSYHRLRDLLLIVTRIVELLG-------RRGWEVLK
YWWNLLQYWSQELKNSAVSLLNATAIAVAEGTDRIIEVIQRICRAIRNIPRRIRQGLERA
LL-
>ENV-M.syn4.3
MRVKETQMNWPNLWKWGTLI--------LGLVIICSASDNLWVTVYYGVPVWKDAETTLF
CASDAKAYDTEVHNVWATYACVPTDPNPQEIHLENVTEEFNMWKNDMVDQMHEDIISLWD
ESLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGYAILKCNDKKFNGTGPCNNVSTVQCTHGIKPVVTTQLLLNGSLAEGEIIIRSEN
ITNNAKTIIVQLNESVVINCTRPNNNTRKSIRIGPGQAFYATGDIIGNIRQAHCNISRAN
WNNTLRQIVEKLGEQFGNNKTIVFNHSSGGDPEIVTHSFNCAGEFFYCNTTKLFNSTWTR
N-NGTWTRN---DTERSNSTE---EHITLPCRIKQIINMWQEVGKAMYAPPIRGQIRCSS
NITGLLLTRDGGNNN-----STNETFRPGGGNMKDNWRSELYKYKVVQIEPLGIAPTKAK
RRVVEREKRAVG-LGAVFLGFLGTAGSTMGAASLTLTVQARQVLSGIVQQQRNLLRAIEA
QQHLLKLTVWGIKQLQARVLAIERYLQDQQLLGMWGCSGKLICTTNVPWNSSWSNKSQTD
IWDNMTWLQWDKEISNYTSLIYTLIEESQNQQEKNEQDLLALDKWASLWSWFDISNWLWY
IKIFIIIVGGLIGLRIVFAVLSIINRVRQGYSPLSLQTLIPNPRGPDRLGRIEEEGGEQD
RDRSIRLVSGFLALAWDDLRSLCIFSYHRLRDFILIAARTVELLGHSSLKGLRLGWEGLK
YLGNLLLYWGQELKNSAINLLDTIAIAVAGWTDRVIEIGQRAGRAILNIPRRIRQGFERA
LL-
>ENV-M.syn4.4
MRVTGIRKNYQHLWRWGTMLLWRWGTMLLGILMICSAAGKLWVTVYYGVPVWRDADTTLF
CASDAKAYDTEAHNVWATHASVPTDPNPQEIVLENVTENFNMWKNNMVEQMHEDIISLWD
QSLKPCVQLTPLCVTLNCTN-VNVTNLKNETNTKSSSGGEKMEEGEMKNCSFNITTEIRD
KKQKVHALFYKLDIVPL-NSNSSE----------YRLINCNTSAITQACPKVSFDPIPIH

Fig. 10 cont'd-11

YCTPAGYAILKCNNKKFNGTGPCKNVSSVQCTHGIKPVISTQLLLNGSLAEEEVVIRSEN
FTNNAKTIMVQLNVSVEINCTRPNNNTRRSIPIGPGRAFYTTGDIIGDIRKAHCNISRAQ
WNNTLKHIVEKLGKQFGNNKTIIFKPSSGGDPEIVMHSFNCGGEFFYCNTSGLFNSTW--
--------N---STSLFNSTN---GTITLQCRIKQIINMWQGVGRAMYAPPIAGNITCKS
NITGLLLVRDGGT---EP--NDTETFRPGGGDMKDNWRSELYKYKVVRIEPLGVAPTRAK
RRVVEREKRAIG-LGAMFLGFLGAAGSTMGAASVTLTVQARLLLSGIVQQQNNLLRAIEA
QQHLLRLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IRIFIMIVGGLVGLRIVFAVLSIVKRVRQGYSPLSFQTRLPAPRGPDRPEGIEEEGGERD
RDRSVRLVDGFLALIWDDLRSLCLFSYHHLRDLLLIVARIVELLG-------RRGWEALK
YWWNLLQYWIQELKNSAISLLNATAVAVAEGTDRVIEALQRACRAILHIPRRIRQGFEAA
LL-
>ENV-M.syn6.1
MRVMGIQRNCQQWWIWGILG--------FWMLMICNVMGNLWVTVYYGVPVWKEANTTLF
CASDAKAYEREVHNVWATHASVPTDPNPQEVVLENVTEDFNMWKNNMVEQMQEDVISLWD
QSLQPCVKLTPLCVTLNCTD-LRNATNGNDTNTTSSS-REMMGGGEMKNCSFNITTEIRD
KKQKVYALFYKLDVVPI-DNDSNNTN--------YRLISCNTSAVTQACPKVTFDPIPIH
YCTPAGFAILKCRDKKFNGTGPCNNVSTVQCTHGIKPVVTTQLLLNGSLAEEEIVIRSEN
FTDNAKTIIVQLKEAVEINCTRPNNNTRKGIHIGPGRAFYATGEIIGDIRQAHCNVSRSE
WNKTLQQVATQLRKHF--NKTIIFNSSSGGDLEITTHSFNCRGEFFYCNTSGLFNSTW--
--NDTTINR----TEGSNNTR----NITLPCRIKQFINMWQEVGRAMYAPPIAGNITCRS
NITGLLLTRDGGNNGNET--NGTEIFRPGGGDMRNNWRSELYKYKVVEIKPLGIAPTKAR
RRVVQREKRAVG-IGAVFLGFLSAAGSTMGAASITLTVQARQLLTGIVQQQSNLLKAIEA
QQHMLQLTVWGVKQLQARVLAVERYLRDQQLLGIWGCSGRLICTTAVPWNTSWSNKSLNE
IWDNMTWMEWEREIDNYTSLIYTLIEESQNQQEKNEQELLELDKWANLWNWFSITNWLWY
IRIFIMIVGGLIGLRIIFGVLSIVKRVRQGYSPLSFQTRLPAPRGPDRPEGIEEEGGERD
RDRSGRLVDGFLALIWDDLRSLCLFSYHRLRDLILIAARIVELLGHSSLKGLRLGWEALK
YLWNLLLYWGQELKNSAISLLNTTAIVVAEGTDRVIEVLQRAGRAILNIPRRIRQGFEAA
LL-
>ENV-M.syn6.2
MRVTGIRKNYQHLWRWGTMLLWRWGTMLLGILMICSAAGKLWVTVYYGVPVWREAKTTLF
CASDAKAYEKEVHNVWATYACVPTDPNPQEMVLENVTENFNMWKNNMVDQMHEDIISLWD
ESLKPCVKLTPLCVTLHCTDL------GNATNT--------MEKGEIKNCSFNTTTEIRD
KKQKVHALFYRLDVVPI-DNDNTS----------YTLINCNTSVITQACPKVTFEPIPIH
YCAPAGFAILKCNNKKFNGTGPCTNVSTVQCTHGIRPVVSTQLLLNGSLAEGEIIIRSEN
LTDNAKTIIVHLNESVEIVCTRPNNNTRKSVRIGPGQTFYATGAIIGDIRQAYCNISRAK
WNNTLKQIVTKLREQFGNNKTIIFKPPSGGDLEITMHHFNCRGEFFYCNTTQLFNSTWNF
--NGTWNKN---FNNTWNNTEGTNDTITLPCKIKQIINMWQGVGRAMYAPPISGQIRCSS
NITGLLLTRDGGT-------NNTEIFRPGGGNMRDNWRSELYKYKVVKIEPLGVAPTKAK
RRVVQREKRAVG-IGALFLGFLGAAGSTMGAASMTLTVQARQVLSGIVQQQRNLLRAIEA
QQHLLQLTVWGIKQLQARILAVERYLKDQKFLGLWGCSGKIICTTAVPWNASWSNKSLDD
IWNNMTWMQWEREIDNYTGLIYSLIEESQTQQEKNEQELLQLDKWASLWNWFDITNWLWY
IRLFIMIVGGLVGLRIVFTVLSIVNRVRKGYSPLSFQTLTHHQREPDRPERIEEGGGEQG
RDRSVRLVSGFLALFWDDLRSLCLFCYHRLRDFILIAARTVELLGHSSLKGLRRGWEGLK
YLWNLLQYWIQELKNSAISLLNATAVAVAEGTDRVIEALQRACRAILHIPRRIRQGLERL
LL-
>ENV-M.syn6.3
MRVRGIQRNWPQWWIWGILG--------FWMIIICRVVGNLWVTVYYGVPVWKDAETTLF
CASDAKSYETEAHNIWATHACVPTDPSPQEVVLGNVTENFNMWKNDMVEQMHEDIISLWD
QSLKPCVELTPLCVTLNCTDDVRNVT-NNATNTNSSW-GEPMEKGEIKNCSFNITTSIRN
KVQKQYALFYKLDVVQI-DDNNSTNTS-------YRLINCNTSAITQACPKVSFDPIPIH
YCAPAGYAILKCNNKTFNGTGPCHNVSTVQCTHGIRPVISTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIIFKPSSGGDPEIVMHSFNCRGEFFYCNTSKLFNSTWTR
N-NGTWTRN---DTERSNSTE---EHITLPCRIKQIINMWQRVGQAMYAPPIAGNITCNS
SITGLLLTRDGGN---DT--SGTEIFRPGGGNIKDNWRSELYKYKVVQIEPLGVAPTRAK

Fig. 10 cont'd-12

RRVVEREKRAVG-IGAMIFGFLGAAGSTMGAASMALTVQARQLLSGIVQQQSNLLMAIEA
QQHLLKLTVWGIKQLRARVLAVERYLKDQQLLGIWGCSGKHICTTNVPWNSSWSNKSLDE
IWNNMTWIEWEREINNYTGLIYNLLEKSQNQQEKNEQDLLALDKWASLWSWFDISNWLWY
IKIFIIIVGGLIGLRIVFAVLSLVNRVRQGYSPLSLQTLLPTPRGPDRPEGTEEEGGEQG
RDRSIRLVSGFLALAWDDLRSLCRFSYHRLRDFILIVARTVELLGRSSLKGLRLGWEGLK
YLGNLLLYWGQELKISAISLLDTTAIAVAGWTDRVIEIGQRLCRAIRNIPRRIRQGAERA
LQ-
>ENV-M.syn6.4
MRVKETQMNWPNLWKWGTLI--------LGLVIICSASDNLWVTVYYGVPVWRDADTTLF
CASDAKAHETEVHNVWATHACVPTDPNPQEIHLENVTEEFNMWKNNMVEQMHTDIISLWD
QSLKPCVRLTPLCVTLNCTDELKNATFRSNTTTNSSW--EKMERGEIKNCSFNITTSIRD
KVQKEYALFYKLDIVPL-NSNSSE----------YRLINCNTSVIKQACPKISFDPIPIH
YCAPAGFAILKCKDKKFNGTGPCQNVSTVQCTHRIKPVVSTQFLLNGSLAEEDIIIRSEN
ITNNAKTIIVQLNESVVINCTRPNNNTRRSIPIGPGRVFYTTEDIIGDIRQAHCNLSRAK
WNDTLKQIVIKLREQFG-NKTIVFNQSSGGDLEIVMHSFNCGGEFFYCNSTQLFNSTWF-
--NSTW------STEGSNNTE-GSDTITLPCRIKQIVNMWQGVGKAMYAPPIRGQIRCSS
NITGILLTRDGGTNGT----NETETFRPGGGNMKDNWRSELYRYKVVKIEPLGIAPTKAK
RRVVEREKRAIG-LGAMFLGFLGTAGSTMGAASLTLTVQARQLMSGIVQQQNNLLRAIEA
QQHMLKLTVWGIKQLQARVLALERYLKDQQLLGLWGCSGKLICTTTVPWNSSWSNKSQTD
IWDNMTWMQWDREISNYTNTIYRLLEDSQNQQEKNEKDLLALDSWKNLWNWFDITKWLWY
IKIFIMIVGGLIGLKIVFAVLSIINRVRQGYSPLSFQTLIPNPRGPDRPGGIEEEGGEQD
RDRSIRLVNGFLALIWVDLRSLFLFSYHRLRDLLLIVTRIVELLG-------RRGWEALK
YWWNLLQYWSQELKNSAINLLDTIAIAVAEGTDRIIEVIQRICRAIRNIPTRIRQGLERA
LL-
>ENV-M.syn6.5
MRVKGIRKNYQHLWKWGTML--------LGMLMICSATEKLWVTVYYGVPVWKEATTTLF
CASDAKAYDTEVHNVWATYACVPTDPNPQELVLENVTENFDMWKNNMVEQMHEDIINLWD
QSLKPCVKLTPICVTLNCTDYVKNIT-NNATSTNSSW-GKPMEKGEIKNCSFNMTTELRD
KKQKVYSLFYKLDVVQM-DEDNTS----------YRLISCNTSVITQACPKISFEPIPIH
YCTPAGYAILKCNDKNFNGTGPCKNVSSVQCTHGIKPVISTQLLLNGSLAEEEIIIRSEN
LTNNVKTIIVHLNKSVEINCTRPSNNTRTSIRIGPGQAFYATGDIIGDIRKAHCNISRAN
WNNTLRQIVEKLGEQFGNNKTIVFNHSSGGDPEITTHSFNCGGEFFYCNTTKLFNSTWTW
N-NSTW--N---NTKRSNDTE---EIITLPCRIKQIINMWQEVGKAMYAPPIQGVIRCES
NITGLILTRDGGNNN-----STNETFRPGGGDMRDNWRSELYKYKVVRIEPLGVAPTEAK
RRVVQREKRAVGTIGAMFLGFLGAAGSTMGAASVTLTVQARLLLSGIVQQQNNLLKAIEA
QQHLLRLTVWGIKQLQARVLAIERYLQDQQLLGIWGCSGKLICTTNVPWNTSWSNRSLNE
IWNNMTWMEWEKEIDNYTNLIYNLLEESQIQQEKNEQELLALDKWANLWNWFDISNWLWY
IRIFIIIVGGLVGLRIVFAVLSIVNKVRQGYSPLSFQTHLPAQRGPDRPEGIEEGGGEQD
RDRSVRLVDGFLAIIWVDLRSLCLFSYHHLRDLLLIVARIVELLG-------RRGWEVLK
YWWNLLKYWSQELKNSAVSLLNATAIAVAEGTDRIIELIQRICRAICNIPRRIRQGFERA
LL-
>ENV-M.syn6.6
MRVKETRKNYQHLWRWGIML--------LGMLMICSAAEQLWVTVYYGVPVWKEAKTTLF
CASNAKAYDTEAHNVWATHACIPTDPNPQEIVLENVTESFNMWKNDMVDQMHEDVISLWD
QSLKPCVQLTPLCVTLNCTN-VNVTNLKNETNTKSSSGGEKMEEGEMKNCSFNVTTELRD
KKKKEYALFYRLDIVPL-NEGNNSNSSY------YRLINCNTSTITQACPKVSFEPIPIH
FCAPAGFAILKCNDKKFNGTGPCKNVSTVQCTHGIKPVVSTQLLLNGSLAEKEIIIRSEN
LTNNAKIIIVQLNESVEINCTRPGNNTRKSIRIGPGQTFYATGDIIGNIRQAHCNISRTQ
WNNTLKQIAIKLREQFG-NKTIIFNQSSGGDPEIVTHSFNCGGEFFYCKSTKLFNSTW--
---------N---STSLFNSTN---GTITLQCRIKQIINRWQEVGKAMYAPPIEGNITCKS
NITGLLLVRDGGINVTNN--TGTEVFRPGGGDMKDNWRNELYKYKVVEIKPLGVAPTRAR
RRVVEREKRAVG-LGAVFLGFLGAAGSTMGAAAVTLTVQARQLLFGIVQQQSNLLRAIEA
QQRMLQLTVWGIKQLQTRVLAIERYLKDQQLLGMWGCSGKLICTTAVPWNSSWSNKTYND
IWDNMTWLQWDKEISNYTDTIYRLLEESQNQQERNEKDLLELDKWASLWNWFNITNWLWY
IKIFIMIIGGLIGLRIIFAVLSIVNRVRQGYSPLSFQTLTPNPRGPDRLGRIEEEGGEQD
KDRSIRLVNGFSALIWDDLRNLCLFSYHQLRDFILVTARAVELLGRSSLRGLQRGWEALK
YLGSLVQYWGLELKKSAISLLDTIAIAVANWTDRVIEVVQRAYRAILHIPTRIRQGFEAA
LQ-

Fig. 10 cont'd-13

>POL-B.syn1.1
FFRENLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGHKAIGTVLVGPTPVNIIGRNLLTQIGCTLNFPISPIE
TVPVKLKPGMDGPKVKQWPLTEEKIKALVEICTEMEKEGKISKIGPENPYNTPVFAIKKK
DSTKWRKLVDFRELNKRTQDFWEVQLGIPHPAGLKKKKSVTVLDVGDAYFSVPLDKDFRK
YTAFTIPSINNETPGIRYQYNVLPQGWKGSPAIFQSSMTKILEPFRKQNPDIVIYQYMDD
LYVGSDLEIGQHRTKIEELRQHLLRWGFTTPDKKHQKEPPFLWMGYELHPDKWTVQPIVL
PEKDSWTVNDIQKLVGKLNWASQIYAGIKVKQLCKLLRGTKALTEVIPLTEEAELELAEN
REILKEPVHGVYYDPSKDLIAEIQKQGQGQWTYQIYQEPFKNLKTGKYARMRGAHTNDVK
QLTEAVQKIATESIVIWGKTPKFKLPIQKETWETWWTEYWQATWIPEWEFVNTPPLVKLW
YQLEKEPIVGAETFYVDGAANRETKLGKAGYVTDRGRQKVVSLTDTTNQKTELQAIHLAL
QDSGLEVNIVTDSQYALGIIQAQPDKSESELVSQIIEQLIKKEKVYLAWVPAHKGIGGNE
QVDKLVSAGIRKVLFLDGIDKAQEEHEKYHSNWRAMASDFNLPPVVAKEIVASCDKCQLK
GEAMHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIGQVR
DQAEHLKTAVQMAVFIHNFKRKGGIGGYSAGERIVDIIATDIQTKELQKQITKIQNFRVY
YRDSRDPLWKGPAKLLWKGEGAVVIQDNSDIKVVPRRKAKIIRDYGKQMAGDDCVASRQD
ED-
>POL-B.syn3.1
FFRENLAFPQGKAREFPSEQTRANSPTSR--------------ELQVWGGDNNSLSEAGD
DR----QGTVS-FSFPQITLWQRPIVTIKIGGQQKEALLDTGADDTVLEEMNLPGRWKPK
IIGGIGGFIKVKQYDQILIEICGHKAIGTVLVGPTPANIIGRNLLTQIGCTLNFPISPIE
TVPVRLKPGMDGPKVKQWPLTEEKIKALIEICTELENEGKISKIGPENPYNTPVFAIKKK
DGTKWRKLVDFRELNKRTQDFWEVQLGIPHPAGLKKKKSVTVLDVGDAYFSVPLDKEFRK
YTAFTIPSINNETPGIRYQYNVLPQGWKGSPSIFQSSMTKILEPFRKQNPEIVIYQYMDD
LYVGSDLEIEQHRTKIEELRQHLLKWGFYTPDKKHQKEPPFLWMGYELHPDKWTVQPIVL
PEKDSWTVNDIQKLVGKLNWASQIYAGIKVKQLCRLLRGTKALTEVVPLTEEAELELAEN
REILKEPVHGVYYDPSKDLVAEIQKQGLGQWTYQIYQEPYKNLKTGKYAKMRGAHTNDVK
QLTEAVQKIATESIVIWGKTPKFRLPIQKETWEAWWMEYWQATWIPEWEFVNTPPLVKLW
YQLEKEPIVGAETFYVDGAANRDTKLGKAGYVTDRGRQKVVSLTDTTNQKTELQAIHLAL
QDSGLEVNIVTDSQYAIGIIQAQPDRSESELVSQIIEQLIKKEKVYLAWVPAHKGIGGNE
QVDKLVSSGIRKVLFLDGIDKAQEDHEKYHSNWKAMASDFNLPPVVAKEIVACCDKCQLK
GEAMHGQVDCSPGIWQLDCTHLEGKVILVAVHVASGYIEAEVIPAETGQETAYFILKLAG
RWPVTTIHTDNGSNFTSTAVKAACWWAGIKQEFGIPYNPQSQGVVESINKELKKIIKQVR
DQAEHLKTAVQMAVFVHNFKRKGGIGGYSAGERMIDIIATDIQTTELQKQITKLQNFRVY
FRDSRDPLWKGPAKLLWKGEGAVVIQDNSEIKVVPRRKAKIIRDYGKQMAGDDCVASRQD
ED-
>POL-B.syn3.2
FFREDLAFLQGKAREFSSEQTRANSPTRG--------------ELQVWGRDNNSLSEAGA
DR----QGTVS-LSFPQITLWQRPLVTVKIGGQLKEALLDTGADDTVLEEMSLPGRWKPK
MIGGIGGFIKVRQYDQILVEICGHKAIGTVLIGPTPVNIIGRDLLTQIGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKQKKSVTVLDVGDAYFSVPLDEDFRK
YTAFTIPSTNNETPGIRYQYNVLPQGWKGSPAIFQSSMTRILEPFRKQNPDLVIYQYMDD
LYVGSDLEIGQHRTKIEELREHLLKWGFTTPDKKHQKEPPFLWMGYELHPDKWTVQPIML
PEKDSWTVNDIQKLVGKLNWASQIYPGIKVKQLCKLLRGAKALTEVIPLTKEAELELAEN
REILKEPVHGAYYDPSKDLIAEIQKQGQGQWTYQIYQDPFKNLKTGKYARMRGAHTNDVR
QLTEAVQKITTESIVIWGKIPKFKLPIQKETWETWWTEYWQATWIPEWEFVNTPPLVKLW
YQLEKEPIIGAETFYVDGAANRETKLGKAGYVTNKGRQKVVSITDTTNQKTELQAILLAL
QDSGLEVNIVTDSQYAIGIIQAQPDKSESELVSQIIEELIKKEKVYLTWVPAHKGIGGNE
QIDKLVSAGIRKVLFLDGIDQAQEEHEKYHSNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTVHTDNGSNFTSTTVKAACWWAGVKQEFGIPYNPQSQGVVESMNNELKKIIGQIR
DQAEHLKTAVQMAVFIHNFKRKGGIGGYSAGERIVDIIATDIQTKELQKQITKIQNFRVY
YRDNRDPLWKGPAKLLWKGEGAVVIQENSDIKVVPRRKVKIIRDYGKQMAGDDCVASGQD
ED-

Fig. 10 cont'd-14

>POL-B.syn3.3
FFREDLAFPQGEAREFSSEQTRANSPTRR--------------ELQVWGRDSNSLSEAGA
DR----QGTVS-FNFPQITLWQRPLVTIKIGGQLKEALLDTGADDTVLEDMNLPGKWKPK
MIGGIGGFIKVRQYDQIPIEICGHKAVGTVLVGPTPVNIIGRNLLTQLGCTLNFPISPIE
TVPVKLKPGMDGPKVKQWPLTEEKIKALVEICTELEKEGKISKIGPENPYNTPVFAIKKK
DSTKWRKVVDFRELNKKTQDFWEVQLGIPHPSGLKKKKSVTVLDVGDAYFSVPLDKDFRK
YTAFTIPSVNNETPGVRYQYNVLPQGWKGSPAIFQCSMTKILEPFRKQNPDIVIYQYMDD
LYVGSDLEIGQHRAKIEELRQHLLRWGFTTPDKKHQNEPPFLWMGYELHPDKWTVQPIEL
PEKDSWTVNDIQKLVGKLNWASQIYPGIKVRQLCKLLRGTKALTEVIPLTEEAELELAEN
REILREPVHGVYYDPTKDLIAEIQKQEQGQWTYQIYQEPFKNLKTGKYARTRGAHTNDVK
QLTEAVQKVATESIVIWGKTPKFKLPIQKETWEAWWTEYWQATWIPEWEFVNTPPLVKLW
YQLEKEPIEGAETFYVDGASNRETKLGKAGYVTNRGRQKVVPLTDTTNQKTELQAIYLAL
QDSGSEVNIVTDSQYALGIIQAQPDKSESELVNQIIEQLIKKEKIYLAWVPAHKGIGGNE
QVDKLVSAGIRKILFLDGIDKAQEEHEKYHNNWRAMASDFNLPPIVAKEIVASCDKCQLK
GEAIHGQVDCSPGIWQLDCTHLEGKVILVAVHVASGYIEAEVIPAETGQETAYFILKLAG
RWPVKTIHTDNGSNFTSATVKAACWWAGIKQEFGIPYNPQSQGVVESMNKELKKIIGQVR
DQAEHLKTAVQMAVFIHNFKRKGGIGEYSAGERIIDIIATDIQTRELQKQITKIQNFRVY
YRDSRDPLWKGPAKLLWKGEGAVVIQDNSDIKVVPRRKAKIIRDYGKQMAGDDCVAGRQD
ED- >POL-B.syn4.1
FFRENLAFPQGEAREFSSEQNRANSPTRR--------------ELQVWGGDNNSLSEAGA
DR----QGTVS-LSFPQITLWQRPLVTIRIGGQLKEALLDTGADDTVLEEMSLPGRWKPK
MIGGIGGFIKVRQYDQILIEICGHKAIGTVLIGPTPVNIIGRNLLTQLGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPSGLKKKKSVTVLDVGDAYFSVPLDKDFRK
YTAFTIPSINNETPGVRYQYNVLPQGWKGSPAIFQSSMTKILEPFRKQNPDMVIYQYMDD
LYVGSDLEIGQHRTKIEELRQHLLRWGLTTPDKKHQKEPPFLWMGYELHPDKWTVQPIKL
PEKDSWTVNDIQKLVGKLNWASQIYAGIKVRQLCKLLRGAKALTEVIPLTAEAELELAEN
REILREPVHGVYYDPSKDLIAEIQKQGQGQWTYQIYQDPFKNLKTGKYAKMRGAHTNDVK
QLTEAVQKVATESIVIWGKTPKFRLPIQKETWEAWWTEYWQATWIPEWEFVNTPPLVKLW
YQLEKEPIEGAETFYVDGAANRDTKLGKAGYVTDRGRQKVVSLTDTTNQKTELQAIHLAL
QDSGLEVNIVTDSQYALGIIQAQPDKSESELVSQIIEELIKKEKVYLAWVPAHKGIGGNE
QIDKLVSAGIRRVLFLDGIDQAQEEHEKYHSNWRAMASDFNLPPIVAKEIVASCDKCQLK
GEAIHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIEQVR
DQAEHLKTAVQMAVFIHNFKRKGGIGEYSAGERIIDIIATDIQTRELQKQITKIQNFRVY
YRDNRDPLWKGPAKLLWKGEGAVVIQDNSDIKVVPRRKAKIIRDYGKQMAGDDCVAGRQD
ED- >POL-B.syn4.2
FFRENLAFPQGKAREFPSEQTRANSPTSR--------------ELQVWGRDNNSLSEAGD
DR----QGTVS-FSFPQITLWQRPLVTVKIGGQLKEALLDTGADDTVLEEMNLPGRWKPK
MIGGIGGFIKVRQYDQIPIEICGHKAVGTVLVGPTPVNIIGRDLLTQIGCTLNFPISPIE
TVPVKLKPGMDGPKVKQWPLTEEKIKALIEICTELENEGKISKIGPENPYNTPVFAIKKK
DGTKWRKLVDFRELNKRTQDFWEVQLGIPHPAGLKQKKSVTVLDVGDAYFSVPLDKEFRK
YTAFTIPSTNNETPGIRYQYNVLPQGWKGSPAIFQCSMTKILEPFRKQNPDLVIYQYMDD
LYVGSDLEIEQHRTKIEELREHLLKWGFTTPDKKHQNEPPFLWMGYELHPDKWTVQPIML
PEKDSWTVNDIQKLVGKLNWASQIYAGIKVKQLCKLLRGTKALTEVVPLTEEAELELAEN
REILKVPVHGVYYDPSKDLVAEIQKQGLGQWTYQIYQEPFKNLKTGKYARTRGAHTNDVR
QLTEAVQKIATESIVIWGKTPKFKLPIQKETWEAWWMEYWQATWIPEWEFVNTPPLVKLW
YQLEKEPIVGAETFYVDGAANRETKLGKAGYVTDKGRQKVVPLTDTTNQKTELQAINLAL
QDSGSEVNIVTDSQYAIGIIQAQPDRSESELVSQIIEQLINKEKVYLAWVPAHKGIGGNE
QVDKLVSSGIRKVLFLDGIDKAQEDHEKYHSNWRAMAGDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFISTTVKAACWWAGVKQEFGIPYNPQSQGVVESMNNELKKIIGQVR
DQAEHLKTAVQMAVFVHNFKRKGGIGGYTAGERIVDIIASDIQTKELQKQITKIQNFRVY

Fig. 10 cont'd-15

YRDSRDPIWKGPAKLLWKGEGAVVIQDNSEIKVVPRRKAKIIRDYGKQMAGDDCVASRQN
ED-
>POL-B.syn4.3
FFREDLAFLQGKAREFSSEQTRANSPTRR--------------ELQVWGRDNNSPSEAGA
DR----QGTVS-FNFPQITLWQRPIVTIKIGGQLKEALLDTGADDTVLEDMNLPGKWKPK
MIGGIGGFIKVRQYDQILVEICGHKAIGTVLVGPTPANIIGRNLLTQIGCTLNFPISPIE
TVPVKLKSGMDGPKVKQWPLTEEKIKALIEICTEMEKEGKISKIGPENPYNTPVFAIKKK
DSTKWRKLVDFRELNKRTQDFWEVQLGIPHPSGLKKKKSVTVLDVGDAYFSVPLDEDFRK
YTAFTIPSVNNETPGIRYQYNVLPQGWKGSPAIFQSSMTRILEPFRKQNPDIVIYQYMDD
LYVGSDLEIGQHRAKIEELRQHLLRWGFTTPDKKHQKEPPFLWMGYELHPDKWTVQPIEL
PEKDSWTVNDIQKLVGKLNWASQIYPGIKVRQLCKLLRGTKALTEVIPLTEEAELELAEN
REILKEPVHGVYYDPSKELIAEIQKQEQGQWTYQIYQEPFKNLKTGKYARMRGTHTNDVK
QLTEAVQKITTESIVIWGRTPKFKLPIQKETWESWWTEYWQATWIPEWEFVNTPPLVKLW
YQLEREPIAGAETFYVDGASNRETKLGKAGYVTNRGRQKVVSLPDTTNQKTELQAIYLAL
QDSGLEVNIVTDSQYAIGIIQAQPDKSESELVNQIIEQLIKKEKIYLAWVPAHKGIGGNE
QVDKLVSNGIRKILFLDGIDKAQDEHEKYHSNWKAMASDFNLPPVVAKEIVACCDKCQLK
GEAMHGQVDCSPGIWQLDCTHLEGKIILVAVHVASGYIEAEVIPAETGQETAYFLLKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERMIDIIATDIQTTELQKQITKLQNFRVY
FRDSRDPLWKGPAKLLWKGEGAVVIQDNNDIKVVPRRKVKIIRDYGKQMAGDDCVASGQD
ED-
>POL-B.syn4.4
FFREDLAFPQGKARELSSEQTRANSPTRG--------------ELQVWGRDSNSLSEAGA
DR----PGTVS-FSFPQITLWQRPLVTIKIGGQQKEALLDTGADDTVLEEINLPGRWKPK
IIGGIGGFIKVKQYDQIPIEICGHKVIGTVLVGPTPANIIGRNLLTQLGCTLNFPISPIE
TVPVRLKPGMDGPKVKQWPLTEEKIKALVEICTELEKEGKISKIGPENPYNTPVFAIKKK
DSTKWRKVVDFRELNKKTQDFWEVQLGIPHPAGLKKKKSVTVLDVGDAYFSVPLDENFRK
YTAFTIPSINNETPGIRYQYNVLPQGWKGSPSIFQSSMTKILEPFRKQNPEIVIYQYMDD
LYVGSDLELGQHRTKIEELRQHLLKWGFYTPDKKHQKEPPFLWMGYELHPDKWTVQPIVL
PEKDSWTVNDIQKLVGKLNWASQIYPGIKVKQLCRLLRGAKALTEVIPLTKEAELELAEN
REILKEPVHGAYYDPTKDLIAEIQKQGEGQWTYQIYQEPYKNLKTGKYARMRGAHTNDVK
QLTETVQKITTESIVIWGKIPKFKLPIQKETWETWWTEYWQATWIPEWEFVNTPPLVKLW
YQLEKEPIIGAETFYVDGAASRETKLGKAGYVTNKGRQKVVSITDTTNQKTELQAILLAL
QDSGLEVNIVTDSQYAIGIIQAQPDKSESEIVSQIIEQLIKKEKVYLTWVPAHKGIGGNE
QVDKLVSAGIRKVLFLDGIDKAQEEHEKYHNNWRAMASDFNIPPVVAKEIVASCDKCQLK
GEAMHGQVDCSPGIWQLDCTHLEGKVILVAVHVASGYIEAEIIPTETGQETAYFILKLAG
RWPVTTIHTDNGSNFTSATVKAACWWAGVKQEFGIPYNPQSQGVIESMNKELKKIIGQIR
DQAEHLKTAVQMAVFIHNFKRKGGIGGYSAGERIVDIIATDIQTKELQNQITKIQNFRVY
YRDSRDPLWKGPAKLLWKGEGAVVIQENSDIKVVPRRKVKIIRDYGKQMAGDDCVASRQD
ED- >POL-B.syn6.1
FFREDLAFPQGEAREFCSEQTRANSPATR--------------ELQVWGRDNTSLSEAGA
DR----PGTVS-FSFPQITLWQRPIVTVKIEGQLKEALLDTGADDTVLEEMNLPGKWKPK
MIGGIGGFIKVRQYDQVSIEICGHKAIGTVLVGPTPANIIGRNLLTQIGCTLNFPISPIE
TVPVKLKPGMDGPKVKQWPLTEEKIKALVEICTELEKEGKISKIGPENPYNTPVFAIKKK
DSTKWRKVVDFRELNKRTQDFWEVQLGIPHPSGLKKKKSVTVLDVGDAYFSVPLDENFRK
YTAFTIPSINNETPGIRYQYNVLPQGWKGSPAIFQSSMTKILEPFRKQNPDIIIYQYMDD
LYVGSDLEIGQHRAKIEELRQHLLKWGFTTPDKKHQKEPPFLWMGYELHPDKWTVQPIEL
PEKDSWTVNDIQKLVGKLNWASQIYAGIKVKELCKLLRGTKALTEVVPLTEEAELELAEN
REILKEPVHGVYYDPSKDLIAELQKQGQGQWTYQIYQEPYKNLKTGKYARTRGAHTNDVR
QLTEAVQKIATEGIVIWGKTPKFKLPIQKETWEAWWTEYWQATWIPEWEFVNTPPLVKLW
YQLEKEPILGAETFYVDGASNRETKLGKAGYVTDRGRQKVVSLTDTTNQKTELQAINLAL
QDSGLEVNIVTDSQYALGIIQAQPDRSESELVSQIIEQLINKEKVYLAWVPAHKGIGGNE
QVDKLVSTGIRRVLFLDGIDKAQEEHEKYHSNWRAMASDFNLPPIVAKEIVASCDKCQLK
GEAIHGQVDCSPGIWQLDCTHLEGKVILVAVHVASGYIEAEVIPAETGQETAYFILKLAG

Fig. 10 cont'd-16

RWPVKTIHTDNGSNFTSTTVKAACWWAGIKQEFGIPYNPQSQGVVESMNKELKKIIEQVR
DQAEHLKTAVQMAVFVHNFKRKGGIGEYSAGERIVDIIATDIQTKELQKHITKIQNFRVY
YRDSRDPLWKGPAKLLWKGEGAVVIQDNSEIKVVPRRKAKIIRDYGKQMAGDDCVASRQD
ED-
>POL-B.syn6.2
FFREDLAFPQGKARELSSEQTRANSPTSPTRG-----------ELQVWGRDSNSLSEAGA
DR----QGPVS-FSFPQITLWQRPIVTIKIGGQLKEALLDTGADDTVLEDMNLPGRWKPK
MIGGIGGFIKVKQYDEILVEICGHKAIGTVLIGPTPVNIIGRNLLTQLGCTLNFPISPIE
TVPVKLKSGMDGPKVKQWPLTEEKIKALVEICTELEKEGKISKIGPENPYNTPIFAIKKK
DSTKWRKLVDFRELNKRTQDFWEVQLGIPHPAGLKKKKSVTVLDVGDAYFSVPLDKDFRK
YTAFTIPSVNNETPGIRYQYNVLPQGWKGSPAIFQCSMTKILEPFRKQNPDMVIYQYMDD
LYVGSDLEIGQHRIKIEELREHLLKWGFTTPDKKHQNEPPFLWMGYELHPDKWTVQPIVL
PEKDSWTVNDIQKLVGKLNWASQIYPGIKVRQLCKLLRGTKALTEVIPLTEEAELELAEN
REILREPVHGVYYDPTKDLIAEIQKQGQGQWTYQIYQEPFKNLKTGKYARMRGAHTNDVK
QLTEAVQKITTESIVIWGKIPKFRLPIQKETWEAWWIEYWQATWIPEWEFVNTPPLVKLW
YQLEREPIAGAETFYVDGAANRETKLGKAGYVTNRGRQKVVSITDTTNQKTELQAILLAL
QDSGLEVNIVTDSQYALGIIQAQPDKSESELVNQIIEQLIKKEKIYLAWVPAHKGIGGNE
QIDKLVSAGIRKVLFLDGIDKAQDEHEKYHSNWRAMAGDFNLPPVVAKEIVACCDKCQLK
GEAMHGQVDCSPGIWQLDCTHLEGKIILVAVHVASGYIEAEVIPAETGQETAYFLLKLAG
RWPVTTIHTDNGSNFTSATVKAACWWAGVKQEFGIPYNPQSQGVIESMNKELKKIIGQVR
DQAEHLKTAVQMAVFIHNFKRKGGIGEYSAGERIIDIIATDIQTKELQKQITKIQNFRVY
YRDSRDPIWKGPAKLLWKGEGAVVIQDNSEIKVVPRRKAKIIRDYGKQMAGDDCVAGRQD
ED-
>POL-B.syn6.3
FFRENLAFPQGEAREFSSEQTRANSPTRG--------------ELQVWGRDSNSLSEAGD
DR----QGTVS-FSFPQITLWQRPLVTIKIGGQQKEALLDTGADDTVLEEMNLPGRWKPK
IIGGIGGFIKVTQYDQIPIEICGHKAVGTVLVGPTPVNIIGRDLLTQIGCTLNFPISPIE
TVPVKLKSGMDGPKVKQWPLTEEKIKALIEICTEMEKEGKISKIGPENPYNTPVFAIKKK
DGTKWRKLVDFRELNKKTQDFWEVQLGIPHPAGLKQKKSVTVLDVGDAYFSVPLDREFRK
YTAFTIPSLNNETPGIRYQYNVLPQGWKGSPSIFQSSMTKILEPFRKQNPDLVIYQYMDD
LYVGSDLELGQHRTKIEELRQHLLKWGFYTPDKKHQKEPPFLWMGYELHPDKWTVQPIKL
PEKDSWTVNDIQKLVGKLNWASQIYPGIKVKQLCRLLRGAKALTEVVPLTKEAELELAEN
REILKEPVHGAYYDPTKDLIAEVQKQELGQWTYQIYQEPFKNLKTGKYARMKGAHTNDVK
QLTETVQKITTESIVIWGKTPKFRLPIQKETWESWWTEYWQATWIPEWEFVNTPPLVKLW
YQLEKEPITGAETFYVDGAANRETKIGKAGYVTDKGRQKVVSLPDTTNQKTELQAIHLAL
QDSGSEVNIVTDSQYAIGIIQAQPDRSESEVVNQIIEQLIKKEKVYLAWVPAHKGIGGNE
QVDKLVSNGIRKILFLDGIDKAQEEHERYHSNWKAMASDFNLPPVVAKEIVACCDKCQLK
GEAIHGQVDCSPGIWQLDCTHLEGKVILVAVHVASGYIEAEVIPAETGQETAYFILKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERIIDIIASDIQTKELQNQITKIQNFRVY
YRDSRDPVWKGPAKLLWKGEGAVVIQDNSDIKVVPRRKAKIIRDYGKQMAGDDCVASRQN
ED-
>POL-B.syn6.4
FFRENLAFPQRKAREFSSEQTRANSPTRR--------------ELQVWGGDNNSLSEAGA
DR----QGTVS-LSFPQITLWQRPLVTIKVGGQLKEALLDTGADDTVLEEINLPGRWKPK
MIGGIGGFIKVRQYDQILVEICGHKAIGTVLVGPTPVNIIGRNLLTQIGCTLNFPISPIE
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKKKKSVTVLDVGDAYFSVPLDEDFRK
YTAFTIPSINNETPGVRYQYNVLPQGWKGSPAIFQASMTKILEPFRKQNPDIVIYQYMDD
LYVGSDLEIGQHRIKIEELRQHLLRWGLTTPDKKHQKEPPFLWMGYELHPDKWTVQPIML
PEKDSWTVNDIQKLVGKLNWASQIYAGIKVRQLCKLLRGAKALTEVIPLTAEAELELAEN
REILKVPVHGVYYDPSKELIAEIQKQEQGQWTYQIYQDPFKNLKTGKYARMRGTHTNDVR
QLTEAVQKITTESIVIWGKIPKFKLPIQKETWETWWTEYWQATWIPEWEFVNTPPLVKLW
YQLEKEPIIGAETFYVDGAASRETKLGKAGYVTDRGRQKVISLTDTTNQKTELQAIHLAL
QDSGVEVNIVTDSQYALGIIQAQPDKSESEIVSQIIEQLIKKEKVYLTWVPAHKGIGGNE

Fig. 10 cont'd-17

QVDKLVSTGIRKVLFLDGIDQAQEEHEKYHSNWRTMASDFNLPPIVAKEIVASCDKCQLK
GEAMHGQVDCSPGIWQLDCTHLEGKVILVAVHVASGYIEAEVIPAETGQETAYFLLKLAG
RWPVKTIHTDNGPNFISTTVKAACWWAGIKQEFGIPYNPQSQGVVESMNNELKKIIGQVR
EQAEHLKTAVQMAVFIHNFKRKGGIGGYSAGERMIDIIATDIQTTELQKQITKLQNFRVY
FRDSRDPLWKGPAKLLWKGEGAVVIQENSDIKVVPRRKAKIIRDYGKQMAGDDCVAGRQD
ED-
>POL-B.syn6.5
FFRENLAFPQGKAREFPSEQTRANSPTSR--------------ELQVWGRDNNSLSEAGA
NR----QGTVS-FSFPQITLWQRPLVTVKIGGQLKEALLDTGADDTVLEDMDLPGRWKPK
MIGGIGGFIKVRQYDQIPIEICGHKVIGTVLVGPTPANIIGRNLLTQIGCTLNFPISPIE
TVPVRLKPGMDGPKVKQWPLTEEKIKALVEICTELEKEGKISKIGPENPYNTPVFAIKKK
DSTKWRKLVDFRELNKKTQDFWEVQLGIPHPSGLKKKKSVTVLDVGDAYFSVPLDKEFRK
YTAFTIPSTNNETPGIRYQYNVLPQGWKGSPAIFQASMTKILEPFRKQNPEIVIYQYMDD
LYVGSDLEIEQHRTKIEELRQHLLRWGFTTPDKKHQKEPPFLWMGYELHPDKWTVQPIVL
PDKDSWTVNDIQKLVGKLNWASQIYPGIKIRQLCKLLRGAKALTEVIPLTKEAELELAEN
REILKEPVHGVYYDPSKDLIAEIQKQGEGQWTYQIYQEPFKNLKTGKYAKMRGAHTNDVK
QLTEAVQKVATESIVIWGKTPKFKLPIQKETWEAWWMEYWQATWIPEWEFVNTPPLVKLW
YQLEKEPIEGAETFYVDGAANRDTKLGKAGYVTNKGRQKVVTLTDTTNQKTELQAIHLAL
QDSGLEVNIVTDSQYALGIIQAQPDKSESEIVNQIIEQLIKKEKVYLAWVPAHKGIGGNE
QVDKLVSSGIRKVLFLDGIDKAQEDHEKYHSNWRAMANDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFTSNTVKAACWWAGIKQEFGIPYNPQSQGVVESMNKQLKQIIGQVR
DQAEHLKTAVQMAVFIHNFKRKGGIGGYTAGERIVDIIATDIQTRELQKQITKIQNFRVY
YRDSREPLWKGPAKLLWKGEGAVVIQDNSDIKVVPRRKAKIIRDYGKQMAGDDCVASGQD
ED-
>POL-B.syn6.6
FFREDLAFLQGKAREFSSEQTRAISPTRR--------------ELQVWGRDNNSPSEAGA
DR----QGTVS-FNFPQITLWQRPLVTIRIGGQLKEALLDTGADDTVLEEMSLPGRWKPK
MIGGIGGFIKVRQYDQILIEICGHKAVGTVLIGPTPVNIIGRNLLTQIGCTLNFPISPID
TVPVKLKPGMDGPKVKQWPLTEEKIKALIEICTELENEGKISKIGPENPYNTPIFAIKKK
DSTKWRKLVDFRELNKRTQDFWEVQLGIPHPSGLKKKKSVTVLDVGDAYFSIPLDEDFRK
YTAFTIPSINNETPGTRYQYNVLPQGWKGSPAIFQSSMTRILEPFRKQNPDIVIYQYVDD
LYVGSDLEIGQHRTKIEELREHLLRWGFTTPDKKHQKEPPFLWMGYELHPDKWTVQPITL
PEKDSWTVNDIQKLVGKLNWASQIYAGIKVKQLCKLLRGTKSLTEVVPLTAEAELELAEN
REILKEPVHGAYYDPSKDLVAEIQKQGLGQWTYQIYQEPFKNLKTGKYAKMRGTHTNDVK
QLTEAVQKIATESIVIWGRTPKFKLPIQKETWDAWWTEYWQATWIPEWEFVNTPPLVKLW
YQLEKEPIVGAETFYVDGAANRETRLGKAGYVTDRGRQKVVPLTDTTNQKTELQAIYLAL
QDSGLEVNIVTDSQYALGIIQAQPDKSESELVSQIIEELIKKEKVYLAWVPAHKGIGGNE
QVDKLVSAGIRRVLFLDGIDKAQEEHEKYHNNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTIHTDNGRNFTSNSVKAACWWAGIKQEFGIPYNPQSQGVVESMNRELKKIIGQIR
DQAEHLKTAVQMAVFIHNFKRKGGIGGYSAGERIVDIIASDIQTKELQKQITKIQNFRVY
YRDNRDPLWKGPAKLLWKGEGAVVIQDNNDIKVVPRRKVKIIRDYGKQMAGDDCVASRQD
ED- >POL-C.syn1.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQILIEICGKKAIGTVLVGPTPVNIIGRNMLTQLGCTLNFPISPIE
TVPVKLKPGMDGPKVKQWPLTEEKIKALTAICEEMEKEGKITKIGPENPYNTPVFAIKKK
DSTKWRKLVDFRELNKRTQDFWEVQLGIPHPAGLKKKKSVTVLDVGDAYFSVPLDEGFRK
YTAFTIPSINNETPGIRYQYNVLPQGWKGSPAIFQSSMTKILEPFRAQNPEIVIYQYMDD
LYVGSDLEIGQHRAKIEELREHLLKWGFTTPDKKHQKEPPFLWMGYELHPDKWTVQPIQL
PEKDSWTVNDIQKLVGKLNWASQIYPGIKVRQLCKLLRGAKALTDIVPLTEEAELELAEN
REILKEPVHGVYYDPSKDLIAEIQKQGHDQWTYQIYQEPFKNLKTGKYAKMRTAHTNDVK

Fig. 10 cont'd-18

QLTEAVQKIAMESIVIWGKTPKFRLPIQKETWETWWTDYWQATWIPEWEFVNTPPLVKLW
YQLEKEPIAGAETFYVDGAANRETKIGKAGYVTDRGRQKIVSLTETTNQKTELQAIQLAL
QDSGSEVNIVTDSQYALGIIQAQPDKSESELVNQIIEQLIKKERVYLSWVPAHKGIGGNE
QVDKLVSSGIRKVLFLDGIDKAQEEHEKYHSNWRAMASEFNLPPIVAKEIVASCDKCQLK
GEAIHGQVDCSPGIWQLDCTHLEGKIILVAVHVASGYIEAEVIPAETGQETAYYILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQIIKIQNFRVY
YRDSRDPIWKGPAKLLWKGEGAVVIQDNSDIKVVPRRKVKIIKDYGKQMAGADCVAGRQD
EDQ
>POL-C.syn3.1
FFRENLAFPQGEAREFPPEQTRANSPT-RANSPTSR-------KLQV--RGDNPCSEAGA
ER----QGT---FNFPQITLWQRPLVTIKVGGQVKEALLDTGADDTVLEEINLPGKWKPK
MIGGIGGFIKVRQYDQIVIEICGKKAIGTVLIGPTPVNIIGRNMLTQLGCTLNFPISPIE
TVPVKLKPGMDGPKIKQWPLTEEKIKALTAICDEMEKEGKIEKIGPENPYNTPIFAIKKK
DSTKWRKLVDFKELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAKNPEIVIYQYMDD
LYIGSDLEIGQHRAKVEELREHLLRWGFTTPDKKHQKEPPFLWMGYELHPDKWTVQPIQL
PEKDSWTVNDIQRLVGKLNWASQIYPGIKVRQLCKLLRGTKALTDIVPLTEEAELELAEN
REILKEPVHGVYYDPSKDLIAEIQKQGDDQWTYQIYQESFKNLKTGKYAKMRSAHTNDVK
QLTEAVQKIALESIVIWGKAPKFRLPIQKETWEIWWTDYWQATWIPDWEFVNTPPLVKLW
YQLEKEPIAGAETFYVDGAANRETKIGKAGYVTDRGRQKVVTLTETTNQKTELQAIQLAL
QDSGLEVNIVTDSQYALGIIQAQPDKSESELVNQIIEELIKKERVYLSWVPAHKGIGENE
QVDKLVSNGIRKVLFLDGIDKAQEEHEKYHSNWRAMANEFNLPPVVAKEIVASCDKCQLK
GEAIHGQVDCSPGMWQLDCTHLEGKVILVAVHVASGYVEAEVIPAETGQETAYFILKLAG
RWPVKIIHTDNGSNFTSNAVKAACWWAGIQQEFGIPYNPQSQGVVESMNKELKKIIGQVR
EQAEHLKTAVQMAVFIHNFKRRGGIGGYSAGERIIDIIASDIQTKELQKQITKIQNFRVY
YRDSRDPVWKGPAKLLWKGEGAVVIQDNGDIKVVPRRKAKIIKDYGKQMAGDDCVAGRQD
EDQ
>POL-C.syn3.2
FFRENLAFQQGEAREFPSEQTRANSPTSRANSPTSRTNSPTSRELQV--RGDNPRSEAGV
ER----QGT---LNFPQITLWQRPLVSIKVGGQIKEALLDTGADDTVLEDINLPGKWKPR
MIGGIGGFIKVRQYDQIPIEICGKKAIGTVLVGPTPVNIIRRNMLTQLRCTLNFPISPIK
TVPVKLKPGMDGPKVKQWPLTEEKIKALTEICEEMEKEGKITKIGPENPYNTPVFAIKKK
DSTKWRKLVDFRELNKRTQDFWEVQLGIPHPSGLKKKKSVTVLDVEDAYFSVPLDEGFRK
YTAFTIPSTNNETPGIRYQYNVLPQGWKGSPAIFQCSMTKILEPFRTQNPDIVIYQYMDD
LYVGSDLEIGQHRAKIEELRAHLLKWGLTTPDKKHQKEPPFLWMGYELHPDKWTVQPIKL
PEKDSWTVNDIQKIVGKLNWASQIYPGIKVKQLCKLLRGAKALTDIIPLTEEAELELAEN
REILKEPVHGAYYDPSKDLVAEIQKQGHDQWTYQIYQEPYKNLKTGKYAKMRTAHTNDVR
QLTEAVQKIAQESIVIWGKTPKFRLPIQKETWETWWTDYWQATWIPEWEFINTPPLVKLW
YQLEKEPIVGAETFYVDGAANRETKMGKAGYVTDKGRQKIVSLTETTNQKAELQAIQLAL
QDSGPEVNIVTDSQYALGIIQAQPDRSESELVNQIIEQLINKERIYLSWVPAHKGIGGNE
QVDKLVSSGIRKVLFLDGIDKAQEDHEKYHNNWRAMASDFNLPPIVAREIVASCDKCQLK
GEAMHGQVDCSPGVWQLDCTHLEGKIILVAVHVASGYMEAEVIPAETGQETAYYILKLAG
RWPVKVIHTDNGSNFTSTAVKAACWWAGIKQEFGIPYNPQSQGVVEAMNKELKKIIEQVR
DQAEHLKTAVQMAVLIHNFKRKGGIGGYSAGERIVDIIATDIQTRELQKQIIQIQNFRVY
YRDSRDPIWKGPAKLLWKGEGAVVIQDNSDIKVVPRRKVKIIKDYGKQMAGADCVASRQD
ED-
>POL-C.syn3.3
FFRENLAFPQGKAREFPSEQARANSPTSRANSPTSR-------ELQV--RRDNPRSEAGA
ER----QGT---LNCPQITLWQRPLVSIKIGGQTREALLDTGADDTVLEEISLPGKWKPK
MIGGIGGFIKVRQYDQILIEICGKKAIGSVLVGPTPVNIIGRNLLTQLGCTLNFPISPIE
TIPVKLKPGMDGPRVKQWPLTEEKIKALTAICEEMEKEGKISKIGPENPYNTPIFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAQNPEIVIYQYMDD
LYVGSDLEIEQHRAKIEELREHLLKWGFTTPDKKHQKEPPFLWMGCELHPDKWTVQPIQL

Fig. 10 cont'd-19

PEKESWTVNDIQKLVGKLNWASQIYAGIKVKQLCRLLRGAKALTDIVPLTAEAELELAEN
REILREPVHGVYYDPSKELIAEIQKQGQDQWTYQIYQEPFKNLKTGKYAKRRTAHTNDVK
QLAEAVQKIAMESIVIWGKIPKFRLPIQKETWEAWWTDYWQATWIPEWEFVNTPPLVKLW
YQLEKDPIAGVETFYVDGAANRETKLGKAGYVTDRGRQKIVSLSETTNQKTELHAIQLAL
QDSGSEVNIVTDSQYALRIIQAQPDKSESEIVNQIIEQLIKKERVYLAWVPAHKGIGENE
QVDKLVSKGIRKVLFLDGIEKAQEEHERYHSNWRAMASEFNLPPIVAKEIVASCDKCQLK
GEATHGQVDCSPGIWQLDCTHLEGKVIIVAVHVASGYIEAEVIPAETGQETAYFLLKLAG
RWPVKTIHTDNGSNFTSAAVKAACWWAGIHQEFGIPYNPQSQGVVESMNKELKKIIGQVR
DQAEHLKTAVLMAVFIHNFKRKGGIGDYSAGERIIDIIATDIQTKELQKQIIKIQNFRVY
YRDNRDPIWKGPAKLLWKGEGAVVLQDNSDIKVIPRRKAKIIRDYGKQMAGADCVAGRQD
ENQ

>POL-C.syn4.1
FFRENLAFPQGKAREFPSEQARANSPTSRANSPTSR-------ELQV--RRDNPRSEAGA
ER----QGT---LNLPQITLWQRPLVSIKVGGQIKEALLDTGADDTVLEDINLPGKWKPK
MIGGIGGFIKVRQYDQIPIEICGKKAIGTVLVGPTPVNIIGRNMLTQLGCTLNFPISPIE
TIPVKLKPGMDGPKVKQWPLTEEKIKALTEICKEMEKEGKIEKIGPENPYNTPVFAIKKK
DSTKWRKLVDFRELNKRTQDFWEVQLGIPHPSGLKKKKSVTVLDVEDAYFSVPLDENFRK
YTAFTIPSVNNETPGIRYQYNVLPQGWKGSPAIFQCSMTKILEPFRTQNPEIVIYQYMDD
LYVGSDLEIGQHRAKIEKLREHLLKWGFTTPDKKHQKEPPFLWMGYELHPDKWTVQPIKL
PEKDSWTVNDIQRLVGKLNWASQIYAGIKVRQLCKLLRGAKALTDIVPLTKEAELELAEN
REILKEPVHGVYYDPSKELIAEIQKQGQDQWTYQIYQEPFKNLKTGKYAKRRTAHTNDVK
QLAEAVQKITMESIVIWGRTPKFRLPIQKETWEAWWTDYWQATWIPEWEFVNTPPLVKLW
YQLEKEPIAEAETFYVDGAANRETKMGKAGYVTDKGRQKIVSLTETTNQKTELHAIQLAL
QDSGPEVNIVTDSQYALGIIQAQPDKSESELVSQIIEQLINKERIYLSWVPAHKGIGGNE
QVDKLVSKGIRKVLFLDGIDKAQEEHERYHSNWRAMANEFNLPPIVAREIVASCDKCQLK
GEAIHGQVDCSPGVWQLDCTHLEGKIILVAVHVASGYVEAEVIPAETGQETAYFLLKLAG
RWPVKTIHTDNGSNFTSAAVKAACWWAGVQQEFGIPYNPQSQGVVESMNKELKKIIGQIR
DQAEHLKTAVQMAVFIHNFKRKGGIGDYSAGERIIDIIATDIQTRELQKQIIQIQNFRVY
YRDSRDPVWKGPAKLLWKGEGAVVLQDNSDIKVVPRRKVKIIKDYGKQMAGADCVAGRQD
ENQ
>POL-C.syn4.2
FFRENLAFPEGEAREFPSEQTRANSPT-RANSPTSR-------KLQV--RGDNPRSEAGV
ER----QGT---LNFPQITLWQRPLVSIKIGGQTREALLDTGADDTVLEEIKLPGNWKPK
MIGGIGGFIKVRQYDQILIEICGKKAIGTVLIGPTPVNIIGRNLLTQLGCTLNFPISPIK
TVPVKLKPGMDGPKVKQWPLSEEKIKALTEICEEMEKEGKISKIGPENPYNTPVFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAKNPEIVIYQYMDD
LYVGSDLEIGQHRAKVEELREHLLKWGLTTPDKKHQKEPPFLWMGYELHPDKWTVQPIQL
PDKDSWTVNDIQKLVGKLNWASQIYPGIKVKQLCKLLRGTKALTDIVPLTAEAELELAEN
REILREPVHGVYYDPSKDLVAEIQKQGNDQWTYQIYQEPYKNLKTGKYAKMRSAHTNDVK
QLTEAVQKIALESIVIWGKAPKFRLPIQKETWEIWWTDYWQATWIPDWEFVNTPPLVKLW
YQLEKDPIAGVETFYVDGAANRETKLGKAGYVTDRGRQKIVSLSETTNQKTELQAIQLAL
QDSGLEVNIVTDSQYALGIIQAQPDKSESELVNQIIEELIKKEKVYLSWVPAHKGIGENE
QVDKLVSSGIRKVLFLDGIEKAQEEHEKYHNNWRAMASEFNLPPIVAKEIVASCDKCQLK
GEATHGQVDCSPGMWQLDCTHLEGKIIIVAVHVASGYLEAEVIPAETGQDTAYYILKLAG
RWPVKVIHTDNGTNFTSAAVKAACWWAGIQQEFGIPYNPQSQGVVESMNKELKKIIGQVR
EQAEHLKTAVLMAVFIHNFKRKGGIGEYSAGERIIDMIATDIQTKELQNQITKIQNFRVY
YRDSRDPIWKGPAKLLWKGEGAVVIQDNGDIKVVPRRKVKIIRDYGKQMAGDDCVAGRQD
EDQ
>POL-C.syn4.3
FFRENLAFPQGEAREFPPEQTRANSPTSRTNSPTSR-------ELQV--RGDNPHSEAGA
ERQGTLQGT---LNCPQITLWQRPLVSIRVGGQIKEALLDTGADDTVLEEISLPGKWKPK
MIGGIGGFIKVRQYDQIVIEICGKKAIGSVLVGPTPVNIIRRNMLTQLRCTLNFPISSIE
TVPVKLKPGMDGPRVKQWPLTEEKIKALTAICEEMEKEGKITKIGPDNPYNTPVFAIKKK

Fig. 10 cont'd-20

DSTKWRKLVDFKELNKRTQDFWEVQLGIPHPAGLKRKKSVTVLDVGDAYFSVPLDEGFRK
YTAFTIPSTNNETPGIRYQYNVLPQGWKGSPAIFQSSMIKILEPFRAQNPDIVIYQYMDD
LYIGSDLEIGQHRAKIEELRAHLLKWGFTTPDKKHQKEPPFLWMGCELHPDKWTVQPIQL
PEKESWTVNDIQRLVGKLNWASQIYSGIKVRQLCKLLRGVKALTDIVPLTEEAELELAEN
REILKETVHGAYYDPSKDLIAEIQKQGHDQWTYQIYQEPFKNLKTGKYAKMRTAHTNDIK
QLTEAVQKIAMESIVIWGKTPKFRLPIQKETWETWWTDYWQATWIPEWEFINTPPLVKLW
YQLEKEPIVGAETFYVDGAANRDTKLGKAGYITDRGRQKVVTLTETTNQKAELQAIQLAL
QDSGSKVNIVTDSQYALGIIQAQPDRSESELVNQIIEQLIKKERVYLSWVPAHKGIGGNE
QIDKLVSSGIRRVLFLDGIDKAQEDHEKYHSNWRAMASDFNLPPIVAKEIIASCDKCQLK
GEAMHGQVDCSPGIWQLDCTHLEGKVIIVAVHVASGYIEAEVIPAETGQETAYYILKLAG
RWPVKIIHTDNGSNFTSNAVKAACWWAGIHQEFGIPYNPQSQGVVEAMNKELKKIIGQVR
DQAEHLKTAVLMAVFIHNFKRRGGIGGYSAGERIIDIIASDIQTKELQKQITKIQNFRVY
YRDSRDPIWKGPAKLLWKGEGAVVIQDNSDIKVIPRRKAKIIKDYGKQMAGADCVAGGQD
EN-
>POL-C.syn4.4
FFRENLAFQQGEAREFPSEQTRAISPTSR--------------ELQV--RGDNPCSEAGA
ER----QGT---FNFPQITLWQRPLVTIKVGGQVKEALLDTGADDTVLEEINLPGKWKPR
MIGGIGGFIKVRQYEQILIEICGKRAIGTVLVGPTPINIIGRNMLTQIGCTLNFPISPIE
TVPVKLKPGMDGPKIKQWPLTEEKIKALTAICDEMEKEGKITKIGPENPYNTPIFAIKKK
DSTKWRKLVDFRELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAQNPEIVIYQYMDD
LYVGSDLEIEQHRAKIEELREHLLRWGFTTPDKKHQKEPPFLWMGYELHPDKWTVQPIQL
PEKDSWTVNDIQKIVGKLNWASQIYPGIKVRQLCRLLRGAKALTDIIPLTEEAELELAEN
REILKEPVHGAYYDPSKDLIAEIQKQGDDQWTYQIYQESFKNLKTGKYAKMRTAHTNDVR
QLTEAVQKIAQESIVIWGKIPKFRLPIQKDTWETWWTDYWQATWIPDWEFVNTPPLVKLW
YQLEKEPIAGAETFYVDGAANRETKIGKAGYVTDRGRQKVITLTETTNQKTELQAIHLAL
QDSGSEVNIVTDSQYALRIIQAQPDKSESEIVNQIIEQLINKERVYLSWVPAHKGIGGNE
QVDKLVSNGIRKVLFLDGIDKAQEEHEKYHSNWRAMASEFNLPPVVAKEIVASCDKCQQK
GEAIHGQVDCSPRIWQLDCTHLEGKVILVAVHVASGYMEAEVIPAETGQETAYFILKLAG
RWPVKVIHTDNGSNFTSTAVKAACWWAGIKQEFGIPYNPQSQGVVESMNKELKKIIEQVR
DQAEHLKTAVQMAVLIHNFKRKGGIGGYSAGERIVDIIATDIQTKELQKQIIKIQNFRVY
YRDNRDPIWKGPAKLLWKGEGAVVIQDNSEIKVVPRRKAKIIRDYGKQMAGADCVASRQD
ED-
>POL-C.syn6.1
FFRENLAFPQGKAREFPSEQTRAISPTSR--------------ELQV--RGNNPRSEAGA
ER----QGT---LNLPQITLWQRPLVSIKIGGQTREALLDTGADDTVLEEIKLPGNWKPK
MIGGIGGFIKVRQYDQILIEICGKRAIGTVLVGPTPVNIIGRNMLTQIGCTLNFPISSIE
TVPVKLKPGMDGPKVKQWPLTEEKIKALTEICEEMEKEGKITKIGPDNPYNTPVFAIKKK
DSTKWRKLVDFKELNKRTQDFWEVQLGIPHPAGLKKNKSVTVLDVGDAYFSVPLDESFRK
YTAFTIPSINNETPGIRYQYNVLPQGWKGSPAIFQSSMTRILEPFRAQNPDIVIYQYMDD
LYVGSDLEIEQHRAKIEELREHLLRWGFTTPDKKHQKEPPFLWMGCELHPDKWTVQPIQL
PEKDSWTVNDIQKLVGKLNWASQIYSGIKVRQLCKLLRGVKALTDIVPLTKEAELELAEN
REILREPVHGVYYDPAKDLIAEIQKQGQDQWTYQIYQEPFKNLKTGKYAKRRTAHTNDVK
QLTEAVQKIATESIVIWGKIPKFRLPIQKDTWETWWTDYWQATWIPDWEFVNTPPLVKLW
YQLEKEPIAEAETFYVDGAASRETKMGKAGYVTDRGRQKVITLTETTNQKTELQAIKLAL
QDSGSEVNVVTDSQYALGIIQAQPDKSESEIVNQIIEQLINKERVYLSWVPAHKGIGGNE
QVDKLVSRGIRKVLFLDGIDKAQDEHEKYHSNWRAMASEFNLPPIVAREIVASCDKCQLK
GEATHGQVDCSPGIWQLDCTHLEGKIILVAVHVASGYIEAEVIPTETGQETAYYILKLAG
RWPVKIIHTDNGSNFTSSAVKAACWWAGIQQEFGIPYNPQSQGVVESMNKELKKIIGQVG
DQAEHLKTAVQMAVFIHNFKRRGGIGGYSAGERIIDIIATDIQTRELQKQIIKIQNFQVY
YRDSRDPIWKGPAKLLWKGEGAVVIQDNSEIKVVPRRKVKIIKDYGKQMAGADCMASRQD
ED-
>POL-C.syn6.2
FFRENLAFPQGEARELPSEQTRANGPTSR--------------ELQV--RGDNPCSEAGA
ER----QGT---FNFPQITLWQRPLVTIKVGGQVKEALLDTGADDTVLEEINLPGKWKPK

Fig. 10 cont'd-21

MIGGIGGFIKVRQYDQIPIEICGKRAIGTVLVGPTPINIIGRNMLTQLGCTLNFPISPIE
TVPVQLKPGMDGPRVKQWPLTEEKIKALTEICKEMEKEGKISKIGPENPYNTPIFAIKKK
DSTKWRKLVDFRELNKRTQDFWEVQLGIPHPAGLKKKRSVTVLDVGDAYFSVPLDEDFRK
YTAFTIPSINNETPGVRYQYNVLPQGWKGSPSIFQSSMTKILEPFRTQNPEIVIYQYMDD
LYIGSDLEIGQHREKIEELREHLLKWGFTTPDKKHQKEPPFLWMGYELHPDKWTVQPIKL
PEKDSWTVNDIQRLVGKLNWASQIYAGIKVRQLCKLLKGAKALTDIVTLTEEAELELAEN
REILKEPVYGVYYDPSKDLVAEIQKQGNDQWTYQIYQESFKNLKTGKYAKMRTAHTNDIK
QLTEAVQKIAQESIVIWGKTPKFRLPIQKETWEAWWTDYWQATWIPDWEFVNTPPLVKLW
YQLEKEPMAGVETFYVDGAANRETKIGKAGYVTDRGRQKVVTITETTNQKTELQAIYLAL
QDSGSKVNIVTDSQYALGIIQAQPDKSESELVSQIIEQLINKEKIYLSWVPAHKGIGGNE
QVDKLVSSGIRKVLFLDGIDKAQEDHERYHSNWRAMASDFNLPPIVAKEIVASCDQCQLK
GEAMHGQVDCSPGMWQLDCTHLEGKIIIVAVHVASGYIEAEVISAETGQETAYYILKLAG
RWPVKVVHTDNGSNFTSAAVKAACWWAGVQQEFGIPYNPQSQGVVESMNKELKRIIGQVR
DQAEHLKTAVQMAVFIHNFKRKGGIGGYSAGERIIDMIATDIQTKELQKQIIQIQNFRVY
YRDSRDPIWKGPAKLLWKGEGAVVIQDKGDIKVVPRRKAKIIRDYGKQMAGADCMAGRQD
EDQ
>POL-C.syn6.3
FFREDLAFPQGEARKFPPEQTRANSPTSRANSPTSR-------KLQV--RGDNPRSEAGV
ER----QGT---LNFPQITLWQRPLVSIKVGGQIREALLDTGADDTVLEEMSLPGKWKPK
MIGGIGGFIKVKQYEQILIEICGKKAIGSVLVGPTPVNIIGRNLLTQLGCTLNFPISPIE
TVPVKLKPGMDGPKVKQWPLTEEKIKALTAICDEMEKEGKITKIGPENPYNTPVFAIKKK
DSTKWRKLVDFKELNKRTQDFWEVQLGIPHPAGLKKKKSVTVLDVGDAYFSVPLDENFRK
YTAFTIPSRNNETPGIRYQYNVLPQGWKGSPAIFQASMTKILEPFRAKNPEIVIYQYMDD
LYVGSDLEIGQHRAKIEELRDHLLKWGFTTPDKKHQKEPPFLWMGYELHPDKWTVQPIEL
PEKDSWTVNDIQKLVGKLNWASQIYPGIQVKQLCKLLRGAKALTDVVPLTEEAELELAEN
REILKEPVHGAYYDPSKDLIAEIQKQGHDQWTYQIYQEPYKNLKTGKYAKRRAAHTNDVK
QLTEAVQKIAMESIVIWGKTPKFRLPIQKETWETWWTEYWQATWIPEWEFVNTPPLVKLW
YQLEKEPIAGAETFYVDGAANRETKMGKAGYITDRGRQKIISLTETTNQKTELHAIQLAL
QDSGSEANIVTDSQYALGIIQAQPDRSESELVNQIIEQLIKKERVYLAWVPAHKGIGENE
QVDKLVSSGIRKILFLDGIDKAQEEHEKYHSNWKAMASEFNLPPVVAREIVASCDKCQLK
GEAMHGQVDCSPRIWQLDCTHLERKVILVAVHVASGYMEAEVIPAETGQETAYFILKLAG
RWPVKVIHTDNGSNFTSNAVKAACWWAGIHQEFGIPYNPQSQGVVESMNKELKKIIEQVR
DQAEHLKTAVQMAVLIHNFKRKGGIGGYTAGERIIDIIATDIQTKELQNQITKIQNFRVY
YRDNRDPIWKGPAKLLWKGEGAVVLQDNSDIKVVPRRKVKIIRDYGKQMAGADCVAGRQD
ED-
>POL-C.syn6.4
FFRKNLAFPQGEAREFPPEQTRANSPTSR--------------ELQV--RGDNPLSEAGA
ERQGTLQGT---LNCPQITLWQRPLVSIKVGGQIKEALLDTGADDTVLEEISLPGKWKPK
MIGGIGGFIKVRQYDQIVIEICGKKAIGAVLVGPTPVNIIRRNMLTQLRCTLNFPISPIK
TVPVKLKPGMDGPKVKQWPLSEEKIKALTAICEDMEKEGKITKIGPENPYNTPIFAIKKK
DSTKWRKLVDFRELNKRTQDFWEVQLGIPHPSGLKKKKSVTVLDVEDAYFSVPLDEGFRK
YTAFTIPSINNATPGIRYQYNVLPQGWKGSPAIFQSSMTKILEPFRTKNPDIVIYQYMDD
LYVGSDLEIGQHRAKIEKLREHLLRWGLTTPDKKHQKEPPFLWMGYELHPDKWTVQPIQL
PDKDSWTVNDIQKLVGKLNWASQIYAGIKVKQLCRLLRGAKALTDIIPLTEEAELELAEN
REILKEPVHGAYYDPSKDLIAEIQKQGQGQWTYQIYQEPYKNLKTGKYAKMRTAHTNDVK
QLAEAVQKITMESIVIWGRTPKFRLPIQKETWETWWTDYWQATWIPEWEFINTPPLVKLW
YQLEKEPIVGAETFYVDGAANRETKLGKAGYVTDKGRQKIVSLTETTNQKTELQAIHLAL
QDSGSEVNIVTDSQYALRIIQAQPDKSESELVNQIIEQLINKERIYLSWVPAHKGIGGNE
QVDKLVSNGIRKVLFLDGIEKAQEEHERYHSNWRAMANEFNLPPIVAREIVASCDKCQIK
GEAMHGQVDCSPGVWQLDCTHLEGKVILVAVHVASGYVEAEVIPAETGQEAAYFILKLAG
RWPVKTIHTDNGSNFTSTAVKAACWWAGIKQEFGIPYNPQSQGVVESMNKELKKIIGQVR
DQAEHLKTAVQMAVLIHNFKRKGGIGDYSAGERIIDIIATDMQTKELQKQIIKVQNFRVY
YRDSRDPIWKGPAKLLWKGEGAVVIQDNGDIKVVPRRKVKIIKDYGRQMAGADCVASRQD
ED-

Fig. 10 cont'd-22

```
>POL-C.syn6.5
FFRENLAFPEGEAREFPSEQARANSPTSR--------------ELQV--RRDNPRSEAGA
EG----QGT---LNFPQITLWQRPLVSIRVGGQIKEALLDTGADDTVLEEINLPGRWKPK
MIGGIGGFIKVRQYDQITIEICGKKAIGTVLVGPTPINIIGRNMLTQIGCTLNFPISPIE
TVPVKLKPGMDGPKIKQWPLTEEKIKALKAICEEMEKEGKIEKIGPENPYNTPVFAIKKK
DSTKWRKLVDFRELNKRTQDFWEIQLGIPHPAGLKRKKSVTVLDVGDAYFSVPLYEDFRK
YTAFTIPSVNNETPGIRYQYNVLPQGWKGSPAIFQCSMTKILEPFRAQNPEIVIYQYMDD
LYVGSDLEIGQHRAKVEELREHLLKWGLTTPDKKHQKEPPFLWMGYELHPDKWTVQPIQL
PEKESWTVNDIQKIVGKLNWASQIYPGIKVRQLCRLLRGAKALTDIVPLTAEAELELAEN
REILKEPVHGVYYDPSKELIAEIQKQGDDQWTYQIYQEPFKNLKTGKYAKMRSAHTNDVK
QLTEAVQKIALESIVIWGKAPKFRLPIQKETWEIWWTDYWQATWIPEWEFINTPPLVKLW
YQLEKEPIAGVETFYVDGAANRDTKIGKAGYVTDRGRQKIVSLSETTNQKTELQAIQLAL
QDSGLEVNIVTDSQYALGIIQAQPDNSESELVNQIIEELIKKERVYLSWVPAHKGIGGNE
QVDKLVSKGIRKVLFLDGIDKAQEEHEKYHNNWRAMASDFNLPPVVAKEIVACCDKCQLK
GEAIHGQVDCSPGIWQLDCTHLEGKVIIVAVHVASGYLEAEVIPAETGQETAYFLLKLAG
RWPVKVIHTDNGPNFTSAAVKAACWWAGINQEFGIPYNPQSQGVVESMNKELKKIIGQVR
EQAEHLKTAVQMAVFIHNFKRKGGIGGYSAGERIVDIIATDIQTKELQNQIIKIQNFRVY
YRDSRDPIWKGPAKLLWKGEGAVVIQENSDIKVVPRRKAKIIKDYGKQMAGDDCVAGRQD
EDQ
>POL-C.syn6.6
FFRENLAFQQGEAREFPSEQTRANSPT-RANSPTSRTNSPTSRELQV--RGDNPHSEAGA
ER----QGS---LNFPQITLWQRPLVTIKIGGQLKEALLDTGADDTVLEDINLPGKWKPR
MIGGIGGFIKVRQYEQIPIEICGKKAIGTVLIGPTPVNIIGRNLLTQLGCTLNFPISPIE
TIPVKLKPGMDGPKVKQWPLTEEKIKALTAICEEMEKEGKITKIGPDNPYNTPVFAIKKK
DSTKWRKLVDFRELNKRTQDFWEVQLGIPHPAGLKKKKSVTVLDVGDAYFSVPLDKDFRK
YTAFTIPSTNNETPGIRYQYNVLPQGWKGSPAIFQSSMIKILEPFRAKNPELVIYQYMDD
LYVGSDLEIMQHRAKIEELRAHLLKWGFTTPDKKHQKEPPFLWMGYELHPDKWTVQPIVL
PEKDSWTVNDIQKLVGKLNWASQIYPGIKVKQLCKLLRGTKALTDIVPLTEEAELELAEN
REILKETVHGAYYDPSKDLIAEIQKQGYDQWTYQIYQEPFKNLKTGKYAKKRTAHTNDVR
QLTEAVQKIAIESIVIWGKTPKFRLPIQKETWETWWADYWQATWIPEWEFVNTPPLVKLW
YQLEKDPIAGAETFYVDGAANRETKKGKAGYVTDKGRQKVVTLTETTNQKAELQAIQLAL
QDSGPEVNIVTDSQYALRIIQAQPDKSESGLVNQIIEQLIKKEKVYLSWVPAHKGIGGNE
QIDKLVSSGIRRVLFLDGIDKAQEDHEKYHSNWRAMAGEFNLPPVVAKEIVASCDKCQQK
GEAIHGQVDCSPGIWQLDCTHLEGKIILVAVHVASGYIEAEVIPAETGQDTAYYILKLAG
RWPVKVIHTDNGTNFTSAAVKAACWWASIQQEFGIPYNPQSQGVVEAMNKELKKIIGQIR
DQAEHLKTAVLMAVFIHNFKRKGGIGEYSAGERIIDIIASDIQTKELQKQITKIQNFRVY
YRDSRDPVWKGPAKLLWKGEGAVVIQDNSDIKVIPRRKAKIIRDYGKQMAGADCVAGGQD
ED-
>POL-M.syn1.1
FFRENLAFPQGEAREFPSEQTRANSPTSRANSPTSR-------ELQV--RGDNPRSEAGA
ER----QGT---LNFPQITLWQRPLVTIKIGGQLKEALLDTGADDTVLEDINLPGKWKPK
MIGGIGGFIKVRQYDQILIEICGKKAIGTVLVGPTPVNIIGRNMLTQIGCTLNFPISPIE
TVPVKLKPGMDGPKVKQWPLTEEKIKALTEICTEMEKEGKISKIGPENPYNTPVFAIKKK
DSTKWRKLVDFRELNKRTQDFWEVQLGIPHPAGLKKKKSVTVLDVGDAYFSVPLDESFRK
YTAFTIPSINNETPGIRYQYNVLPQGWKGSPAIFQSSMTKILEPFRKQNPDIVIYQYMDD
LYVGSDLEIGQHRAKIEELREHLLKWGFTTPDKKHQKEPPFLWMGYELHPDKWTVQPIQL
PEKDSWTVNDIQKLVGKLNWASQIYPGIKVKQLCKLLRGAKALTDIVPLTEEAELELAEN
REILKEPVHGVYYDPSKDLIAEIQKQGQDQWTYQIYQEPFKNLKTGKYAKMRTAHTNDVK
QLTEAVQKIATESIVIWGKTPKFRLPIQKETWETWWTDYWQATWIPEWEFVNTPPLVKLW
YQLEKEPIVGAETFYVDGAANRETKLGKAGYVTDRGRQKVVSLTETTNQKTELQAIQLAL
QDSGSEVNIVTDSQYALGIIQAQPDKSESELVNQIIEQLIKKEKVYLSWVPAHKGIGGNE
QVDKLVSSGIRKVLFLDGIDKAQEEHEKYHSNWRAMASDFNLPPIVAKEIVASCDKCQLK
GEAMHGQVDCSPGIWQLDCTHLEGKVILVAVHVASGYIEAEVIPAETGQETAYFILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQITKIQNFRVY
```

Fig. 10 cont'd-23

YRDSRDPIWKGPAKLLWKGEGAVVIQDNSDIKVVPRRKAKIIRDYGKQMAGDDCVAGRQD
EDQ

>POL-M.syn3.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQIPIEICGKRAIGTVLVGPTPINIIGRNMLTQLGCTLNFPISPIK
TVPVKLKPGMDGPKVKQWPLTEEKIKALTAICEEMEKEGKITKIGPENPYNTPVFAIKKK
DGTKWRKLVDFRELNKRTQDFWEVQLGIPHPSGLKKKKSVSVLDVGDAYFSVPLDESFRK
YTAFTIPSINNETPGIRYCYNVLPQGWKGSPAIFQCSMTKILEPFRAQNPEIVIYQYMDD
LYIGSDLEIGQHRAKIEELREHLLRWGFTTPDKKHQKEPPFLWMGCELHPDKWTVQPIQL
PEKDSWTVNDIQKIVGKLNWASQIYPGIKVRQLCKLLRGAKALTDIVPLTEEAELELAEN
REILREPVHGVYYDPSKDLVAEIQKQGQDQWTYQIYQEPFKNLKTGKYAKMRTAHTNDVK
QLTEAVQKIALESIVIWGKIPKFRLPIQKETWEAWWMEYWQATWIPEWEFINTPPLVKLW
YQLEKEPIAGAETFYVDGAANRETKIGKAGYVTDRGRQKIVSLTETTNQKAELQAIQLAL
QDSGPEVNIVTDSQYALGIIQAHPDKSESELVNQIIEQLIKKERVYLSWVPAHKGIGENE
QVDKLVSNGIRKILFLDGIDKAQEEHEKYHSNWRAMASEFNLPPIVAKEIVASCNKCQLK
GEALHGQVDCSPGMWQLDCTHLEGKVILVAVHVASGYMEAEVIPAETGQETAYYILKLAG
RWPVKVVHTDNGSNFTSTAVKAACWWAGIQQEFGIPYNPQSQGVIESMNKELKKIIGQIR
DQAEHLKTAVQMAVFIHNFKRKGGIGEYSAGERIIDIIATDIQTRELQKQIIKIQNFRVY
YRDSRDPIWKGPAKLLWKGEGAVVLQDNSDIKVVPRRKVKIIKDYGKQMAGADCVAGRQD
ENQ
>POL-M.syn3.2
FFRENLAFQQGEARKFSSEQTGANSPTSR--------------ELRV-RRGDNPLSEAGA
ER----RGTVPSLSFPQITLWQRPLVTVKIGGQLIEALLDTGADDTVLEDINLPGKWKPR
MIGGIGGFIKVKQYDQILIEICGKKAIGTVLVGPTPVNIIGRNMLTQIGCTLNFPISPID
TVPVTLKPGMDGPKIKQWPLTEEKIKALTEICTEMEKEGKISRIGPENPYNTPIFAIKKK
DSTKWRKLVDFRELNKKTQDFWEVQLGIPHPAGLKKKRSVTVLDVGDAYFSVPLDKDFRK
YTAFTIPSTNNETPGIRYQYNVLPQGWKGSPSIFQSSMTRILEPFRAKNPEIVIYQYMDD
LYVGSDLEIEQHRTKIEELRQHLLRWGLTTPDKKHQKEPPFLWMGYELHPDRWTVQPIEL
PEKESWTVNDIQKLVGKLNWASQIYAGIKVKQLCKLLRGTKALTEVVPLTEEAELELEEN
REILKDPVHGAYYDPSKDLIAEIQKQGHDQWTYQIYQEQYKNLKTGKYARKRSAHTNDVR
QLTEAVQKIATESIVIWGKTPKFRLPIQRETWETWWTDYWQATWIPEWEFVNTPPLVKLW
YQLEKDPIAGVETFYVDGASNRETKKGKAGYVTDKGRQKVVSLTETTNQKTELHAIHLAL
QDSGSEVNIVTDSQYALGIIQAQPDRSESELVNQIIEELIKKEKVYLSWVPAHKGIGGNE
QVDKLVSSGIRKVLFLDRIDKAQEEHERYHSNWRTMASDFNLPPIVAKEIVANCDKCQLK
GEAMHGQVDCSPGIWQIDCTHLEGKVIIVAVHVASGYIEAEVIPAETGQETAYFLLKLAG
RWPVKVIHTDNGSNFTSAAVKAACWWANVTQEFGIPYNPQSQGVVESMNKELKKIIGQVR
EQAEHLKTAVQMAVLIHNFKRKGGIGGYSAGERIIDIIASDIQTKELQKQIIKVQNFRVY
YRDSRDPVWKGPAKLLWKGEGAVVIQDNSDIKVVPRRKVKIIRDYGKQMAGDDCVAGRQD
EDQ
>POL-M.syn3.3
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQILIEICGHKAIGTVLIGPTPVNIIGRNLLTQIGCTLNFPISPIE
TVPVKLKPGMDGPRVKQWPLTEEKIKALVEICTEMEKEGKISKIGPENPYNTPVFAIKKK
DSTRWRKLVDFRELNKRTQDFWEIQLGIPHPAGLKKKKSVTVLDVGDAYFSVPLDEGFRK
YTAFTIPSVNNETPGVRYQYNVLPQGWKGSPAIFQSSMTKILEPFRKQNPDIVIYQYMDD
LYVGSDLEIGQHRTKIEELREHLLKWGFTTPDKKHQNEPPFLWMGYELHPDKWTVQPIVL
PEKDSWTVNDLQKLVGKLNWASQIYPGIKVKQLCRLLRGAKALTEVIPLTKEAELELAEN
REILKEPVHGVYYDPSKELIAEIQKQGQGQWTYQIYQEPYKNLKTGKYARMRGAHTNDVK
QLTEVVQKIAMESIVIWGKTPKFKLPIQKETWETWWTEYWQATWIPDWEFVNTPPLVKLW
YQLEKEPIVGAETFYVDGAANRETKLGKAGYVTDRGRQKVVSLTDTTNQKTELQAIHLAL
QDSGLEVNIVTDSQYAIGIIQAQPDKSESELVSQIIEQLIKKEKVYLAWVPAHKGIGGNE
QVDKLVSAGIRKVLFLDGIDKAQEDHEKYHNNWRAMASDFNLPPVVAKEIVASCDKCQLK

Fig. 10 cont'd-24

GEAIHGQVDCSPGIWQLDCTHLEGKIILVAVHVASGYLEAEVIPAETGQETAYFILKLAG
RWPVKTIHTDNGSNFTSTTVKAACWWAGIKQEFGIPYNPQSQGVVESINKELKKIIGQVR
DQAEHLKTAVLMAVFIHNFKRRGGIGGYSAGERIVDIIATDIQTKELQKQITKIQNFRVY
YRDSRDPLWKGPAKLLWKGEGAVVIQDNSEIKVVPRRKAKIIRDYGKQMAGDDCVASRQD
ED-

>POL-M.syn4.1
FFRENLAFQQGEARKFSSEQTRANSPTRG--------------ELQVWGRDNNPLSEAGA
ER----RGTVPSLSFPQITLWQRPLVTVKIGGQLIEALLDTGADDTVLEDINLPGKWKPK
MIGGIGGFIKVKQYDQILIEICGKKAIGTVLVGPTPVNIIGRNMLTQIGCTLNFPISPID
TVPVTLKPGMDGPRIKQWPLTEEKIKALTEICKEMEEEGKISKIGPENPYNTPIFAIKKK
NSTRWRKLVDFRELNKKTQDFWEVQLGIPHPAGLKRKKSVTVLDVEDAYFSVPLDESFRK
YTAFTIPSINNETPGVRYQYNVLPQGWKGSPAIFQCSMTKILEPFRIKNPEMVIYQYMDD
LYVGSDLEIGQHRIKIEELRAHLLSWGFTTPDKKHQKDPPFLWMGYELHPDRWTVQPIEL
PEKDSWTVNDIQKLVEKLNWASQIYSGIKVRQLCRLLRGAKALTDIVPLTEEAELELAEN
REILKEPVHGAYYDPSKDLVAEIQKQGQDQWTYQIYQEPFKNLKTGKYARKRSAHTNDVK
QLTEVVQKIATESIVIWGKTPKFRLPIQRETWETWWTEYWQATWIPEWEFVNTPPLVKLW
YQLEKDPIAGVETFYVDGAASRETKLGKAGYVTDRGRQKVVSLTETTNQKTELHAIHLAL
QDSGSEVNIVTDSQYVLGIIQAQPDRSESELVNQIIEELIKKEKVYLSWVPAHKGIGGNE
QVDKLVSSGIRKVLFLNGIDKAQEEHERYHSNWRTMASDFNLPPIVAKEIVANCDKCQLK
GEAMHGQVDCSPGVWQLDCTHLEGKVIIVAVHVASGYIEAEVIPAETGQEAAYFILKLAG
RWPVKVVHTDNGSNFTSAAVKAACWWANVRQEFGIPYNPQSQGVVESMNNELKKIIGQIR
DQAEHLKTAVLMAVFIHNFKRKGGIGEYSAGERIIDIIATDIQTRELQKQITKIQNFRVY
FRDSRDPIWKGPAKLLWKGEGAVVIQDNSEIKVVPRRKVKIIRDYGKQMAGDDCVAGRQD
EN- >POL-M.syn4.2
FFRENLAFPQGEAREFPSEQARANSPTSRANSPTSR-------DLWDGGRDNLP-SEAGA
ER----QGT---LNFPQITLWQRPLVTVRIGGQLREALLDTGADDTVLEDIDLPGKWKPK
IIGGIGGFIKVRQYEQIPIEICGHKAIGTVLVGPTPINIIGRNMLTQLGCTLNFPISPIK
TVPVKLKPGMDGPRVKQWPLTEEKIKALTAICEEMEKEGKITKIGPENPYNTPVFAIKKK
DSTRWRKLVDFRELNRRTQDFWEVQLGIPHPAGLKKKRSVTVLDVGDAYFSVPLDEGFRK
YTAFTIPSVNNETPGIRYQYNVLPQGWKGSPSIFQSSMTRILEPFRAKNPEIVIYQYIDD
LYVRSDLEIGQHRAKIEELREHLLRWGFTTPDKKHQKEPPFLWMGCELHPDKWTVQPIQL
PEKDSWTINDIQKLVGKLNWASQIYPGIKVRQLCKLLRGTKALTDIVTLTEEAELELAEN
REILKDPVHGVYYDPSKELIAEIQKQGDDQWTYQIYQEQYKNLKTGKYAKRRTAHTNDVR
QLTEAVQKIALESIVIWGKIPKFRLPIQKETWEAWWMEYWQATWIPEWEYVNTPPLVKLW
YQLEKEPIIGAETFYVDGAANRETKLGKAGYVTNRGRQKVVSLTDTTNQKTELQAIQLAL
QDSGSEVNVVTDSQYALGIIQAHPDKSESELVNQIIEQLIKKERVYLSWVPAHKGIGGNE
QVDKLVSAGIRKVLFLDGIDKAQEDHERYHSNWRAMASDFNLPPVVAKEIVASCNKCQLK
GEAIHGQVDCSPGIWQLDCTHLEGKIIIVAVHVASGYMEAEVIPAETGQETAYFILKLAG
RWPVKIIHTDNGSNFTSATVKAACWWANVTQEFGIPYNPQSQGVVESINKELKKIIGQVR
DQAEHLRTAVQMAVFIHNFKRRGGIGGYSAGERIVDIIATDIQTKELQKQITKIQKFRVY
YRDSRDPLWKGPAKLLWKGEGAVVIQDNSDIKVIPRRKAKIIKDYGKQMAGADCVAGRQD
EDQ >POL-M.syn4.3
FFRENLAFPQGKAREFPSEQTRANSPTSRANSPTSR-------ELQV--RGDNPRSEAGA
ER----QGT---FNFPQITLWQRPLVSIKVGGQIKEALLDTGADDTVLEEINLPGKWKPR
MIGGIGGFIKVRQYDQILIEICGKRAIGTVLVGPTPANIIGRNLLTQLGCTLNFPISPIE
TVPVKLKPGMDGPKIKQWPLTEEKIKALTEICTEMEKEGKISKIGPENPYNTPIFAIKKK
DSTKWRKLVDFKELNKRTQDFWEVQLGIPHPSGLKKKKSVTVLDVGDAYFSVPLDEDFRK
YTAFTIPSTNNETPGIRYQYNVLPQGWKGSPAIFQASMTKILEPFRAQNPEIVIYQYMDD
LYVGSDLEIEQHRAKVEELREHLLKWGFTTPDKKHQNEPPFLWMGYELHPDKWTVQPIKL
PEKESWTVNDIQKLVGKLNWASQIYPGIKVKQLCRLLRGTKALTEVIPLTKEAELELAEN
REILREPVHGVYYDPTKDLIAEIQKQGHDQWTYQIYQEPHKNLKTGKYAKMRTAHTNDVK
QLAEAVQKIAMESIVIWGKIPKFKLPIQKETWETWWTDYWQATWIPDWEFVNTPPLVKLW

Fig. 10 cont'd-25

YQLEKEPIAGAETFYVDGAANRETKIGKAGYVTDRGRQKIVSLTETTNQKAELQAIQLAL
QDSGPEVNIVTDSQYALGIIQAQPDKSESEIVNQIIEKLIEKDKVYLSWVPAHKGIGGNE
QIDKLVSNGIRKVLFLDGIEKAQEEHEKYHSNWRAMASEFNLPPIVAKEIVASCDKCQLK
GEATHGQVDCSPGMWQLDCTHLEGKIILVAVHVASGYIEAEVIPTETGQETAYYILKLAG
RWPVKVIHTDNGSNFTSTAVKAACWWAGIQQEFGIPYNPQGQGVVESMNKELKKIIGQVR
EQAEHLKTAVQMAVLIHNFKRKGGIGGYSAGERIIDIIASDIQTKELQKQIIKVQNFRVY
YRDSRDPIWKGPAKLLWKGEGAVVLQDNSDIKVVPRRKVKIIKDYGKQMAGADCVASRQD
EN-
>POL-M.syn4.4
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGKKAIGTVLIGPTPVNIIGRNLLTQIGCTLNFPISPIE
TIPVKLKPGMDGPKVKQWPLTEEKIKALVEICTEMEKEGKISRIGPENPYNTPVFAIKKK
DGTKWRKLVDFRELNKRTQDFWEIQLGIPHPAGLKKKKSVSVLDVGDAYFSVPLDKDFRK
YTAFTIPSINNETPGIRYCYNVLPQGWKGSPAIFQSSMTKILEPFRKQNPDIVIYQYMDD
LYIGSDLEIGQHRTKIEELRQHLLRWGLTTPDKKHQNEPPFLWMGYELHPDKWTVQPIVL
PEKDSWTVNDLQKLVGKLNWASQIYAGIKVKQLCKLLRGAKALTEVVPLTEEAELELEEN
REILKEPVHGVYYDPSKDLIAEIQKQGQGQWTYQIYQEPYKNLKTGKYARMRGAHTNDVK
QLTEAVQKIAQECIVIWGKTPKFKLPIQKETWETWWMDYWQATWIPEWEFINTPPLVKLW
YQLEKEPIVGAETFYVDGASNRETKKGKAGYVTDKGRQKVVTLTETTNQKTELQAIHLAL
QDSGLEVNIVTDSQYAIGIIQAQPDKSESELVSQIIEQLIKKEKVYLAWVPAHKGIGGNE
QVDKLVSNGIRKILFLDGIDKAQEEHEKYHNNWRAMASDFNIPPVVAKEIVACCDKCQLK
GEALHGQVDCSPRIWQLDCTHLEGKVILVAVHVASGYLEAEVIPAETGQETAYFLLKLAG
RWPVKTIHTDNGSNFTSTTVKAACWWAGIKQEFGIPYNPQSQGVIESMNKELKKIIEQVR
DQAEHLKTAVQMAVFVHNFKRKGGIGDYSAGERIIDIISTDIQTRELQKQIIKIQNFRVY
YRDSRDPVWKGPAKLLWKGEGAVVIQDNNEIKVVPRRKAKIIRDYGKQMAGDDCVASRQD
ED- >POL-M.syn6.1
FFREDLAFPQGEARKFPSEQTRANSPTRG--------------ELQVWGRDNNSLSEAGD
DR----QGTVS-FNLPQITLWQRPLVTVRIGGQLIEALLDTGADDTVLEDMNLPGKWKPK
MIGGIGGFIKVRQYEQIPIEICGHKAIGTVLIGPTPVNIIGRNLLTQIGCTLNFPISPID
TVPVTLKPGMDGPKIKQWPLTEEKIKALTEICTEMEKEGKISRIGPENPYNTPVFAIKKK
NSTRWRKLVDFRELNKRTQDFCEVQLGIPHPAGLKKKRSVTVLDVGDAYFSVPLDENFRK
YTAFTIPSINNETPGVRYQYNVLPQGWKGSPAIFQASMTKILEPFRTKNPELVIYQYMDD
LYVGSDLEIEQHRTKIEELRAHLLSWGFTTPDKKHQKEPPFLWMGYELHPDKWTVQPIEL
PEKDSWTVNDIQKIVGKLNWASQIYPGIKVRQLCRLLRGTKALTDIVPLTAEAELELAEN
REILREPVHGVYYDPSKELIAEIQKQGHDQWTYQIYQDPFKNLKTGKYARKRSAHTNDVR
QLTEAVQKITTESIVIWGKTPKFRLPIQRETWEAWWMEYWQATWIPEWEFINTPPLVKLW
YQLEKDPIVGAETFYVDGAASRETKLGKAGYVTNKGRQKVVSLNETTNQKTELHAIHLAL
QDSGSEANIVTDSQYALGIIQAQPDRSESEVVNQIIEELIKKEKVYLSWVPAHKGIGGNE
QVDKLVSSGIRKVLFLDGIDKAQEDHERYHSNWRTMASDFNLPPIVAREIVASCDKCQQK
GEAMHGQVDCGPGIWQLDCTHLERKVILVAVHVASGYIEAEVIPAETGQETAYFVLKLAG
RWPVKVIHTDNGSNFTSAAVKAACWWANVTQEFGIPYNPQSQGVVESMNNELKKIIGQVR
EQAEHLKTAVLMAVFIHNFKRKRGIGGYSAGERIVDIIASDIQTKELQNQITKIQNFRVY
FRDSRDPIWKGPAKLLWKGEGAVVIQDNNDIKVVPRRKVKIIRDYGKQMAGDDCVAGRQD
EN-
>POL-M.syn6.2
FFREDLAFQQGEARKFSSEQTRANSPTSR--------------ELRVWG-GDNTLSETGA
ER----QGT---LNFPQITLWQRPLVTIKVGGQIKEALLDTGADDTVLEDINLPGKWKPR
MIGGIGGFIKVRQYDQIPIEICGKKAIGSVLVGPTPVNIIGRNMLTQLGCTLNFPISPIK
TVPVKLKPGMDGPKVKQWPLSEEKIKALTAICDEMEKEGKITKIGPDNPYNTPVFAIKKK
DGTKWRKLVDFKELNKRTQDFWEIQLGIPHPAGLKKKKSVSVLDVGDAYFSVPLDESFRK
YTAFTIPSLNNETPGIRYCYNVLPQGWKGSPAIFQSSMTKILEPFRAQNPEIVIYQYIDD
LYVRSDLEIGQHRAKIEELREHLLKWGLTTPDKKHQKEPPFLWMGYELHPDRWTVQPIQL

Fig. 10 cont'd-26

PDKDSWTVNDLQKLVGKLNWASQIYPGIRVKQLCKLLKGAKALTDIVTLTEEAELELAEN
REILKNPVHGVYYDPAKDLIAEIQKQGNDQWTYQIYQEPHKNLKTGKYAKMRTAHTNDVK
QLTEVVQKIAMESIVIWGKVPKFRLPIQKETWETWWTDYWQATWIPDWEFVNTPPLVKLW
YQLEKEPIAGAETFYVDGAANRETKMGKAGYVTDRGRQKVVSLTETTNQKTELQAIQLAL
QDSGPEVNIVTDSQYAIGIIQAQPDKSESEIVNQIIEQLIKKERVYLSWVPAHKGIGENE
QVDKLVSTGIRRVLFLDGIDKAQEEHERYHSNWRAMASEFNLPPIVAKEIVASCDQCQLK
GEAMHGQVDCSPGVWQLDCTHLEGKIILVAVHVASGYMEAEVIPAETGQETAYFILKLAA
RWPVKVIHTDNGPNFTSATVKAACWWANITQEFGIPYNPQGQGVVESMNKELKKIIKQVR
DQAEHLKTAVQMAVLIHNFKRKGGIGGYSAGERIIDIIASDIQTKELQKQIIKIQNFQVY
YRDSRDPIWKGPAKLLWKGEGAVVLQDNSDIKVVPRRKVKIIKDYGKQMAGADCVAGGQD
ED-
>POL-M.syn6.3
FFRENLAFPQGKAREFPSEQTRAISPTSR--------------ELQVWGGDNNSLSEAGA
ER----QGTVS-FSFPQITLWQRPIVTIKIGGQLREALLDTGADDTVLEEMNLPGRWKPK
MIGGIGGFIKVKQYDNILIEICGHKAVGTVLVGPTPANIIGRNLLTQLGCTLNFPISPIE
TVPVKLKPGIDGPKVKQWPLTEEKIKALVEICTEMEKEGKISKIGPENPYNTPIFAIKKK
DSTRWRKLVDFRELNRRTQDFWEVQLGIPHPAGLKRKKSVTVLDVGDAYFSVPLDKEFRK
YTAFTIPSINNETPGIRYQYNVLPQGWKGSPSIFQSSMTKILEPFRIKNPEMVIYQYMDD
LYIGSDLEIGQHRIKIEELREHLLKWGFTTPDKKHQKEPPFLWMGCELHPDKWTVQPIML
PEKDSWTVNDIQKLVGKLNWASQIYAGIKVRQLCKLLRGTKALTEVVPLTEEAELELAEN
REILKEPVHGAYYDPSKDLIAEVQKQGQDQWTYQIYQEPFKNLKTGKYAKKRSAHTNDVK
QLTEAVQKIALESIVIWGKAPKFRLPIQKETWEAWWTEYWQATWVPEWEFVNTPPLVKLW
YQLETEPIAGAETYYVDGAANRETKLGKAGYVTNRGRQKVVSLTDTTNQKTELQAIHLAL
QDSGLEVNIVTDSQYALGIIHAQPDKSESELVNQIIEQLINKERIYLSWVPAHKGIGENE
QVDKLVSKGIRKVLFLDGIEKAQEEHEKYHSNWKAMASEFNLPPVVAKEIVACCDKCQLK
GEALHGQVDCSPGMWQLDCTHLEGKIIIVAVHVASGYIEAEVIPTETGQETAYFLLKLAG
RWPVKTIHTDNGSNFTSTTVKAACWWAGIKQEFGIPYNPQSQGVVESINKELKKIIGQIR
DQAEHLKTAVLMAVFIHNFKRKGGIGGYTAGERIVDIIATDIQTKELQKQITKVQNFRVY
YRDSREPLWKGPAKLLWKGEGAVVIQDNNEIKVVPRRKAKILRDYGKQMAGADCVASRQD
EN-
>POL-M.syn6.4
FFRENLAFQQGEAREFSSEQTRTNSPTSR--------------ELWDGGRDNLP-SEAGA
ER----RGTVPSLSFPQITLWQRPLVTVKIGGQLKEALLDTGADDTVLEEINLPGKWKPK
LIGGIGGFIKVRQYDQILIEICGKKAIGTVLVGPTPINIIGRNMLTQIGCTLNFPISPIE
TIPVKLKPGMDGPRVKQWPLTEEKIKALIEICTEMEKEGKISRVGPENPYNTPIFAIKKK
NSNRWRKLVDFRELNKRTQDFWEVQLGIPHPGGLKKKKSVTILDVGDAYFSVPLDEDFRK
YTAFTIPSINNATPGIRYQYNVLPQGWKGSPAIFQCSMTKILEPFRKQNPEIIIYQYMDD
LYVRSDLEIGQHRTKIEELRQHLLKWGFYTPDKKHQKEPPFLWMGYELHPDKWTVQPIKL
PEKESWTVNDIQKLVEKLNWASQIYPGIKVKQLCRLLRGAKALTEVIPLTEEAELELEEN
REILKDPVHGVYYDPTKDLIAEIQKQGDDQWTYQIYQEPYKNLKTGKYAKRRTAHTNDVR
QLTEVVQKVATESIVIWGKIPKFKLPIQKETWEIWWTDYWQATWIPEWEFVNTPHLVKLW
YQLEKEPIIGAETFYVDGASNRETKKGKAGYVTDRGRQKIVSLTETTNQKAELQAIQLAL
QDSGSEVNIVTDSQYALGIIQAHPDKSESELVSQIIEQLIKKEKVYLAWVPAHKGIGGNE
QIDKLVSNGIRKILFLDGIDKAQEEHEKYHNNWRAMASDFNLPPVVAKEIVASCNKCQLK
GEAIHGQVDCSPRIWQLDCTHLEGKVIMVAVHVASGYVEAEVIPAETGQDTAYFILKLAG
RWPVKVVHTDNGSNFTSAAFKAACWWANVQQEFGIPYNPQSQGVVEAMNKELKKIIEQVR
DQAEHLKTAVQMAVFVHNFKRKGGIGDYSAGERIIDIIATDIQTRELQKQIIKIQNFRVY
YRDNRDPIWKGPAKLLWKGEGAVVIQDNSDIKVIPRRKAKIIRDYGKQMAGDDCMAGRQD
EDQ
>POL-M.syn6.5
FFREDLAFLQGKAREFSSEQTRANSPTRR--------------ELQVWGRDSNSLSEAGA
DR----QGTVS-FNFPQITLWQRPLVTIKIGGQLKEALLDTGADDTVLEDIDLPGKWKPK
IIGGIGGFIKVKQYDQILIEICGKRAIGTVLVGPTPVNIIGRNILTQIGCTLNFPISPID
TVPVKLKPGMDGPRIKQWPLTEEKIKALTEICKEMEEEGKISKIGPENPYNTPVFAIKKK

Fig. 10 cont'd-27

DSTKWRKVVDFRELNKGTQDFWEVQLGIPHPAGLKQKKSVTVLDVEDAYFSVPLDKDFRK
YTAFTIPSVNNETPGIRYQYNVLPQGWKGSPAIFQSSMTRILEPFRKQNPDIVIYQYMDD
LYVGSDLEIGQHRTKVEELRQHLLRWGFTTPDKKHQKDPPFLWMGYELHPDKWTVQPIVL
PEKDSWTINDIQKLVGKLNWASQIYSGIKVRQLCKCLRGTKALTEVIPLTKEAELELAEN
KEILKEPVHGVYYDPSKDLVAEIQKQGQGQWTYQIYQEQYKNLKTGKYARMRGAHTNDVK
QLAEAVQKIATESIVIWGKIPKFRLPIQRETWETWWTEYWQATWIPEWEYVNTPPLVKLW
YQLEKEPIVGAETFYVDGAANRDTKLGKAGYVTDRGRQKVVPLTDTTNQKTELQAINLAL
QDSGSKVNIVTDSQYVLGIIQAQPDRSESEIVNQIIEKLIEKDKVYLSWVPAHKGIGGNE
QVDKLVSAGIRKVLFLDGIDKAQDEHEKYHSNWRAMASDFNLPPVIAKEIVASCDKCQLK
GEATHGQVDCSPGIWQLDCTHLEGKVIIVAVHVASGYIEAEVISAETGQETAYYILKLAG
RWPVKIIHTDNGSNFTSTAVKAACWWAGIQQEFGIPYSPQSQGVVESMNKQLKQIIGQVR
DQAEQLKTAVQMAVFIHNFKRKGGIGEYSAGERIIDIISTDIQTRELQKQITKIQNFRVY
YRDSRDPVWKGPAKLLWKGEGAVVIQDNSEIKVVPRRKAKIIRHYGKQMAGDDCVASRQD
EDQ
>POL-M.syn6.6
FFRENLAFPQGEAREFPSEQARANSPTSRANSPTSR-------ELQV--RGDNPRSEAGA
ERQGTLQGT---LNCPQITLWQRPLVSIKVGGQVKEALLDTGADDTVLEEMSLPGKWKPK
MVGGIGGFIKVRQYDQILVEICGHKAIGTVLVGPTPVNIIRRNMLTQLRCTLNFPISPIE
TVPVTLKPGMDGPKVRQWPLTEEKIKALTAICEEMEKEGKITKIGPENPYNTPVFAIRKK
DSTKWRKLVDFRELNKKTQDFWEVQLGIPHPSGLKKKKSVTVLDVGDAYFSVPLDEGFRK
YTAFTIPSTNNETPGIRYQYNVLPQGWKGSPAIFQSSMIKILEPFRAKNPEIVIYQYMDD
LYVGSDLEIGQHRAKVEELREHLLRWGFTTPDKKHQNEPPFLWMGYELHPDKWTVQPIQL
PEKDSWTVNDIQRLVGKLNWASQIYAGIKVKQLCKLLRGAKALTDIVPLTEEAELELAEN
REILKTPVHGVYYDPSKDLIAEIQKQGQDQWSYQIYQEPFKNLKTGKYARTRGAHTNDVR
QLTEAVQKIAQECIVIWGKTPKFKLPIQKDTWETWWMDYWQATWIPKWEFVNTPPLVKLW
YQLEKDPIAGVETFYVDGAANRETKIGKAGYVTDKGRQKVVTLTETTNQKTELHAIYLAL
QDSGSEVNVVTDSQYALGIIQAQPDRSESELVNQIIEKLIGKDKVYLSWVPAHKGIGENE
QVDKLVSNGIRKVLFLDGIDKAQEDHEKYHSNWRAMANEFNLPPIVAKEIVANCDKCQLK
GEAMHGQVDCSPGIWQIDCTHLEGKVILVAVHVASGYLEAEVIPAETGQEAAYFILKLAG
RWPVKTVHTDNGSNFTSNAVKAACWWANVRQEFGIPYNPQSQGVIESMNKELKKIIGQVR
DQAEHLRTAVQMAVFIHNFKRRGGIGGYSAGERMIDIIATDIQTTELQKQITKIQKFRVY
YRDSRDPLWKGPAKLLWKGEGAVVIQENSDIKVVPRRKAKIIKDYGKQVAGADCVAGRQD
EDQ

Fig. 11

This plot is alignment independent, based on splintering all M group proteins, (database and CHAVI, one sequence per person) into all possible 9-mers, attending to their frequencies, and then looking for matches and near matches in each vaccine antigen or cocktail with the database

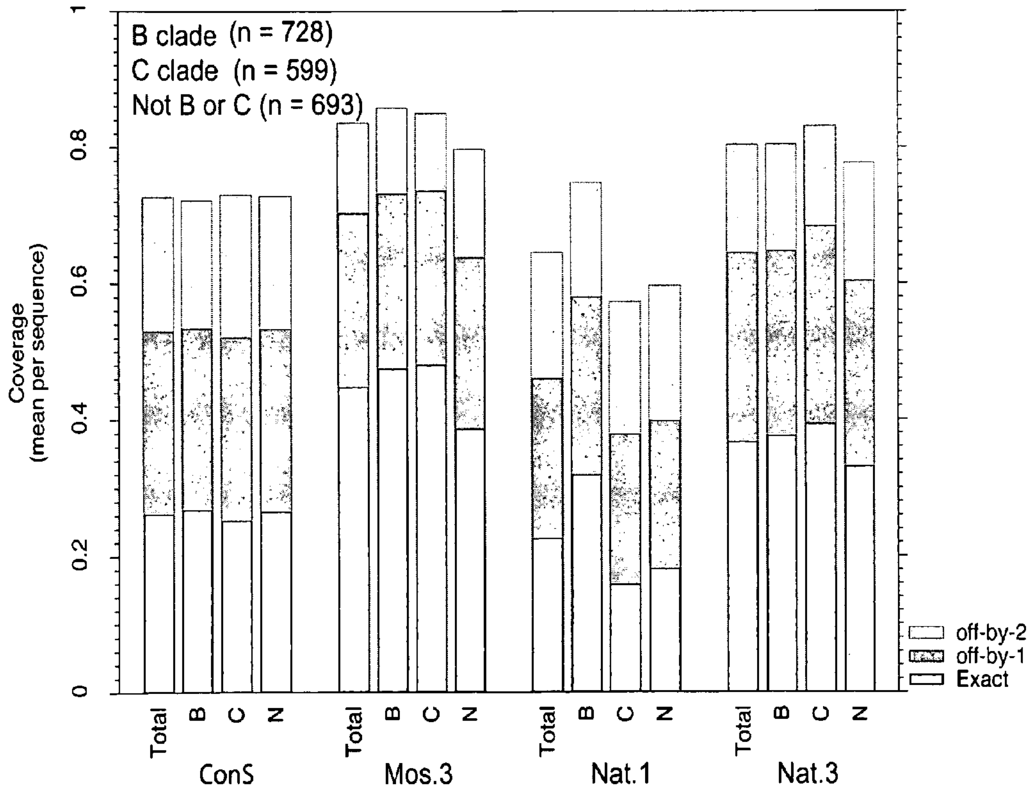

| Vaccine | subset | Off-by0 | Off-by1 | Off-by2 | (<3,>1) | unique | absent | rare < 3 |
|---|---|---|---|---|---|---|---|---|
| ConSgp160 | Total | 0.2628 | 0.5301 | 0.7267 | 9 | 12 | 45 | 66 |
| ConSgp160 | B | 0.2682 | 0.5344 | 0.7223 | 2 | 8 | 45 | |
| ConSgp160 | C | 0.2526 | 0.5214 | 0.7302 | 1 | 0 | 45 | |
| ConSgp160 | N | 0.2662 | 0.5332 | 0.7283 | 7 | 4 | 45 | |
| Mos.3 | Total | 0.4485 | 0.7032 | 0.8358 | 15 | 164 | 8 | 179 |
| Mos.3 | B | 0.4749 | 0.7319 | 0.8576 | 3 | 40 | 8 | |
| Mos.3 | C | 0.4809 | 0.7363 | 0.8498 | 8 | 65 | 8 | |
| Mos.3 | N | 0.3868 | 0.6383 | 0.7970 | 11 | 59 | 8 | |
| Nat.1.acute | Total | 0.2258 | 0.4598 | 0.6458 | 125 | 0 | 0 | 125 |
| Nat.1.acute | B | 0.3190 | 0.5803 | 0.7482 | 125 | 0 | 0 | |
| Nat.1.acute | C | 0.1589 | 0.3781 | 0.5726 | 0 | 0 | 0 | |
| Nat.1.acute | N | 0.1815 | 0.3979 | 0.5968 | 0 | 0 | 0 | |
| Nat.3.acute | Total | 0.3673 | 0.6449 | 0.8036 | 164 | 252 | 0 | 416 |
| Nat.3.acute | B | 0.3765 | 0.6483 | 0.8045 | 130 | 0 | 0 | |
| Nat.3.acute | C | 0.3940 | 0.6840 | 0.8307 | 19 | 102 | 0 | |
| Nat.3.acute | N | 0.3311 | 0.6036 | 0.7766 | 21 | 150 | 0 | |

Fig. 15A
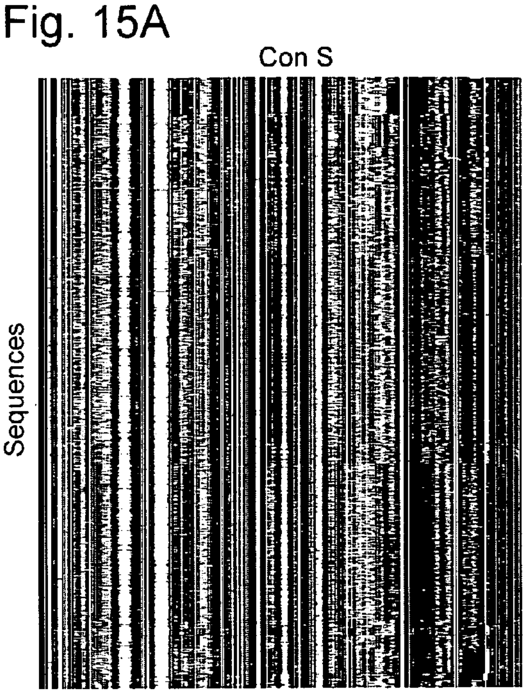
Fig. 15C
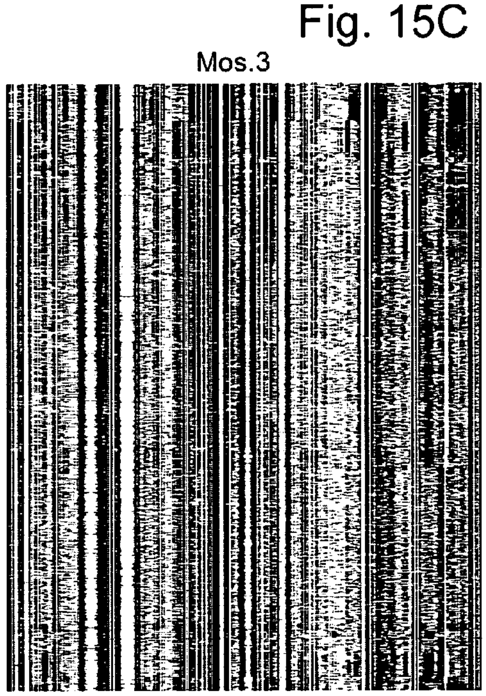
Fig. 15B
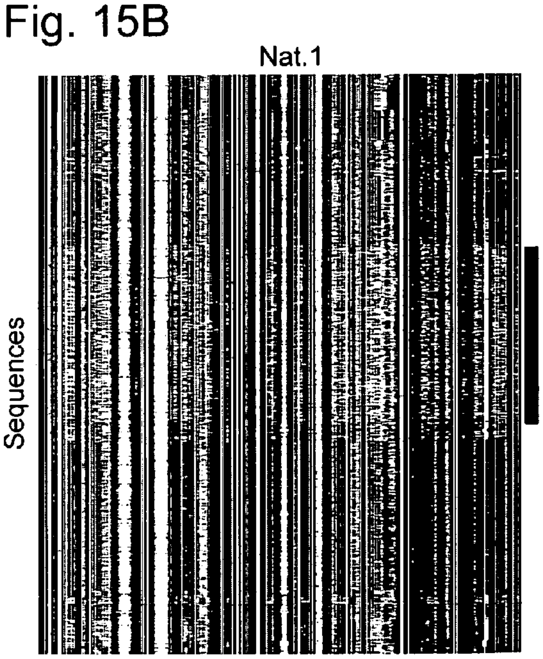
Fig. 15D
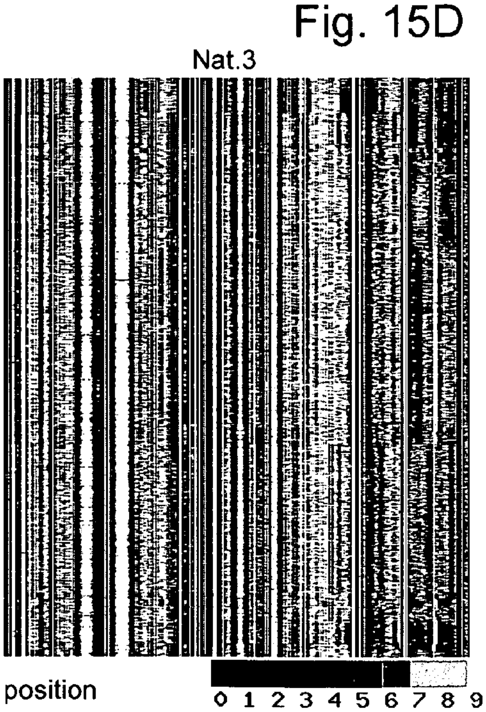
Sequences
Env alignment position
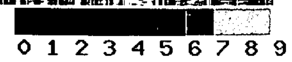
■ B clade
Con S
Mos.3
Nat.1
Nat.3
Env alignment position    0 1 2 3 4 5 6 7 8 9
■ B clade

Fig. 17

Coverage of the HIV database plus CHAVI sequences (N = 2020)

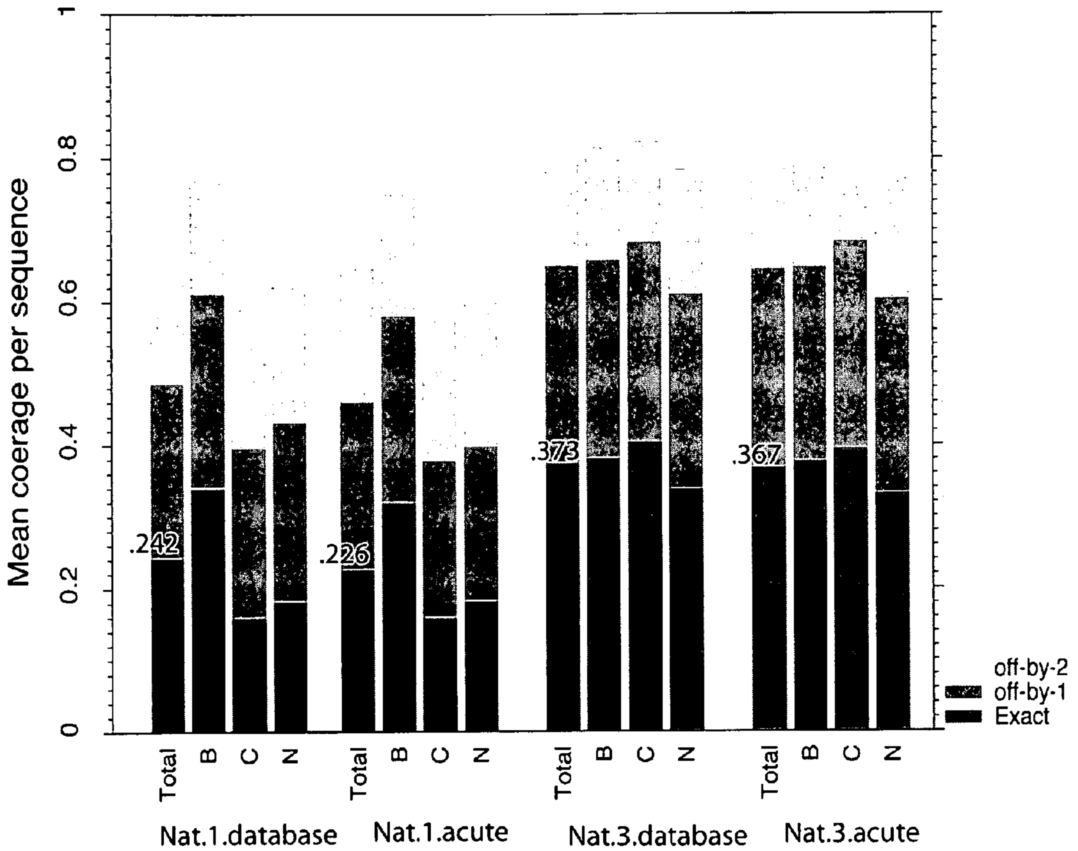

Nat.3.database

Option 1:
B YU2* -- 1986, USA
C DU467, South Africa,
A ML170 -- 1986 Kenya

Optimal for the set after requiring inclusion of one each of subtype A, B and C.

Nat.3.acute

Option 2:
B 1059*
C 0393
A R66201FPB

Optimal for the set after requiring inclusion of one each of subtype A, B and C as well as restricting antigen selection to SGA sequences sampled during acute infection.

Fig. 21

>nefM_4.1Dmyr
MAAKWSKSSIVGWPAVRERMRRAEPAADGVGAVSRDLEKHGAITSSNTAATNADCAWLEAQEE
DSEVGFPVRPHVPLRPMTYKAAVDLSHFLKEQGGLEGLIYSQKRQDILDLWVYHTQGYFPDWQN
YTPGPGIRYPLTFGWCFKLVPVDPREVEEANKGENNCLLHPMSQHGMDDPEKEVLMWKFDSRLA
FHHMAREKHPEFYKDC >nefM_4.2Dmyr
MAAKWSKRSIVGWPAIRERMRRTEPAAEGVGAASQDLDKYGALTSSNTAQTNPDCAWLEAQEE
EEVGFPVRPQVPVRPMTYKGALDLSHFLKEKGGLDGLIYSRKRQEILDLWVYNTQGYFPDWQNY
TPGPGVRYPLTFGWCYKLVPVDPEEVEKANEGENNSLLHPMSLHGMEDPEREVLKWKFDSRLAL
KHRARELHPEFYKDC >nefM_4.3Dmyr
MAANWSKSSIVGWPEIRERIRRTDPAAEGVGAASRDLERHGAITSSNTATTNAACAWLEAQEDEE
VGFPVRPQVPLRPMTFKGAFDLGFFLKEKGGLEGLIYSKKRQDILDLWVYNTQGFFPDWQNYTPG
PGTRFPLTFGWCFELVPVDPKEVEEANEGENNCLLHPICQHGMDDEEREVLMWKFDSSLARRHLA
REKHPEYYKDC >nefM_4.4Dmyr
MASKWSKSSIVGWPQVRERIRQTPPAAEGVGAVSQDLDKHGAVTSSNTAANNADCAWLQAQEE
EEEVGFPVKPQVPLRPMTYKGAFDLSFFLKEKGGLDGLIYSKKRQEILDLWVYHTQGFFPDWHNY
TPGPGTRYPLCFGWCFKLVPMDPAEVEEATEGENNSLLHPICQHGMEDEDREVLVWRFDSSLARR
HIARELHPEYYKDC >Gag-M4.1Dmyr
MAARASVLSGGELDRWEKIRLRPGGKKKYKLKHIVWASRELERFAVNPGLLETSEGCRQILGQLQ
PSLQTGSEELRSLYNTVAVLYCVHQRIDVKDTKEALEKIEEEQNKSQQKTQQAKAADGKVSQNYP
IVQNAQGQMVHQAISPRTLNAWVKVIEEKGFSPEVIPMFSALAEGATPQDLNTMLNTIGGHQAAM
QMLKDTINDEAAEWDRLHPVQAGPVAPGQIREPRGSDIAGTTSNLQEQIGWMTSNPPIPVGDIYKR
WIIMGLNKIVRMYSPTSILDIRQGPKESFRDYVDRFFRTLRAEQASQEVKNWMTETLLVQNSNPDC
KTILKALGPAATLEEMMTACQGVGGPGHKARVLAEAMSQVQQPNIMMQRGNFKGQKRIKCFNC
GREGHLARNCRAPRKKGCWKCGREGHQMKDCTESKANFLGKIWPSNKGRPGNFLQSRPEPSAPP
AESFGFGEEITPSQKQEQKDKELYPLASLKSLFGNDPLSQ >Gag_M4.2 Dmyr
MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQNY
PIVQNIQGQMVHQPISPRTLNAWVKVVEEKAFSPEVIPMFTALSDGATPQDLNSMLNAVGGHQAA
MQILKDTINEEAADWDRLHPVHAGPVAPGQMREPRGSDIAGTTSTLQEQIGWMTNNPPIPVGEIYK
RWIILGLNKIVRMYSPVSILDIKQGPKESFRDYVDRFFKVLRAEQATQDVKNWMTDTLLIQNANPD
CKSILRALGPGATLEEMMTACQGVGGPSHKARILAEAMSQVTNSATIMMQRGNFRNQRKTVKCF
NCGKEGHLARNCKAPRKRGCWKCGKEGHQMKECTERQANFLGKIWPSSKGRPGNFPQSRPEPTA
PPEESFRFGEETTTPSQKQEPIDKELYPLASLRSLFGNDPSSQAS

Fig. 21 cont'd-1

>Gag_M4.3 Dmyr
MAARASILRGGKLDKWEKIRLRPGGKKRYMLKHLIWASRELERFALNPGLLETAEGCQQIIEQLQS
TLKTGSEELKSLFNTVATLYCVHQRIEVKDTKEALDKVEEEQNKSKKKAQQAAADTGNSSQVSQ
NYPIVQNLQGQMVHQALSPRTLNAWVKVIEEKAFSPEIIPMFTALSEGATPSDLNTMLNTVGGHQ
AAMQMLKDTINEEAAEWDRVHPVHAGPIPPGQMREPRGSDIAGTTSSLQEQIAWMTSNPPVPVGE
IYKRWIVLGLNKIVRMYSPVSILDIRQGPKEPFRDYVDRFFKTLRAEQASQDVKNWMTETLLVQN
ANPDCKTILRALGPGASLEEMMTACQGVGGPSHKARVLAEAMSQTNSAILMQRSNFKGSKRIVKC
FNCGKEGHIARNCRAPRKRGCWKCGQEGHQMKDCNERQANFLGKIWPSHKGRPGNFLQNRPEPT
APPEPTAPPAESFRFEETTPAPKQELKDREPLTSLKSLFGSDPLSQAS >Gag_M4.4 Dmyr
MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKVSQ
NYPIVQNLQGQMVHQPLSPRTLNAWVKVVEEKGFNPEVIPMFSALSEGATPQDLNMMLNIVGGH
QAAMQMLKETINEEAAEWDRLHPVHAGPIAPGQMREPRGSDIAGSTSTLQEQIAWMTGNPPVPV
GDIYKRWIILGLNKIVKMYSPTSILDIKQGPKEPFRDYVDRFYKTLRAEQATQEVKNWMTDTLLVQ
NANPDCKSILKALGTGATLEEMMSACQGVGGPAHKARVLAEAMSQANNTNIMMQRSNFKGPKRI
IKCFNCGKEGHIAKNCRAPRKKGCWKCGKEGHQMKDCTERQANFLGRIWPSSKGRPGNFLQSRP
EPTAPPAEPTAPPAESFKFEETTPAPKQEPKDREPLTSLRSLFGSDPLLQAS >M_mos_3_1 (M_mos_Env_3_1)
MRVKGIRKNYQHLWRWGTMLLGMLMICSAAEQLWVTVYYGVPVWRDAETTLFCASDAKAYER
EVHNVWATHACVPTDPNPQEIVLENVTEEFNMWKNNMVDQMHEDIISLWDESLKPCVKLTPLCV
TLNCTDVNVTKTNSTSWGMMEKGEIKNCSFNMTTELRDKKQKVYALFYKLDIVPLEENDTISNST
YRLINCNTSAITQACPKVTFEPIPIHYCTPAGFAILKCNDKKFNGTGPCKNVSTVQCTHGIRPVVTTQ
LLLNGSLAEEEIIIRSENLTNNAKTIIVQLNESVVINCTRPNNNTRKSIRIGPGQTFYATGDIIGNIRQA
HCNISREKWINTTRDVRKKLQEHFNKTIIFNSSSGGDLEITTHSFNCRGEFFYCNTSKLFNSVWGNS
SNVTKVNGTKVKETITLPCKIKQIINMWQEVGRAMYAPPIAGNITCKSNITGLLLVRDGGNVTNNT
EIFRPGGGNMKDNWRSELYKYKVVEIKPLGIAPTKAKRRVVEREKRAVGLGAVFLGFLGAAGST
MGAASMTLTVQARQLLSGIVQQQSNLLRAIEAQQHMLQLTVWGIKQLQARILAVERYLRDQQLL
GIWGCSGKLICTTNVPWNSSWSNKSLDEIWNNMTWMQWEKEIDNYTSLIYTLIEESQNQQEKNEQ
DLLALDKWANLWNWFDISNWLWYIRIFIMIVGGLIGLRIVFAVLSIVNRVRKGYSPLSFQTLTPNPR
GPDRLGRIEEEGGEQDKDRSIRLVNGFLALAWDDLRNLCLFSYHRLRDLLLIVTRIVELLGRRGWE
ALKYLWNLLQYWIQELKNSAVSLLNATAIAVAEGTDRVIEVVQRACRAILHIPRRIRQGLERALL >M_mos_3_2 (M_mos_Env_3_2)
MRVKETQMNWPNLWKWGTLILGLVIICSASDNLWVTVYYGVPVWKEATTTLFCASDAKAYDTE
VHNVWATYACVPTDPNPQEVVLGNVTENFNMWKNNMVEQMHEDIISLWDQSLKPCVRLTPLCV
TLNCSNANTTNTNSTEEIKNCSFNITTSIRDKVQKEYALFYKLDVVPIDNDNTSYRLISCNTSVITQA
CPKVSFEPIPIHYCAPAGFAILKCKDKKFNGTGPCTNVSTVQCTHGIRPVVSTQLLLNGSLAEEEVVI
RSENFTNNAKTIIVHLNKSVEINCTRPNNNTRKSIHIGPGRAFYATGEIIGDIRQAHCNISRAKWNNT
LKQIVKKLKEQFNKTIIFNQSSGGDPEITTHSFNCGGEFFYCNTSGLFNSTWNSTATQESNNTELNG
NITLPCRIKQIVNMWQEVGKAMYAPPIRGQIRCSSNITGLILTRDGGNNNSTNETFRPGGGDMRDN
WRSELYKYKVVKIEPLGVAPTKAKRRVVQREKRAVGTIGAMFLGFLGAAGSTMGAASLTLTVQA
RLLLSGIVQQQNNLLRAIEAQQHLLQLTVWGIKQLQARVLAVERYLKDQQLLGIWGCSGKLICTT
TVPWNTSWSNKSLNEIWDNMTWMEWEREIDNYTGLIYTLLEESQNQQEKNEQELLELDKWASL
WNWFDITKWLWYIKIFIMIVGGLVGLRIVFTVLSIVNRVRQGYSPLSFQTHLPAPRGPDRPEGIEEE
GGERDRDRSGRLVDGFLAIIWVDLRSLCLFSYHQLRDFILIAARTVELLGHSSLKGLRRGWEALKY
WWNLLQYWSQELKNSAISLLNTTAIVVAEGTDRIIEVLQRAGRAILHIPTRIRQGLERLLL

Fig. 21 cont'd-2

>M_mos_3_3 (M_mos_Env_3_3)
MRVRGIQRNWPQWWIWGILGFWMLMICNVVGNLWVTVYYGVPVWKEAKTTLFCASDAKAYEK
EVHNVWATHACVPTDPSPQEVVLENVTENFNMWKNDMVDQMHEDVISLWDQSLKPCVKLTHL
CVTLNCTNATNTNYNNSTNVTSSMIGEMKNCSFNITTEIRDKSRKEYALFYRLDIVPLNEQNSSEY
RLINCNTSTITQACPKVSFDPIPIHYCAPAGYAILKCNNKTFNGTGPCNNVSTVQCTHGIKPVVSTQL
LLNGSLAEGEIIIRSENLTDNAKTIIVHLNESVEIVCTRPNNNTRKSVRIGPGQAFYATGDIIGDIRQA
HCNLSRTQWNNTLKQIVTKLREQFGNKTIVFNQSSGGDPEIVMHSFNCGGEFFYCNTTQLFNSTWE
NSNITQPLTLNRTKGPNDTITLPCRIKQIINMWQGVGRAMYAPPIEGLIKCSSNITGLLLTRDGGNNS
ETKTTETFRPGGGNMRDNWRNELYKYKVVQIEPLGVAPTRAKRRVVEREKRAVGIGAVFLGFLG
TAGSTMGAASITLTVQARQVLSGIVQQQSNLLKAIEAQQHLLKLTVWGIKQLQTRVLAIERYLKD
QQLLGLWGCSGKLICTTAVPWNSSWSNKSQTDIWDNMTWMQWDREISNYTDTIYRLLEDSQNQ
QEKNEKDLLALDSWKNLWNWFDITNWLWYIKIFIIIVGGLIGLRIIFAVLSIVNRCRQGYSPLSLQTL
IPNPRGPDRLGGIEEEGGEQDRDRSIRLVSGFLALAWDDLRSLCLFSYHRLRDFILIVARAVELLGRS
SLRGLQRGWEALKYLGSLVQYWGLELKKSAISLLDTIAIAVAEGTDRIIEVIQRICRAIRNIPRRIRQ
GFEAALL

Fig. 22

| HVI number | Gene name | Nef | Myristylation signal mutated |
|---|---|---|---|
| HV13236 | M.con_Nef01_Dmyr.WLV | Group M (2001) consensus | Yes |
| HV13319 | nefM_4.1Dmyr.wlv | Mosaic No. 1 | Yes |
| HV13231 | nefM_4.2Dmyr.wlv | Mosaic No. 2 | Yes |
| HV13230 | nefM_4.3Dmyr.wlv | Mosaic No. 3 | Yes |
| HV13232 | nefM_4.4Dmyr.wlv | Mosaic No. 4 | Yes |
| HV10001 | No inser | | |

All five constructs were cloned into HV10001 (WLV001AM DNA vaccine plasmid.

M.con_Nef01_Dmyr.WLV (657nt.)(hv13236), 67% GC
XhoI
CTCGAGAAGAAAATGGCGGCCAAGTGGTCGAAGAGCTCCATCGTCGGGTGGCCGGCGGTCCGGGAG
CGCATCCGGCGGACGCACCCCGCGGCCGAGGGGGTCGGCGCGGTCTCGCAAGACCTCGACAAGC
ACGGGGCGATCACGTCGAGCAACACCGCCGCGAACAACCCCGACTGCGCGTGGCTGGAGGCCCA
GGAGGAAGAGGAAGAGGTCGGCTTCCCGGTCCGCCCGCAAGTGCCGCTCAGGCCGATGACGTAC
AAGGCGGCCCTCGACCTCTCGCACTTCCTGAAAGAGAAGGGTGGCCTGGAGGGGCTCATCTACT
CGAAGAAGAGGCAGGAGATCCTCGACCTGTGGGTCTACCACACCCAGGGCTACTTCCCGGACTG
GCAGAACTACACGCCAGGCCCGGGAATCCGCTACCCGCTGACCTTCGGGTGGTGCTTCAAGCTC
GTCCCCGTCGACCCGGAGGAGGTCGAGGAAGCCAACGAGGGCGAGAACAACAGCCTCCTGCACC
CGATGTGCCAGCACGGGATGGAGGACGAGGAGCGCGAGGTGCTGATGTGGAAGTTCGACTCGCG
CCTGGCCCTGCGCCACATCGCCCGGGAGCTCCACCCGGAGTACTACAAGGACTGCTGATAAGCTA
GCGGATCCTGATCA
NheI BamHI BclI MAAKWSKSSIVGWPAVRERIRRTHPAAEGVGAVSQDLDKHGAITSSNTAANNPDCAWLEAQEEE
EEVGFPVRPQVPLRPMTYKAALDLSHFLKEKGGLEGLIYSKKRQEILDLWVYHTQGYFPDWQNY
TPGPGIRYPLTFGWCFKLVPVDPEEVEEANEGENNSLLHPMCQHGMEDEEREVLMWKFDSRLAL
RHIARELHPEYYKDC_

>HV13236 in hv10001, 3953nt.
AAATGGGGGCGCTGAGGTCTGCCTCGTGAAGAAGGTGTTGCTGACTCATACCAGGCCTGAATCGCCCCATCATCCAG
CCAGAAAGTGAGGGAGCCACGGTTGATGAGAGCTTTGTTGTAGGTGGACCAGTTGGTGATTTTGAACTTTTGCTTTG
CCACGGAACGGTCTGCGTTGTCGGGAAGATGCGTGATCTGATCCTTCAACTCAGCAAAAGTTCGATTTATTCAACAA
AGCCGCCGTCCCGTCAAGTCAGCGTAATGCTCTGCCAGTGTTACAACCAATTAACCAATTCTGCGTTCAAAATGGTA
TGCGTTTTGACACATCCACTATATATCCGTGTCGTTCTGTCCACTCCTGAATCCCATTCCAGAAATTCTCTAGCGAT
TCCAGAAGTTTCTCAGAGTCGGAAAGTTGACCAGACATTACGAACTGGCACAGATGGTCATAACCTGAAGGAAGATC
TGATTGCTTAACTGCTTCAGTTAAGACCGACGCGCTCGTCGTATAACAGATGCGATGATGCAGACCAATCAACATGG
CACCTGCCATTGCTACCTGTACAGTCAAGGATGGTAGAAATGTTGTCGGTCCTTGCACACGAATATTACGCCATTTG
CCTGCATATTCAAACAGCTCTTCTACGATAAGGGCACAAATCGCATCGTGGAACGTTTGGGCTTCTACCGATTTAGC
AGTTTGATACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTTCCACTCA
CCGGTTGTCCATTCATGGCTGAACTCTGCTTCCTCTGTTGACATGACACACATCATCTCAATATCCGAATACGGACC
ATCAGTCTGACGACCAAGAGAGCCATAAACACCAATAGCCTTAACATCATCCCCATATTTATCCAATATTCGTTCCT
TAATTTCATGAACAATCTTCATTCTTTCTTCTCTAGTCATTATTATTGGTCCGTTCATAACACCCCTTGTATTACTG
TTTATGTAAGCAGACAGTTTTATTGTTCATGATGATATATTTTTATCTTGTGCAATGTAACATCAGAGATTTTGAGA
CACAACGTGGCTTTCCCCGGCCCATGACCAAAATCCCTTAACGTGAGTTTTCGTTCCACTGAGCGTCAGACCCCGTA
GAAAAGATCAAAGGATCTTCTTGAGATCCTTTTTTTCTGCGCGTAATCTGCTGCTTGCAAACAAAAAAACCACCGCT

Fig. 22 cont'd-1

ACCAGCGGTGGTTTGTTTGCCGGATCAAGAGCTACCAACTCTTTTTCCGAAGGTAACTGGCTTCAGCAGAGCGCAGA
TACCAAATACTGTTCTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACA
CCGAACTGAGATACCTACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGGTATTTCACACCGCATAT
GGTGCACTCTCAGTACAATCTGCTCTGATGCCGCATAGTTAAGCCAGTATCTGCTCCCTGCTTGTGTGTTGGAGGTC
GCTGAGTAGTGCGCGAGCAAAATTTAAGCTACAACAAGGCAAGGCTTGACCGACAATTGCATGAAGAATCTGCTTAG
GGTTAGGCGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTATTGACTA
GTTATTAATAGTAATCAATTACGGGGTCATTAGTTCATAGCCCATATATGGAGTTCCGCGTTACATAACTTACGGTA
AATGGCCCGCCTGGCTGACCGCCCAACGACCCCCGCCCATTGACGTCAATAATGACGTATGTTCCCATAGTAACGCC
AATAGGGACTTTCCATTGACGTCAATGGGTGGAGTATTTACGGTAAACTGCCCACTTGGCAGTACATCAAGTGTATC
ATATGCCAAGTCCGCCCCCTATTGACGTCAATGACGGTAAATGGCCCGCCTGGCATTATGCCCAGTACATGACCTTA
CGGGACTTTCCTACTTGGCAGTACATCTACGTATTAGTCATCGCTATTACCATGGTGATGCGGTTTTGGCAGTACAT
CAATGGGCGTGGATAGCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATGGGCGGTAGGCGTGTA
CGGTGGGAGGTCTATATAAGCAGAGCTCGTTTAGTGAACCGTCAGATCGCCTGGAGACGCCATCCACGCTGTTTTGA
CCTCCATAGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGAGCTCCATCGTCGGGTGGCCGGCGGTCCGGGAGCGCATCCGGCGGAC
GCACCCCGCGGCCGAGGGGGTCGGCGCGGTCTCGCAAGACCTCGACAAGCACGGGGCGATCACGTCGAGCAACACCG
CCGCGAACAACCCCGACTGCGCGTGGCTGGAGGCCCAGGAGGAAGAGGAAGAGGTCGGCTTCCCGGTCCGCCCGCAA
GTGCCGCTCAGGCCGATGACGTACAAGGCGGCCCTCGACCTCTCGCACTTCCTGAAAGAGAAGGGTGGCCTGGAGGG
GCTCATCTACTCGAAGAAGAGGCAGGAGATCCTCGACCTGTGGGTCTACCACACCCAGGGCTACTTCCCGGACTGGC
AGAACTACACGCCAGGCCCGGGAATCCGCTACCCGCTGACCTTCGGGTGGTGCTTCAAGCTCGTCCCCGTCGACCCG
GAGGAGGTCGAGGAAGCCAACGAGGGCGAGAACAACAGCCTCCTGCACCCGATGTGCCAGCACGGGATGGAGGACGA
GGAGCGCGAGGTGCTGATGTGGAAGTTCGACTCGCGCCTGGCCCTGCGCCACATCGCCCGGGAGCTCCACCCGGAGT
ACTACAAGGACTGCTGATAAGCTAGCGGATCCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGGGGGAGGATTGGGAAG
ACAATAGCAGGCATGCTGGGGAATTT

Thursday, August 2, 2007

Sequence 0 Length : 3953

AatII GACGTC
4 Sites
2510 2563 2646
2832
AccI GTMKAC
3 Sites
3050 3433 3535
AflIII ACRYGT
1 Site
1897
AluI AGCT
13 Sites
109 633 1340
1597 1643 1733
1959
2184 2951 3112
3524 3683 3717
AlwNI CAGNNNCTG
2 Sites
1488 2129
AosII GRCGYC
5 Sites
2507 2560 2643
2829 2963

ApaI GGGCCC
1 Site
3075
ApaLI GTGCAC
2 Sites
1583 2081
AvaI CYCGRG
3 Sites
3078 3482 3676
BamHI GGATCC
1 Site
3723
BanI GGYRCC
3 Sites
538 2850 3807
BanII GRGCYC
5 Sites
2953 3075 3114
3391 3685
BclI TGATCA
1 Site
3729
BcnI CCSGG
12 Sites
1173 1521 3021
3139 3298 3457
3484

3485 3541 3678
3679 3691
BglI GCCNNNNNGGC
4 Sites
2475 2597 2668
3320
BglII AGATCT
1 Site
458
Bsp1286 GDGCHC
8 Sites
652 1587 2085
2953 3075 3114
3391
3685
BspHI TCATGA
2 Sites
1007 1105
BspNI CCWGG
13 Sites
52 1738 1751
1872 2475 2668
2977
3270 3381 3444
3478 3657 3801
BssHII GCGCGC
1 Site
3045

Mosaic and Group M nef_Dmyr-Patent.doc

Fig. 22 cont'd-2

BstNI CCWGG
13 Sites
52 1738 1751
1872 2475 2668
2977
3270 3381 3444
3478 3657 3801
Cfr10I RCCGGY
2 Sites
847 3128
CfrI YGGCCR
4 Sites
769 3094 3126
3166
ClaI ATCGAT
1 Site
2287
DdeI CTNAG
12 Sites
12 204 397
711 787 1214 1623
2088 2158 2229
3318 3861
DpnI GATC
13 Sites
190 195 460
1239 1247 1258
1333
2972 3028 3216
3417 3725 3731
DraIII CACNNNGTG
1 Site
1161
Eco47I GGWCC
7 Sites
122 586 919
1048 3021 3133
3298
EcoRII CCWGG
13 Sites
50 1736 1749
1870 2473 2666
2975
3268 3379 3442
3476 3655 3799
EcoRV GATATC
1 Site
2294
Fnu4HI GCNGC
20 Sites
234 769 1283
1489 1492 1557
1700
1855 1973 1976
1994 2110 2250
2279
2262 3094 3166
3235 3315 3340
FnuDII CGCG
17 Sites
494 1273 1854
2169 2257 2281
2445
3039 3045 3047
3062 3165 3183
3237
3255 3625 3653
HaeII RGCGCY
3 Sites
12 1657 2027
HaeIII GGCC
20 Sites
55 771 1175
1423 1857 1875
1886
2268 2469 2662
3073 3096 3128
3168
3267 3323 3342
3379 3481 3660
HgiAI GWGCWC
5 Sites
1587 2085 2953
3114 3685
HhaI GCGC
19 Sites
11 496 1273
1382 1556 1656
1723
1993 2026 2169
2249 3045 3047
3145
3183 3255 3625
3655 3667
HincII GTYRAC
5 Sites
413 886 2369
3051 3536
HinfI GANTC
15 Sites
43 59 357
383 401 725 779
807 1527 1923
1998 2222 2795
3487
3648
HinPI GCGC
19 Sites
9 494 1271
1380 1554 1654
1721
1991 2024 2167
2247 3043 3045
3143
3181 3253 3623
3653 3665
HpaII CCGG
16 Sites
848 1172 1329
1519 1545 1692
3019
3129 3137 3149
3297 3456 3483
3540
3677 3690
MaeI CTAG
7 Sites
378 801 1034
1404 2385 3718
3751
MaeII ACGT
12 Sites
669 1160 1196
2306 2507 2519
2560
2643 2724 2829
3219 3330
MaeIII GTNAC
8 Sites
270 1134 1361
1477 1540 2446
2533
2882
MvaI CCNGG
25 Sites
52 1172 1520
1738 1751 1872
2475
2668 2977 3020
3138 3270 3297
3381
3444 3456 3478
3483 3484 3540
3657
3677 3678 3690
3801
NaeI GCCGGC
1 Site
3130
NciI CCSGG
12 Sites
1172 1520 3020
3138 3297 3456
3483
3484 3540 3677
3678 3690
NcoI CCATGG
1 Site
2745
NdeI CATATG
2 Sites
2076 2619
NheI GCTAGC
1 Site
3717
NlaIII CATG
14 Sites
538 762 864
892 1011 1105 1181
1901 2219 2349
2367 2689 2749
3942
NlaIV GGNNCC
9 Sites
92 540 1630
1869 2852 3023
3073
3725 3809
NruI TCGCGA
1 Site
2257
NsiI ATGCAT
1 Site
796
Nsp7524I RCATGY
2 Sites
1901 3942
NspBII CMGCKG
6 Sites
1314 1559 2281
3039 3165 3500
RsaI GTAC
11 Sites
559 2093 2263
2330 2604 2684
2717
2768 2925 3333
3696
RsrII CGGWCCG
2 Sites
3134 3299
SacI GAGCTC
3 Sites
2953 3114 3685
SacII CCGCGG
3 Sites

Fig. 22 cont'd-3

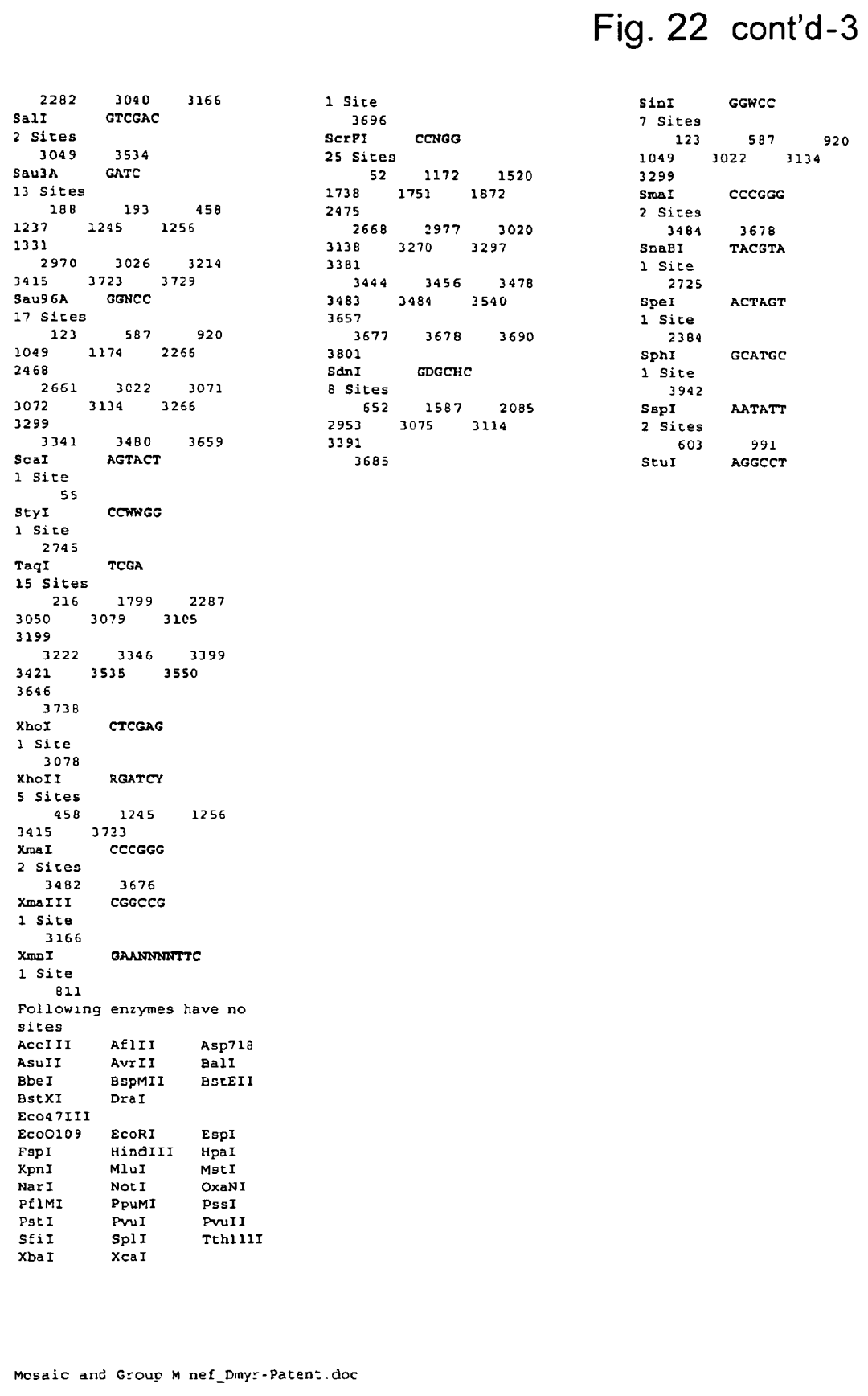

2282 3040 3166
SalI GTCGAC
2 Sites
3049 3534
Sau3A GATC
13 Sites
188 193 458
1237 1245 1256
1331
2970 3026 3214
3415 3723 3729
Sau96A GGNCC
17 Sites
123 587 920
1049 1174 2266
2468
2661 3022 3071
3072 3134 3266
3299
3341 3480 3659
ScaI AGTACT
1 Site
55
StyI CCWWGG
1 Site
2745
TaqI TCGA
15 Sites
216 1799 2287
3050 3079 3105
3199
3222 3346 3399
3421 3535 3550
3646
3738
XhoI CTCGAG
1 Site
3078
XhoII RGATCY
5 Sites
458 1245 1256
3415 3723
XmaI CCCGGG
2 Sites
3482 3676
XmaIII CGGCCG
1 Site
3166
XmnI GAANNNNTTC
1 Site
811
Following enzymes have no sites

| | | |
|---|---|---|
| AccIII | AflII | Asp718 |
| AsuII | AvrII | BalI |
| BbeI | BspMII | BstEII |
| BstXI | DraI | |
| Eco47III | | |
| EcoO109 | EcoRI | EspI |
| FspI | HindIII | HpaI |
| KpnI | MluI | MstI |
| NarI | NotI | OxaNI |
| PflMI | PpuMI | PssI |
| PstI | PvuI | PvuII |
| SfiI | SplI | Tth111I |
| XbaI | XcaI | |

1 Site
3696
ScrFI CCNGG
25 Sites
52 1172 1520
1738 1751 1872
2475
2668 2977 3020
3138 3270 3297
3381
3444 3456 3478
3483 3484 3540
3657
3677 3678 3690
3801
SdnI GDGCHC
8 Sites
652 1587 2085
2953 3075 3114
3391
3685

SinI GGWCC
7 Sites
123 587 920
1049 3022 3134
3299
SmaI CCCGGG
2 Sites
3484 3678
SnaBI TACGTA
1 Site
2725
SpeI ACTAGT
1 Site
2384
SphI GCATGC
1 Site
3942
SspI AATATT
2 Sites
603 991
StuI AGGCCT

Fig. 22 cont'd-4 nefM_4.1Dmyr (hv13225 in), (663nt.), GC=67%

CTCGAGAAGAAAATGGCGGCCAAGTGGTCGAAGAGCTCCATCGTCGGGTGGCCGGCGGTCCGGGAGAGGA
TGCGGAGGGCGGAGCCGGCGGCCGACGGGGTCGGGGCGGTCTCGCGGGACCTGGAGAAGCACGGGGCGAT
CACGTCGAGCAACACCGCCGCGACGAACGCGGACTGCGCGTGGCTGGAGGCCCAGGAGGAGGACTCGGAG
GTCGGCTTCCCGGTCCGGCCGCACGTCCCGCTCCGGCCGATGACGTACAAGGCGGCCGTCGACCTCTCCC
ACTTCCTGAAAGAGCAGGGGGGCCTGGAGGGGCTCATCTACTCGCAGAAGAGGCAGGACATCCTCGACCT
GTGGGTCTACCACACCCAGGGCTACTTCCCGGACTGGCAGAACTACACGCCAGGCCCGGGAATCCGCTAC
CCGCTGACCTTCGGGTGGTGCTTCAAGCTCGTCCCCGTGGACCCGCGGGAGGTCGAGGAAGCCAACAAGG
GGGAGAACAACTGCCTCCTGCACCCGATGTCGCAGCACGGGATGGACGACCCGGAGAAGGAGGTGCTGAT
GTGGAAGTTCGACTCGCGGCTGGCGTTCCACCACATGGCCCGCGAGAAGCACCCGGAGTTCTACAAGGAC
TGCTGATAAGCTAGCTGATCAGGATCCACGCGT

MAAKWSKSSIVGWPAVRERMRRAEPAADGVGAVSRDLEKHGAITSSNTAATNADCAWLEAQEEDSEVGFP
VRPHVPLRPMTYKAAVDLSHFLKEQGGLEGLIYSQKRQDILDLWVYHTQGYFPDWQNYTPGPGIRYPLTF
GWCFKLVPVDPREVEEANKGENNCLLHPMSQHGMDDPEKEVLMWKFDSRLAFHHMAREKHPEFYKDC_

HV13319 (nefM_4.1Dmyr.wlv), 3918nt.

AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA

Fig. 22 cont'd-5

TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGAGAAGAAAATGGCGGCCAAGTGGTCGAA
GAGCTCCATCGTCGGGTGGCCGGCGGTCCGGGAGAGGATGCGGAGGGCGGAGCCGGCGGCCGACGGGGTC
GGGGCGGTCTCGCGGGACCTGGAGAAGCACGGGGCGATCACGTCGAGCAACACCGCCGCGACGAACGCGG
ACTGCGCGTGGCTGGAGGCCCAGGAGGAGGACTCGGAGGTCGGCTTCCCGGTCCGGCCGCACGTCCCGCT
CCGGCCGATGACGTACAAGGCGGCCGTCGACCTCTCCCACTTCCTGAAAGAGCAGGGGGGCCTGGAGGGG
CTCATCTACTCGCAGAAGAGGCAGGACATCCTCGACCTGTGGGTCTACCACACCCAGGGCTACTTCCCGG
ACTGGCAGAACTACACGCCAGGCCCGGGAATCCGCTACCCGCTGACCTTCGGGTGGTGCTTCAAGCTCGT
CCCCGTGGACCCGCGGGAGGTCGAGGAAGCCAACAAGGGGGAGAACAACTGCCTCCTGCACCCGATGTCG
CAGCACGGGATGGACGACCCGGAGAAGGAGGTGCTGATGTGGAAGTTCGACTCGCGGCTGGCGTTCCACC
ACATGGCCCGCGAGAAGCACCCGGAGTTCTACAAGGACTGCTGATAAGCTAGCTGATCAGCCTCGACTGT
GCCTTCTAGTTGCCAGCCATCTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGG
GGGGTGGGGTGGGGCAGGACAGCAAGGGGGAGGATTGGGAAGACAATAGCAGGCATGCTGGGGAATTT

Thursday, August 2, 2007

Sequence 0 Length : 3918

AatII GACGTC
4 Sites
2510 2563 2646
2832
AccI GTMKAC
2 Sites
3317 3404
AflIII ACRYGT
1 Site
1897
AluI AGCT
13 Sites
109 633 1340
1597 1643 1733
1959
2184 2951 3083
3495 3688 3692
AlwNI CAGNNNCTG
2 Sites
1488 2129
AosII GRCGYC
5 Sites
2507 2560 2643
2829 2983
ApaLI GTGCAC
2 Sites
1563 2081
AvaI CYCGRG
1 Site
3453
BanI GGYRCC
3 Sites
538 2850 3772
BanII GRGCYC
3 Sites
2953 3085 3362
BclI TGATCA
1 Site
3694
BcnI CCSGG
10 Sites
1173 1521 3021
3110 3269 3428
3455
3456 3590 3662
BglI GCCNNNNNGGC
3 Sites
2475 2597 2668
BglII AGATCT
1 Site
458
Bsp1286 GDGCHC
6 Sites
652 1587 2085
2953 3085 3362
BspHI TCATGA
2 Sites
1007 1105
BspNI CCWGG
13 Sites
52 1738 1751
1872 2475 2668
2977
3169 3241 3352
3415 3449 3766
BssHII GCGCGC
1 Site
3045
BstNI CCWGG
13 Sites
52 1738 1751
1872 2475 2668
2977
3169 3241 3352
3415 3449 3766
Cfr10I RCCGGY
3 Sites
847 3099 3132
CfrI YGGCCR
7 Sites
769 3065 3097
3137 3274 3292
3311
ClaI ATCGAT
1 Site
2287
DdeI CTNAG
11 Sites
12 204 397
711 787 1214 1623
2088 2158 2229
3826
DpnI GATC
11 Sites
190 195 460
1239 1247 1258
1333
2972 3028 3187
3696
DraIII CACNNNGTG
1 Site
1161
Eco47I GGWCC
9 Sites
122 586 919
1048 3021 3104
3164
3269 3506
Eco0109 RGGNCCY
2 Sites
3165 3348
EcoRII CCWGG

Fig. 22 cont'd-6

13 Sites
50 1736 1749
1870 2473 2666
2975
3167 3239 3350
3413 3447 3764
EcoRV GATATC
1 Site
2294
Fnu4HI GCNGC
22 Sites
234 769 1283
1489 1492 1557
1700
1855 1973 1976
1994 2110 2250
2279
2282 3065 3137
3206 3277 3311
3571
3625
FnuDII CGCG
17 Sites
494 1273 1854
2169 2257 2281
2445
3039 3045 3047
3162 3208 3217
3226
3513 3624 3650
HaeII RGCGCY
3 Sites
12 1657 2027
HaeIII GGCC
20 Sites
55 771 1175
1423 1857 1875
1886
2268 2469 2662
3067 3099 3139
3238
3276 3294 3313
3350 3452 3646
HgiAI GWGCWC
4 Sites
1587 2085 2953
3085
HhaI GCGC
14 Sites
11 496 1273
1382 1556 1656
1723
1993 2026 2169
2249 3045 3047
3226
HincII GTYRAC
4 Sites
413 886 2369
3318
HinfI GANTC
16 Sites
43 59 357
383 401 725 779
807 1527 1923
1998 2222 2795
3250
3458 3619
HinPI GCGC
14 Sites
9 494 1271
1380 1554 1654
1721
1991 2024 2167
2247 3043 3045
3224
HpaII CCGG
17 Sites
848 1172 1329
1519 1545 1692
3019
3100 3108 3133
3268 3273 3291
3427
3454 3589 3661
MaeI CTAG
7 Sites
378 801 1034
1404 2385 3689
3716
MaeII ACGT
13 Sites
669 1160 1196
2306 2507 2519
2560
2643 2724 2829
3190 3281 3301
MaeIII GTNAC
8 Sites
270 1134 1361
1477 1540 2446
2533
2882
MvaI CCNGG
23 Sites
52 1172 1520
1738 1751 1872
2475
2668 2977 3020
3109 3169 3241
3268
3352 3415 3427
3449 3454 3455
3589
3661 3766
NaeI GCCGGC
2 Sites
3101 3134
NciI CCSGG
10 Sites
1172 1520 3020
3109 3268 3427
3454
3455 3589 3661
NcoI CCATGG
1 Site
2745
NdeI CATATG
2 Sites
2076 2619
NheI GCTAGC
1 Site
3688
NlaIII CATG
15 Sites
538 762 864
892 1011 1109 1181
1901 2219 2349
2367 2689 2749
3645
3907
NlaIV GGNNCC
11 Sites
92 540 1830
1869 2852 3023
3131
3166 3349 3509
3774
NruI TCGCGA
1 Site
2257
NsiI ATGCAT
1 Site
796
Nsp7524I RCATGY
2 Sites
1901 3907
NspBII CMGCKG
6 Sites
1314 1559 2281
3039 3471 3513
PflMI CCANNNNNTGG
1 Site
3642
PpuMI RGGWCCY
1 Site
3165
PssI RGGNCCY
2 Sites
3168 3351
RsaI GTAC
10 Sites
559 2093 2263
2330 2604 2684
2717
2768 2925 3304
RsrII CGGWCCG
2 Sites
3105 3270
SacI GAGCTC
2 Sites
2953 3085
SacII CCGCGG
3 Sites
2282 3040 3514
SalI GTCGAC
1 Site
3316
Sau3A GATC
11 Sites
188 193 458
1237 1245 1256
1331
2970 3026 3185
3694
Sau96A GGNCC
17 Sites
123 587 920
1049 1174 2266
2468
2661 3022 3105
3165 3237 3270
3348
3451 3507 3645
ScrFI CCNGG
23 Sites
52 1172 1520
1738 1751 1872
2475
2668 2977 3020
3109 3169 3241
3268

Mosaic and CON nef_Dmyr_final.doc

Fig. 22 cont'd-7

3352 3415 3427
3449 3454 3455
3589
3661 3766
SdnI GDGCHC
6 Sites
652 1587 2085
2953 3085 3362
SinI GGWCC
9 Sites
123 587 920
1049 3022 3105
3165
3270 3507
SmaI CCCGGG
1 Site
3455
SnaBI TACGTA
1 Site
2725
SpeI ACTAGT
1 Site
2384
SphI GCATGC
1 Site 3907
SspI AATATT
2 Sites
603 991
StuI AGGCCT
1 Site
55
StyI CCWWGG
1 Site
2745
TaqI TCGA
11 Sites
216 1799 2287
3050 3076 3193
3317
3392 3521 3617
3703
Tth111I GACNNNGTC
1 Site
3145
XhoII RGATCY
3 Sites
458 1245 1256
XmaI CCCGGG
1 Site 3453
XmaIII CGGCCG
4 Sites
3137 3274 3292
3311
XmnI GAANNNNTTC
1 Site
811

Following enzymes have no sites

| | | |
|---|---|---|
| AccIII | AflII | ApaI |
| Asp718 | AsuII | AvrII |
| BalI | BamHI | BbeI |
| BspMII | BstEII | BstXI |
| DraI | Eco47III | EcoRI |
| EspI | FspI | HindIII |
| HpaI | KpnI | MluI |
| MstI | NarI | NotI |
| OxaNI | PstI | PvuI |
| PvuII | ScaI | SfiI |
| SplI | XbaI | XcaI |
| XhoI | | |

nefM_4.2Dmyr (654nt.) hv13231, GC=66% ctcgagAAGAAAATGGCGGCCAAGTGGTCGAAGCGGTCCATCGTCGGGTGGCCGGCGATCCGGGAGAGGA
TGCGGAGGACGGAGCCGGCGGCCGAGGGGGTCGGGGCGGCGTCGCAGGACCTCGACAAATACGGGGCGCT
CACGTCGAGCAACACCGCCCAGACGAACCCGGACTGCGCGTGGCTGGAGGCCCAGGAGGAGGAAGAGGTC
GGCTTCCCGGTCCGGCCGCAAGTCCCAGTCAGGCCGATGACGTACAAGGGCGCCCTGGACCTCTCCCACT
TCCTGAAAGAGAAGGGGGGCCTGGACGGGCTCATCTACTCGCGGAAGAGGCAGGAGATCCTCGACCTGTG
GGTCTACAACACCCAGGGCTACTTCCCCGACTGGCAGAACTACACGCCAGGCCCCGGAGTGCGGTACCCG
CTGACCTTCGGGTGGTGCTACAAGCTCGTCCCCGTGGACCCGGAGGAGGTCGAGAAGGCCAACGAGGGGG
AGAACAACTCCCTCCTGCACCCGATGTCGCTCCACGGGATGGAGGACCCCGAGAGGGAGGTGCTGAAGTG
GAAGTTCGACTCGCGGCTGGCGCTCAAGCACCGGGCCCGGGAGCTCCACCCGGAGTTCTACAAGGACTGC
TGATAAGCTAGCGGATCCTGATCA MAAKWSKRSIVGWPAIRERMRRTEPAAEGVGAASQDLDKYGALTSSNTAQTNPDCAWLEAQEEEEVGFPV
RPQVPVRPMTYKGALDLSHFLKEKGGLDGLIYSRKRQEILDLWVYNTQGYFPDWQNYTPGPGVRYPLTFG
WCYKLVPVDPEEVEKANEGENNSLLHPMSLHGMEDPEREVLKWKFDSRLALKHRARELHPEFYKDC_

>HV13231 in hv10001 (nefM_4.2Dmyr.wlv), 3950nt.

AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT

Fig. 22 cont'd-8

```
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGCGGTCCATCGTCGGGTGGCCGGCGATCCGGGAGAGGATGC
GGAGGACGGAGCCGGCGGCCGAGGGGGTCGGGGCGGCGTCGCAGGACCTCGACAAATACGGGGCGCTCAC
GTCGAGCAACACCGCCCAGACGAACCCGGACTGCGCGTGGCTGGAGGCCCAGGAGGAGGAAGAGGTCGGC
TTCCCGGTCCGGCCGCAAGTCCCAGTCAGGCCGATGACGTACAAGGGCGCCCTGGACCTCTCCCACTTCC
TGAAAGAGAAGGGGGGCCTGGACGGGCTCATCTACTCGCGGAAGAGGCAGGAGATCCTCGACCTGTGGGT
CTACAACACCCAGGGCTACTTCCCCGACTGGCAGAACTACACGCCAGGCCCCGGAGTGCGGTACCCGCTG
ACCTTCGGGTGGTGCTACAAGCTCGTCCCCGTGGACCCGGAGGAGGTCGAGAAGGCCAACGAGGGGGAGA
CAACTCCCTCCTGCACCCGATGTCGCTCCACGGGATGGAGGACCCCGAGAGGGAGGTGCTGAAGTGGAA
GTTCGACTCGCGGCTGGCGCTCAAGCACCGGGCCCGGGAGCTCCACCCGGAGTTCTACAAGGACTGC TGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGGGGGAGGATTGG
GAAGACAATAGCAGGCATGCTGGGGAATTT
```

```
Thursday, August 2, 2007        AflIII    ACRYGT           2 Sites
                                1 Site                     1488      2129
Sequence 0   Length : 3950      1897                       AosII     GRCGYC
                                AluI      AGCT             7 Sites
AatII      GACGTC               12 Sites                   2507      2560    2643
4 Sites                         109       633      1340    2829      2983    3186
   2510    2563      2646       1597      1643     1733    3337
2832                            1959                       ApaI      GGGCCC
AccI       GTMKAC                2184     2951     3521    2 Sites
2 Sites                         3680      3714             3075      3674
   3050    3430                 AlwNI     CAGNNNCTG        ApaLI     GTGCAC
```

Mosaic and CON nef_Dmyr_final.doc

Fig. 22 cont'd-9

2 Sites
1583 2081
Asp718 GGTACC
1 Site
3490
AvaI CYCGRG
3 Sites
3078 3615 3673
BamHI GGATCC
1 Site
3720
BanI GGYRCC
5 Sites
538 2850 3336
3490 3804
BanII GRGCYC
5 Sites
2953 3075 3388
3674 3682
BbeI GGCGCC
1 Site
3340
BclI TGATCA
1 Site
3726
BcnI CCSGG
12 Sites
1173 1521 3021
3139 3247 3295
3482
3538 3670 3675
3676 3688
BglI GCCNNNNNGGC
3 Sites
2475 2597 2668
BglII AGATCT
1 Site
458
Bsp1286 GDGCHC
8 Sites
652 1587 2085
2953 3075 3388
3674
3682
BspHI TCATGA
2 Sites
1007 1105
BspNI CCWGG
13 Sites
52 1738 1751
1872 2475 2668
2977
3270 3342 3378
3441 3475 3798
BssHII GCGCGC
1 Site
3045
BstNI CCWGG
13 Sites
52 1738 1751
1872 2475 2668
2977
3270 3342 3378
3441 3475 3798
Cfr10I RCCGGY
3 Sites
847 3128 3161
CfrI YGGCCR
5 Sites
769 3094 3126
3166 3300
Mosaic and CON nef_Dmyr_final.doc ClaI ATCGAT
1 Site
2287
DdeI CTNAG
11 Sites
12 204 397
711 787 1214 1623
2088 2158 2229
3858
DpnI GATC
13 Sites
190 195 460
1239 1247 1258
1333
2972 3028 3135
3414 3722 3728
DraIII CACNNNGTG
1 Site
1161
Eco47I GGWCC
11 Sites
122 586 919
1048 3021 3111
3193
3295 3343 3532
3610
Eco0109 RGGNCCY
4 Sites
3194 3374 3477
3611
EcoRII CCWGG
13 Sites
50 1736 1749
1870 2473 2666
2975
3268 3340 3376
3439 3473 3796
EcoRV GATATC
1 Site
2294
Fnu4HI GCNGC
20 Sites
234 769 1283
1489 1492 1557
1700
1855 1973 1976
1994 2110 2250
2279
2282 3094 3166
3184 3303 3651
FnuDII CGCG
14 Sites
494 1273 1854
2169 2257 2281
2445
3039 3045 3047
3062 3255 3398
3650
HaeII RGCGCY
6 Sites
12 1657 2027
3216 3340 3660
HaeIII GGCC
21 Sites
55 771 1175
1423 1857 1875
1886
2268 2469 2662
3073 3096 3128
3168

3267 3302 3320
3376 3478 3555
3672
HgiAI GWGCWC
4 Sites
1587 2085 2953
3682
HhaI GCGC
17 Sites
11 496 1273
1382 1556 1656
1723
1993 2026 2169
2249 3045 3047
3215
3255 3339 3659
HincII GTYRAC
4 Sites
413 886 2369
3051
HinfI GANTC
14 Sites
43 59 357
383 401 725 779
807 1527 1923
1998 2222 2795
3645
HinPI GCGC
17 Sites
9 494 1271
1380 1554 1654
1721
1991 2024 2167
2247 3043 3045
3213
3253 3337 3657
HpaII CCGG
18 Sites
848 1172 1329
1519 1545 1692
3019
3129 3137 3162
3246 3294 3299
3481
3537 3668 3674
3687
KpnI GGTACC
1 Site
3494
MaeI CTAG
7 Sites
378 801 1034
1404 2385 3715
3748
MaeII ACGT
12 Sites
669 1160 1196
2306 2507 2519
2560
2643 2724 2829
3219 3327
MaeIII GTNAC
8 Sites
270 1134 1361
1477 1540 2446
2533
2882
MvaI CCNGG
25 Sites

Fig. 22 cont'd-10

52 1172 1520
1738 1751 1872
2475
2668 2977 3020
3138 3246 3270
3294
3342 3378 3441
3475 3481 3537
3669
3674 3675 3687
3798
NaeI GCCGGC
2 Sites
3130 3163
NarI GGCGCC
1 Site
3337
NciI CCSGG
12 Sites
1172 1520 3020
3138 3246 3294
3481
3537 3669 3674
3675 3687
NcoI CCATGG
1 Site
2745
NdeI CATATG
2 Sites
2076 2619
NheI GCTAGC
1 Site
3714
NlaIII CATG
14 Sites
538 762 864
892 1011 1109 1181
1901 2219 2349
2367 2689 2749
3939
NlaIV GGNNCC
17 Sites
92 540 1830
1869 2852 3023
3073
3160 3338 3375
3479 3492 3535
3613
3672 3722 3806
NruI TCGCGA
1 Site
2257
NsiI ATGCAT
1 Site
796
Nsp7524I RCATGY
2 Sites
1901 3939
NspBII CMGCKG
5 Sites
1314 1559 2281
3039 3497
PflMI CCANNNNNTGG
1 Site
3605
PpuMI RGGWCCY
2 Sites
3194 3611
PssI RGGNCCY
4 Sites
3197 3377 3480
3614
RsaI GTAC
11 Sites
559 2093 2263
2330 2604 2684
2717
2768 2925 3330
3492
RsrII CGGWCCG
1 Site
3296
SacI GAGCTC
2 Sites
2953 3682
SacII CCGCGG
2 Sites
2282 3040
SalI GTCGAC
1 Site
3049
Sau3A GATC
13 Sites
188 193 458
1237 1245 1256
1331
2970 3026 3133
3412 3720 3726
Sau96A GGNCC
22 Sites
123 587 920
1049 1174 2266
2468
2661 3022 3071
3072 3112 3194
3266
3296 3344 3374
3477 3533 3611
3670
3671
ScrFI CCNGG
25 Sites
52 1172 1520
1738 1751 1872
2475
2668 2977 3020
3138 3246 3270
3294
3342 3378 3441
3475 3481 3537
3669
3674 3675 3687
3798
SdnI GDGCHC
8 Sites
652 1587 2085
2953 3075 3388
3674
3682
SinI GGWCC
11 Sites
123 587 920
1049 3022 3112
3194
3296 3344 3533
3611
SmaI CCCGGG
1 Site
3675
SnaBI TACGTA
1 Site
2725
SpeI ACTAGT
1 Site
2384
SphI GCATGC
1 Site
3939
SspI AATATT
2 Sites
603 991
StuI AGGCCT
1 Site
55
StyI CCWWGG
1 Site
2745
TaqI TCGA
12 Sites
216 1799 2287
3050 3079 3105
3199
3222 3418 3547
3643 3735
XhoI CTCGAG
1 Site
3078
XhoII RGATCY
5 Sites
458 1245 1256
3412 3720
XmaI CCCGGG
1 Site
3673
XmaIII CGGCCG
2 Sites
3166 3300
XmnI GAANNNNTTC
1 Site
811

Following enzymes have no sites

| | | |
|---|---|---|
| AccIII | AflII | AsuII |
| AvrII | BalI | BspMII |
| BstEII | BstXI | DraI |
| Eco47III | EcoRI | EspI |
| FspI | HindIII | HpaI |
| MluI | MstI | NotI |
| OxaNI | PstI | PvuI |
| PvuII | ScaI | SfiI |
| SplI | Tth111I | XbaI |
| XcaI | | |

>nefM_4.3Dmyr(654nt.), hv13230, GC=66%
ctcgagAAGAAAATGGCGGCCAACTGGTCGAAGAGCTCCATCGTCGGGTGGCCGGAGATCCGGGAGCGCA
TCCGGAGGACGGACCCGGCGGCCGAGGGGGTCGGGGCGGCCTCGCGGGACCTGGAGCGCCACGGGGCGAT Mosaic and CON nef_Dmyr_final.doc

Fig. 22 cont'd-11

CACGTCGAGCAACACCGCCACCACGAACGCGGCCTGCGCGTGGCTGGAGGCCCAGGAGGACGAGGAAGTC
GGCTTCCCGGTCCGGCCGCAAGTCCCGCTCAGGCCGATGACGTTCAAGGGGGCCTTCGACCTCGGCTTCT
TCCTGAAAGAGAAGGGGGGCCTGGAGGGGCTCATCTACTCGAAGAAGAGGCAGGACATCCTCGACCTGTG
GGTCTACAACACCCAGGGGTTCTTCCCGGACTGGCAGAACTACACGCCAGGCCCGGGAACCCGGTTCCCG
CTGACCTTCGGGTGGTGCTTCGAGCTCGTCCCCGTGGACCCGAAGGAGGTCGAGGAAGCCAACGAGGGGG
AGAACAACTGCCTCCTGCACCCGATCTGCCAGCACGGGATGGACGACGAGGAGCGCGAGGTGCTGATGTG
GAAGTTCGACTCGTCCCTGGCCCGGCGCCACCTCGCCCGGGAGAAGCACCCGGAGTACTACAAGGACTGC
TGATAAGCTAGCGGATCCTGATCA

MAANWSKSSIVGWPEIRERIRRTDPAAEGVGAASRDLERHGAITSSNTATTNAACAWLEAQEDEEVGFPV
RPQVPLRPMTFKGAFDLGFFLKEKGGLEGLIYSKKRQDILDLWVYNTQGFFPDWQNYTPGPGTRFPLTFG
WCFELVPVDPKEVEEANEGENNCLLHPICQHGMDDEEREVLMWKFDSSLARRHLAREKHPEYYKDC_

>hv13230 in hv10001 (nefM_4.3Dmyr.wlv)(3950nt.)
AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT

Fig. 22 cont'd-12

GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGCCCACTC
GAGAAGAAAATGGCGGCCAACTGGTCGAAGAGCTCCATCGTCGGGTGGCCGGAGATCCGGGAGCGCATCC
GGAGGACGGACCCGGCGGCCGAGGGGGTCGGGGCGGCCTCGCGGGACCTGGAGCGCCACGGGGCGATCAC
GTCGAGCAACACCGCCACCACGAACGCGGCCTGCGCGTGGCTGGAGGCCCAGGAGGACGAGGAAGTCGGC
TTCCCGGTCCGGCCGCAAGTCCCGCTCAGGCCGATGACGTTCAAGGGGGCCTTCGACCTCGGCTTCTTCC
TGAAAGAGAAGGGGGGCCTGGAGGGGCTCATCTACTCGAAGAAGAGGCAGGACATCCTCGACCTGTGGGT
CTACAACACCCAGGGGTTCTTCCCGGACTGGCAGAACTACACGCCAGGCCCGGGAACCCGGTTCCCGCTG
ACCTTCGGGTGGTGCTTCGAGCTCGTCCCCGTGGACCCGAAGGAGGTCGAGGAAGCCAACGAGGGGGAGA
ACAACTGCCTCCTGCACCCGATCTGCCAGCACGGGATGGACGACGAGGAGCGCGAGGTGCTGATGTGGAA
GTTCGACTCGTCCCTGGCCCGGCGCCACCTCGCCCGGGAGAAGCACCCGGAGTACTACAAGGACTGCTGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGGGGGAGGATTGG
GAAGACAATAGCAGGCATGCTGGGAATTT

Thursday, August 2, 2007

Sequence 0 Length : 3950

AatII GACGTC
4 Sites
2510 2563 2646
2832
AccI GTMKAC
2 Sites
3050 3430
AccIII TCCGGA
1 Site
3148
AflIII ACRYGT
1 Site
1897
AluI AGCT
12 Sites
109 633 1340
1597 1643 1733
1959
2184 2951 3112
3521 3714
AlwNI CAGNNNCTG
2 Sites
1488 2129
AosII GRCGYC
6 Sites
2507 2560 2643
2829 2983 3662
ApaI GGGCCC
1 Site
3075
ApaLI GTGCAC
2 Sites
1583 2081
AvaI CYCGRG
3 Sites
3078 3479 3673
BamHI GGATCC
1 Site
3720

BanI GGYRCC
4 Sites
538 2850 3661
3804
BanII GRGCYC
5 Sites
2953 3075 3114
3388 3523
BbeI GGCGCC
1 Site
3665
BclI TGATCA
1 Site
3726
BcnI CCSGG
14 Sites
1173 1521 3021
3139 3163 3295
3454
3481 3482 3489
3660 3675 3676
3688
BglI GCCNNNNNGGC
3 Sites
2475 2597 2668
BglII AGATCT
1 Site
458
Bsp1286 GDGCHC
8 Sites
652 1587 2085
2953 3075 3114
3388
3523
BspHI TCATGA
2 Sites
1007 1105
BspMII TCCGGA
1 Site
3148
BspNI CCWGG
14 Sites 52 1738 1751
1872 2475 2668
2977
3198 3270 3378
3441 3475 3654
3798
BssHII GCGCGC
1 Site
3045
BstNI CCWGG
14 Sites
52 1738 1751
1872 2475 2668
2977
3198 3270 3378
3441 3475 3654
3798
Cfr10I RCCGGY
1 Site
847
CfrI YGGCCR
5 Sites
769 3094 3126
3166 3300
ClaI ATCGAT
1 Site
2287
DdeI CTNAG
12 Sites
12 204 397
711 787 1214 1623
2088 2158 2229
3315 3858
DpnI GATC
14 Sites
190 195 460
1239 1247 1258
1333
2972 3028 3135
3216 3591 3722
3728
DraIII CACNNNGTG
1 Site Mosaic and CON nef_Dmyr_final.doc

Fig. 22 cont'd-13

1161
Eco47I GGWCC
9 Sites
122 586 919
1048 3021 3157
3193
3295 3532
EcoO109 RGGNCCY
3 Sites
3194 3337 3374
EcoRII CCWGG
14 Sites
50 1736 1749
1870 2473 2666
2975
3196 3268 3376
3439 3473 3652
3796
EcoRV GATATC
1 Site
2294
Fnu4HI GCNGC
20 Sites
234 769 1283
1489 1492 1557
1700
1855 1973 1976
1994 2110 2250
2279
2282 3094 3166
3184 3247 3303
FnuDII CGCG
15 Sites
494 1273 1854
2169 2257 2281
2445
3039 3045 3047
3062 3191 3246
3255
3622
HaeII RGCGCY
5 Sites
12 1657 2027
3206 3665
HaeIII GGCC
23 Sites
55 771 1175
1423 1857 1875
1886
2268 2469 2662
3073 3096 3128
3168
3186 3249 3267
3302 3320 3339
3376
3478 3657
HgiAI GWGCWC
5 Sites
1587 2085 2953
3114 3523
HhaI GCGC
18 Sites
11 496 1273
1382 1556 1656
1723
1993 2026 2169
2249 3045 3047
3145
3205 3255 3622
3664
HincII GTYRAC
4 Sites
413 886 2369
3051
HinfI GANTC
14 Sites
43 59 357
383 401 725 779
807 1527 1923
1998 2222 2795
3645
HinPI GCGC
18 Sites
9 494 1271
1380 1554 1654
1721
1991 2024 2167
2247 3043 3045
3143
3203 3253 3620
3662
HpaII CCGG
19 Sites
848 1172 1329
1519 1545 1692
3019
3129 3137 3149
3162 3294 3299
3453
3480 3488 3659
3674 3687
MaeI CTAG
7 Sites
378 801 1034
1404 2385 3715
3748
MaeII ACGT
12 Sites
669 1160 1196
2306 2507 2519
2560
2643 2724 2829
3219 3327
MaeIII GTNAC
8 Sites
270 1134 1361
1477 1540 2446
2533
2882
MvaI CCNGG
28 Sites
52 1172 1520
1738 1751 1872
2475
2668 2977 3020
3138 3162 3198
3270
3294 3378 3441
3453 3475 3480
3481
3488 3654 3659
3674 3675 3687
3798
NarI GGCGCC
1 Site
3662
NciI CCSGG
14 Sites
1172 1520 3020
3138 3162 3294
3453
3480 3481 3488
3659 3674 3675
3687
NcoI CCATGG
1 Site
2745
NdeI CATATG
2 Sites
2076 2619
NheI GCTAGC
1 Site
3714
NlaIII CATG
14 Sites
538 762 864
892 1011 1109 1181
1901 2219 2349
2367 2689 2749
3939
NlaIV GGNNCC
17 Sites
92 540 1830
1869 2852 3023
3073
3160 3195 3338
3375 3485 3492
3535
3663 3722 3806
NruI TCGCGA
1 Site
2257
NsiI ATGCAT
1 Site
796
Nsp7524I RCATGY
2 Sites
1901 3939
NspBII CMGCKG
5 Sites
1314 1559 2281
3039 3497
PpuMI RGGWCCY
1 Site
3194
PssI RGGNCCY
3 Sites
3197 3340 3377
RsaI GTAC
10 Sites
559 2093 2263
2330 2604 2684
2717
2768 2925 3693
RsrII CGGWCCG
1 Site
3296
SacI GAGCTC
3 Sites
2953 3114 3523
SacII CCGCGG
2 Sites
2282 3040
SalI GTCGAC
1 Site
3049
Sau3A GATC
14 Sites
188 193 458
1237 1245 1256
1331

Mosaic and CON nef_Dmyr_final.doc

Fig. 22 cont'd-14

2970 3026 3133
3214 3589 3720
3726
Sau96A GGNCC
20 Sites
123 587 920
1049 1174 2266
2468
2661 3022 3071
3072 3158 3194
3266
3296 3337 3374
3477 3533 3656
ScaI AGTACT
1 Site
3693
ScrFI CCNGG
28 Sites
52 1172 1520
1738 1751 1872
2475
2668 2977 3020
3138 3162 3198
3270
3294 3378 3441
3453 3475 3480
3481
3488 3654 3659
3674 3675 3687
3798
SdnI GDGCHC
8 Sites
652 1587 2085
2953 3075 3114
3388

3523
SinI GGWCC
9 Sites
123 587 920
1049 3022 3158
3194
3296 3533
SmaI CCCGGG
2 Sites
3481 3675
SnaBI TACGTA
1 Site
2725
SpeI ACTAGT
1 Site
2384
SphI GCATGC
1 Site
3939
SspI AATATT
2 Sites
603 991
StuI AGGCCT
1 Site
55
StyI CCWWGG
1 Site
2745
TaqI TCGA
14 Sites
216 1799 2287
3050 3079 3105
3222

3343 3396 3418
3517 3547 3643
3735
XhoI CTCGAG
1 Site
3078
XhoII RGATCY
5 Sites
458 1245 1256
3133 3720
XmaI CCCGGG
2 Sites
3479 3673
XmaIII CGGCCG
2 Sites
3166 3300
XmnI GAANNNNTTC
1 Site
811

Following enzymes have no sites

| | | |
|---|---|---|
| AflII | Asp718 | AsuII |
| AvrII | BalI | BstEII |
| BstXI | DraI | |
| Eco47III | EcoRI | EspI |
| FspI | | |
| HindIII | HpaI | KpnI |
| MluI | MstI | NaeI |
| NotI | OxaNI | PflMI |
| PstI | PvuI | PvuII |
| SfiI | SplI | Tth111I |
| XbaI | XcaI | |

nefM_4.4Dmyr (657nt.) hv13232, GC=66% ctcgagAAGAAAATGGCCTCCAAGTGGTCGAAGAGCTCCATCGTCGGGTGGCCGCAAGTCCGGGAGCGCA
TCCGGCAGACGCCCCCCGCGGCCGAGGGGGTCGGCGCGGTCTCGCAGGACCTCGACAAGCACGGGGCGGT
CACGTCGAGCAACACCGCCGCGAACAACGCGGACTGCGCGTGGCTGCAGGCCCAGGAGGAAGAGGAAGAG
GTCGGCTTCCCGGTCAAGCCGCAAGTGCCGCTCAGGCCGATGACGTACAAGGGGGCCTTCGACCTCTCGT
TCTTCCTGAAAGAGAAGGGTGGCCTGGACGGGCTCATCTACTCGAAGAAGAGGCAGGAGATCCTCGACCT
GTGGGTCTACCACACCCAGGGGTTCTTCCCGGACTGGCACAACTACACGCCAGGCCCGGGAACCCGCTAC
CCGCTGTGCTTCGGGTGGTGCTTCAAGCTCGTCCCCATGGACCCGGCCGAGGTCGAGGAAGCCACCGAGG
GCGAGAACAACTCCCTCCTGCACCCGATCTGCCAGCACGGGATGGAGGACGAGGACCGCGAGGTGCTGGT
CTGGCGGTTCGACTCGTCCCTGGCCCGGCGCCACATCGCCCGGGAGCTCCACCCGGAGTACTACAAGGAC
TGCTGATAAGCTAGCGGATCCTGATCA MASKWSKSSIVGWPQVRERIRQTPPAAEGVGAVSQDLDKHGAVTSSNTAANNADCAWLQAQEEEEEVGFP
VKPQVPLRPMTYKGAFDLSFFLKEKGGLDGLIYSKKRQEILDLWVYHTQGFFPDWHNYTPGPGTRYPLCF
GWCFKLVPMDPAEVEEATEGENNSLLHPICQHGMEDEDREVLVWRFDSSLARRHIARELHPEYYKDC_

>HV13232 in hv10001 (nefM_4.4Dmyr.wlv), 3953nt.

AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC

Fig. 22 cont'd-15

GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCCTCCAAGTGGTCGAAGAGCTCCATCGTCGGGTGGCCGCAAGTCCGGGAGCGCATCC
GGCAGACGCCCCCCGCGGCCGAGGGGGTCGGCGCGGTCTCGCAGGACCTCGACAAGCACGGGGCGGTCAC
GTCGAGCAACACCGCCGCGAACAACGCGGACTGCGCGTGGCTGCAGGCCCAGGAGGAAGAGGAAGAGGTC
GGCTTCCCGGTCAAGCCGCAAGTGCCGCTCAGGCCGATGACGTACAAGGGGGCCTTCGACCTCTCGTTCT
TCCTGAAAGAGAAGGGTGGCCTGGACGGGCTCATCTACTCGAAGAAGAGGCAGGAGATCCTCGACCTGTG
GGTCTACCACACCCAGGGGTTCTTCCCGGACTGGCACAACTACACGCCAGGCCCGGGAACCCGCTACCCG
CTGTGCTTCGGGTGGTGCTTCAAGCTCGTCCCCATGGACCCGGCCGAGGTCGAGGAAGCCACCGAGGGCG
AGAACAACTCCCTCCTGCACCCGATCTGCCAGCACGGGATGGAGGACGAGGACCGCGAGGTGCTGGTCTG
GCGGTTCGACTCGTCCCTGGCCCGGCGCCACATCGCCCGGGAGCTCCACCCGGAGTACTACAAGGACTGC
TGATAAGCTAGCGGATCCTGATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGGGGGAGGAT
TGGGAAGACAATAGCAGGCATGCTGGGGAATTT

THURSDAY, AUGUST 2, 2007 SEQUENCE 0 LENGTH : 3953
Mosaic and CON nef_Dmyr_final.doc

Fig. 22 cont'd-16

AATII GACGTC
4 SITES
2510 2563 2646
2832
ACCI GTMKAC
2 SITES
3050 3433
AFLIII ACRYGT
1 SITE
1897
ALUI AGCT
13 SITES
109 633 1340
1597 1643 1733
1959
2184 2951 3112
3524 3683 3717
ALWNI CAGNNNCTG
2 SITES
1488 2129
AOSII GRCGYC
7 SITES
2507 2560 2643
2829 2983 3156
3665
APAI GGGCCC
1 SITE
3075
APALI GTGCAC
2 SITES
1583 2081
AVAI CYCGRG
3 SITES
3078 3482 3676
BAMHI GGATCC
1 SITE
3723
BANI GGYRCC
4 SITES
538 2850 3664
3807
BANII GRGCYC
5 SITES
2953 3075 3114
3391 3685
BBEI GGCGCC
1 SITE
3668
BCLI TGATCA
1 SITE
3729
BCNI CCSGG
13 SITES
1173 1521 3021
3139 3298 3457
3484
3485 3541 3663
3678 3679 3691
BGLI GCCNNNNNGGC
4 SITES
2475 2597 2668
3320
BGLII AGATCT
1 SITE
458
BSP1286 GDGCHC
8 SITES
652 1587 2085
2953 3075 3114
3391

3685
BSPHI TCATGA
2 SITES
1007 1105
BSPNI CCWGG
13 SITES
52 1738 1751
1872 2475 2668
2977
3270 3381 3444
3478 3657 3801
BSSHII GCGCGC
1 SITE
3045
BSTNI CCWGG
13 SITES
52 1738 1751
1872 2475 2668
2977
3270 3381 3444
3478 3657 3801
CFR10I RCCGGY
1 SITE
847
CFRI YGGCCR
4 SITES
769 3126 3166
3541
CLAI ATCGAT
1 SITE
2287
DDEI CTNAG
12 SITES
12 204 397
711 787 1214 1623
2088 2158 2229
3318 3861
DPNI GATC
13 SITES
190 195 460
1239 1247 1258
1333
2972 3028 3417
3594 3725 3731
DRAIII CACNNNGTG
1 SITE
1161
ECO47I GGWCC
8 SITES
122 586 919
1048 3021 3193
3535
3619
ECO0109 RGGNCCY
2 SITES
3194 3340
ECORII CCWGG
13 SITES
50 1736 1749
1870 2473 2666
2975
3268 3379 3442
3476 3655 3799
ECORV GATATC
1 SITE
2294
FNU4HI GCNGC
21 SITES
234 769 1283
1489 1492 1557
1700

1855 1973 1976
1994 2110 2250
2279
2282 3129 3166
3235 3261 3306
3315
FNUDII CGCG
17 SITES
494 1273 1854
2169 2257 2281
2445
3039 3045 3047
3062 3165 3183
3237
3246 3255 3625
HAEII RGCGCY
4 SITES
12 1657 2027
3668
HAEIII GGCC
21 SITES
55 771 1175
1423 1857 1875
1886
2268 2469 2662
3073 3093 3128
3168
3267 3323 3342
3379 3481 3543
3660
HGIAI GWGCWC
5 SITES
1587 2085 2953
3114 3685
HHAI GCGC
17 SITES
11 496 1273
1382 1556 1656
1723
1993 2026 2169
2249 3045 3047
3145
3183 3255 3667
HINCII GTYRAC
4 SITES
413 886 2369
3051
HINFI GANTC
14 SITES
43 59 357
383 401 725 779
807 1527 1923
1998 2222 2795
3648
HINPI GCGC
17 SITES
9 494 1271
1380 1554 1654
1721
1991 2024 2167
2247 3043 3045
3143
3181 3253 3665
HPAII CCGG
16 SITES
848 1172 1329
1519 1545 1692
3019
3137 3149 3297
3456 3483 3540
3662

Fig. 22 cont'd-17

```
   3677    3690
MAEI       CTAG
7 SITES
    378      801     1034
1404     2385    3718
3751
MAEII      ACGT
12 SITES
    669     1160     1196
2306     2507     2519
2560
   2643     2724     2829
3219     3330
MAEIII     GTNAC
9 SITES
    270     1134     1361
1477     1540     2446
2533
   2882     3215
MVAI       CCNGG
26 SITES
     52     1172     1520
1738     1751     1872
2475
   2668     2977     3020
3138     3270     3297
3381
   3444     3456     3478
3483     3484     3540
3657
   3662     3677     3678
3690     3801
NARI       GGCGCC
1 SITE
   3665
NCII       CCSGG
13 SITES
   1172     1520     3020
3138     3297     3456
3483
   3484     3540     3662
3677     3678     3690
NCOI       CCATGG
2 SITES
   2745     3532
NDEI       CATATG
2 SITES
   2076     2619
NHEI       GCTAGC
1 SITE
   3717
NLAIII     CATG
15 SITES
    538      762      864
892     1011     1109     1181
   1901     2219     2349
2367     2689     2749
3536
   3942
NLAIV      GGNNCC
13 SITES
     92      540     1830
1869     2852     3023
3073
   3341     3488     3538
3666     3725     3809
NRUI       TCGCGA
1 SITE
   2257
NSII       ATGCAT
1 SITE
    796
NSP7524I   RCATGY
2 SITES
   1901     3942
NSPBII     CMGCKG
6 SITES
   1314     1559     2281
3039     3165     3500
PPUMI      RGGWCCY
1 SITE
   3194
PSSI       RGGNCCY
2 SITES
   3197     3343
PSTI       CTGCAG
1 SITE
   3265
RSAI       GTAC
11 SITES
    559     2093     2263
2330     2604     2684
2717
   2768     2925     3333
3696
SACI       GAGCTC
3 SITES
   2953     3114     3685
SACII      CCGCGG
3 SITES
   2282     3040     3166
SALI       GTCGAC
1 SITE
   3049
SAU3A      GATC
13 SITES
    188      193      458
1237     1245     1256
1331
   2970     3026     3415
3592     3723     3729
SAU96A     GGNCC
18 SITES
    123      587      920
1049     1174     2266
2468
   2661     3022     3071
3072     3194     3266
3340
   3480     3536     3620
3659
SCAI       AGTACT
1 SITE
   3696
SCRFI      CCNGG
26 SITES
     52     1172     1520
1738     1751     1872
2475
   2668     2977     3020
3138     3270     3297
3381
   3444     3456     3478
3483     3484     3540
3657
   3662     3677     3678
3690     3801
SDNI       GDGCHC
8 SITES
    652     1587     2085
2953     3075     3114
3391
   3685
SINI       GGWCC
8 SITES
    123      587      920
1049     3022     3194
3536
   3620
SMAI       CCCGGG
2 SITES
   3484     3678
SNABI      TACGTA
1 SITE
   2725
SPEI       ACTAGT
1 SITE
   2384
SPHI       GCATGC
1 SITE
   3942
SSPI       AATATT
2 SITES
    603      991
STUI       AGGCCT
1 SITE
     55
STYI       CCWWGG
2 SITES
   2745     3532
TAQI       TCGA
14 SITES
    216     1799     2287
3050     3079     3105
3199
   3222     3346     3399
3421     3550     3646
3738
XHOI       CTCGAG
1 SITE
   3078
XHOII      RGATCY
5 SITES
    458     1245     1256
3415     3723
XMAI       CCCGGG
2 SITES
   3482     3676
XMAIII     CGGCCG
2 SITES
   3166     3541
XMNI       GAANNNNTTC
1 SITE
    811

FOLLOWING ENZYMES HAVE NO
SITES
ACCIII     AFLII      ASP718
ASUII      AVRII      BALI
BSPMII     BSTEII     BSTXI
DRAI       ECO47III   ECORI
ESPI       FSPI       HINDIII
HPAI       KPNI       MLUI
MSTI       NAEI       NOTI
OXANI      PFLMI      PVUI
PVUII      RSRII      SFII
SPLI       TTH111I    XBAI
XCAI
```

Mosaic and CON nef_Dmyr_final.doc

Fig. 22 cont'd-18

Gag gene constructs:

| HVI number | Gene name | Gag | Myristylation signal mutated |
|---|---|---|---|
| HV13234 | M.con_Gag01_Dmyr.wlv | Group M (2001) | Yes |
| HV13309 | Gag-M4.1 Dmyr.wlv | Mosaic No. 1 | Yes |
| HV13316 | Gag_M4.2 Dmyr.wlv | Mosaic No. 2 | Yes |
| HV13317 | Gag_M4.3 Dmyr.wlv | Mosaic No. 3 | Yes |
| HV13318 | Gag_M4.4 Dmyr.wlv | Mosaic No. 4 | Yes |

All five constructs were cloned into HV10001 (WLV001AM DNA vaccine plasmid.

M.con_Gag01_Dmyr

MAARASVLSGGKLDAWEKIRLRPGGKKKYRLKHLVWASRELERFALNPGLLETSEGCQQIIGQLQPALQT
GSEELRSLYNTVATLYCVHQRIEVKDTKEALEKIEEEQNKSQQKTQQAAADKGNSSKVSQNYPIVQNLQG
QMVHQAISPRTLNAWVKVIEEKAFSPEVIPMFSALSEGATPQDLNTMLNTVGGHQAAMQMLKDTINEEAA
EWDRLHPVHAGPIPPGQMREPRGSDIAGTTSTLQEQIAWMTSNPPIPVGEIYKRWIILGLNKIVRMYSPV
SILDIRQGPKEPFRDYVDRFFKTLRAEQATQDVKNWMTDTLLVQNANPDCKTILKALGPGATLEEMMTAC
QGVGGPSHKARVLAEAMSQVTNAAIMMQRGNFKGQRRIIKCFNCGKEGHIARNCRAPRKKGCWKCGKEGH
QMKDCTERQANFLGKIWPSNKGRPGNFLQSRPEPTAPPAESFGFGEEITPSPKQEPKDKEPPLASLKSLF
GNDPLSQ_

HV13234 (M.con_Gag01_Dmyr.wlv) (1527nt)

XhoI

CTCGAGAAGAAAATGGCGGCTCGCGCCTCGGTCCTCAGCGGGGGCAAGTTGGATGCGTGGGAGAA
GATCCGCTTGAGGCCAGGAGGGAAGAAGAAGTACCGGCTCAAGCACCTGGTCTGGGCGAGCAGG
GAGCTGGAGCGCTTCGCGCTGAACCCGGGCCTGCTGGAGACATCCGAGGGCTGTCAGCAGATCA
TCGGGCAGCTTCAGCCAGCGCTCCAGACGGGCAGCGAGGAGCTGCGCTCGCTATACAACACGGT
AGCGACCCTCTACTGCGTGCACCAGCGGATCGAGGTCAAGGACACGAAGGAGGCTCTTGAGAAG
ATCGAGGAGGAGCAGAACAAGTCGCAGCAGAAGACCCAGCAGGCGGCGGCCGACAAGGGCAACT
CCTCAAAAGTATCTCAGAACTACCCGATCGTGCAGAACCTGCAGGGACAGATGGTCCACCAGGC
CATCAGCCCACGGACGCTTAACGCCTGGGTCAAGGTGATCGAGGAGAAGGCCTTCTCGCCGGAG
GTCATCCCCATGTTCTCGGCACTCTCCGAGGGAGCCACCCCGCAGGACCTGAACACGATGTTGA
ACACGGTCGGCGGGCACCAGGCGGCCATGCAGATGCTCAAGGATACCATCAACGAGGAGGCTGC
GGAGTGGGACCGCCTGCACCCAGTGCACGCGGGGCCCATCCCCCCGGGCCAGATGAGAGAGCCG
CGGGGATCGGACATCGCGGGCACGACCAGCACCTTGCAGGAGCAAATCGCCTGGATGACTAGCA
ACCCCCCGATCCCGGTCGGGGAGATCTACAAGCGGTGGATCATCCTCGGGTTGAACAAGATCGT
GCGGATGTACAGCCCTGTCTCAATCCTGGACATCCGGCAGGGGCCCAAGGAGCCCTTCCGCGAC
TACGTCGACCGGTTCTTCAAGACTCTCCGGGCGGAGCAGGCGACGCAGGACGTCAAGAACTGGA
TGACGGACACCTTGTTGGTCCAGAACGCTAACCCGGACTGCAAGACGATCCTGAAGGCTCTCGG
CCCGGGAGCGACCTTGGAGGAGATGATGACCGCGTGCCAGGGGGTCGGGGGACCCAGCCACAAG
GCGCGGGTCTTGGCCGAGGCGATGTCCCAGGTCACGAACGCCGCGATCATGATGCAGCGGGGGA
ACTTCAAGGGCCAGCGCCGGATCATCAAGTGCTTCAACTGCGGCAAGGAGGGCCACATCGCCCG
GAACTGCCGGGCCCCGCGGAAGAAGGGCTGCTGGAAGTGCGGAAAGGAGGGGCACCAGATGAAG
GACTGCACGGAGCGCCAGGCGAATTTCCTCGGGAAGATCTGGCCGTCCAACAAGGGGCGGCCAG
GGAACTTCCTGCAATCGCGGCCAGAGCCGACGGCCCCTCCCGCGGAGAGCTTCGGGTTCGGCGA

Fig. 22 cont'd-19

GGAGATCACGCCCAGCCCCAAGCAAGAGCCGAAGGACAAGGAGCCGCCCCTTGCGTCCCTCAAG
TCGCTCTTCGGCAACGACCCGCTCTCCCAATGATAAGCTAGCGGATCCTGATCA
NheI BamHI BclI

Cut with XhoI and NheI site for VSV subcloning.

>HV13234 in hv10001 (4,822bp)

AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCTCGCGCCTCGGTCCTCAGCGGGGGCAAGTTGGATGCGTGGGAGAAGATCCGCT
TGAGGCCAGGAGGGAAGAAGAAGTACCGGCTCAAGCACCTGGTCTGGGCGAGCAGGGAGCTGGAGCGCTT
CGCGCTGAACCCGGGCCTGCTGGAGACATCCGAGGGCTGTCAGCAGATCATCGGGCAGCTTCAGCCAGCG
CTCCAGACGGGCAGCGAGGAGCTGCGCTCGCTATACAACACGGTAGCGACCCTCTACTGCGTGCACCAGC

Fig. 22 cont'd-20

GGATCGAGGTCAAGGACACGAAGGAGGCTCTTGAGAAGATCGAGGAGGAGCAGAACAAGTCGCAGCAGAA
GACCCAGCAGGCGGCGGCCGACAAGGGCAACTCCTCAAAAGTATCTCAGAACTACCCGATCGTGCAGAAC
CTGCAGGGACAGATGGTCCACCAGGCCATCAGCCCACGGACGCTTAACGCCTGGGTCAAGGTGATCGAGG
AGAAGGCCTTCTCGCCGGAGGTCATCCCCATGTTCTCGGCACTCTCCGAGGGAGCCACCCCGCAGGACCT
GAACACGATGTTGAACACGGTCGGCGGGCACCAGGCGGCCATGCAGATGCTCAAGGATACCATCAACGAG
GAGGCTGCGGAGTGGGACCGCCTGCACCCAGTGCACGCGGGGCCCATCCCCCCGGCCAGATGAGAGAGC
CGCGGGGATCGGACATCGCGGGCACGACCAGCACCTTGCAGGAGCAAATCGCCTGGATGACTAGCAACCC
CCCGATCCCGGTCGGGGAGATCTACAAGCGGTGGATCATCCTCGGGTTGAACAAGATCGTGCGGATGTAC
AGCCCTGTCTCAATCCTGGACATCCGGCAGGGGCCCAAGGAGCCCTTCCGCGACTACGTCGACCGGTTCT
TCAAGACTCTCCGGGCGGAGCAGGCGACGCAGGACGTCAAGAACTGGATGACGGACACCTTGTTGGTCCA
GAACGCTAACCCGGACTGCAAGACGATCCTGAAGGCTCTCGGCCCGGGAGCGACCTTGGAGGAGATGATG
ACCGCGTGCCAGGGGGTCGGGGGACCCAGCCACAAGGCGCGGGTCTTGGCCGAGGCGATGTCCCAGGTCA
CGAACGCCGCGATCATGATGCAGCGGGGGAACTTCAAGGGCCAGCGCCGGATCATCAAGTGCTTCAACTG
CGGCAAGGAGGGCCACATCGCCCGGAACTGCCGGGCCCCGCGGAAGAAGGGCTGCTGGAAGTGCGGAAAG
GAGGGGCACCAGATGAAGGACTGCACGGAGCGCCAGGCGAATTTCCTCGGGAAGATCTGGCCGTCCAACA
AGGGGCGGCCAGGGAACTTCCTGCAATCGCGGCCAGAGCCGACGGCCCCTCCCGCGGAGAGCTTCGGGTT
CGGCGAGGAGATCACGCCCAGCCCCAAGCAAGAGCCGAAGGACAAGGAGCCGCCCCTTGCGTCCCTCAAG
TCGCTCTTCGGCAACGACCCGCTCTCCCAATGATAAGCTAGCGGATCCTGATCAGCCTCGACTGTGCCTT
CTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGAATTT

Thursday, August 2, 2007

Sequence 0 Length : 4823

AatII GACGTC
5 Sites
2510 2563 2646
2832 4027
AccI GTMKAC
2 Sites
3050 3979
AflIII ACRYGT
1 Site
1897
AluI AGCT
14 Sites
109 633 1340
1597 1643 1733
1959
2184 2951 3209
3278 3311 4471
4587
AlwNI CAGNNNCTG
4 Sites
1488 2129 3500
3638
AosII GRCGYC
6 Sites
2507 2560 2643
2829 2983 4024
ApaI GGGCCC
4 Sites
3075 3754 3955
4307
ApaLI GTGCAC
4 Sites
1583 2081 3351
3741
AvaI CYCGRG
6 Sites
3078 3230 3761
3891 4103 4386
BamHI GGATCC
1 Site
4593

BanI GGYRCC
5 Sites
538 2850 3667
4345 4677
BanII GRGCYC
6 Sites
2953 3075 3754
3955 3964 4307
BclI TGATCA
1 Site
4599
BcnI CCSGG
14 Sites
1173 1521 3021
3232 3233 3763
3764
3859 4003 4072
4105 4106 4293
4303
BglI GCCNNNNNGGC
3 Sites
2475 2597 2668
BglII AGATCT
3 Sites
458 3868 4393
Bsp1286 GDGCHC
14 Sites
652 1587 2085
2953 3075 3355
3670
3745 3754 3804
3955 3964 4307
4348
BspHI TCATGA
3 Sites
1007 1105 4213
BspNI CCWGG
19 Sites
52 1738 1751
1872 2475 2668
2977
3157 3189 3522
3551 3672 3833
3936

4140 4194 4374
4420 4671
BssHII GCGCGC
1 Site
3045
BstNI CCWGG
19 Sites
52 1738 1751
1872 2475 2668
2977
3157 3189 3522
3551 3672 3833
3936
4140 4194 4374
4420 4671
Cfr10I RCCGGY
3 Sites
847 3175 3982
CfrI YGGCCR
7 Sites
769 3445 3676
4177 4398 4416
4440
ClaI ATCGAT
1 Site
2287
DdeI CTNAG
13 Sites
12 204 397
711 787 1214 1623
2088 2158 2229
3111 3475 4731
DpnI GATC
27 Sites
190 195 460
1239 1247 1258
1333
2972 3028 3144
3267 3363 3399
3489
3564 3788 3855
3870 3885 3906
4086
4212 4251 4395
4491 4595 4601

Fig. 22 cont'd-21

DraIII CACNNNGTG
2 Sites
1161 3740
Eco47I GGWCC
11 Sites
122 586 919
1048 3021 3106
3514
3634 3724 4054
4151
Eco47III AGCGCT
2 Sites
3216 3289
EcoO109 RGGNCCY
5 Sites
3635 3750 3951
4152 4304
EcoRII CCWGG
19 Sites
50 1736 1749
1870 2473 2666
2975
3155 3187 3520
3549 3670 3831
3934
4138 4192 4372
4418 4669
EcoRV GATATC
1 Site
2294
Fnu4HI GCNGC
32 Sites
234 769 1283
1489 1492 1557
1700
1855 1973 1976
1994 2110 2250
2279
2282 3094 3276
3302 3312 3423
3442
3445 3676 3715
3780 4207 4221
4271
4322 4416 4440
4530
FnuDII CGCG
23 Sites
494 1273 1854
2169 2257 2281
2445
3039 3045 3047
3062 3100 3222
3747
3782 3798 3970
4134 4169 4209
4310
4439 4464
HaeII RGCGCY
7 Sites
12 1657 2027
3218 3291 4247
4373
HaeIII GGCC
29 Sites
55 771 1175
1423 1857 1875
1886
2268 2469 2662
3073 3155 3235
3447
3525 3576 3678
3752 3766 3953
4102
Mosaic and Group M Gag_dmyr-patent.doc 4179 4240 4282
4305 4400 4418
4442
4455
HgiAI GWGCWC
5 Sites
1587 2085 2953
3355 3745
HhaI GCGC
21 Sites
11 496 1273
1382 1556 1656
1723
1993 2026 2169
2249 3045 3047
3102
3217 3224 3290
3316 4169 4246
4372
HincII GTYRAC
5 Sites
413 886 2369
3051 3980
HinfI GANTC
14 Sites
43 59 357
383 401 725 779
807 1527 1923
1998 2222 2795
3995
HinPI GCGC
21 Sites
9 494 1271
1380 1554 1654
1721
1991 2024 2167
2247 3043 3045
3100
3215 3222 3288
3314 4167 4244
4370
HpaII CCGG
20 Sites
848 1172 1329
1519 1545 1692
3019
3176 3231 3585
3762 3858 3944
3983
4001 4071 4104
4247 4292 4301
MaeI CTAG
8 Sites
378 801 1034
1404 2385 3841
4588
4621
MaeII ACGT
12 Sites
669 1160 1196
2306 2507 2519
2560
2643 2724 2829
3976 4024
MaeIII GTNAC
9 Sites
270 1134 1361
1477 1540 2446
2533
2882 4196
MvaI CCNGG
33 Sites 52 1172 1520
1738 1751 1872
2475
2668 2977 3020
3157 3189 3231
3232
3522 3551 3672
3762 3763 3833
3858
3936 4002 4071
4104 4105 4140
4194
4292 4302 4374
4420 4671
NciI CCSGG
14 Sites
1172 1520 3020
3231 3232 3762
3763
3858 4002 4071
4104 4105 4292
4302
NcoI CCATGG
1 Site
2745
NdeI CATATG
2 Sites
2076 2619
NheI GCTAGC
1 Site
4587
NlaIII CATG
17 Sites
538 762 864
892 1011 1109 1181
1901 2219 2349
2367 2689 2749
3602
3683 4217 4812
NlaIV GGNNCC
24 Sites
92 540 1830
1869 2852 3023
3073
3623 3669 3726
3751 3752 3952
3953
3961 4153 4154
4305 4306 4347
4456
4528 4595 4679
NruI TCGCGA
1 Site
2257
NsiI ATGCAT
1 Site
796
Nsp7524I RCATGY
2 Sites
1901 4812
NspBII CMGCKG
10 Sites
1314 1559 2281
3039 3115 3359
3782
4223 4310 4464
PpuMI RGGWCCY
2 Sites
3635 4152
PssI RGGNCCY
5 Sites
3638 3753 3954
4155 4307
PstI CTGCAG

Fig. 22 cont'd-22

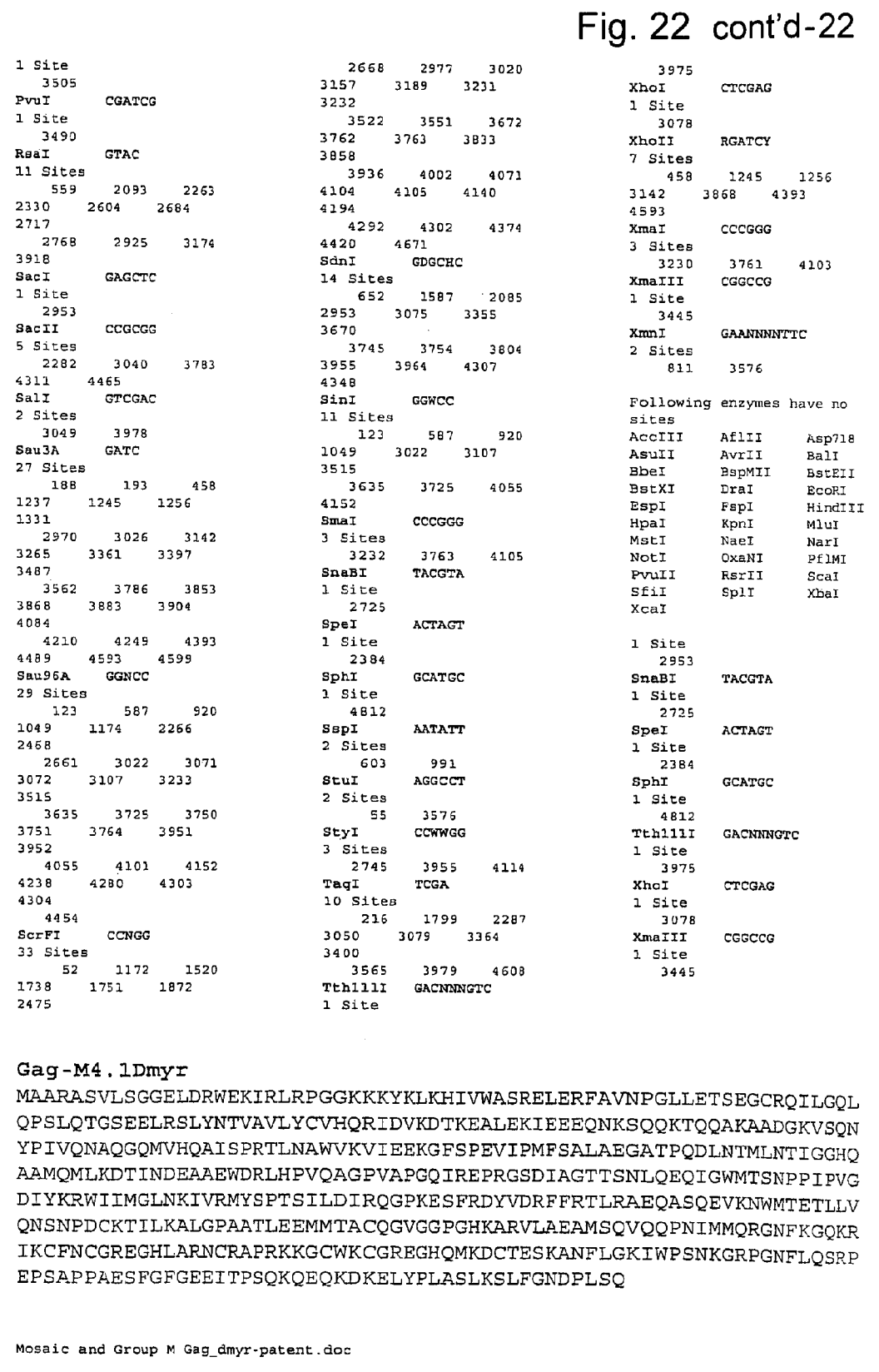

1 Site
3505
PvuI CGATCG
1 Site
3490
RsaI GTAC
11 Sites
559 2093 2263
2330 2604 2684
2717
2768 2925 3174
3918
SacI GAGCTC
1 Site
2953
SacII CCGCGG
5 Sites
2282 3040 3783
4311 4465
SalI GTCGAC
2 Sites
3049 3978
Sau3A GATC
27 Sites
188 193 458
1237 1245 1256
1331
2970 3026 3142
3265 3361 3397
3487
3562 3786 3853
3868 3883 3904
4084
4210 4249 4393
4489 4593 4599
Sau96A GGNCC
29 Sites
123 587 920
1049 1174 2266
2468
2661 3022 3071
3072 3107 3233
3515
3635 3725 3750
3751 3764 3951
3952
4055 4101 4152
4238 4280 4303
4304
4454
ScrFI CCNGG
33 Sites
52 1172 1520
1738 1751 1872
2475
2668 2977 3020
3157 3189 3231
3232
3522 3551 3672
3762 3763 3833
3858
3936 4002 4071
4104 4105 4140
4194
4292 4302 4374
4420 4671
SdnI GDGCHC
14 Sites
652 1587 2085
2953 3075 3355
3670
3745 3754 3804
3955 3964 4307
4348
SinI GGWCC
11 Sites
123 587 920
1049 3022 3107
3515
3635 3725 4055
4152
SmaI CCCGGG
3 Sites
3232 3763 4105
SnaBI TACGTA
1 Site
2725
SpeI ACTAGT
1 Site
2384
SphI GCATGC
1 Site
4812
SspI AATATT
2 Sites
603 991
StuI AGGCCT
2 Sites
55 3576
StyI CCWWGG
3 Sites
2745 3955 4114
TaqI TCGA
10 Sites
216 1799 2287
3050 3079 3364
3400
3565 3979 4608
Tth111I GACNNNGTC
1 Site
3975
XhoI CTCGAG
1 Site
3078
XhoII RGATCY
7 Sites
458 1245 1256
3142 3868 4393
4593
XmaI CCCGGG
3 Sites
3230 3761 4103
XmaIII CGGCCG
1 Site
3445
XmnI GAANNNNTTC
2 Sites
811 3576

Following enzymes have no sites

| | | |
|---|---|---|
| AccIII | AflII | Asp718 |
| AsuII | AvrII | BalI |
| BbeI | BspMII | BstEII |
| BstXI | DraI | EcoRI |
| EspI | FspI | HindIII |
| HpaI | KpnI | MluI |
| MstI | NaeI | NarI |
| NotI | OxaNI | PflMI |
| PvuII | RsrII | ScaI |
| SfiI | SplI | XbaI |
| XcaI | | |

1 Site
2953
SnaBI TACGTA
1 Site
2725
SpeI ACTAGT
1 Site
2384
SphI GCATGC
1 Site
4812
Tth111I GACNNNGTC
1 Site
3975
XhoI CTCGAG
1 Site
3078
XmaIII CGGCCG
1 Site
3445

Gag-M4.1Dmyr

MAARASVLSGGELDRWEKIRLRPGGKKKYKLKHIVWASRELERFAVNPGLLETSEGCRQILGQL
QPSLQTGSEELRSLYNTVAVLYCVHQRIDVKDTKEALEKIEEEQNKSQQKTQQAKAADGKVSQN
YPIVQNAQGQMVHQAISPRTLNAWVKVIEEKGFSPEVIPMFSALAEGATPQDLNTMLNTIGGHQ
AAMQMLKDTINDEAAEWDRLHPVQAGPVAPGQIREPRGSDIAGTTSNLQEQIGWMTSNPPIPVG
DIYKRWIIMGLNKIVRMYSPTSILDIRQGPKESFRDYVDRFFRTLRAEQASQEVKNWMTETLLV
QNSNPDCKTILKALGPAATLEEMMTACQGVGGPGHKARVLAEAMSQVQQPNIMMQRGNFKGQKR
IKCFNCGREGHLARNCRAPRKKGCWKCGREGHQMKDCTESKANFLGKIWPSNKGRPGNFLQSRP
EPSAPPAESFGFGEEITPSQKQEQKDKELYPLASLKSLFGNDPLSQ

Fig. 22 cont'd-23

HV13309 (Gag-M4.1Dmyr.wlv)

CTCGACAAGAAAATGGCGGCGCGCGCCTCGGTCCTTAGCGGGGGCGAGTTGGATCGGTG
GGAAAAGATCCGCTTGAGGCCAGGAGGGAAGAAGAAGTACAAGCTCAAGCACATCGTCT
GGGCGAGCAGAGAGCTCGAGCGGTTCGCGGTCAACCCGGGCCTGCTTGAGACATCGGAG
GGCTGTCGGCAAATCCTGGGGCAGCTTCAACCGTCCTTGCAAACGGGCAGCGAGGAGCT
GCGATCGCTATACAACACGGTAGCGGTCCTCTACTGCGTGCACCAGCGGATCGACGTCA
AGGACACGAAGGAGGCTCTTGAGAAGATTGAGGAAGAGCAGAACAAGTCGCAGCAGAAG
ACGCAGCAGGCGAAGGCCGCAGACGGCAAAGTATCTCAGAACTACCCGATCGTGCAGAA
CGCGCAGGGACAGATGGTCCACCAGGCCATCTCCCCACGGACGCTTAACGCCTGGGTCA
AAGTAATCGAGGAGAAGGGATTCAGCCCGGAAGTGATCCCCATGTTCTCGGCACTTGCG
GAGGGAGCCACCCCGCAGGACCTGAACACGATGTTGAACACCATCGGCGGGCACCAGGC
GGCCATGCAGATGCTTAAGGACACCATCAACGACGAGGCTGCGGAGTGGGACCGGCTTC
ACCCGGTGCAGGCGGGGCCCGTCGCGCCGGGCCAGATCAGAGAGCCGCGGGGATCGGAC
ATCGCGGGAACCACCAGCAACTTGCAGGAGCAAATCGGGTGGATGACTTCGAACCCCCC
GATCCCGGTCGGGGACATCTACAAGAGATGGATCATCATGGGGTTGAACAAGATCGTGA
GGATGTACAGCCCGACCAGCATCCTGGACATCCGACAGGGACCGAAGGAGTCGTTCAGA
GACTACGTAGACCGGTTCTTCCGGACTCTCCGGGCGGAGCAGGCGTCGCAGGAGGTCAA
GAACTGGATGACGGAGACCTTGTTGGTCCAGAACTCGAACCCGGACTGCAAGACCATCC
TGAAGGCTCTCGGCCCGGCGGCGACGTTGGAAGAGATGATGACGGCGTGCCAGGGAGTC
GGGGGACCCGGCCACAAGGCGCGGGTCTTGGCCGAGGCGATGAGCCAGGTGCAGCAGCC
GAACATCATGATGCAGCGGGGCAACTTCAAGGGACAGAAGCGGATCAAGTGTTTCAACT
GTGGCAGGGAGGGACACCTCGCCAGGAACTGCCGGGCCCCGCGGAAGAAGGGCTGCTGG
AAGTGCGGAAGGGAGGGGCACCAAATGAAGGACTGCACGGAGTCGAAGGCGAATTTCCT
CGGGAAGATCTGGCCGTCCAACAAGGGGCGGCCAGGGAACTTTCTGCAAAGCCGGCCGG
AGCCGTCGGCCCCGCCGGCGGAGTCCTTTGGGTTCGGGGAGGAGATCACGCCCTCGCAG
AAGCAAGAGCAAAAGGACAAGGAGCTCTACCCTCTTGCGTCCCTCAAGTCGCTCTTCGGC
AACGACCCGCTTTCGCAATGATAAGCTAGCGGATCCTGATCAGGCGCGCC

NheI AscI

HV13309 in HV10001, 4836bp

AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG

Fig. 22 cont'd-24

CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGACAAGAAAATGGCGGCGCGCGCCTCGGTCCTTAGCGGGGGCGAGTTGGAT
CGGTGGGAAAAGATCCGCTTGAGGCCAGGAGGGAAGAAGAAGTACAAGCTCAAGCACAT
CGTCTGGGCGAGCAGAGAGCTCGAGCGGTTCGCGGTCAACCCGGGCCTGCTTGAGACAT
CGGAGGGCTGTCGGCAAATCCTGGGGCAGCTTCAACCGTCCTTGCAAACGGGCAGCGAG
GAGCTGCGATCGCTATACAACACGGTAGCGGTCCTCTACTGCGTGCACCAGCGGATCGA
CGTCAAGGACACGAAGGAGGCTCTTGAGAAGATTGAGGAAGAGCAGAACAAGTCGCAGC
AGAAGACGCAGCAGGCGAAGGCCGCAGACGGCAAAGTATCTCAGAACTACCCGATCGTG
CAGAACGCGCAGGGACAGATGGTCCACCAGGCCATCTCCCCACGGACGCTTAACGCCTG
GGTCAAAGTAATCGAGGAGAAGGGATTCAGCCCGGAAGTGATCCCCATGTTCTCGGCAC
TTGCGGAGGGAGCCACCCCGCAGGACCTGAACACGATGTTGAACACCATCGGCGGGCAC
CAGGCGGCCATGCAGATGCTTAAGGACACCATCAACGACGAGGCTGCGGAGTGGGACCG
GCTTCACCCGGTGCAGGCGGGGCCCGTCGCGCCGGGCCAGATCAGAGAGCCGCGGGGAT
CGGACATCGCGGGAACCACCAGCAACTTGCAGGAGCAAATCGGGTGGATGACTTCGAAC
CCCCCGATCCCGGTCGGGGACATCTACAAGAGATGGATCATCATGGGGTTGAACAAGAT
CGTGAGGATGTACAGCCCGACCAGCATCCTGGACATCCGACAGGGACCGAAGGAGTCGT
TCAGAGACTACGTAGACCGGTTCTTCCGGACTCTCCGGGCGGAGCAGGCGTCGCAGGAG

Fig. 22 cont'd-25

GTCAAGAACTGGATGACGGAGACCTTGTTGGTCCAGAACTCGAACCCGGACTGCAAGAC
CATCCTGAAGGCTCTCGGCCCGGCGGCGACGTTGGAAGAGATGATGACGGCGTGCCAGG
GAGTCGGGGGACCCGGCCACAAGGCGCGGGTCTTGGCCGAGGCGATGAGCCAGGTGCAG
CAGCCGAACATCATGATGCAGCGGGGCAACTTCAAGGGACAGAAGCGGATCAAGTGTTT
CAACTGTGGCAGGGAGGGACACCTCGCCAGGAACTGCCGGGCCCCGCGGAAGAAGGGCT
GCTGGAAGTGCGGAAGGGAGGGGCACCAAATGAAGGACTGCACGGAGTCGAAGGCGAAT
TTCCTCGGGAAGATCTGGCCGTCCAACAAGGGGCGGCCAGGGAACTTTCTGCAAAGCCG
GCCGGAGCCGTCGGCCCCGCCGGCGGAGTCCTTTGGGTTCGGGGAGGAGATCACGCCCT
CGCAGAAGCAAGAGCAAAAGGACAAGGAGCTCTACCCTCTTGCGTCCCTCAAGTCGCTC
TTCGGCAACGACCCGCTTTCGCAATGATAAGCTAGCGGATCCTGATCAGGCGCGCCGAGCTCGC
TGATCAGCCTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGGGGAGGAT
TGGGAAGACAATAGCAGGCATGCTGGGGAATTT

Thursday, August 2, 2007

Sequence 0 Length : 4836

AatII GACGTC
5 Sites
2510 2563 2646
2832 3370
AccI GTMKAC
2 Sites
3050 3970
AccIII TCCGGA
1 Site
3982
AflII CTTAAG
1 Site
3681
AflIII ACRYGT
1 Site
1897
AluI AGCT
16 Sites
109 633 1340
1597 1643 1733
1959
2184 2951 3179
3209 3278 3311
4517
4578 4606
AlwNI CAGNNNCTG
4 Sites
1488 2129 3629
4285
AosII GRCGYC
7 Sites
2507 2560 2643
2829 2983 3367
4005
ApaI GGGCCC
3 Sites
3075 3745 4295
ApaLI GTGCAC
3 Sites
1583 2081 3351
AsuII TTCGAA
1 Site
3834
AvaI CYCGRG
3 Sites
3210 3230 4374
BamHI GGATCC
1 Site
4584
BanI GGYRCC
5 Sites
538 2850 3658
4333 4690
BanII GRGCYC
7 Sites
2953 3075 3211
3745 4295 4519
4608
BclI TGATCA
2 Sites
4590 4612
BcnI CCSGG
14 Sites
1173 1521 3021
3232 3233 3577
3730
3755 3850 3994
4063 4096 4148
4291
BglI GCCNNNNNGGC
4 Sites
2475 2597 2668
4449
BglII AGATCT
2 Sites
458 4381
Bsp1286 GDGCHC
13 Sites
652 1587 2085
2953 3075 3211
3355
3661 3745 4295
4336 4519 4608
BspHI TCATGA
3 Sites
1007 1105 4204
BspMII TCCGGA
1 Site
3982
BspNI CCWGG
18 Sites
52 1738 1751
1872 2475 2668
2977
3157 3270 3513
3542 3663 3927
4131
4185 4280 4408
4684
BssHII GCGCGC
4 Sites
3045 3098 3100
4599
BstNI CCWGG
18 Sites
52 1738 1751
1872 2475 2668
2977
3157 3270 3513
3542 3663 3927
4131
4185 4280 4408
4684
BstXI CCANNNNNNTGG
1 Site
3926
Cfr10I RCCGGY
5 Sites
847 3718 3973
4426 4448
CfrI YGGCCR
7 Sites
769 3667 4148
4168 4386 4404
4428
ClaI ATCGAT
1 Site
2287
DdeI CTNAG
13 Sites
12 204 397
711 787 1214 1623
2088 2158 2229
3111 3466 4744
DpnI GATC
26 Sites
190 195 460
1239 1247 1258
1333
2972 3028 3130
3144 3317 3363
3480
3585 3762 3779
3846 3876 3897
4242
4383 4479 4586
4592 4614
DraIII CACNNNGTG

Fig. 22 cont'd-26

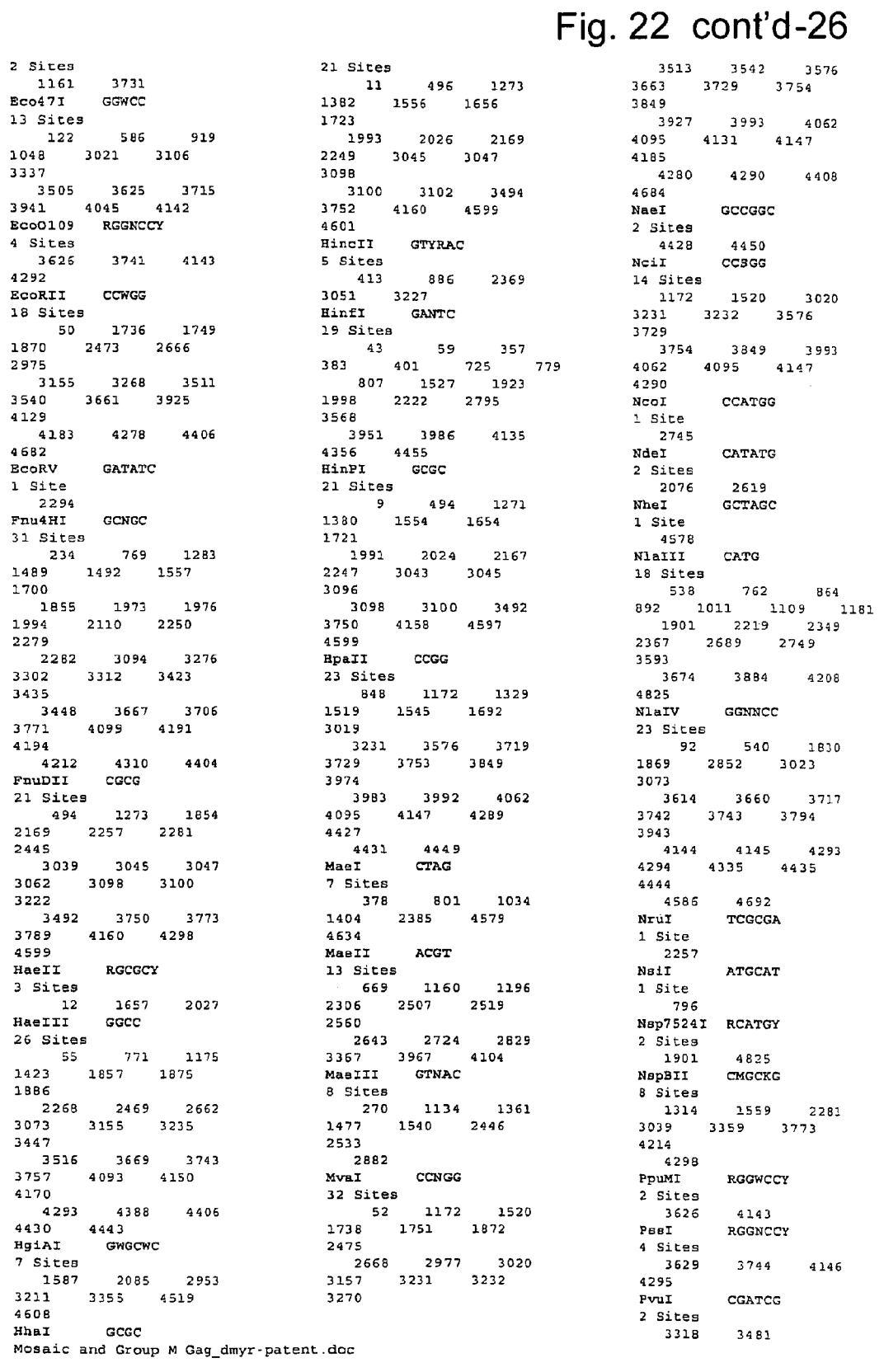

2 Sites
1161 3731
Eco47I GGWCC
13 Sites
122 586 919
1048 3021 3106
3337
3505 3625 3715
3941 4045 4142
EcoO109 RGGNCCY
4 Sites
3626 3741 4143
4292
EcoRII CCWGG
18 Sites
50 1736 1749
1870 2473 2666
2975
3155 3268 3511
3540 3661 3925
4129
4183 4278 4406
4682
EcoRV GATATC
1 Site
2294
Fnu4HI GCNGC
31 Sites
234 769 1283
1489 1492 1557
1700
1855 1973 1976
1994 2110 2250
2279
2282 3094 3276
3302 3312 3423
3435
3448 3667 3706
3771 4099 4191
4194
4212 4310 4404
FnuDII CGCG
21 Sites
494 1273 1854
2169 2257 2281
2445
3039 3045 3047
3062 3098 3100
3222
3492 3750 3773
3789 4160 4298
4599
HaeII RGCGCY
3 Sites
12 1657 2027
HaeIII GGCC
26 Sites
55 771 1175
1423 1857 1875
1886
2268 2469 2662
3073 3155 3235
3447
3516 3669 3743
3757 4093 4150
4170
4293 4388 4406
4430 4443
HgiAI GWGCWC
7 Sites
1587 2085 2953
3211 3355 4519
4608
HhaI GCGC
Mosaic and Group M Gag_dmyr-patent.doc 21 Sites
11 496 1273
1382 1556 1656
1723
1993 2026 2169
2249 3045 3047
3098
3100 3102 3494
3752 4160 4599
4601
HincII GTYRAC
5 Sites
413 886 2369
3051 3227
HinfI GANTC
19 Sites
43 59 357
383 401 725 779
807 1527 1923
1998 2222 2795
3568
3951 3986 4135
4356 4455
HinPI GCGC
21 Sites
9 494 1271
1380 1554 1654
1721
1991 2024 2167
2247 3043 3045
3096
3098 3100 3492
3750 4158 4597
4599
HpaII CCGG
23 Sites
848 1172 1329
1519 1545 1692
3019
3231 3576 3719
3729 3753 3849
3974
3983 3992 4062
4095 4147 4289
4427
4431 4449
MaeI CTAG
7 Sites
378 801 1034
1404 2385 4579
4634
MaeII ACGT
13 Sites
669 1160 1196
2306 2507 2519
2560
2643 2724 2829
3367 3967 4104
MaeIII GTNAC
8 Sites
270 1134 1361
1477 1540 2446
2533
2882
MvaI CCNGG
32 Sites
52 1172 1520
1738 1751 1872
2475
2668 2977 3020
3157 3231 3232
3270

3513 3542 3576
3663 3729 3754
3849
3927 3993 4062
4095 4131 4147
4185
4280 4290 4408
4684
NaeI GCCGGC
2 Sites
4428 4450
NciI CCSGG
14 Sites
1172 1520 3020
3231 3232 3576
3729
3754 3849 3993
4062 4095 4147
4290
NcoI CCATGG
1 Site
2745
NdeI CATATG
2 Sites
2076 2619
NheI GCTAGC
1 Site
4578
NlaIII CATG
18 Sites
538 762 864
892 1011 1109 1181
1901 2219 2349
2367 2689 2749
3593
3674 3884 4208
4825
NlaIV GGNNCC
23 Sites
92 540 1830
1869 2852 3023
3073
3614 3660 3717
3742 3743 3794
3943
4144 4145 4293
4294 4335 4435
4444
4586 4692
NruI TCGCGA
1 Site
2257
NsiI ATGCAT
1 Site
796
Nsp7524I RCATGY
2 Sites
1901 4825
NspBII CMGCKG
8 Sites
1314 1559 2281
3039 3359 3773
4214
4298
PpuMI RGGWCCY
2 Sites
3626 4143
PssI RGGNCCY
4 Sites
3629 3744 4146
4295
PvuI CGATCG
2 Sites
3318 3481

Fig. 22 cont'd-27

RsaI GTAC
11 Sites
559 2093 2263
2330 2604 2684
2717
2768 2925 3174
3909
SacI GAGCTC
4 Sites
2953 3211 4519
4608
SacII CCGCGG
4 Sites
2282 3040 3774
4299
SalI GTCGAC
1 Site
3049
Sau3A GATC
26 Sites
188 193 458
1237 1245 1256
1331
2970 3026 3128
3142 3315 3361
3478
3583 3760 3777
3844 3874 3895
4240
4381 4477 4584
4590 4612
Sau96A GGNCC
27 Sites
123 587 920
1049 1174 2266
2468
2661 3022 3071
3072 3107 3233
3338
3506 3626 3716
3741 3742 3755
3942
4046 4092 4143
4291 4292 4442

ScrFI CCNGG
32 Sites
52 1172 1520
1738 1751 1872
2475
2668 2977 3020
3157 3231 3232
3270
3513 3542 3576
3663 3729 3754
3849
3927 3993 4062
4095 4131 4147
4185
4280 4290 4408
4684
SdnI GDGCHC
13 Sites
652 1587 2085
2953 3075 3211
3355
3661 3745 4295
4336 4519 4608
SinI GGWCC
13 Sites
123 587 920
1049 3022 3107
3338
3506 3626 3716
3942 4046 4143
SmaI CCCGGG
1 Site
3232
SnaBI TACGTA
2 Sites
2725 3968
SpeI ACTAGT
1 Site
2384
SphI GCATGC
1 Site
4825
SspI AATATT
2 Sites 603 991
StuI AGGCCT
1 Site
55
StyI CCWWGG
1 Site
2745
TaqI TCGA
12 Sites
216 1799 2287
3050 3079 3211
3364
3556 3834 4056
4359 4621
XhoI CTCGAG
1 Site
3210
XhoII RGATCY
6 Sites
458 1245 1256
3142 4381 4584
XmaI CCCGGG
1 Site
3230
XmaIII CGGCCG
1 Site
4428
XmnI GAANNNNTTC
2 Sites
811 3557

Following enzymes have no sites

| | | |
|---|---|---|
| Asp718 | AvrII | BalI |
| BbeI | BstEII | DraI |
| Eco47III | EcoRI | EspI |
| FspI | HindIII | HpaI |
| KpnI | MluI | MstI |
| NarI | NotI | OxaNI |
| PflMI | PstI | PvuII |
| RsrII | ScaI | SfiI |
| SplI | Tth111I | XbaI |
| XcaI | | |

Gag_M4.2 Dmyr

MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQN
YPIVQNIQGQMVHQPISPRTLNAWVKVVEEKAFSPEVIPMFTALSDGATPQDLNSMLNAVGGHQ
AAMQILKDTINEEAADWDRLHPVHAGPVAPGQMREPRGSDIAGTTSTLQEQIGWMTNNPPIPVG
EIYKRWIILGLNKIVRMYSPVSILDIKQGPKESFRDYVDRFFKVLRAEQATQDVKNWMTDTLLI
QNANPDCKSILRALGPGATLEEMMTACQGVGGPSHKARILAEAMSQVTNSATIMMQRGNFRNQR
KTVKCFNCGKEGHLARNCKAPRKRGCWKCGKEGHQMKECTERQANFLGKIWPSSKGRPGNFPQS
RPEPTAPPEESFRFGEETTTPSQKQEPIDKELYPLASLRSLFGNDPSSQAS

HV13316 (Gag_M4.2 Dmyr.wlv) cloned in to XhoI

GTCGAGAAGAAAATGGCGGCTCGCGCCTCGGTCCTTAGCGGGGGCAAGTTGGATGCGTGGGAAA
AGATCCGCTTGAGGCCAGGAGGGAAGAAGAAGTACCGGCTCAAGCACCTTGTCTGGGCGAGCAG
AGAGCTCGACCGGTTCGCGCTGAACCCGTCGCTGCTTGAGACAGCCGAGGGCTGCAAGCAAATC
ATGAAGCAGCTTCAACCGGCGTTGAAGACGGGCACGGAGGAGCTGAAGTCGCTATACAACACGG
TAGCGACGCTCTACTGCGTGCACGAGAAGATCGACGTCAGGGACACGAAGGAGGCTCTTGACAA

Fig. 22 cont'd-28

GATTGAGGAAGAGCAGAACAAGATCCAGCAGAAGACGCAGCAGGCGAAGGAGGCAGACGGCAAA
GTATCTCAGAACTACCCGATCGTGCAGAACATCCAGGGACAGATGGTCCACCAGCCGATCTCCC
CACGGACGCTTAACGCCTGGGTCAAAGTAGTCGAGGAGAAGGCATTCAGCCCGGAAGTGATCCC
CATGTTCACTGCACTTAGCGACGGAGCCACCCCGCAGGACCTGAACAGCATGTTGAACGCCGTC
GGCGGGCACCAGGCGGCCATGCAGATCCTTAAGGACACCATCAACGAGGAGGCTGCGGACTGGG
ACCGGCTTCACCCGGTGCACGCGGGGCCCGTCGCGCCGGGCCAGATGAGAGAGCCGCGGGGATC
GGACATCGCGGGAACCACCAGCACCTTGCAGGAGCAAATCGGGTGGATGACTAACAACCCCCCG
ATCCCGGTCGGGGAGATCTACAAGAGATGGATCATCCTGGGGTTGAACAAGATCGTGAGGATGT
ACAGCCCAGTCAGCATCCTGGACATCAAGCAGGGACCGAAGGAGTCGTTCAGAGACTACGTCGA
CCGGTTCTTCAAAGTCCTCCGGGCGGAGCAGGCGACGCAGGACGTCAAGAACTGGATGACGGAC
ACCTTGTTGATCCAGAACGCGAACCCGGACTGCAAGTCGATCCTGCGGGCTCTCGGCCCGGGAG
CGACGTTGGAAGAGATGATGACGGCGTGCCAGGGAGTCGGGGGACCCTCGCACAAGGCGCGGAT
CTTGGCCGAGGCGATGTCACAAGTGACTAACAGCGCGACCATCATGATGCAGCGGGGCAACTTC
CGGAACCAGCGGAAGACGGTGAAGTGTTTCAACTGTGGCAAGGAGGGACACCTCGCCAGGAACT
GCAAGGCCCCGCGGAAGCGGGGCTGCTGGAAGTGCGGAAAGGAGGGGCACCAAATGAAGGAGTG
CACGGAGCGGCAGGCGAATTTCCTCGGGAAGATCTGGCCGTCCTCGAAGGGGCGGCCAGGGAAC
TTTCCGCAAAGCCGGCCGGAGCCGACGGCCCCGCCGGAGGAGTCCTTTCGGTTCGGGGAGGAGA
CGACCACGCCCTCGCAGAAGCAAGAGCCGATCGACAAGGAGCTCTACCCTCTTGCGTCCCTCCG
GTCGCTCTTCGGCAACGACCCGTCGTCGCAAGCGTCG*TGATAA*GCTAGCGGATCCGGCGCGCC
NheI AscI

>HV13316 in HV10001 4816bp

AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT

Fig. 22 cont'd-29

TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTAGCGGGGGCAAGTTGGATGCGTGGGAAAAGATCCGCTTGAGGCCAGGAGGGA
AGAAGAAGTACCGGCTCAAGCACCTTGTCTGGGCGAGCAGAGAGCTCGACCGGTTCGCGCTGAA
CCCGTCGCTGCTTGAGACAGCCGAGGGCTGCAAGCAAATCATGAAGCAGCTTCAACCGGCGTTG
AAGACGGGCACGGAGGAGCTGAAGTCGCTATACAACACGGTAGCGACGCTCTACTGCGTGCACG
AGAAGATCGACGTCAGGGACACGAAGGAGGCTCTTGACAAGATTGAGGAAGAGCAGAACAAGAT
CCAGCAGAAGACGCAGCAGGCGAAGGAGGCAGACGGCAAAGTATCTCAGAACTACCCGATCGTG
CAGAACATCCAGGGACAGATGGTCCACCAGCCGATCTCCCCACGGACGCTTAACGCCTGGGTCA
AAGTAGTCGAGGAGAAGGCATTCAGCCCGGAAGTGATCCCCATGTTCACTGCACTTAGCGACGG
AGCCACCCCGCAGGACCTGAACAGCATGTTGAACGCCGTCGGCGGGCACCAGGCGGCCATGCAG
ATCCTTAAGGACACCATCAACGAGGAGGCTGCGGACTGGGACCGGCTTCACCCGGTGCACGCGG
GGCCCGTCGCGCCGGGCCAGATGAGAGAGCCGCGGGGATCGGACATCGCGGGAACCACCAGCAC
CTTGCAGGAGCAAATCGGGTGGATGACTAACAACCCCCCGATCCCGGTCGGGGAGATCTACAAG
AGATGGATCATCCTGGGGTTGAACAAGATCGTGAGGATGTACAGCCCAGTCAGCATCCTGGACA
TCAAGCAGGGACCGAAGGAGTCGTTCAGAGACTACGTCGACCGGTTCTTCAAAGTCCTCCGGGC
GGAGCAGGCGACGCAGGACGTCAAGAACTGGATGACGGACACCTTGTTGATCCAGAACGCGAAC
CCGGACTGCAAGTCGATCCTGCGGGCTCTCGGCCCGGGAGCGACGTTGGAAGAGATGATGACGG
CGTGCCAGGGAGTCGGGGGACCCTCGCACAAGGCGCGGATCTTGGCCGAGGCGATGTCACAAGT
GACTAACAGCGCGACCATCATGATGCAGCGGGGCAACTTCCGGAACCAGCGGAAGACGGTGAAG
TGTTTCAACTGTGGCAAGGAGGGACACCTCGCCAGGAACTGCAAGGCCCCGCGGAAGCGGGGCT
GCTGGAAGTGCGGAAAGGAGGGGCACCAAATGAAGGAGTGCACGGAGCGGCAGGCGAATTTCCT
CGGGAAGATCTGGCCGTCCTCGAAGGGGCGGCCAGGGAACTTTCCGCAAAGCCGGCCGGAGCCG
ACGGCCCCGCCGGAGGAGTCCTTTCGGTTCGGGGAGGAGACGACCACGCCCTCGCAGAAGCAAG
AGCCGATCGACAAGGAGCTCTACCCTCTTGCGTCCCTCCGGTCGCTCTTCGGCAACGACCCGTC
GTCGCAAGCGTCG*TGATAA*GCTAGCGGATCCGGCGCGCCGAGCTCGCTGATCAGCCTCGACTGT
GCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAG
GCATGCTGGGGAATTT

Thursday, August 2, 2007 Sequence 1 Length : 4816 AatII GACGTC
6 Sites

Mosaic and Group M Gag_dmyr-patent.doc

Fig. 22 cont'd-30

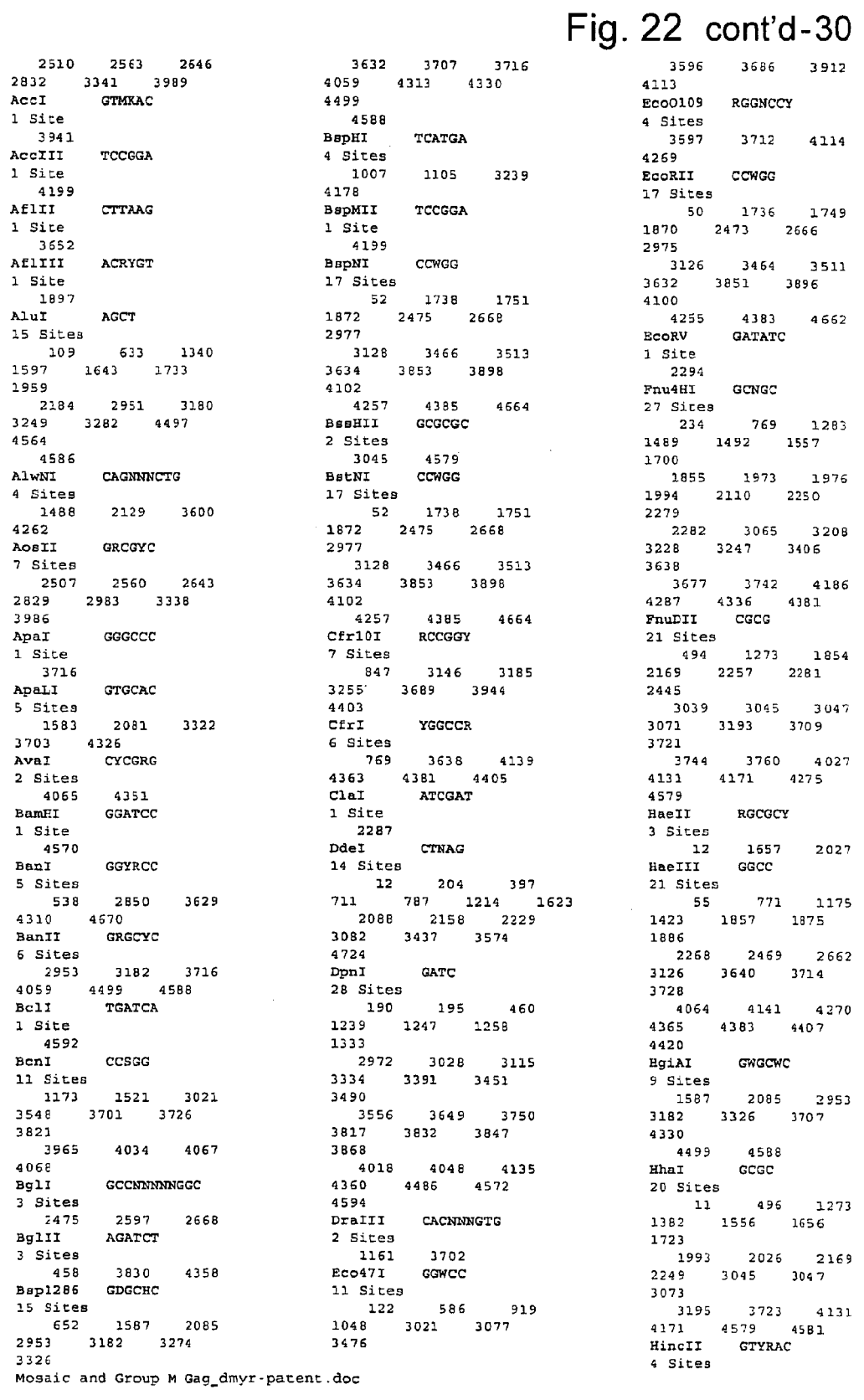

2510 2563 2646
2832 3341 3989
AccI GTMKAC
1 Site
3941
AccIII TCCGGA
1 Site
4199
AflII CTTAAG
1 Site
3652
AflIII ACRYGT
1 Site
1897
AluI AGCT
15 Sites
109 633 1340
1597 1643 1733
1959
2184 2951 3180
3249 3282 4497
4564
4586
AlwNI CAGNNNCTG
4 Sites
1488 2129 3600
4262
AosII GRCGYC
7 Sites
2507 2560 2643
2829 2983 3338
3986
ApaI GGGCCC
1 Site
3716
ApaLI GTGCAC
5 Sites
1583 2081 3322
3703 4326
AvaI CYCGRG
2 Sites
4065 4351
BamHI GGATCC
1 Site
4570
BanI GGYRCC
5 Sites
538 2850 3629
4310 4670
BanII GRGCYC
6 Sites
2953 3182 3716
4059 4499 4588
BclI TGATCA
1 Site
4592
BcnI CCSGG
11 Sites
1173 1521 3021
3548 3701 3726
3821
3965 4034 4067
4068
BglI GCCNNNNNGGC
3 Sites
2475 2597 2668
BglII AGATCT
3 Sites
458 3830 4358
Bsp1286 GDGCHC
15 Sites
652 1587 2085
2953 3182 3274
3326

3632 3707 3716
4059 4313 4330
4499
4588
BspHI TCATGA
4 Sites
1007 1105 3239
4178
BspMII TCCGGA
1 Site
4199
BspNI CCWGG
17 Sites
52 1738 1751
1872 2475 2668
2977
3128 3466 3513
3634 3853 3898
4102
4257 4385 4664
BssHII GCGCGC
2 Sites
3045 4579
BstNI CCWGG
17 Sites
52 1738 1751
1872 2475 2668
2977
3128 3466 3513
3634 3853 3898
4102
4257 4385 4664
Cfr10I RCCGGY
7 Sites
847 3146 3185
3255 3689 3944
4403
CfrI YGGCCR
6 Sites
769 3638 4139
4363 4381 4405
ClaI ATCGAT
1 Site
2287
DdeI CTNAG
14 Sites
12 204 397
711 787 1214 1623
2088 2158 2229
3082 3437 3574
4724
DpnI GATC
28 Sites
190 195 460
1239 1247 1258
1333
2972 3028 3115
3334 3391 3451
3490
3556 3649 3750
3817 3832 3847
3868
4018 4048 4135
4360 4486 4572
4594
DraIII CACNNNGTG
2 Sites
1161 3702
Eco47I GGWCC
11 Sites
122 586 919
1048 3021 3077
3476

3596 3686 3912
4113
EcoO109 RGGNCCY
4 Sites
3597 3712 4114
4269
EcoRII CCWGG
17 Sites
50 1736 1749
1870 2473 2666
2975
3126 3464 3511
3632 3851 3896
4100
4255 4383 4662
EcoRV GATATC
1 Site
2294
Fnu4HI GCNGC
27 Sites
234 769 1283
1489 1492 1557
1700
1855 1973 1976
1994 2110 2250
2279
2282 3065 3208
3228 3247 3406
3638
3677 3742 4186
4287 4336 4381
FnuDII CGCG
21 Sites
494 1273 1854
2169 2257 2281
2445
3039 3045 3047
3071 3193 3709
3721
3744 3760 4027
4131 4171 4275
4579
HaeII RGCGCY
3 Sites
12 1657 2027
HaeIII GGCC
21 Sites
55 771 1175
1423 1857 1875
1886
2268 2469 2662
3126 3640 3714
3728
4064 4141 4270
4365 4383 4407
4420
HgiAI GWGCWC
9 Sites
1587 2085 2953
3182 3326 3707
4330
4499 4588
HhaI GCGC
20 Sites
11 496 1273
1382 1556 1656
1723
1993 2026 2169
2249 3045 3047
3073
3195 3723 4131
4171 4579 4581
HincII GTYRAC
4 Sites

Fig. 22 cont'd-31

```
       413     886    2369         3964    4033    4066         3940
3942                              4067                         Sau3A    GATC
HinfI    GANTC                    NcoI     CCATGG              28 Sites
16 Sites                          1 Site                            188     193     458
     43      59     357                2745                    1237    1245    1256
   383     401     725     779    NdeI     CATATG              1331
   807    1527    1923             2 Sites                          2970    3026    3113
  1998    2222    2795                 2076    2619            3332    3389    3449
  3922                             NheI     GCTAGC              3488
  4106    4432                     1 Site                           3554    3647    3748
HinPI    GCGC                          4564                    3815    3830    3845
20 Sites                          NlaIII   CATG                3866
       9     494    1271           19 Sites                         4016    4046    4133
  1380    1554    1654                  538     762     864    4358    4484    4570
  1721                                892    1011    1109    1181    4592
  1991    2024    2167                 1901    2219    2349    Sau96A   GGNCC
  2247    3043    3045                 2367    2689    2749    21 Sites
  3071                             3243                             123     587     920
  3193    3721    4129                 3564    3612    3645    1049    1174    2266
  4169    4577    4579             4182    4805                2468
HpaII    CCGG                      NlaIV    GGNNCC                  2661    3022    3078
25 Sites                          22 Sites                     3477    3597    3687
       848    1172    1329              92     540    1830    3712
  1519    1545    1692             1869    2852    3023             3713    3726    3913
  3019                             3585                        4063    4114    4269
  3147    3186    3256             3631    3688    3713        4419
  3547    3690    3700             3714    3765    3914        ScrFI    CCNGG
  3724                             4115                        28 Sites
  3820    3945    3963                 4116    4204    4271         52    1172    1520
  4033    4066    4200             4312    4412    4421        1738    1751    1872
  4404                             4572                        2475
  4408    4426    4518             4672                             2668    2977    3020
  4574                             NruI     TCGCGA              3128    3466    3513
MaeI     CTAG                      1 Site                      3547
7 Sites                               2257                          3634    3700    3725
       378    801    1034         NsiI     ATGCAT              3820    3853    3898
  1404    2385    4565             1 Site                      3964
  4614                                 796                          4033    4066    4067
MaeII    ACGT                      Nsp7524I  RCATGY             4102    4257    4385
14 Sites                          3 Sites                      4664
       669    1160    1196             1901    3612    4805   SdnI     GDGCHC
  2306    2507    2519            NspBII   CMGCKG              15 Sites
  2560                             8 Sites                          652    1587    2085
  2643    2724    2829                 1314    1559    2281    2953    3182    3274
  3338    3938    3986             3039    3744    4188        3326
  4075                             4209                             3632    3707    3716
MaeIII   GTNAC                     4275                        4059    4313    4330
10 Sites                          PpuMI    RGGWCCY             4499
       270    1134    1361         2 Sites                         4588
  1477    1540    2446                 3597    4114            SinI     GGWCC
  2533                             PssI     RGGNCCY             11 Sites
  2882    4151    4158              4 Sites                         123     587     920
MvaI     CCNGG                          3600    3715    4117   1049    3022    3078
28 Sites                          4272                         3477
       52    1172    1520         PvuI     CGATCG                   3597    3687    3913
  1738    1751    1872             2 Sites                      4114
  2475                                 3452    4487            SmaI     CCCGGG
       2668    2977    3020       RsaI     GTAC                1 Site
  3128    3466    3513             11 Sites                         4067
  3547                                 559    2093    2263    SnaBI    TACGTA
       3634    3700    3725        2330    2604    2684        1 Site
  3820    3853    3898             2717                            2725
  3964                                  2768    2925    3145   SpeI     ACTAGT
       4033    4066    4067        3880                        1 Site
  4102    4257    4385            SacI     GAGCTC                   2384
  4664                             4 Sites                     SphI     GCATGC
NaeI     GCCGGC                         2953    3182    4499   1 Site
1 Site                             4588                             4805
     4405                         SacII    CCGCGG              SspI     AATATT
NciI     CCSGG                     4 Sites                     2 Sites
11 Sites                               2282    3040    3745         603     991
       1172    1520    3020        4276                        StuI     AGGCCT
  3547    3700    3725            SalI     GTCGAC              1 Site
  3820                             1 Site                          55
Mosaic and Group M Gag_dmyr-patent.doc
```

Fig. 22 cont'd-32

StyI CCWWGG
1 Site
2745
TaqI TCGA
12 Sites
216 1799 2287
3050 3182 3335
3527
3941 4045 4372
4487 4601

Tth111I GACNNNGTC
1 Site
3537
XhoII RGATCY
10 Sites
458 1245 1256
3113 3389 3647
3830
4133 4358 4570
XmaI CCCGGG 1 Site
4065
XmaIII CGGCCG
1 Site
4405
XmnI GAANNNNTTC
3 Sites
811 3538 4225

Need re-create XhoI site at the 5' end
Primer:
Gag-M2-4-fG/C:
GGGCGCCTCGAGAAGAAAATGGCGGCTCG Gag_M4.3 Dmyr
MAARASILRGGKLDKWEKIRLRPGGKKRYMLKHLIWASRELERFALNPGLLETAEGCQQIIEQL
QSTLKTGSEELKSLFNTVATLYCVHQRIEVKDTKEALDKVEEEQNKSKKKAQQAAADTGNSSQV
SQNYPIVQNLQGQMVHQALSPRTLNAWVKVIEEKAFSPEIIPMFTALSEGATPSDLNTMLNTVG
GHQAAMQMLKDTINEEAAEWDRVHPVHAGPIPPGQMREPRGSDIAGTTSSLQEQIAWMTSNPPV
PVGEIYKRWIVLGLNKIVRMYSPVSILDIRQGPKEPFRDYVDRFFKTLRAEQASQDVKNWMTET
LLVQNANPDCKTILRALGPGASLEEMMTACQGVGGPSHKARVLAEAMSQTNSAILMQRSNFKGS
KRIVKCFNCGKEGHIARNCRAPRKRGCWKCGQEGHQMKDCNERQANFLGKIWPSHKGRPGNFLQ
NRPEPTAPPEPTAPPAESFRFEETTPAPKQELKDREPLTSLKSLFGSDPLSQAS HV13317 (Gag_M4.3 Dmyr.wlv)
GTCGAGAAGAAAATGGCGGCTCGCGCCTCGATCCTTCGAGGGGGCAAGTTGGATAAGTGGGAAA
AGATCCGCTTGAGGCCAGGAGGGAAGAAGAGATACATGCTCAAGCACCTGATCTGGGCGAGCAG
AGAGCTGGAGCGGTTCGCGCTGAACCCGGGCCTGCTTGAGACAGCGGAGGGCTGTCAGCAAATC
ATCGAGCAGCTTCAAAGCACGCTGAAGACGGGCAGCGAGGAGCTGAAGTCGCTATTCAACACGG
TAGCGACCCTCTACTGCGTGCACCAGCGGATCGAGGTCAAGGACACGAAGGAGGCTCTTGACAA
GGTGGAGGAAGAGCAGAACAAGTCGAAGAAGAAGGCGCAGCAGGCGGCGGCCGACACCGGCAAC
TCCTCACAAGTATCTCAGAACTACCCGATCGTGCAGAACCTGCAGGGACAGATGGTCCACCAGG
CCCTCTCCCCACGGACGCTTAACGCCTGGGTCAAAGTAATCGAGGAGAAGGCCTTCAGCCCGGA
AATCATCCCCATGTTCACAGCACTTTCCGAGGGAGCCACCCCGAGCGACCTGAACACGATGTTG
AACACCGTCGGCGGGCACCAGGCGGCCATGCAGATGCTTAAGGACACCATCAACGAGGAGGCTG
CGGAGTGGGACCGGGTGCACCCGGTGCACGCGGGGCCCATCCCACCGGGCCAGATGAGAGAGCC
GCGGGGATCGGACATCGCGGGAACCACCAGCAGCTTGCAGGAGCAAATCGCCTGGATGACTTCG
AACCCCCCGGTCCCGGTCGGGGAGATCTACAAGAGATGGATCGTCCTCGGGTTGAACAAGATCG
TGAGGATGTACAGCCCTGTGTCAATCCTGGACATCCGACAGGGACCGAAGGAGCCCTTCAGAGA
CTACGTCGACCGGTTCTTCAAGACTCTCCGGGCGGAGCAGGCGTCGCAGGACGTCAAGAACTGG
ATGACGGAGACCTTGTTGGTCCAGAACGCTAACCCGGACTGCAAGACCATCCTGCGCGCTCTCG
GCCCGGGAGCGTCCTTGGAAGAGATGATGACGGCGTGCCAGGGAGTCGGGGGACCCTCACACAA
GGCGCGGGTCTTGGCCGAGGCGATGAGCCAGACGAACTCCGCCATCCTCATGCAGCGGTCCAAC
TTCAAGGGAAGCAAGCGGATCGTCAAGTGTTTCAACTGTGGCAAGGAGGGACACATCGCCAGGA
ACTGCCGGGCCCCGCGGAAGCGAGGCTGCTGGAAGTGCGGACAGGAGGGGCACCAAATGAAGGA
CTGCAACGAGCGCCAGGCGAATTTCCTCGGGAAGATCTGGCCGTCCCACAAGGGGCGGCCAGGG
AACTTCCTTCAAAACCGGCCAGAGCCGACGGCCCCTCCCGAGCCGACCGCCCCGCCGGCGGAGT
CCTTTCGCTTCGAGGAGACCACGCCCGCCCCCAAGCAAGAGCTCAAGGACCGCGAGCCTCTTAC

Fig. 22 cont'd-33

CTCCCTCAAGTCGCTCTTCGGCTCCGACCCGCTTTCGCAAGCGTCG*TGATAA*GCTAGCGGATCC
GGCGCGC
AscI NheI
Need re-create XhoI site at the 5' end

HV13317 in HV10001 4824bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG

Fig. 22 cont'd-34

ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGATCCTTCGAGGGGGCAAGTTGGATAAGTGGAAAAGATCCGCTTGAGGCCAGGAGGGA
AGAAGAGATACATGCTCAAGCACCTGATCTGGGCGAGCAGAGAGCTGGAGCGGTTCGCGCTGAA
CCCGGGCCTGCTTGAGACAGCGGAGGGCTGTCAGCAAATCATCGAGCAGCTTCAAAGCACGCTG
AAGACGGGCAGCGAGGAGCTGAAGTCGCTATTCAACACGGTAGCGACCCTCTACTGCGTGCACC
AGCGGATCGAGGTCAAGGACACGAAGGAGGCTCTTGACAAGGTGGAGGAAGAGCAGAACAAGTC
GAAGAAGAAGGCGCAGCAGGCGGCGGCCGACACCGGCAACTCCTCACAAGTATCTCAGAACTAC
CCGATCGTGCAGAACCTGCAGGGACAGATGGTCCACCAGGCCCTCTCCCCACGGACGCTTAACG
CCTGGGTCAAAGTAATCGAGGAGAAGGCCTTCAGCCCGGAAATCATCCCCATGTTCACAGCACT
TTCCGAGGGAGCCACCCCGAGCGACCTGAACACGATGTTGAACACCGTCGGCGGGCACCAGGCG
GCCATGCAGATGCTTAAGGACACCATCAACGAGGAGGCTGCGGAGTGGGACCGGGTGCACCCGG
TGCACGCGGGGCCCATCCCACCGGGCCAGATGAGAGAGCCGCGGGGATCGGACATCGCGGGAAC
CACCAGCAGCTTGCAGGAGCAAATCGCCTGGATGACTTCGAACCCCCCGGTCCCGGTCGGGGAG
ATCTACAAGAGATGGATCGTCCTCGGGTTGAACAAGATCGTGAGGATGTACAGCCCTGTGTCAA
TCCTGGACATCCGACAGGGACCGAAGGAGCCCTTCAGAGACTACGTCGACCGGTTCTTCAAGAC
TCTCCGGGCGGAGCAGGCGTCGCAGGACGTCAAGAACTGGATGACGGAGACCTTGTTGGTCCAG
AACGCTAACCCGGACTGCAAGACCATCCTGCGCGCTCTCGGCCCGGGAGCGTCCTTGGAAGAGA
TGATGACGGCGTGCCAGGGAGTCGGGGGACCCTCACACAAGGCGCGGGTCTTGGCCGAGGCGAT
GAGCCAGACGAACTCCGCCATCCTCATGCAGCGGTCCAACTTCAAGGGAAGCAAGCGGATCGTC
AAGTGTTTCAACTGTGGCAAGGAGGGACACATCGCCAGGAACTGCCGGGCCCCGCGGAAGCGAG
GCTGCTGGAAGTGCGGACAGGAGGGGCACCAAATGAAGGACTGCAACGAGCGCCAGGCGAATTT
CCTCGGGAAGATCTGGCCGTCCCACAAGGGGCGGCCAGGGAACTTCCTTCAAAACCGGCCAGAG
CCGACGGCCCCTCCCGAGCCGACCGCCCCGCCGGCGGAGTCCTTTCGCTTCGAGGAGACCACGC
CCGCCCCCAAGCAAGAGCTCAAGGACCGCGAGCCTCTTACCTCCCTCAAGTCGCTCTTCGGCTC
CGACCCGCTTTCGCAAGCGTCG*TGATAA*GCTAGCGGATCCGGCGCGCGAGCTCGCTGATCAGCC
TCGACTGTGCCTTCTAGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAGAC
AATAGCAGGCATGCTGGGAATTT

Thursday, August 2, 2007

Sequence 2 Length : 4824

AatII GACGTC
5 Sites
2510 2563 2646
2832 3998
AccI GTMKAC
1 Site
3950
AflII CTTAAG
1 Site
3661
AflIII ACRYGT
1 Site
1897
AluI AGCT
16 Sites
109 633 1340
1597 1643 1733
1959

2184 2951 3180
3249 3282 3785
4497
4573 4594
AlwNI CAGNNNCTG
4 Sites
1488 2129 3471
4265
AosII GRCGYC
7 Sites
2507 2560 2643
2829 2983 3985
3995
ApaI GGGCCC
2 Sites
3725 4275
ApaLI GTGCAC
5 Sites
1583 2081 3322
3703 3712
AsuII TTCGAA
1 Site
3814
AvaI CYCGRG 6 Sites
3201 3600 3862
4074 4354 4429
BamHI GGATCC
1 Site
4579
BanI GGYRCC
5 Sites
538 2850 3638
4313 4678
BanII GRGCYC
6 Sites
2953 3725 3935
4275 4499 4596
BclI TGATCA
1 Site
4600
BcnI CCSGG
16 Sites
1173 1521 3021
3203 3204 3557
3701

Mosaic and Group M Gag_dmyr-patent.doc

Fig. 22 cont'd-35

3710 3735 3824
3830 3974 4043
4076
4077 4271
BglI GCCNNNNNGGC
4 Sites
2475 2597 2668
4447
BglII AGATCT
3 Sites
458 3839 4361
Bsp1286 GDGCHC
14 Sites
652 1587 2085
2953 3326 3641
3707
3716 3725 3935
4275 4316 4499
4596
BspHI TCATGA
2 Sites
1007 1105
BspNI CCWGG
18 Sites
52 1738 1751
1872 2475 2668
2977
3128 3493 3522
3643 3804 3907
4111
4260 4342 4388
4672
BssHII GCGCGC
3 Sites
3045 4064 4588
BstNI CCWGG
18 Sites
52 1738 1751
1872 2475 2668
2977
3128 3493 3522
3643 3804 3907
4111
4260 4342 4388
4672
Cfr10I RCCGGY
5 Sites
847 3424 3953
4406 4446
CfrI YGGCCR
7 Sites
769 3416 3647
4148 4366 4384
4408
ClaI ATCGAT
1 Site
2287
DdeI CTNAG
12 Sites
12 204 397
711 787 1214 1623
2088 2158 2229
3446 4732
DpnI GATC
22 Sites
190 195 460
1239 1247 1258
1333
2972 3028 3079
3115 3163 3334
3460
3759 3841 3856
3877 4219 4363
4581
Mosaic and Group M Gag_dmyr-patent.doc 4602
DraIII CACNNNGTG
2 Sites
1161 3711
Eco47I GGWCC
13 Sites
122 586 919
1048 3021 3485
3695
3824 3921 4025
4122 4192 4502
EcoO109 RGGNCCY
4 Sites
3495 3721 4123
4272
EcoRII CCWGG
18 Sites
50 1736 1749
1870 2473 2666
2975
3126 3491 3520
3641 3802 3905
4109
4258 4340 4386
4670
EcoRV GATATC
1 Site
2294
Fnu4HI GCNGC
28 Sites
234 769 1283
1489 1492 1557
1700
1855 1973 1976
1994 2110 2250
2279
2282 3065 3247
3273 3406 3413
3416
3647 3686 3751
3783 4189 4290
4384
FnuDII CGCG
21 Sites
494 1273 1854
2169 2257 2281
2445
3039 3045 3047
3071 3193 3718
3753
3769 4064 4140
4278 4508 4588
4590
HaeII RGCGCY
4 Sites
12 1657 2027
4341
HaeIII GGCC
25 Sites
55 771 1175
1423 1857 1875
1886
2268 2469 2662
3126 3206 3418
3496
3547 3649 3723
3737 4073 4150
4273
4368 4386 4410
4423
HgiAI GWGCWC
8 Sites 1587 2085 2953
3326 3707 3716
4499
4596
HhaI GCGC
22 Sites
11 496 1273
1382 1556 1656
1723
1993 2026 2169
2249 3045 3047
3073
3195 3405 4064
4066 4140 4340
4588
4590
HincII GTYRAC
4 Sites
413 886 2369
3951
HinfI GANTC
16 Sites
43 59 357
383 401 725 779
807 1527 1923
1998 2222 2795
3966
4115 4453
HinPI GCGC
22 Sites
9 494 1271
1380 1554 1654
1721
1991 2024 2167
2247 3043 3045
3071
3193 3403 4062
4064 4138 4338
4586
4588
HpaII CCGG
23 Sites
848 1172 1329
1519 1545 1692
3019
3202 3425 3556
3699 3709 3733
3823
3829 3954 3972
4042 4075 4269
4407
4447 4583
MaeI CTAG
7 Sites
378 801 1034
1404 2385 4574
4622
MaeII ACGT
12 Sites
669 1160 1196
2306 2507 2519
2560
2643 2724 2829
3947 3995
MaeIII GTNAC
8 Sites
270 1134 1361
1477 1540 2446
2533
2882
MvaI CCNGG
34 Sites

Fig. 22 cont'd-36

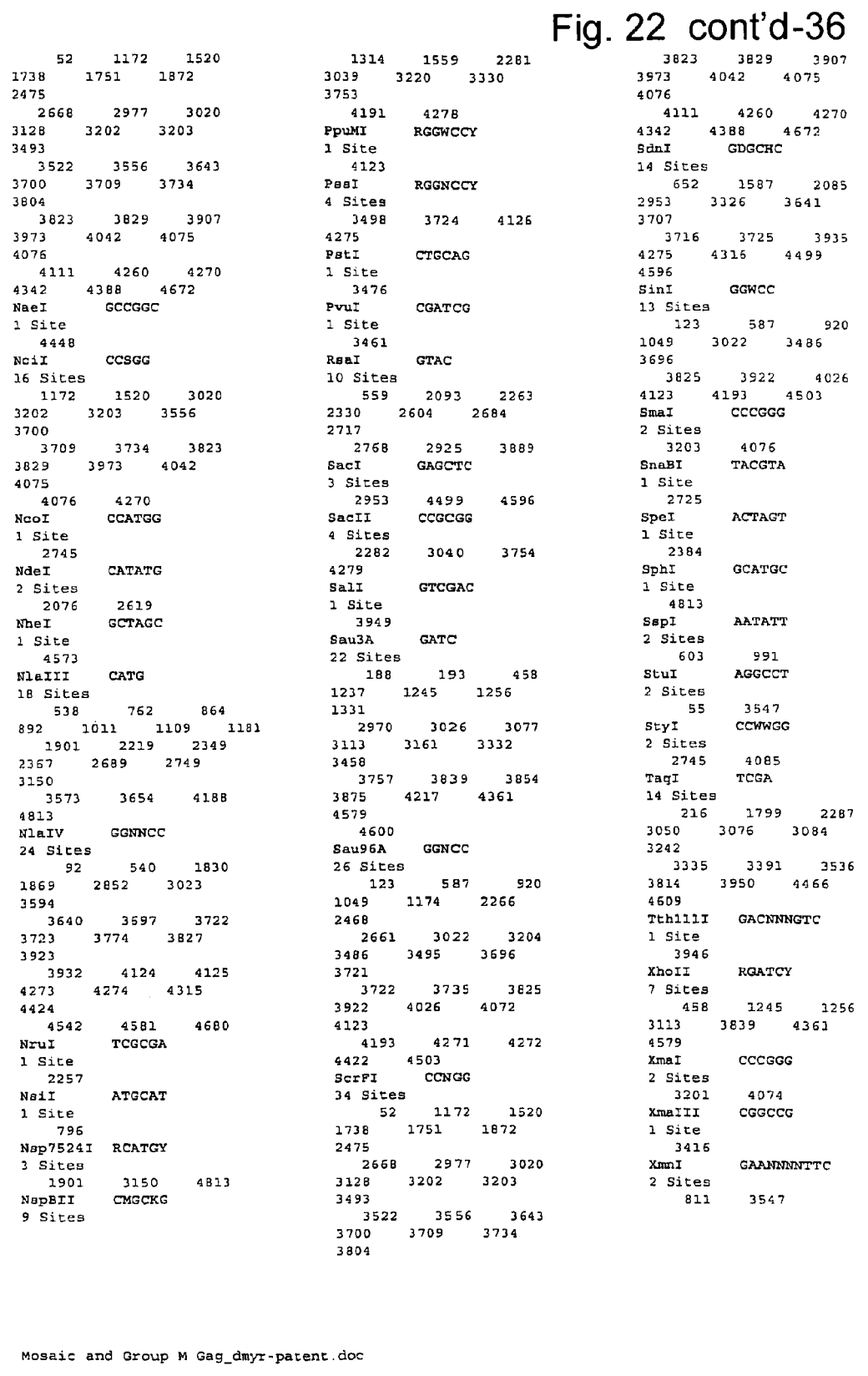

52 1172 1520
1738 1751 1872
2475
2668 2977 3020
3128 3202 3203
3493
3522 3556 3643
3700 3709 3734
3804
3823 3829 3907
3973 4042 4075
4076
4111 4260 4270
4342 4388 4672
NaeI GCCGGC
1 Site
4448
NciI CCSGG
16 Sites
1172 1520 3020
3202 3203 3556
3700
3709 3734 3823
3829 3973 4042
4075
4076 4270
NcoI CCATGG
1 Site
2745
NdeI CATATG
2 Sites
2076 2619
NheI GCTAGC
1 Site
4573
NlaIII CATG
18 Sites
538 762 864
892 1011 1109 1181
1901 2219 2349
2367 2689 2749
3150
3573 3654 4188
4813
NlaIV GGNNCC
24 Sites
92 540 1830
1869 2852 3023
3594
3640 3697 3722
3723 3774 3827
3923
3932 4124 4125
4273 4274 4315
4424
4542 4581 4680
NruI TCGCGA
1 Site
2257
NsiI ATGCAT
1 Site
796
Nsp7524I RCATGY
3 Sites
1901 3150 4813
NspBII CMGCKG
9 Sites
1314 1559 2281
3039 3220 3330
3753
4191 4278
PpuMI RGGWCCY
1 Site
4123
PssI RGGNCCY
4 Sites
3498 3724 4126
4275
PstI CTGCAG
1 Site
3476
PvuI CGATCG
1 Site
3461
RsaI GTAC
10 Sites
559 2093 2263
2330 2604 2684
2717
2768 2925 3889
SacI GAGCTC
3 Sites
2953 4499 4596
SacII CCGCGG
4 Sites
2282 3040 3754
4279
SalI GTCGAC
1 Site
3949
Sau3A GATC
22 Sites
188 193 458
1237 1245 1256
1331
2970 3026 3077
3113 3161 3332
3458
3757 3839 3854
3875 4217 4361
4579
4600
Sau96A GGNCC
26 Sites
123 587 920
1049 1174 2266
2468
2661 3022 3204
3486 3495 3696
3721
3722 3735 3825
3922 4026 4072
4123
4193 4271 4272
4422 4503
ScrFI CCNGG
34 Sites
52 1172 1520
1738 1751 1872
2475
2668 2977 3020
3128 3202 3203
3493
3522 3556 3643
3700 3709 3734
3804
3823 3829 3907
3973 4042 4075
4076
4111 4260 4270
4342 4388 4672
SdnI GDGCHC
14 Sites
652 1587 2085
2953 3326 3641
3707
3716 3725 3935
4275 4316 4499
4596
SinI GGWCC
13 Sites
123 587 920
1049 3022 3486
3696
3825 3922 4026
4123 4193 4503
SmaI CCCGGG
2 Sites
3203 4076
SnaBI TACGTA
1 Site
2725
SpeI ACTAGT
1 Site
2384
SphI GCATGC
1 Site
4813
SspI AATATT
2 Sites
603 991
StuI AGGCCT
2 Sites
55 3547
StyI CCWWGG
2 Sites
2745 4085
TaqI TCGA
14 Sites
216 1799 2287
3050 3076 3084
3242
3335 3391 3536
3814 3950 4466
4609
Tth111I GACNNNGTC
1 Site
3946
XhoII RGATCY
7 Sites
458 1245 1256
3113 3839 4361
4579
XmaI CCCGGG
2 Sites
3201 4074
XmaIII CGGCCG
1 Site
3416
XmnI GAANNNNTTC
2 Sites
811 3547

Fig. 22 cont'd-37

Gag_M4.4 Dmyr
MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKV
SQNYPIVQNLQGQMVHQPLSPRTLNAWVKVVEEKGFNPEVIPMFSALSEGATPQDLNMMLNIVG
GHQAAMQMLKETINEEAAEWDRLHPVHAGPIAPGQMREPRGSDIAGSTSTLQEQIAWMTGNPPV
PVGDIYKRWIILGLNKIVKMYSPTSILDIKQGPKEPFRDYVDRFYKTLRAEQATQEVKNWMTDT
LLVQNANPDCKSILKALGTGATLEEMMSACQGVGGPAHKARVLAEAMSQANNTNIMMQRSNFKG
PKRIIKCFNCGKEGHIAKNCRAPRKKGCWKCGKEGHQMKDCTERQANFLGRIWPSSKGRPGNFL
QSRPEPTAPPAEPTAPPAESFKFEETTPAPKQEPKDREPLTSLRSLFGSDPLLQAS HV13318 (Gag_M4.4 Dmyr.wlv)
GTCGAGAAGAAAATGGCGGCTCGCGCCTCGGTCCTTCGAGGGGAGAAGTTGGATAAGTGGGAAC
GGATCCGCTTGAGGCCAGGAGGGAAGAAGCACTACATGCTCAAGCACCTGGTCTGGGCGAGCAG
AGAGCTGGAGAAGTTCGCGCTGAACCCGGGCCTGCTTGAGACATCCGAGGGCTGTAAGCAAATC
ATCAAGCAGCTTCAACCAGCGCTCCAGACGGGCACCGAGGAGCTGCGCTCGCTATTCAACACGG
TAGCGACCCTCTACTGCGTGCACGCCGGAATCGAAGTTCGTGACACGAAGGAGGCTCTTGACAA
GATCGAGGAAATCCAGAACAAGTCGAAGCAGAAGACCCAGCAGGCGGCGGCCGGGACCGGCTCG
TCCTCAAAAGTATCTCAGAACTACCCGATCGTGCAGAACCTGCAGGGACAGATGGTCCACCAGC
CGCTCTCCCCACGGACGCTTAACGCCTGGGTCAAAGTAGTCGAGGAGAAGGGGTTCAACCCGGA
AGTCATCCCCATGTTCTCGGCACTTTCCGAGGGAGCCACCCCGCAGGACCTGAACATGATGTTG
AACATCGTCGGCGGGCACCAGGCGGCCATGCAGATGCTTAAGGAGACCATCAACGAGGAGGCTG
CGGAGTGGGACCGCCTGCACCCGGTGCACGCGGGGCCCATCGCACCGGGCCAGATGAGAGAGCC
GCGGGGATCGGACATCGCGGGATCCACCAGCACCTTGCAGGAGCAAATCGCCTGGATGACTGGG
AACCCCCCGGTCCCGGTCGGGGACATCTACAAGAGATGGATCATCCTCGGGTTGAACAAGATCG
TGAAGATGTACAGCCCTACGTCAATCCTGGACATCAAGCAGGGCCCCAAGGAGCCCTTCAGAGA
CTACGTCGACCGGTTCTACAAGACTCTCCGGGCGGAGCAGGCGACGCAGGAGGTCAAGAACTGG
ATGACGGACACCTTGTTGGTCCAGAACGCTAACCCGGACTGCAAGAGCATCCTGAAGGCTCTCG
GCACGGGAGCGACCTTGGAAGAGATGATGTCCGCGTGCCAGGGAGTCGGGGGACCCGCGCACAA
GGCGCGGGTCTTGGCCGAGGCGATGTCCCAGGCCAACAACACGAACATCATGATGCAGCGGTCC
AACTTCAAGGGACCGAAGCGGATCATCAAGTGTTTCAACTGTGGCAAGGAGGGACACATCGCCA
AGAACTGCCGGGCCCCGCGGAAGAAGGGCTGCTGGAAGTGCGGAAAGGAGGGGCACCAAATGAA
GGACTGCACGGAGCGCCAGGCGAATTTCCTCGGGCGGATCTGGCCGTCCTCGAAGGGGCGGCCA
GGGAACTTCCTTCAATCGCGGCCAGAGCCGACGGCCCCTCCCGCGGAGCCGACCGCCCCGCCGG
CGGAGTCCTTTAAGTTCGAGGAGACCACGCCCGCCCCCAAGCAAGAGCCGAAGGACCGCGAGCC
TCTTACCTCCCTCCGGTCGCTCTTCGGCTCCGACCCGCTTCTGCAAGCGTCGTGATAAGCTAGC
GGATCCGGCGCGCC NheI
AscI HV13318 in in HV10001 4831bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT

Fig. 22 cont'd-38

ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTCGAGGGGAGAAGTTGGATAAGTGGGAACGGATCCGCTTGAGGCCAGGAGGGA
AGAAGCACTACATGCTCAAGCACCTGGTCTGGGCGAGCAGAGAGCTGGAGAAGTTCGCGCTGAA
CCCGGGCCTGCTTGAGACATCCGAGGGCTGTAAGCAAATCATCAAGCAGCTTCAACCAGCGCTC
CAGACGGGCACCGAGGAGCTGCGCTCGCTATTCAACACGGTAGCGACCCTCTACTGCGTGCACG
CCGGAATCGAAGTTCGTGACACGAAGGAGGCTCTTGACAAGATCGAGGAAATCCAGAACAAGTC
GAAGCAGAAGACCCAGCAGGCGGCGGCCGGGACCGGCTCGTCCTCAAAAGTATCTCAGAACTAC
CCGATCGTGCAGAACCTGCAGGGACAGATGGTCCACCAGCCGCTCTCCCCACGGACGCTTAACG
CCTGGGTCAAAGTAGTCGAGGAGAAGGGGTTCAACCCGGAAGTCATCCCCATGTTCTCGGCACT
TTCCGAGGGAGCCACCCCGCAGGACCTGAACATGATGTTGAACATCGTCGGCGGGCACCAGGCG
GCCATGCAGATGCTTAAGGAGACCATCAACGAGGAGGCTGCGGAGTGGGACCGCCTGCACCCGG
TGCACGCGGGGCCCATCGCACCGGGCCAGATGAGAGAGCCGCGGGGATCGGACATCGCGGGATC

CACCAGCACCTTGCAGGAGCAAATCGCCTGGATGACTGGGAACCCCCCGGTCCCGGTCGGGGAC
ATCTACAAGAGATGGATCATCCTCGGGTTGAACAAGATCGTGAAGATGTACAGCCCTACGTCAA
TCCTGGACATCAAGCAGGGCCCCAAGGAGCCCTTCAGAGACTACGTCGACCGGTTCTACAAGAC
TCTCCGGGCGGAGCAGGCGACGCAGGAGGTCAAGAACTGGATGACGGACACCTTGTTGGTCCAG
AACGCTAACCCGGACTGCAAGAGCATCCTGAAGGCTCTCGGCACGGGAGCGACCTTGGAAGAGA
TGATGTCCGCGTGCCAGGGAGTCGGGGGACCCGCGCACAAGGCGCGGGTCTTGGCCGAGGCGAT
GTCCCAGGCCAACAACACGAACATCATGATGCAGCGGTCCAACTTCAAGGGACCGAAGCGGATC
ATCAAGTGTTTCAACTGTGGCAAGGAGGGACACATCGCCAAGAACTGCCGGGCCCCGCGGAAGA
AGGGCTGCTGGAAGTGCGGAAAGGAGGGGCACCAAATGAAGGACTGCACGGAGCGCCAGGCGAA
TTTCCTCGGGCGGATCTGGCCGTCCTCGAAGGGGCGGCCAGGGAACTTCCTTCAATCGCGGCCA
GAGCCGACGGCCCCTCCCGCGGAGCCGACCGCCCCGCCGGCGGAGTCCTTTAAGTTCGAGGAGA
CCACGCCCGCCCCCAAGCAAGAGCCGAAGGACCGCGAGCCTCTTACCTCCCTCCGGTCGCTCTT
CGGCTCCGACCCGCTTCTGCAAGCGTCG*TGATAA*GCTAGCGGATCCGGCGCGCCGAGCTCGCTG
ATCAGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATT
GTCTGAGTAGGTGTCATTCTATTCTGGGGGGTGGGGTGGGGCAGGACAGCAAGGGGGAGGATTG
GGAAGACAATAGCAGGCATGCTGGGGAATTT

Primers:

HV1001-F2892
CCGCCCCATTGACGCAAATGG

HV1001-R3113
GCTGGCAACTAGAAGGCACAG
(+ strand: CTGTGCCTTCTAGTTGCCAGC

Thursday, August 2, 2007

Sequence 4 Length : 4831

AatII GACGTC
4 Sites
2510 2563 2646
2832
AccI GTMKAC
1 Site
3950
AflII CTTAAG
1 Site
3661
AflIII ACRYGT
1 Site
1897
AluI AGCT
14 Sites
109 633 1340
1597 1643 1733
1959
2184 2951 3180
3249 3282 4579
4601
AlwNI CAGNNNCTG
4 Sites
1488 2129 3471
3609
AosII GRCGYC
5 Sites
2507 2560 2643
2829 2983
ApaI GGGCCC
3 Sites
3725 3925 4278
ApaLI GTGCAC
4 Sites
1583 2081 3322
3712
AvaI CYCGRG
3 Sites
3201 3862 4357
BamHI GGATCC
3 Sites
3113 3772 4585
BanI GGYRCC
6 Sites
538 2850 3271
3638 4316 4685
BanII GRGCYC
6 Sites
2953 3725 3925
3935 4278 4603
BclI TGATCA
1 Site
4607
BcnI CCSGG
14 Sites
1173 1521 3021
3203 3204 3421
3557
3710 3735 3824
3830 3974 4043
4274
BglI GCCNNNNNGGC
4 Sites
2475 2597 2668
4453
BglII AGATCT
1 Site
458
Bsp1286 GDGCHC
14 Sites
652 1587 2085
2953 3274 3326
3641
3716 3725 3925
3935 4278 4319
4603
BspHI TCATGA
3 Sites
1007 1105 4184
BspNI CCWGG
18 Sites
52 1738 1751
1872 2475 2668
2977
3128 3160 3522
3643 3804 3907
4111
4165 4345 4391
4679
BssHII GCGCGC
2 Sites
3045 4594
BstNI CCWGG
18 Sites
52 1738 1751
1872 2475 2668
2977

Mosaic and Group M Gag_dmyr-patent.doc

Fig. 22 cont'd-40

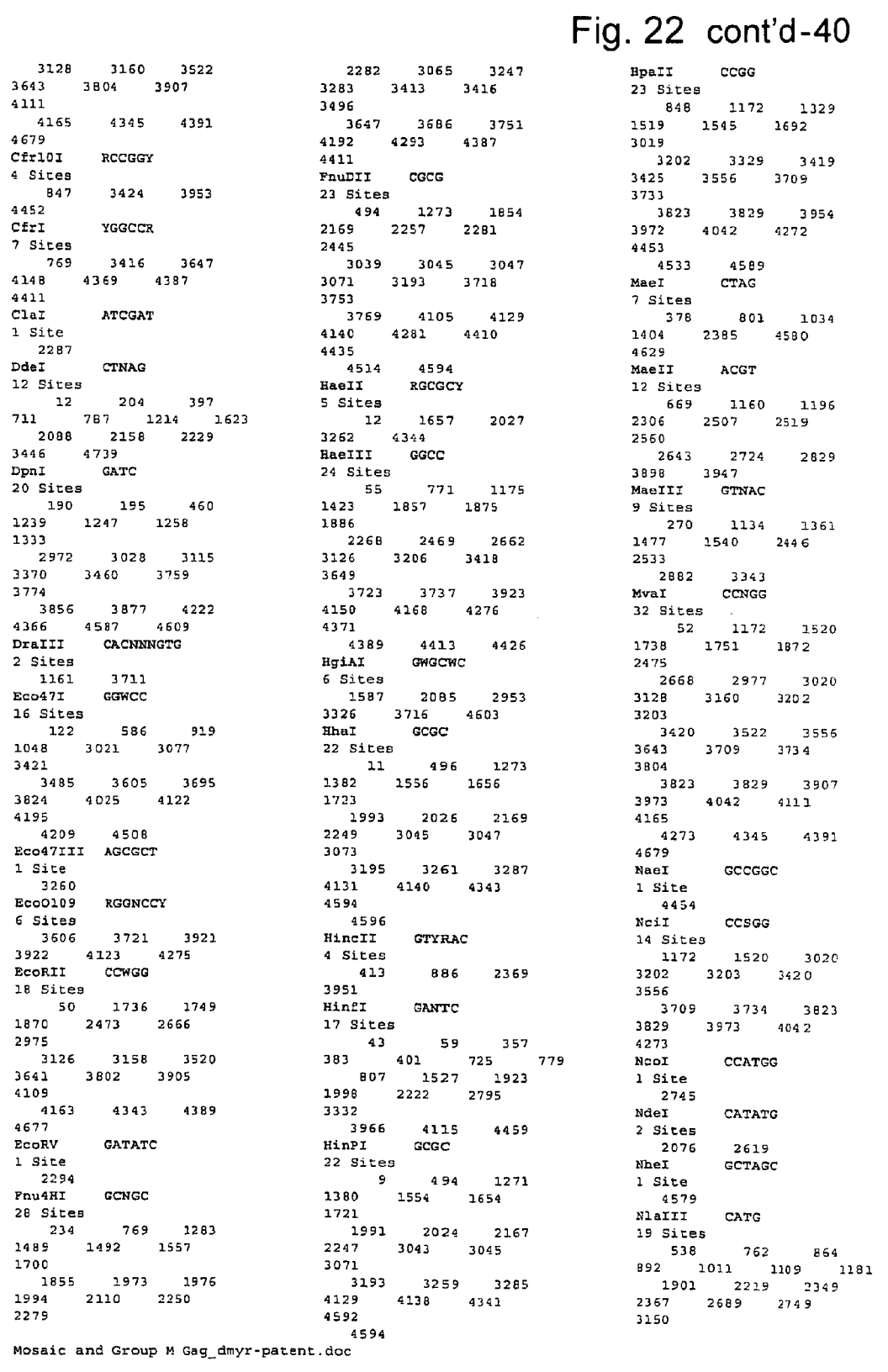

3128 3160 3522
3643 3804 3907
4111
4165 4345 4391
4679
Cfr10I RCCGGY
4 Sites
847 3424 3953
4452
CfrI YGGCCR
7 Sites
769 3416 3647
4148 4369 4387
4411
ClaI ATCGAT
1 Site
2287
DdeI CTNAG
12 Sites
12 204 397
711 787 1214 1623
2088 2158 2229
3446 4739
DpnI GATC
20 Sites
190 195 460
1239 1247 1258
1333
2972 3028 3115
3370 3460 3759
3774
3856 3877 4222
4366 4587 4609
DraIII CACNNNGTG
2 Sites
1161 3711
Eco47I GGWCC
16 Sites
122 586 919
1048 3021 3077
3421
3485 3605 3695
3824 4025 4122
4195
4209 4508
Eco47III AGCGCT
1 Site
3260
EcoO109 RGGNCCY
6 Sites
3606 3721 3921
3922 4123 4275
EcoRII CCWGG
18 Sites
50 1736 1749
1870 2473 2666
2975
3126 3158 3520
3641 3802 3905
4109
4163 4343 4389
4677
EcoRV GATATC
1 Site
2294
Fnu4HI GCNGC
28 Sites
234 769 1283
1489 1492 1557
1700
1855 1973 1976
1994 2110 2250
2279

2282 3065 3247
3283 3413 3416
3496
3647 3686 3751
4192 4293 4387
4411
FnuDII CGCG
23 Sites
494 1273 1854
2169 2257 2281
2445
3039 3045 3047
3071 3193 3718
3753
3769 4105 4129
4140 4281 4410
4435
4514 4594
HaeII RGCGCY
5 Sites
12 1657 2027
3262 4344
HaeIII GGCC
24 Sites
55 771 1175
1423 1857 1875
1886
2268 2469 2662
3126 3206 3418
3649
3723 3737 3923
4150 4168 4276
4371
4389 4413 4426
HgiAI GWGCWC
6 Sites
1587 2085 2953
3326 3716 4603
HhaI GCGC
22 Sites
11 496 1273
1382 1556 1656
1723
1993 2026 2169
2249 3045 3047
3073
3195 3261 3287
4131 4140 4343
4594
4596
HincII GTYRAC
4 Sites
413 886 2369
3951
HinfI GANTC
17 Sites
43 59 357
383 401 725 779
807 1527 1923
1998 2222 2795
3332
3966 4115 4459
HinPI GCGC
22 Sites
9 494 1271
1380 1554 1654
1721
1991 2024 2167
2247 3043 3045
3071
3193 3259 3285
4129 4138 4341
4592
4594

HpaII CCGG
23 Sites
848 1172 1329
1519 1545 1692
3019
3202 3329 3419
3425 3556 3709
3733
3823 3829 3954
3972 4042 4272
4453
4533 4589
MaeI CTAG
7 Sites
378 801 1034
1404 2385 4580
4629
MaeII ACGT
12 Sites
669 1160 1196
2306 2507 2519
2560
2643 2724 2829
3898 3947
MaeIII GTNAC
9 Sites
270 1134 1361
1477 1540 2446
2533
2882 3343
MvaI CCNGG
32 Sites
52 1172 1520
1738 1751 1872
2475
2668 2977 3020
3128 3160 3202
3203
3420 3522 3556
3643 3709 3734
3804
3823 3829 3907
3973 4042 4111
4165
4273 4345 4391
4679
NaeI GCCGGC
1 Site
4454
NciI CCSGG
14 Sites
1172 1520 3020
3202 3203 3420
3556
3709 3734 3823
3829 3973 4042
4273
NcoI CCATGG
1 Site
2745
NdeI CATATG
2 Sites
2076 2619
NheI GCTAGC
1 Site
4579
NlaIII CATG
19 Sites
538 762 864
892 1011 1109 1181
1901 2219 2349
2367 2689 2749
3150

Mosaic and Group M Gag_dmyr-patent.doc

Fig. 22 cont'd-41

3573 3618 3654
4188 4820
NlaIV GGNNCC
31 Sites
92 540 1830
1869 2852 3023
3115
3273 3423 3594
3640 3697 3722
3723
3774 3817 3827
3923 3924 3932
4124
4125 4211 4276
4277 4318 4427
4439
4548 4587 4687
NruI TCGCGA
1 Site
2257
NsiI ATGCAT
1 Site
796
Nsp7524I RCATGY
3 Sites
1901 3150 4820
NspBII CMGCKG
8 Sites
1314 1559 2281
3039 3753 4194
4281
4435
PpuMI RGGWCCY
2 Sites
3606 4123
PssI RGGNCCY
6 Sites
3609 3724 3924
3925 4126 4278
PstI CTGCAG
1 Site
3476
PvuI CGATCG
1 Site
3461
RsaI GTAC
10 Sites
559 2093 2263
2330 2604 2684
2717
2768 2925 3889
SacI GAGCTC
2 Sites
2953 4603
SacII CCGCGG
5 Sites
2282 3040 3754
4282 4436
SalI GTCGAC
1 Site
3949
Sau3A GATC
20 Sites
188 193 458
1237 1245 1256
1331
2970 3026 3113
3368 3458 3757
3772
3854 3875 4220
4364 4585 4607
Sau96A GGNCC
29 Sites
123 587 920
1049 1174 2266
2468
2661 3022 3078
3204 3422 3486
3606
3696 3721 3722
3735 3825 3921
3922
4026 4123 4196
4210 4274 4275
4425
4509
ScrFI CCNGG
32 Sites
52 1172 1520
1738 1751 1872
2475
2668 2977 3020
3128 3160 3202
3203
3420 3522 3556
3643 3709 3734
3804
3823 3829 3907
3973 4042 4111
4165
4273 4345 4391
4679
SdnI GDGCHC
14 Sites
652 1587 2085
2953 3274 3326
3641
3716 3725 3925
3935 4278 4319
4603
SinI GGWCC
16 Sites
123 587 920
1049 3022 3078
3422
3486 3606 3696
3825 4026 4123
4196
4210 4509
SmaI CCCGGG
1 Site
3203
SnaBI TACGTA
1 Site
2725
SpeI ACTAGT
1 Site
2384
SphI GCATGC
1 Site
4820
SspI AATATT
2 Sites
603 991
StuI AGGCCT
1 Site
55
StyI CCWWGG
3 Sites
2745 3926 4085
TaqI TCGA
13 Sites
216 1799 2287
3050 3084 3335
3371
3391 3536 3950
4378 4472 4616
Tth111I GACNNNGTC
1 Site
3946
XhoII RGATCY
7 Sites
458 1245 1256
3113 3772 4364
4585
XmaI CCCGGG
1 Site
3201
XmaIII CGGCCG
1 Site
3416
XmnI GAANNNNTTC
2 Sites
811 3547

Following enzymes have no sites

| | | |
|---|---|---|
| AccIII | Asp718 | AsuII |
| AvrII | BalI | BbeI |
| BspMII | BstEII | BstXI |
| DraI | EcoRI | EspI |
| FspI | HindIII | HpaI |
| KpnI | MluI | MstI |
| NarI | NotI | OxaNI |
| PflMI | PvuII | RsrII |
| ScaI | SfiI | SplI |
| XbaI | XcaI | XhoI |

Primer below can be used for Gag-M4.1 through 4.4 to generate XhoI site:

Gag-M2-4-fG/C: GGGCGCCTCGAGAAGAAAATGGCGGCTCG

WLV001AM (vector sequence), hv10001
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA

Fig. 22 cont'd-42

GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGAGAGGCGCGCCGAGCTCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTT

Fig. 22 cont'd-43

CCTAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGAATTT

MOSAIC CLADE M HUMAN IMMUNODEFICIENCY VIRUS TYPE 1 (HIV-1) GAG IMMUNOGENS

This application is the U.S. national phase of International Application No. PCT/US2009/004664, filed 14 Aug. 2009, which designated the U.S. and is a continuation of U.S. application Ser. No. 12/192,015, filed 14 Aug. 2008 (issued as U.S. Pat. No. 7,951,377), the entire contents of each of which are hereby incorporated by reference.

This application is a continuation-in-part of U.S. application Ser. No. 11/990,222, filed Feb. 8, 2008 (issued as U.S. Pat. No. 8,119,140), which is the U.S. national phase of International Application No. PCT/US2006/032907, filed Aug. 23, 2006, which designated the U.S. and claims priority from U.S. Provisional Application No. 60/710,154, filed Aug. 23, 2005, and U.S. Provisional Application No. 60/739,413, filed Nov. 25, 2005, the entire contents of which applications are incorporated herein by reference.

TECHNICAL FIELD

The present invention relates, in general, to an immunogenic composition (e.g., a vaccine) and, in particular, to a polyvalent immunogenic composition, such as a polyvalent HIV vaccine, and to methods of using same. The invention further relates to methods that use a genetic algorithm to create sets of polyvalent antigens suitable for use, for example, in vaccination strategies.

BACKGROUND

Designing an effective HIV vaccine is a many-faceted challenge. The vaccine preferably elicits an immune response capable of either preventing infection or, minimally, controlling viral replication if infection occurs, despite the failure of immune responses to natural infection to eliminate the virus (Nabel, Vaccine 20:1945-1947 (2002)) or to protect from superinfection (Altfeld et al, Nature 420:434-439 (2002)). Potent vaccines are needed, with optimized vectors, immunization protocols, and adjuvants (Nabel, Vaccine 20:1945-1947 (2002)), combined with antigens that can stimulate cross-reactive responses against the diverse spectrum of circulating viruses (Gaschen et al, Science 296:2354-2360 (2002), Korber et al, Br. Med. Bull. 58:19-42 (2001)). The problems that influenza vaccinologists have confronted for decades highlight the challenge posed by HIV-1: human influenza strains undergoing antigenic drift diverge from one another by around 1-2% per year, yet vaccine antigens often fail to elicit cross-reactive B-cell responses from one year to the next, requiring that contemporary strains be continuously monitored and vaccines be updated every few years (Korber et al, Br. Med. Bull. 58:19-42 (2001)). In contrast, co-circulating individual HIV-1 strains can differ from one another by 20% or more in relatively conserved proteins, and up to 35% in the Envelope protein (Gaschen et al, Science 296:2354-2360 (2002), Korber et al, Br. Med. Bull. 58:19-42 (2001)).

Different degrees of viral diversity in regional HIV-1 epidemics provide a potentially useful hierarchy for vaccine design strategies. Some geographic regions recapitulate global diversity, with a majority of known HIV-1 subtypes, or clades, co-circulating (e.g., the Democratic Republic of the Congo (Mokili & Korber, J. Neurovirol 11(Suppl. 1):66-75 (2005)); others are dominated by two subtypes and their recombinants (e.g., Uganda (Barugahare et al, J. Virol. 79:4132-4139 (2005)), and others by a single subtype (e.g., South Africa (Williamson et al, AIDS Res. Hum. Retroviruses 19:133-144 (2003)). Even areas with predominantly single-subtype epidemics must address extensive within-clade diversity (Williamson et al, AIDS Res. Hum. Retroviruses 19:133-44 (2003)) but, since international travel can be expected to further blur geographic distinctions, all nations would benefit from a global vaccine.

Presented herein is the design of polyvalent vaccine antigen sets focusing on T lymphocyte responses, optimized for either the common B and C subtypes, or all HIV-1 variants in global circulation [the HIV-1 Main (M) group]. Cytotoxic T-lymphocytes (CTL) directly kill infected, virus-producing host cells, recognizing them via viral protein fragments (epitopes) presented on infected cell surfaces by human leukocyte antigen (HLA) molecules. Helper T-cell responses control varied aspects of the immune response through the release of cytokines. Both are likely to be crucial for an HIV-1 vaccine: CTL responses have been implicated in slowing disease progression (Oxenius et al, J. Infect. Dis. 189:1199-208 (2004)); vaccine-elicited cellular immune responses in nonhuman primates help control pathogenic SIV or s SHIV, reducing the likelihood of disease after challenge (Barouch et al, Science 290:486-92 (2000)); and experimental depletion of CD8+ T-cells results in increased viremia in SIV infected rhesus macaques Schmitz et al, Science 283:857-60 (1999)). Furthermore, CTL escape mutations are associated with disease progression (Barouch et al, J. Virol. 77:7367-75 (2003)), thus vaccine-stimulated memory responses that block potential escape routes may be valuable.

The highly variable Env protein is the primary target for neutralizing antibodies against HIV; since immune protection will likely require both B-cell and T-cell responses (Moore and Burton, Nat. Med. 10:769-71 (2004)), Env vaccine antigens will also need to be optimized separately to elicit antibody responses. T-cell-directed vaccine components, in contrast, can target the more conserved proteins, but even the most conserved HIV-1 proteins are diverse enough that variation is an issue. Artificial central-sequence vaccine approaches (e.g., consensus sequences, in which every amino acid is found in a plurality of sequences, or maximum likelihood reconstructions of ancestral sequences (Gaschen et al, Science 296:2354-60 (2002), Gao et al, J. Virol. 79:1154-63 (2005), Doria-Rose et al, J. Virol. 79:11214-24 (2005), Weaver et al, J. Virol., in press)) are promising; nevertheless, even centralized strains provide limited coverage of HIV-1 variants, and consensus-based reagents fail to detect many autologous T-cell responses (Altfeld et al, J. Virol. 77:7330-40 (2003)).

Single amino acid changes can allow an epitope to escape T-cell surveillance; since many T-cell epitopes differ between HIV-1 strains at one or more positions, potential responses to any single vaccine antigen are limited. Whether a particular mutation results in escape depends upon the specific epitope/T-cell combination, although some changes broadly affect between-subtype cross-reactivity (Norris et al, AIDS Res. Hum. Retroviruses 20:315-25 (2004)). Including multiple variants in a polyvalent vaccine could enable responses to a broader range of circulating variants, and could also prime the immune system against common escape mutants (Jones et al, J. Exp. Med. 200:1243-56 (2004)). Escape from one T-cell receptor may create a variant that is susceptible to another (Allen et al, J. Virol. 79:12952-60 (2005), Feeney et al, J. Immunol. 174:7524-30 (2005)), so stimulating polyclonal responses to epitope variants may be beneficial (Killian et al, Aids 19:887-96 (2005)). Escape mutations that inhibit processing (Milicic et al, J. Immunol. 175:4618-26 (2005)) or HLA binding (Ammaranond et al, AIDS Res. Hum. Retroviruses 21:395-7 (2005)) cannot be directly countered by a T-cell with a different specificity, but responses to overlapping epitopes may block even some of these escape routes.

The present invention relates to a polyvalent vaccine comprising several "mosaic" proteins (or genes encoding these proteins). The candidate vaccine antigens can be cocktails of k composite proteins (k being the number of sequence variants in the cocktail), optimized to include the maximum number of potential T-cell epitopes in an input set of viral proteins. The mosaics are generated from natural sequences: they resemble natural proteins and include the most common forms of potential epitopes. Since CD8+ epitopes are contiguous and typically nine amino-acids long, sets of mosaics can be scored by "coverage" of nonamers (9-mers) in the natural sequences (fragments of similar lengths are also well represented). 9-Mers not found at least three times can be excluded. This strategy provides the level of diversity coverage achieved by a massively polyvalent multiple-peptide vaccine but with important advantages: it allows vaccine delivery as intact proteins or genes, excludes low-frequency or unnatural epitopes that are not relevant to circulating strains, and its intact protein antigens are more likely to be processed as in a natural infection.

SUMMARY OF THE INVENTION

In general, the present invention relates to an immunogenic composition. More specifically, the invention relates to a polyvalent immunogenic composition (e.g., an HIV vaccine), and to methods of using same. The invention further relates to methods that involve the use of a genetic algorithm to design sets of polyvalent antigens suitable for use as vaccines.

Objects and advantages of the present invention will be clear from the description that follows.

BRIEF DESCRIPTION OF THE DRAWINGS

In FIGS. 1A, 1C and 1E, the scores for each consecutive 9-mer are plotted in their natural order to show how diversity varies in different protein regions; both p24 in the center of Gag and the central region of Nef are particularly highly conserved. In FIGS. 1B, 1D and 1F, the scores for each 9-mer are reordered by coverage (a strategy also used in FIG. 4), to provide a sense of the overall population coverage of a given protein. Coverage of gp120, even with 8 variant 9-mers, is particularly poor (FIGS. 1E and 1F).

FIG. 2A) A set of k populations is generated by random 2-point recombination of natural sequences (1-6 populations of 50-500 sequences each have been tested). One sequence from each population is chosen (initially at random) for the mosaic cocktail, which is subsequently optimized. The cocktail sequences are scored by computing coverage (defined as the mean fraction of natural-sequence 9-mers included in the cocktail, averaged over all natural sequences in the input data set). Any new sequence that covers more epitopes will increase the score of the whole cocktail. FIG. 2B) The fitness score of any individual sequence is the coverage of a cocktail containing that sequence plus the current representatives from other populations. FIG. 2C) Optimization: 1) two "parents" are chosen: the higher-scoring of a randomly chosen pair of recombined sequences, and either (with 50% probability) the higher-scoring sequence of a second random pair, or a randomly chosen natural sequence. 2) Two-point recombination between the two parents is used to generate a "child" sequence. If the child contains unnatural or rare 9-mers, it is immediately rejected, otherwise it is scored (Gaschen et al, Science 296:2354-2360 (2002)). If the score is higher than that of any of four randomly-selected population members, the child is inserted in the population in place of the weakest of the four, thus evolving an improved population; 4) if its score is a new high score, the new child replaces the current cocktail member from its population. Ten cycles of child generation are repeated for each population in turn, and the process iterates until improvement stalls.

FIG. 4A) Non-optimal natural sequences selected from among strains being used in vaccine studies (Kong et al, J. Virol.77:12764-72 (2003)) including an individual clade A, B, and C viral sequences (Gag: GenBank accession numbers AF004885, K03455, and U52953; Nef core: AF069670, K02083, and U52953). FIG. 4B) Optimum set of natural sequences [isolates US2 (subtype B, USA), 70177 (subtype C, India), and 99TH.R2399 (subtype CRF15 01B, Thailand); accession numbers AY173953, AF533131, and AF530576] selected by choosing the single sequence with maximum coverage, followed by the sequence that had the best coverage when combined with the first (i.e. the best complement), and so on, selected for M group coverage FIG. 4C) Consensus sequence cocktail (M group, B- and C-subtypes). FIG. 4D) 3 mosaic sequences, FIG. 4E) 4 mosaic sequences, FIG. 4F) 6 mosaic sequences. FIGS. 4D-4F were all optimized for M group coverage.

FIG. 7A: frequencies from 0-60% (for 9-mer frequencies >60%, the distributions are equivalent for all methods). FIG. 7B: Details of low-frequency 9-mers. Natural sequences have large numbers of rare or unique-to-isolate 9-mers (bottom right, FIGS. 7A and 7B); these are unlikely to induce useful vaccine responses. Selecting optimal natural sequences does select for more common 9-mers, but rare and unique 9-mers are still included (top right, FIGS. 7A and 7B). Consensus cocktails, in contrast, under-represent uncommon 9-mers, especially below 20% frequency (bottom left, FIGS. 7A and 7B). For mosaic sequences, the number of lower-frequency 9-mers monotonically increases with the number of sequences (top left, each panel), but unique-to-isolate 9-mers are completely excluded (top left of right panel: * marks the absence of 9-mers with frequencies <0.005).

FIGS. 8A and 8B) HLA binding motif counts. FIGS. 8C and 8D) number of unfavorable amino acids. In all graphs: natural sequences are marked with black circles (λ);consensus sequences with blue triangles (σ); inferred ancestral sequences with green squares (ν); and mosaic sequences with red diamonds (♥). Left panel (FIGS. 8A and 8C) shows HLA-binding-motif counts (FIG. 8A) and counts of unfavorable amino acids (FIG. 8C) calculated for individual sequences; Right panel (FIGS. 8B and 8D) shows HLA binding motifs counts (FIG. 8B) and counts of unfavorable amino acids (FIG. 8D) calculated for sequence cocktails. The top portion of each graph (box-and-whiskers graph) shows the distribution of respective counts (motif counts or counts of unfavorable amino acids) based either on alignment of M group sequences (for individual sequences, FIGS. 8A and 8C) or on 100 randomly composed cocktails of three sequences, one from each A, B and C subtypes (for sequence cocktails, FIGS. 8B and 8D). The alignment was downloaded from the Los Alamos HIV database. The box extends from the 25 percentile to the 75 percentile, with the line at the median. The whiskers extending outside the box show the highest and lowest values. Amino acids that are very rarely found as C-terminal anchor residues are G, S, T, P, N, Q, D, E, and H, and tend to be small, polar, or negatively charged (Yusim et al, J. Virol. 76:8757-8768 (2002)). Results are shown for Gag, but the same qualitative results hold for Nef core and complete Nef. The same procedure was done for supertype motifs with results qualitatively similar to the results for HLA binding motifs (data not shown).

FIG. 9. Mosaic protein sets limited to 4 sequences (k=4), spanning Gag and the central region of Nef, optimized for subtype B, subtype C, and the M group. Figure discloses SEQ ID NOs: 1-84, respectively, in order of appearance.

FIG. 10. Mosaic sets for Env and Pol. Figure discloses SEQ ID NOs: 85-168, respectively, in order of appearance.

FIG. 11. This plot is alignment independent, based on splintering all M group proteins, (database and CHAVI, one sequence per person) into all possible 9-mers, attending to their frequencies, and then looking for matches and near matches in each vaccine antigen or cocktail with the database.

FIGS. 15A-5D. Plots mapping every amino acid in every sequence in the full database alignment.

FIG. 17. Coverage of the HIV database plus CHAVI sequences (N=2020).

FIG. 21. Gag, Nef and Env sequences. Figure discloses SEQ ID NOs: 169-179, respectively, in order of appearance.

FIG. 22. Mosaic gag and nef genes and M consensus gag and nef genes. Figure discloses SEQ ID NOs: 180-187, 183, 188, 184, 189-191, 183, 188, 184, 192-194, 183-184, 195-197, 183-184, 198-200, 183-184, 201-204, 183-184, 205-207, 183-184, 208-211, 183-184, 212-217, 183-184, 208 and 218, respectively, in order of appearance.

DETAILED DESCRIPTION OF THE INVENTION

Figures 1A, 1B, 1C, 1D, 1E, 1F:
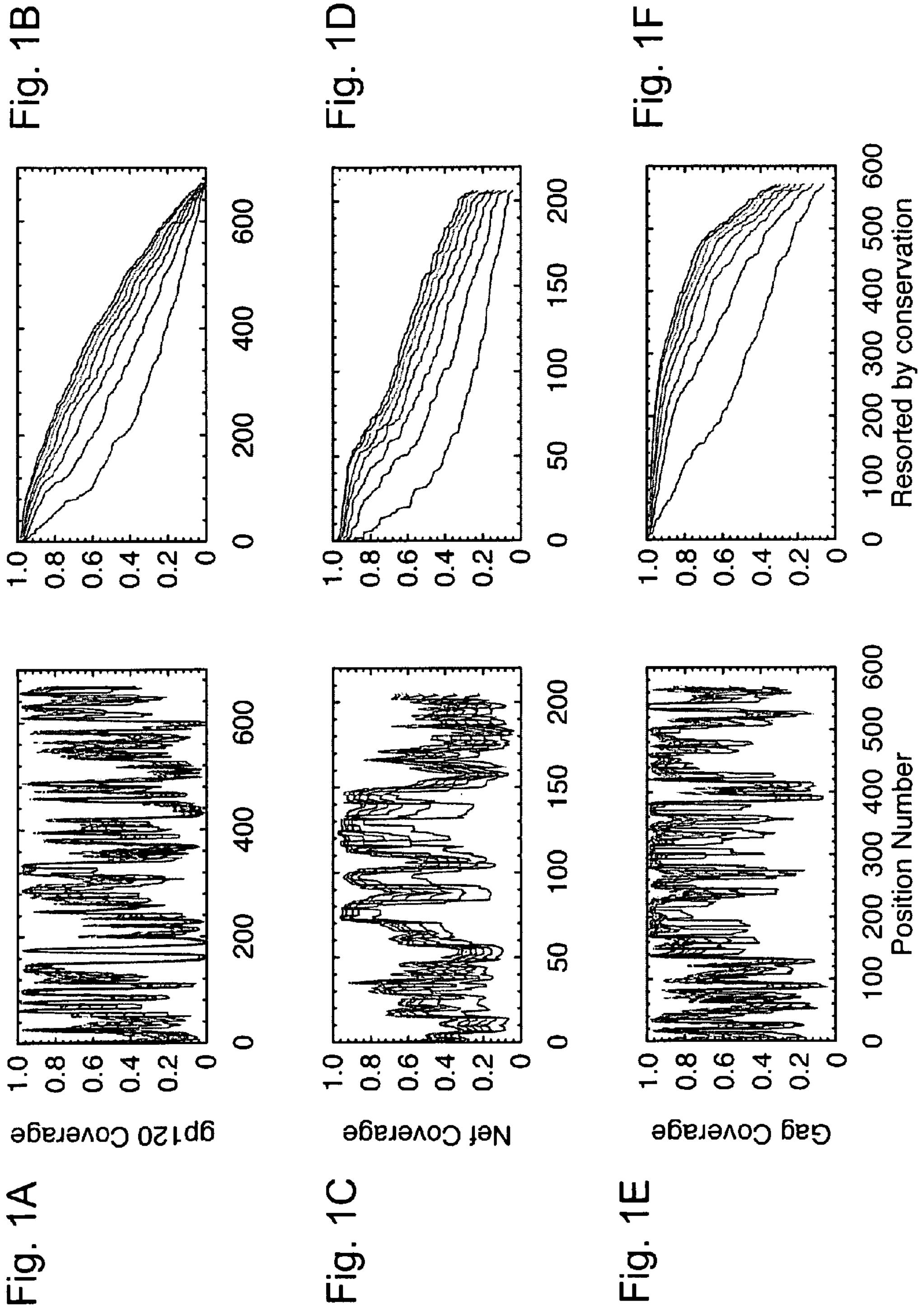
FIGS. 1A-1F. The upper bound of potential epitope coverage of the HIV-1 M group. The upper bound for population coverage of 9-mers for increasing numbers of variants is shown, for k=1-8 variants. A sliding window of length nine was applied across aligned sequences, moving down by one position. Different colors denote results for different numbers of sequences. At each window, the coverage given by the k most common 9-mers is plotted for Gag (FIGS. 1A and 1B), Nef (FIGS. 1C and 1D) and Env gp120 (FIGS. 1E and 1F). Gaps inserted to maintain the alignment are treated as characters. The diminishing returns of adding more variants are evident, since, as k increases, increasingly rare forms are added.

The present invention results from the realization that a polyvalent set of antigens comprising synthetic viral proteins, the sequences of which provide maximum coverage of non-rare short stretches of circulating viral sequences, constitutes a good vaccine candidate. The invention provides a "genetic algorithm" strategy to create such sets of polyvalent antigens as mosaic blends of fragments of an arbitrary set of natural protein sequences provided as inputs. In the context of HIV, the proteins Gag and Nef are ideal candidates for such antigens. To expand coverage, Pol and/or Env can also be used. The invention further provides optimized sets for these proteins.

The genetic algorithm strategy of the invention uses unaligned protein sequences from the general population as an input data set, and thus has the virtue of being "alignment independent". It creates artificial mosaic proteins that resemble proteins found in nature—the success of the consensus antigens in small animals models suggest this works well. 9 Mers are the focus of the studies described herein, however, different length peptides can be selected depending on the intended target. In accordance with the present approach, 9 mers (for example) that do not exist in nature or that are very rare can be excluded—this is an improvement relative to consensus sequences since the latter can contain some 9 mers (for example) that have not been found in nature, and relative to natural strains that almost invariably contain some 9 mers (for example) that are unique to that strain. The definition of fitness used s for the genetic algorithm is that the most "fit" polyvalent cocktail is the combination of mosaic strains that gives the best coverage (highest fraction of perfect matches) of all of the 9 mers in the population and is subject to the constraint that no 9 mer is absent or rare in the population.

The mosaics protein sets of the invention can be optimized with respect to different input data sets—this allows use of current data to assess virtues of a subtype or region specific vaccines from a T cell perspective. By way of example, options that have been compared include:

1) Optimal polyvalent mosaic sets based on M group, B clade and C clade. The question presented was how much better is intra-clade coverage than inter-clade or global.
2) Different numbers of antigens: 1, 3, 4, 6
3) Natural strains currently in use for vaccine protocols just to exemplify "typical" strains (Merck, VRC)
4) Natural strains selected to give the best coverage of 9-mers in a population
5) Sets of consensus: A+B+C.
6) Optimized cocktails that include one "given" strain in a polyvalent antigen, one ancestral+3 mosaic strains, one consensus+3 mosaic strains.
7) Coverage of 9 mers that were perfectly matched was compared with those that match 8/9, 7/9, and 6/9 or less.

This is a computationally difficult problem, as the best set to cover one 9-mer may not be the best set to cover overlapping 9-mers.

It will be appreciated from a reading of this disclosure that the approach described herein can be used to design peptide reagents to test HIV immune responses, and be applied to other variable pathogens as well. For example, the present approach can be adapted to the highly variable virus Hepatitis C.

The proteins/polypeptides/peptides ("immunogens") of the invention can be formulated into compositions with a pharmaceutically acceptable carrier and/or adjuvant using techniques well known in the art. Suitable routes of administration include systemic (e.g. intramuscular or subcutaneous), oral, intravaginal, intrarectal and intranasal.

The immunogens of the invention can be chemically synthesized and purified using methods which are well known to the ordinarily skilled artisan. The immunogens can also be synthesized by well-known recombinant DNA techniques.

Nucleic acids encoding the immunogens of the invention can be used as components of, for example, a DNA vaccine wherein the encoding sequence is administered as naked DNA or, for example, a minigene encoding the immunogen can be present in a viral vector. The encoding sequences can be expressed, for example, in mycobacterium, in a recombinant chimeric adenovirus, or in a recombinant attenuated vesicular stomatitis virus. The encoding sequence can also be present, for example, in a replicating or non-replicating adenoviral vector, an adeno-associated virus vector, an attenuated *mycobacterium tuberculosis* vector, a *Bacillus Calmette Guerin* (BCG) vector, a vaccinia or Modified Vaccinia Ankara (MVA) vector, another pox virus vector, recombinant polio and other enteric virus vector, *Salmonella* species bacterial vector, *Shigella* species bacterial vector, Venezuelean Equine Encephalitis Virus (VEE) vector, a Semliki Forest Virus vector, or a Tobacco Mosaic Virus vector. The encoding sequence, can also be expressed as a DNA plasmid with, for example, an active promoter such as a CMV promoter. Other live vectors can also be used to express the sequences of the invention. Expression of the immunogen of the invention can be induced in a patient's own cells, by introduction into those cells of nucleic acids that encode the immunogen, preferably using codons and promoters that optimize expression in human cells. Examples of methods of making and using DNA vaccines are disclosed in U.S. Pat. Nos. 5,580,859, 5,589,466, and 5,703,055. Examples of methods of codon optimization are described in Haas et al, Current Biology 6:315-324 (1996) and in Andre et al, J. Virol. 72(2):1497-1503 (1998).

It will be appreciated that adjuvants can be included in the compositions of the invention (or otherwise administered to enhance the immunogenic effect). Examples of suitable adjuvants include TRL-9 agonists, TRL-4 agonists, and TRL-7, 8 and 9 agonist combinations (as well as alum). Adjuvants can take the form of oil and water emulsions. Squalene adjuvants can also be used.

The composition of the invention comprises an immunologically effective amount of the immunogen of this invention, or nucleic acid sequence encoding same, in a pharmaceutically acceptable delivery system. The compositions can be used for prevention and/or treatment of virus infection (e.g. HIV infection). As indicated above, the compositions of the invention can be formulated using adjuvants, emulsifiers, pharmaceutically-acceptable carriers or other ingredients routinely provided in vaccine compositions. Optimum formulations can be readily designed by one of ordinary skill in the art and can include formulations for immediate release and/or for sustained release, and for induction of systemic immunity and/or induction of localized mucosal immunity (e.g, the formulation can be designed for intranasal, intravaginal or intrarectal administration). As noted above, the present compositions can be administered by any convenient route including subcutaneous, intranasal, oral, intramuscular, or other parenteral or enteral route. The immunogens can be administered as a single dose or multiple doses. Optimum immunization schedules can be readily determined by the ordinarily skilled artisan and can vary with the patient, the composition and the effect sought.

The invention contemplates the direct use of both the immunogen of the invention and/or nucleic acids encoding same and/or the immunogen expressed as as indicated above. For example, a minigene encoding the immunogen can be used as a prime and/or boost.

The invention includes any and all amino acid sequences disclosed herein, as well as nucleic acid sequences encoding same (and nucleic acids complementary to such encoding sequences).

Specifically disclosed herein are vaccine antigen sets optimized for single B or C subtypes, targeting regional epidemics, as well as for all HIV-1 variants in global circulation [the HIV-1 Main (M) group]. In the study described in Example 1 that follows, the focus is on designing polyvalent vaccines specifically for T-cell responses. HIV-1 specific T-cells are likely to be crucial to an HIV-1-specific vaccine response: CTL responses are correlated with slow disease progression in humans (Oxenius et al, J. Infect. Dis. 189:1199-1208 (2004)), and the importance of CTL responses in non-human primate vaccination models is well-established. Vaccine elicited cellular immune responses help control pathogenic SIV or SHIV, and reduce the likelihood of disease after challenge with pathogenic virus (Barouch et al, Science 290:486-492 (2000)). Temporary depletion of CD8+ T cells results in increased viremia in SIV-infected rhesus macaques (Schmitz et al, Science 283:857-860 (1999)). Furthermore, the evolution of escape mutations has been associated with disease progression, indicating that CTL responses help constrain viral replication in vivo (Barouch et al, J. Virol. 77:7367-7375 (2003)), and so vaccine-stimulated memory responses that could block potential escape routes may be of value. While the highly variable Envelope (Env) is the primary target for neutralizing antibodies against HIV, and vaccine antigens will also need to be tailored to elicit these antibody responses (Moore & Burton, Nat. Med. 10:769-771 (2004)), T-cell vaccine components can target more conserved proteins to trigger responses that are more likely to cross-react. But even the most conserved HIV-1 proteins are diverse enough that variation will be an issue. Artificial central-sequence vaccine approaches, consensus and ancestral sequences (Gaschen et al, Science 296:2354-2360 (2002), Gao et al, J. Virol. 79:1154-1163 (2005), Doria-Rose et al, J. Virol. 79:11214-11224 (2005)), which essentially "split the differences" between strains, show promise, stimulating responses with enhanced cross-reactivity compared to natural strain vaccines (Gao et al, J. Virol. 79:1154-1163 (2005)) (Liao et al. and Weaver et al., submitted.) Nevertheless, even central strains cover the spectrum of HIV diversity to a very limited extent, and consensus-based peptide reagents fail to detect many autologous CD8+ T-cell responses (Altfeld et al, J. Virol. 77:7330-7340 (2003)).

A single amino acid substitution can mediate T-cell escape, and as one or more amino acids in many T-cell epitopes differ between HIV-1 strains, the potential effectiveness of responses to any one vaccine antigen is limited. Whether a particular mutation will diminish T-cell cross-reactivity is epitope- and T-cell-specific, although some changes can broadly affect between-clade cross-reactivity (Norris et al, AIDS Res. Hum. Retroviruses 20:315-325 (2004)). Including more variants in a polyvalent vaccine could enable responses to a broader range of circulating variants. It could also prime the immune system against common escape variants (Jones et al, J. Exp. Med. 200:1243-1256 (2004)); escape from one T-cell receptor might create a variant that is susceptible to another (Lee et al, J. Exp. Med. 200:1455-1466 (2004)), thus stimulating polyclonal responses to epitope variants may be beneficial (Killian et al, AIDS 19:887-896 (2005)). Immune escape involving avenues that inhibit processing (Milicic et al, J. Immunol. 175:4618-4626 (2005)) or HLA binding (Amaranond et al, AIDS Res. Hum. Retroviruses 21:395-397 (2005)) prevent epitope presentation, and in such cases the escape variant could not be countered by a T-cell with a different specificity. However, it is possible the presence of T-cells that recognize overlapping epitopes may in some cases block these even escape routes.

Certain aspects of the invention can be described in greater detail in the non-limiting Examples that follow.

EXAMPLE 1

Experimental Details

HIV-1 sequence data. The reference alignments from the 2005 HIV sequence database (http://hiv.lanl.gov), which contain one sequence per person, were used, supplemented by additional recently available C subtype Gag and Nef sequences from Durban, South Africa (GenBank accession numbers AY856956-AY857186) (Kiepiela et al, Nature 432: 769-75 (2004)). This set contained 551 Gag and 1,131 Nef M group sequences from throughout the globe; recombinant sequences were included as well as pure subtype sequences for exploring M group diversity. The subsets of these alignments that contained 18 A, 102 B, 228 C, and 6 G subtype (Gag), and 62 A, 454 B, 284 C, and 13 G subtype sequences (Nef) sequences were used for within- and between-single-clade optimizations and comparisons.

The genetic algorithm. GAs are computational analogues of biological processes (evolution, populations, selection, recombination) used to find solutions to problems that are difficult to solve analytically (Holland, Adaptation in Natural and Artificial Systems: An Introductory Analysis with Applicatins to Biology, Control, and Artificial Intelligence, (M.I.T. Press, Cambridge, Mass. (1992))). Solutions for a given input are "evolved" though a process of random modification and selection according to a "fitness" (optimality) criterion. GAs come in many flavors; a "steady-state co-evolutionary multi-population" GA was implemented. "Steady-state" refers to generating one new candidate solution at a time, rather than a whole new population at once; and "co-evolutionary" refers to simultaneously evolving several distinct populations that work together to form a complete solution. The input is an unaligned set of natural sequences; a candidate solution is a set of k pseudo-natural "mosaic" sequences, each of which is formed by concatenating sections of natural sequences. The fitness criterion is population coverage, defined as the proportion of all 9-amino-acid sequence fragments (potential epitopes) in the input sequences that are found in the s cocktail.

Figures 2A, 2B, 2C:
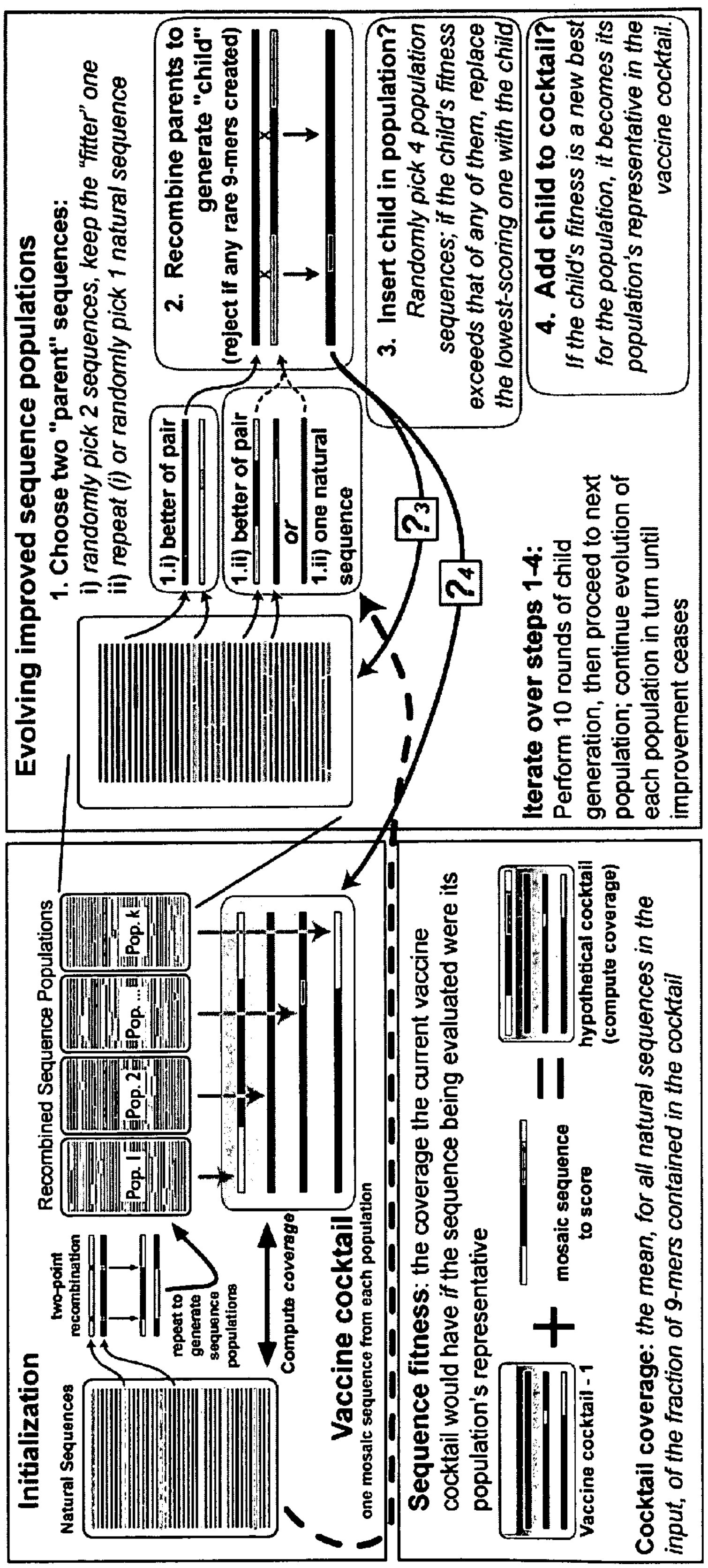
FIGS. 2A-2C. Mosaic initialization, scoring, and optimization.

To initialize the GA (FIG. 2), k populations of n initial candidate sequences are generated by 2-point recombination between randomly selected natural sequences. Because the input natural sequences are not aligned, "homologous" crossover is used: crossover points in each sequence are selected by searching for short matching strings in both sequences; strings of c-1=8, were used where a typical epitope length is c=9. This ensures that the recombined sequences resemble natural proteins: the boundaries between sections of sequence derived from different strains are seamless, the local sequences spanning the boundaries are always found in nature, and the mosaics are prevented from acquiring large insertions/deletions or unnatural combinations of amino acids. Mosaic sequence lengths fall within the distribution of natural sequence lengths as a consequence of mosaic construction: recombination is only allowed at identical regions, reinforced by an explicit software prohibition against excessive lengths to prevent reduplication of repeat regions. (Such "in frame" insertion of reduplicated epitopes could provide another way of increasing coverage without generating unnatural 9-mers, but their inclusion would create "unnatural" proteins.) Initially, the cocktail contains one randomly chosen "winner" from each population. The fitness score for any individual sequence in a population is the coverage value for the cocktail consisting of that sequence plus the current winners from the other populations. The individual fitness of any sequence in a population therefore depends dynamically upon the best sequences found in the other populations.

Optimization proceeds one population at a time. For each iteration, two "parent" sequences are chosen. The first parent is chosen using "2-tournament" selection: two sequences are picked at random from the current population, scored, and the better one is chosen. This selects parents with a probability inversely proportional to their fitness rank within the population, without the need to actually compute the fitness of all individuals. The second parent is chosen in the same way (50% of the time), or is selected at random from the set of natural sequences. 2-point homologous crossover between the parents is then used to generate a "child" sequence. Any child containing a 9-mer that was very rare in the natural population (found less than 3 times) is rejected immediately. Otherwise, the new sequence is scored, and its fitness is compared with the fitnesses of four randomly chosen sequences from the same population. If any of the four randomly chosen sequences has a score lower than that of the new sequence, it is replaced in the population by the new sequence. Whenever a sequence is encountered that yields a better score than the current population "winner", that sequence becomes the winner for the current population and so is subsequently used in the cocktail to evaluate sequences in other populations. A few such optimization cycles (typically 10) are applied to each population in turn, and this process continues cycling through the populations until evolution stalls (i.e., no improvement has been made for a defined number of generations). At this point, the entire procedure is restarted using newly generated random starting populations, and the restarts are continued until no further improvement is seen. The GA was run on each data set with n=50 or 500; each run was continued until no further improvement occurred for 12-24 hours on a 2 GHz Pentium processor. Cocktails were generated having k=1, 3, 4, or 6 mosaic sequences.

The GA also enables optional inclusion of one or more fixed sequences of interest (for example, a consensus) in the cocktail and will evolve the other elements of the cocktail in order to optimally complement that fixed strain. As these solutions were suboptimal, they are not included here. An additional program selects from the input file the k best natural strains that in combination provide the best population coverage.

Comparison with other polyvalent vaccine candidates. Population coverage scores were computed for other potential mono- or polyvalent vaccines to make direct comparisons with the mosaic-sequence vaccines, tracking identities with population 9-mers, as well as similarities of 8/9 and 7/9 amino acids. Potential vaccine candidates based on natural strains include single strains (for example, a single C strain for a vaccine for southern Africa (Williamson et al, AIDS Res. Hum. Retroviruses 19:133-44 (2003))) or combinations of natural strains (for example, one each of subtype A, B, and C (Kong et al, J. Virol. 77:12764-72 (2003)). To date, natural-strain vaccine candidates have not been systematically selected to maximize potential T-cell epitope coverage; vaccine candidates were picked from the literature to be representative of what could be expected from unselected vaccine candidates. An upper bound for coverage was also determined using only intact natural strains: optimal natural-sequence cocktails were generated by selecting the single sequence with the best coverage of the dataset, and then successively adding the most complementary sequences up to a given k. The comparisons included optimal natural-sequence cocktails of various sizes, as well as consensus sequences, alone or in combination (Gaschen et al, Science 296:2354-60 (2002)), to represent the concept of central, synthetic vaccines. Finally, using the fixed-sequence option in the GA, consensus-plus-mosaic combinations in the comparisons; these scores were essentially equivalent to all-mosaic combinations were included for a given k (data not shown). The code used for performing these analyses are available at: ftp://ftp-t10/pub/btk/mosaics.

Results

Protein Variation. In conserved HIV-1 proteins, most positions are essentially invariant, and most variable positions have only two to three amino acids that occur at appreciable frequencies, and variable positions are generally well dispersed between conserved positions. Therefore, within the boundaries of a CD8+ T-cell epitope (8-12 amino acids, typically nine), most of the population diversity can be covered with very few variants. FIG. 1 shows an upper bound for population coverage of 9-mers (stretches of nine contiguous amino acids) comparing Gag, Nef, and Env for increasing numbers of variants, sequentially adding variants that provide the best coverage. In conserved regions, a high degree of population coverage is achieved with 2-4 variants. By contrast, in variable regions like Env, limited population coverage is possible even with eight variants. Since each new addition is rarer, the relative benefits of each addition diminish as the number of variants increases.

Vaccine design optimization strategies. FIG. 1 shows an idealized level of 9-mer coverage. In reality, high-frequency 9-mers often conflict: because of local co-variation, the optimal amino acid for one 9-mer may differ from that for an overlapping 9-mer. To design mosaic protein sets that optimize population coverage, the relative benefits of each amino acid must be evaluated in combination with nearby variants. For example, Alanine (Ala) and Glutamate (Glu) might each frequently occur in adjacent positions, but if the Ala-Glu combination is never observed in nature, it should be excluded from the vaccine. Several optimization strategies were investigated: a greedy algorithm, a semi-automated compatible-9mer assembly strategy, an alignment-based genetic algorithm (GA), and an alignment-independent GA.

The alignment-independent GA generated mosaics with the best population coverage. This GA generates a user-specified number of mosaic sequences from a set of unaligned protein sequences, explicitly excluding rare or unnatural epitope-length fragments (potentially introduced at recombination breakpoints) that could induce non-protective vaccine-antigen-specific responses. These candidate vaccine sequences resemble natural proteins, but are assembled from frequency-weighted fragments of database sequences recombined at homologous breakpoints (FIG. 2); they approach maximal coverage of 9-mers for the input population.

Figure 3:
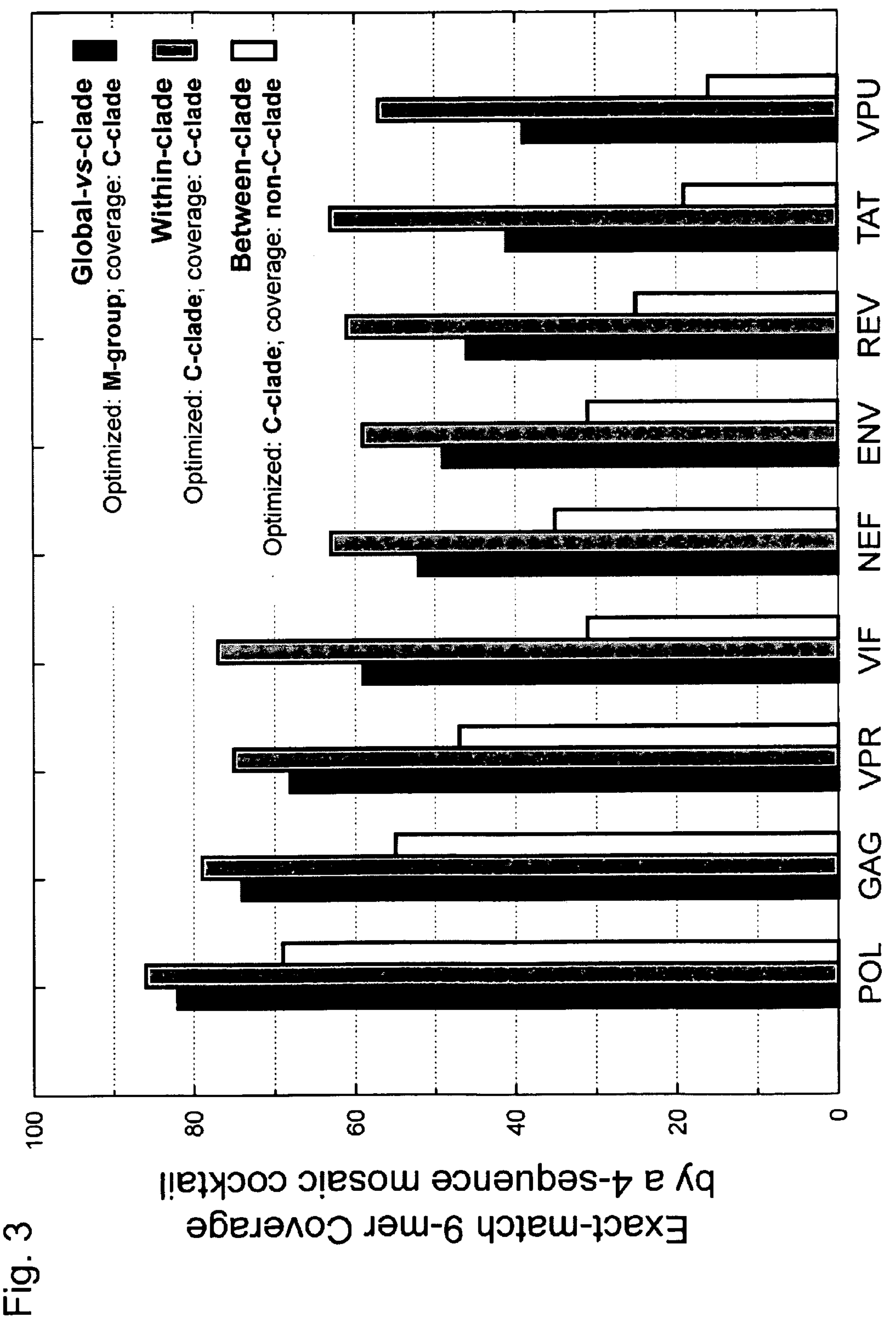
FIG. 3. Mosaic strain coverage for all HIV proteins. The level of 9-mer coverage achieved by sets of four mosaic proteins for each HIV protein is shown, with mosaics optimized using either the M group or the C subtype. The fraction of C subtype sequence 9-mers covered by mosaics optimized on the C subtype (within-clade optimization) is shown in gray. Coverage of 9-mers found in non-C subtype M-group sequences by subtype-C-optimized mosaics (between-clade coverage) is shown in white. Coverage of subtype C sequences by M-group optimized mosaics is shown in black. B clade comparisons gave comparable results (data not shown).
Figure 4A:
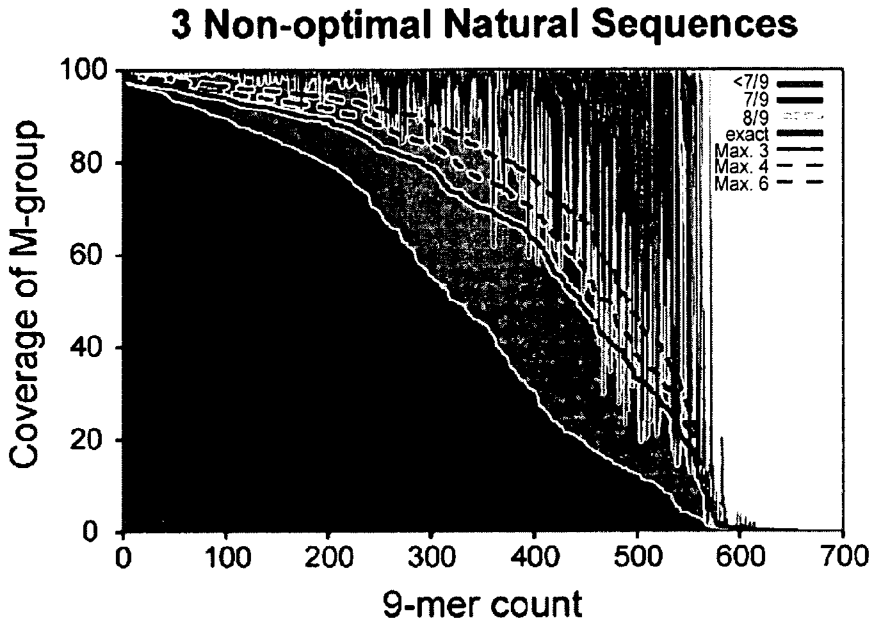
FIGS. 4A-4F. Coverage of M group sequences by different vaccine candidates, nine-mer by nine-mer. Each plot presents site-by-site coverage (i.e., for each nine-mer) of an M-group natural-sequence alignment by a single tri-valent vaccine candidate. Bars along the x-axis represent the proportion of sequences matched by the vaccine candidate for a given alignment position: 9/9 matches (in red), 8/9 (yellow), 7/9 (blue). Aligned 9-mers are sorted along the x-axis by exact-match coverage value. 656 positions include both the complete Gag and the central region of Nef. For each alignment position, the maximum possible matching value (i.e. the proportion of aligned sequences without gaps in that nine-mer) is shown in gray.
Figure 4B:
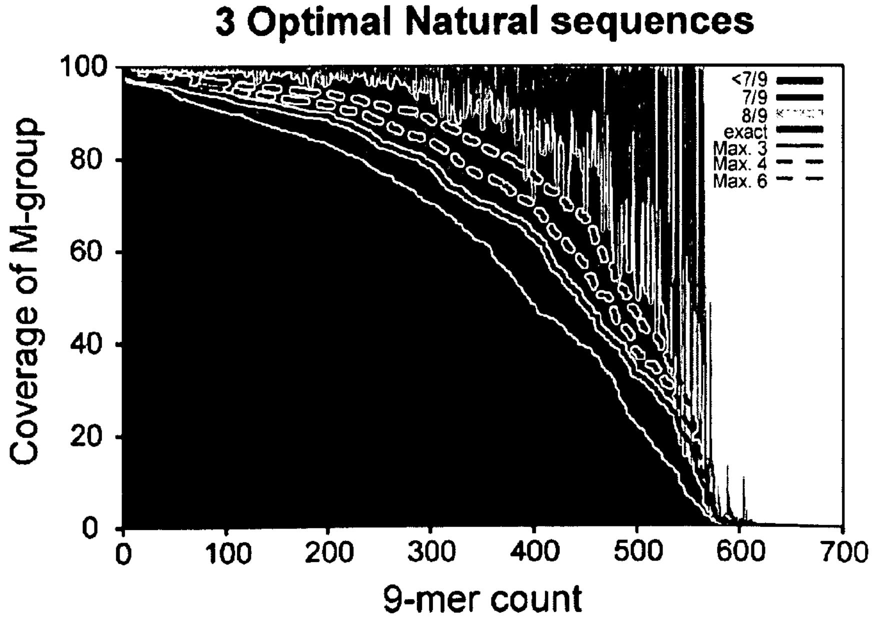
Figure 4C:
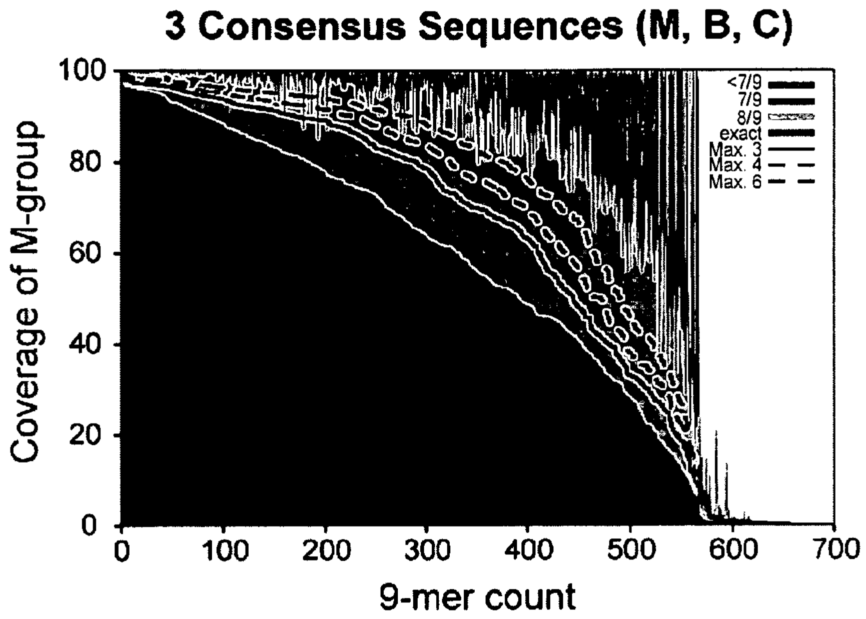
Figure 4D:
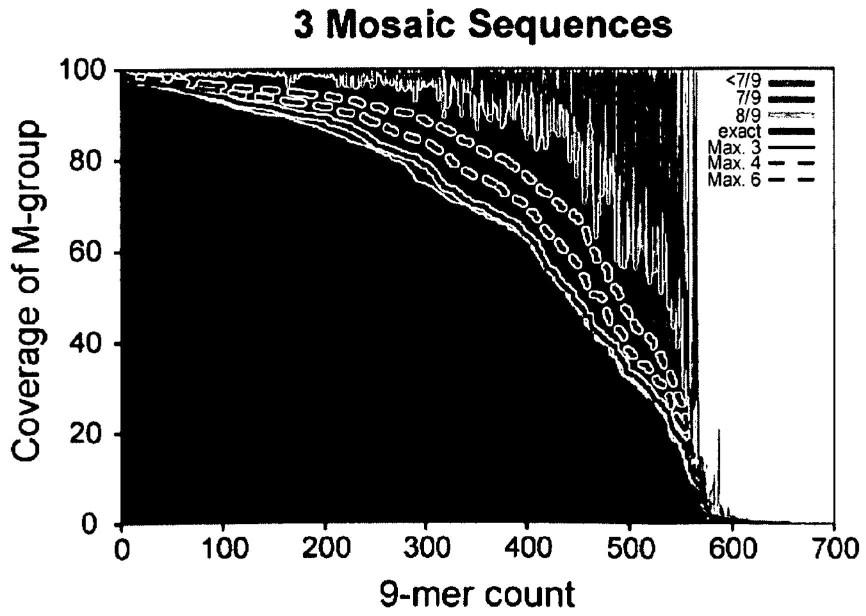
Figure 4E:
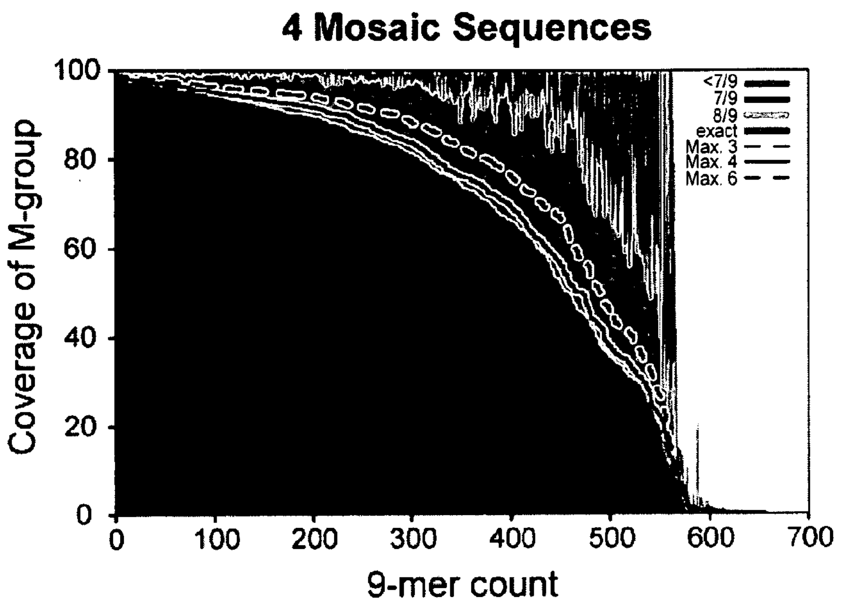
Figure 4F:
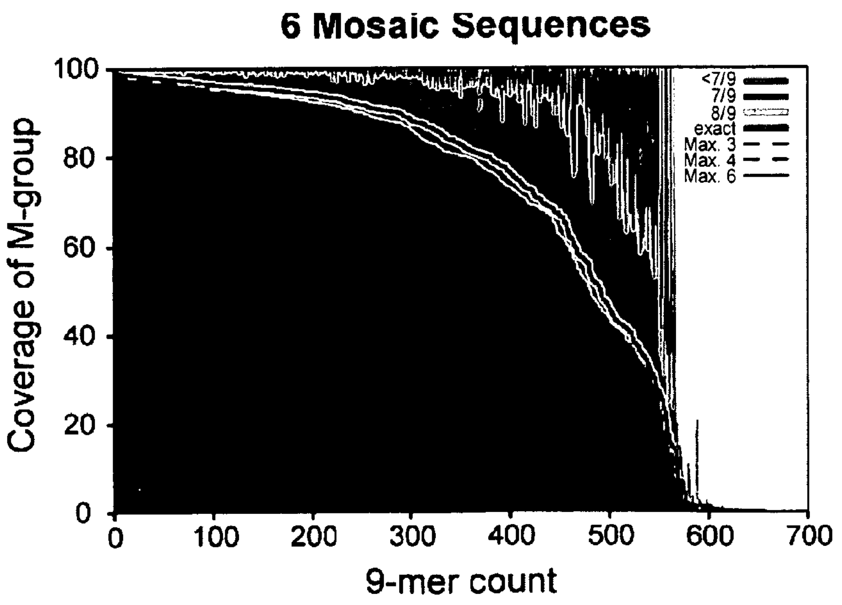

Selecting HIV protein regions for an initial mosaic vaccine. The initial design focused on protein regions meeting specific criteria: i) relatively low variability, ii) high levels of recognition in natural infection, iii) a high density of known epitopes and iv) either early responses upon infection or CD8+ T-cell responses associated with good outcomes in infected patients. First, an assessment was made of the level of 9-mer coverage achieved by mosaics for different HIV proteins (FIG. 3). For each protein, a set of four mosaics was generated using either the M group or the B- and C-subtypes alone; coverage was scored on the C subtype. Several results are notable: i) within-subtype optimization provides the best within-subtype coverage, but substantially poorer between-subtype coverage—nevertheless, B-subtype-optimized mosaics provide better C-subtype coverage than a single natural B subtype protein (Kong et al, J. Virol. 77:12764-72 (2003)); ii) Pol and Gag have the most potential to elicit broadly cross-reactive responses, whereas Rev, Tat, and Vpu have even fewer conserved 9-mers than the highly variable Env protein, iii) within-subtype coverage of M-group-optimized mosaic sets approached coverage of within-subtype optimized sets, particularly for more conserved proteins.

Gag and the central region of Nef meet the four criteria listed above. Nef is the HIV protein most frequently recognized by T-cells (Frahm et al, J. Virol. 78:2187-200 (2004)) and the target for the earliest response in natural infection (Lichterfeld et al, Aids 18:1383-92 (2004)). While overall it is variable (FIG. 3), its central region is as conserved as Gag (FIG. 1). It is not yet clear what optimum proteins for inclusion in a vaccine might be, and mosaics could be designed to maximize the potential coverage of even the most variable proteins (FIG. 3), but the prospects for global coverage are better for conserved proteins. Improved vaccine protection in macaques has been demonstrated by adding Rev, Tat, and Nef to a vaccine containing Gag, Pol, and Env (Hel et al, J. Immunol. 176:85-96 (2006)), but this was in the context of homologous challenge, where variability was not an issue. The extreme variability of regulatory proteins in circulating virus populations may preclude cross-reactive responses; in terms of conservation, Pol, Gag (particularly p24) and the central region of Nef (HXB2 positions 65-149) are promising potential immunogens (FIGS. 1,3). Pol, however, is infrequently recognized during natural infection (Frahm et al, J. Virol. 78:2187-200 (2004)), so it was not included in the initial immunogen design. The conserved portion of Nef that were included contains the most highly recognized peptides in HIV-1 (Frahm et al, J. Virol. 78:2187-200 (2004)), but as a protein fragment, would not allow Nef's immune inhibitory functions (e.g. HLA class I down-regulation (Blagoveshchenskaya, Cell 111:853-66 (2002))). Both Gag and Nef are densely packed with overlapping well-characterized CD8+ and CD4+ T-cell epitopes, presented by many different HLA molecules (http://www.hiv.lanl.gov//content/immunology/maps/maps.html), and Gag-specific CD8+ (Masemola et al, J. Virol. 78:3233-43 (2004)) and CD4+ (Oxenius et al, J. Infect. Dis. 189:1199-208 (2004)) T-cell responses have been associated with low viral set points in infected individuals (Masemola et al, J. Virol. 78:3233-43 (2004)).

To examine the potential impact of geographic variation and input sample size, a limited test was done using published subtype C sequences. The subtype C Gag data were divided into three sets of comparable size—two South African sets (Kiepiela et al, Nature 432:769-75 (2004)), and one non-South-African subtype C set. Mosaics were optimized independently on each of the sets, and the resulting mosaics were tested against all three sets. The coverage of 9-mers was slightly better for identical training and test sets (77-79% 9/9 coverage), but essentially equivalent when the training and test sets were the two different South African data sets (73-75%), or either of the South African sets and the non-South African C subtype sequences (74-76%). Thus between- and within-country coverage approximated within-clade coverage, and in this case no advantage to a country-specific C subtype mosaic design was found.

Designing mosaics for Gag and Nef and comparing vaccine strategies. To evaluate within- and between-subtype cross-reactivity for various vaccine design strategies, a calculation was made of the coverage they provided for natural M-Group sequences. The fraction of all 9-mers in the natural sequences that were perfectly matched by 9-mers in the vaccine antigens were computed, as well as those having 8/9 or 7/9 matching amino acids, since single (and sometimes double) substitutions within epitopes may retain cross-reactivity. FIG. 4 shows M group coverage per 9-mer in Gag and the central region of Nef for cocktails designed by various strategies: a) three non-optimal natural strains from the A, B, and C subtypes that have been used as vaccine antigens (Kong et al, J. Virol. 77:12764-72 (2003)); b) three natural strains that were computationally selected to give the best M group coverage; c) M group, B subtype, and C subtype consensus sequences; and, d,e,f) three, four and six mosaic proteins. For cocktails of multiple strains, sets of k=3, k=4, and k=6, the mosaics clearly perform the best, and coverage approaches the upper bound for k strains. They are followed by optimally selected natural strains, the consensus protein cocktail, and finally, non-optimal natural strains. Allowing more antigens provides greater coverage, but gains for each addition are reduced as k increases (FIGS. 1 and 4).

Figure 5A:
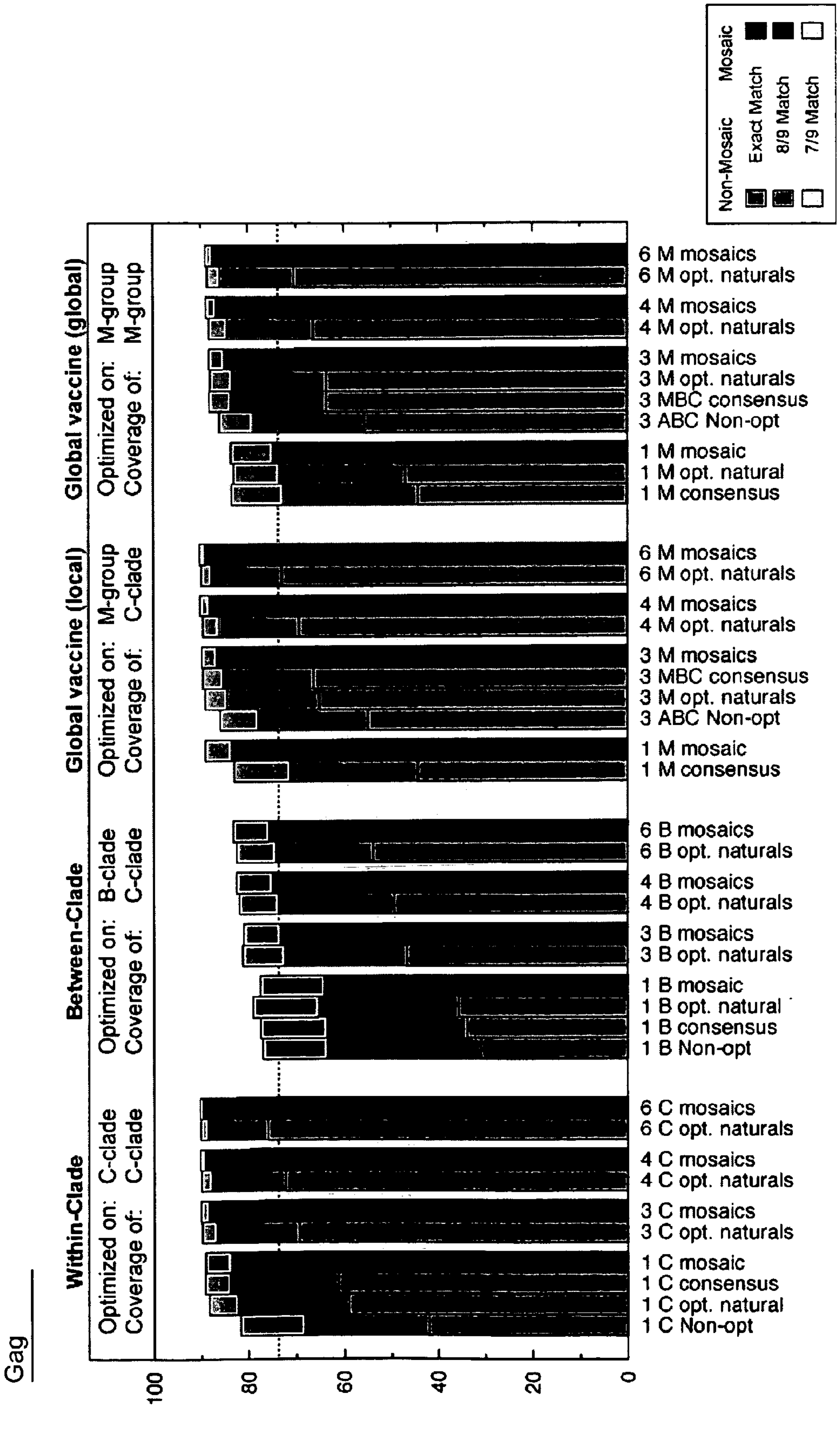
FIGS. 5A and 5B. Overall coverage of vaccine candidates: coverage of 9-mers in C clade sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 5A) and Nef (core) (FIG. 5B) for four test situations: within-clade (C-clade-optimized candidates scored for C-clade coverage), between-clade (B-clade-optimized candidates scored for C-clade coverage), global-against-single-subtype (M-group-optimized candidates scored for C-clade coverage), global-against-global (M-group-optimized candidates scored for global coverage). Within each set of results, vaccine candidates are o grouped by number of sequences in the cocktail (1-6); mosaic sequences are plotted with darker colors. "Non-opt" refers to one set of sequences moving into vaccine trials (Kong et al, J. Virol. 77:12764-72 (2003)); "mosaic" denotes sequences generated by the genetic algorithm; "opt. natural" denotes intact natural sequences selected for maximum 9-mer coverage; "MBC is consensus" denotes a cocktail of 3 consensus sequences, for M-group, B-subtype, and C-subtype. For ease of comparison, a dashed line marks the coverage of a 4-sequence set of M-group mosaics (73.7-75.6%). Over 150 combinations of mosaic-number, virus subset, protein region, and optimization and test sets were tested. The C clade/B clade/M group comparisons illustrated in this figure are generally representative of within-clade, between-clade, and M group coverage. In particular, levels of mosaic coverage for B and C clade were very similar, despite there being many more C clade sequences in the Gag collection, and many more B clade sequences in the Nef collection (see FIG. 6 for a full B and C clade comparison). There were relatively few A and G clade sequences in the alignments (24 Gag, 75 Nef), and while 9-mer coverage by M-group optimized mosaics was not as high as for subtypes for B and C clades (4-mosaic coverage for A and G subtypes was 63% for Gag, 74% for Nef), it was much better than a non-optimal cocktail (52% Gag, 52% for Nef).
Figure 5B:
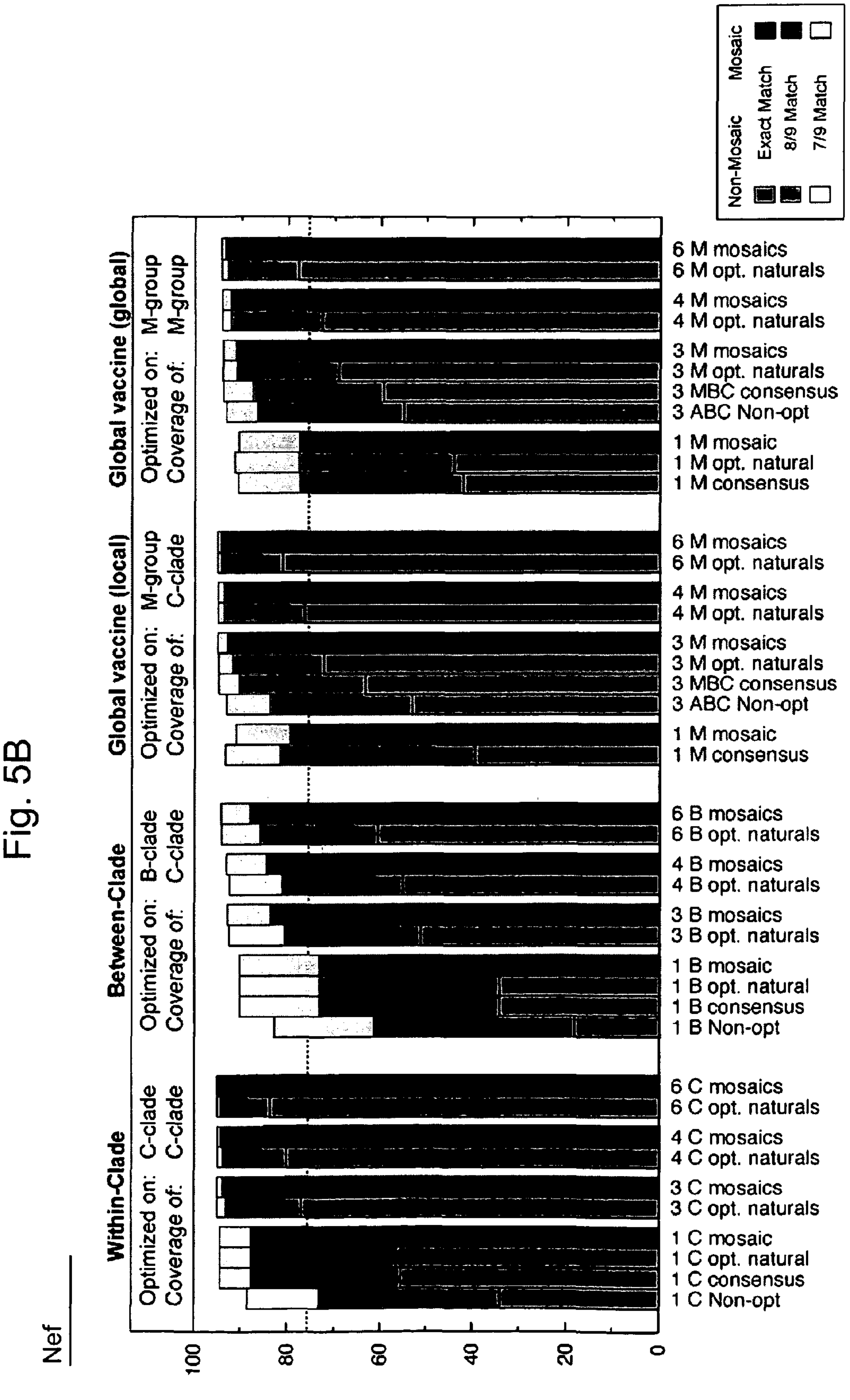
Figure 6A:
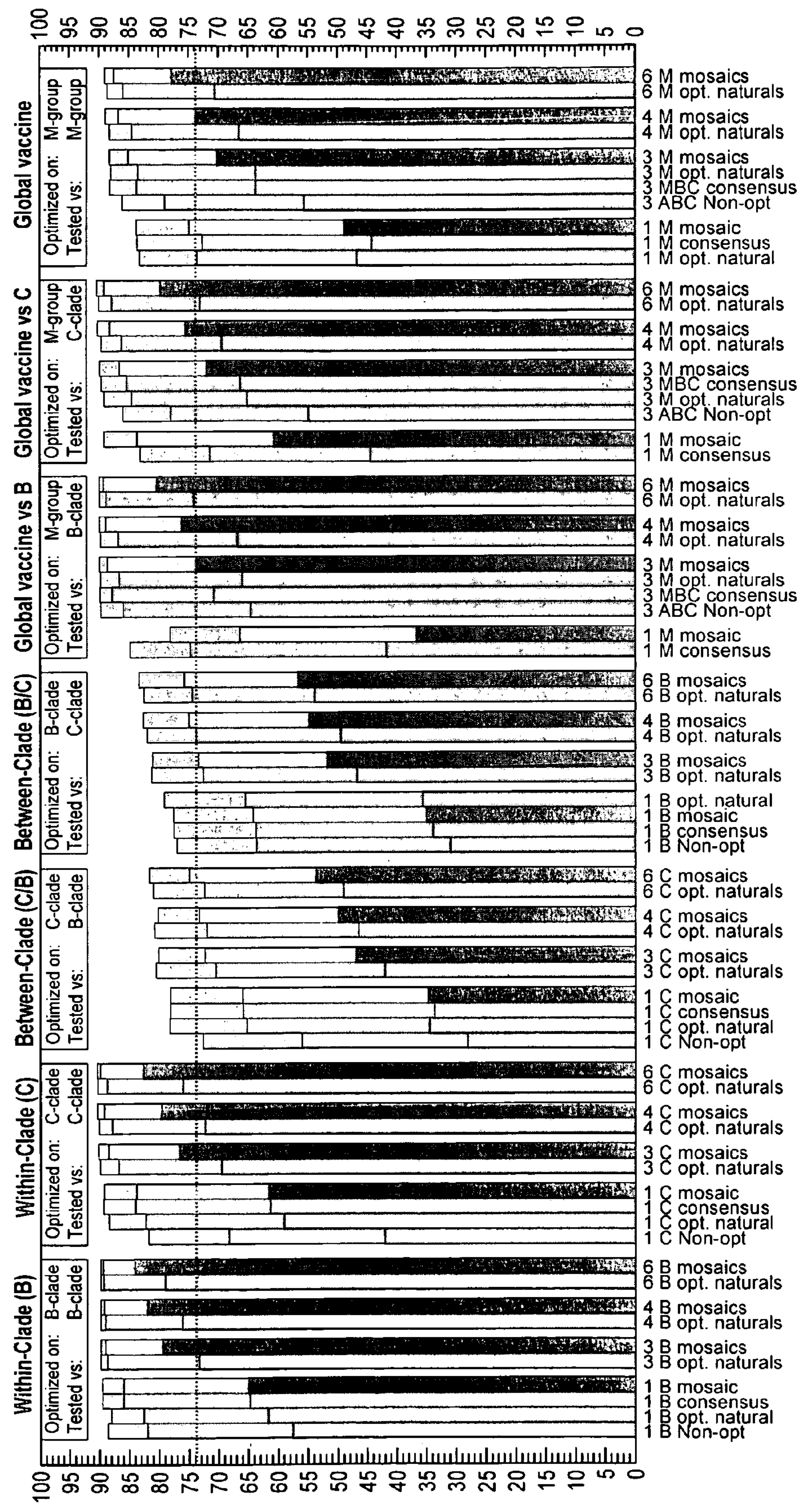
FIGS. 6A and 6B. Overall coverage of vaccine candidates: coverage of 9-mers in B-clade, C-clade, and M-group sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 6A) and Nef (core) (FIG. 6B) for seven test situations: within-clade (B- or C-clade-optimized candidates scored against the same clade), between-clade (B- or C-clade-optimized candidates scored against the other clade), global vaccine against single subtype (M-group-optimized candidates scored against B- or C-clade), global vaccine against global viruses (M-group-optimized candidates scored against all M-group sequences). Within each set of results, vaccine candidates are grouped by number of sequences in the cocktail (1-6); mosaic sequences are plotted with darker colors. "Non-opt" refers to a particular set of natural sequences previously proposed for a vaccine (Kong, W. P. et al. J Virol 77, 12764-72 (2003)); "mosaic" denotes sequences generated by the genetic algorithm; "opt. natural" denotes intact natural sequences selected for maximum 9-mer coverage; "MBC consensus" denotes a cocktail of 3 consensus sequences, for M-group, B-subtype, and C-subtype. A dashed line is shown at the level of exact-match M-group coverage for a 4-valent mosaic set optimized on the M-group.
Figure 6B:
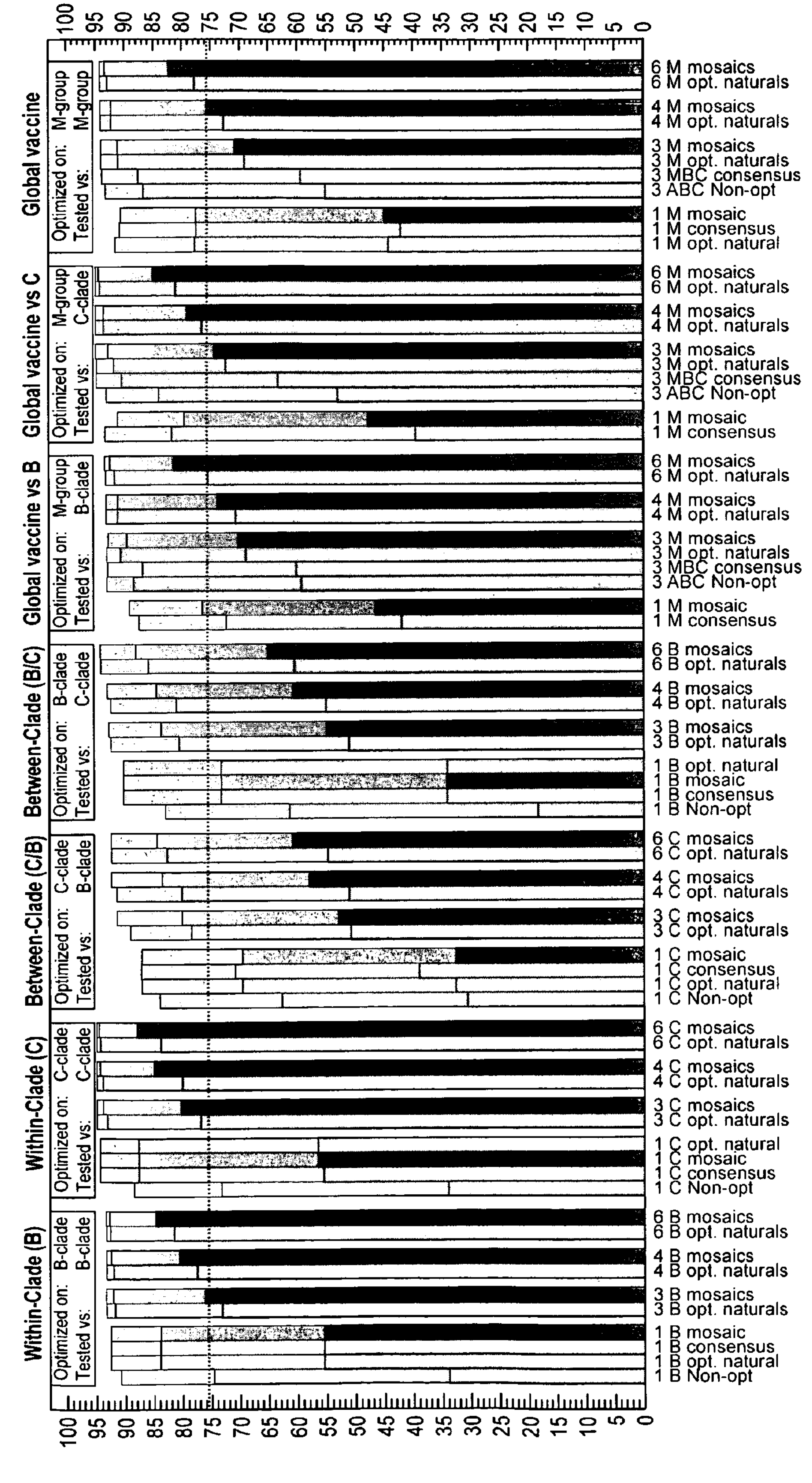

FIG. 5 summarizes total coverage for the different vaccine design strategies, from single proteins through combinations of mosaic proteins, and compares within-subtype optimization to M group optimization. The performance of a single mosaic is comparable to the best single natural strain or a consensus sequence. Although a single consensus sequence out-performs a single best natural strain, the optimized natural-sequence cocktail does better than the consensus cocktail: the consensus sequences are more similar to each other than are natural strains, and are therefore somewhat redundant. Including even just two mosaic variants, however, markedly increases coverage, and four and six mosaic proteins give progressively better coverage than polyvalent cocktails of natural or consensus strains. Within-subtype optimized mosaics perform best—with four mosaic antigens 80-85% of the 9-mers are perfectly matched—but between-subtype coverage of these sets falls off dramatically, to 50-60%. In contrast, mosaic proteins optimized using the full M group give coverage of approximately 75-80% for individual subtypes, comparable to the coverage of the M group as a whole (FIGS. 5 and 6). If imperfect 8/9 matches are allowed, both M group optimized and within-subtype optimized mosaics approach 90% coverage.

Figure 7A:
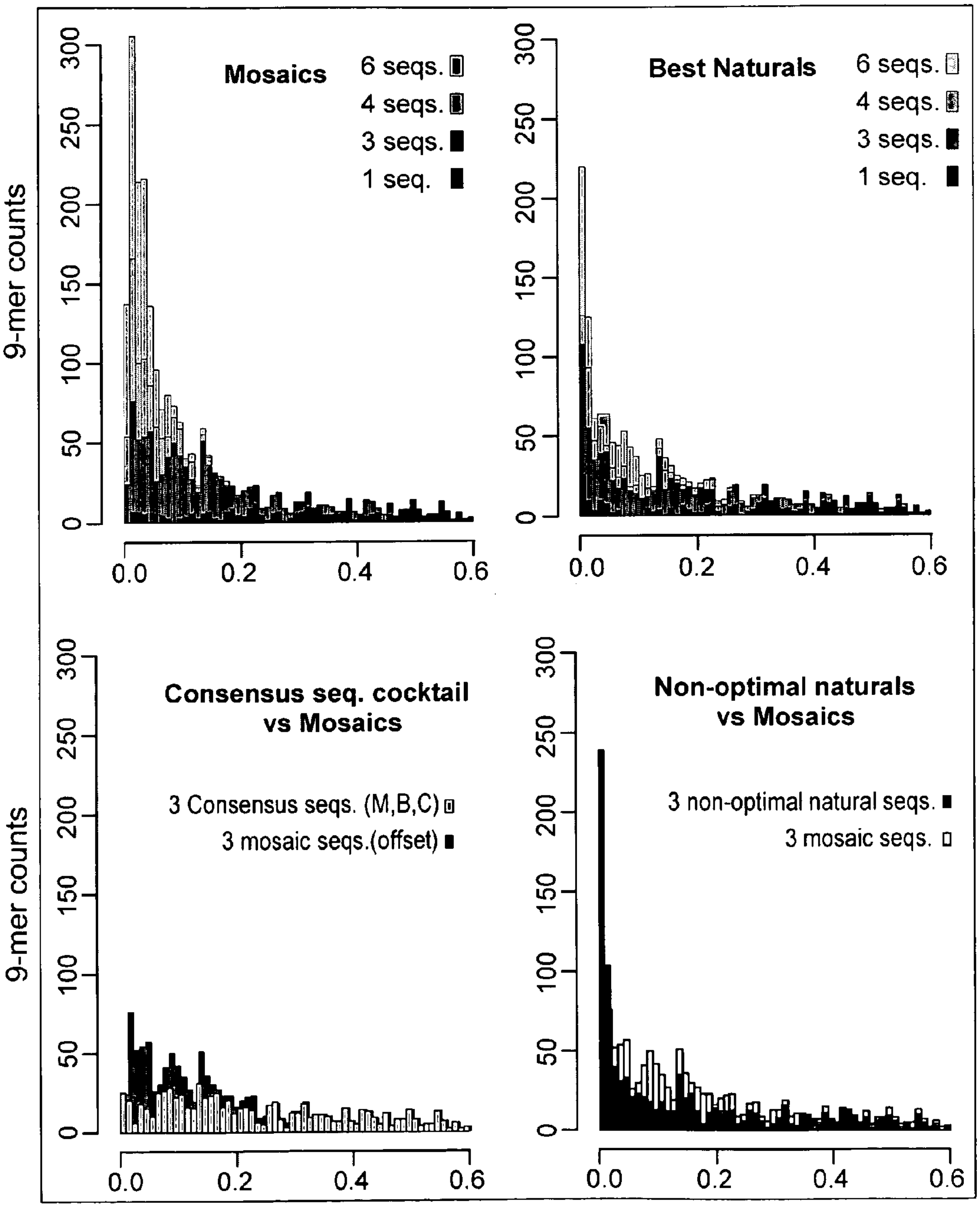
FIGS. 7A and 7B. The distribution of 9-mers by frequency of occurrence in natural, consensus,and mosaic sequences. Occurrence counts (y-axis) for different 9-mer frequencies (x-axis) for vaccine cocktails produced by several methods.
Figure 7B:
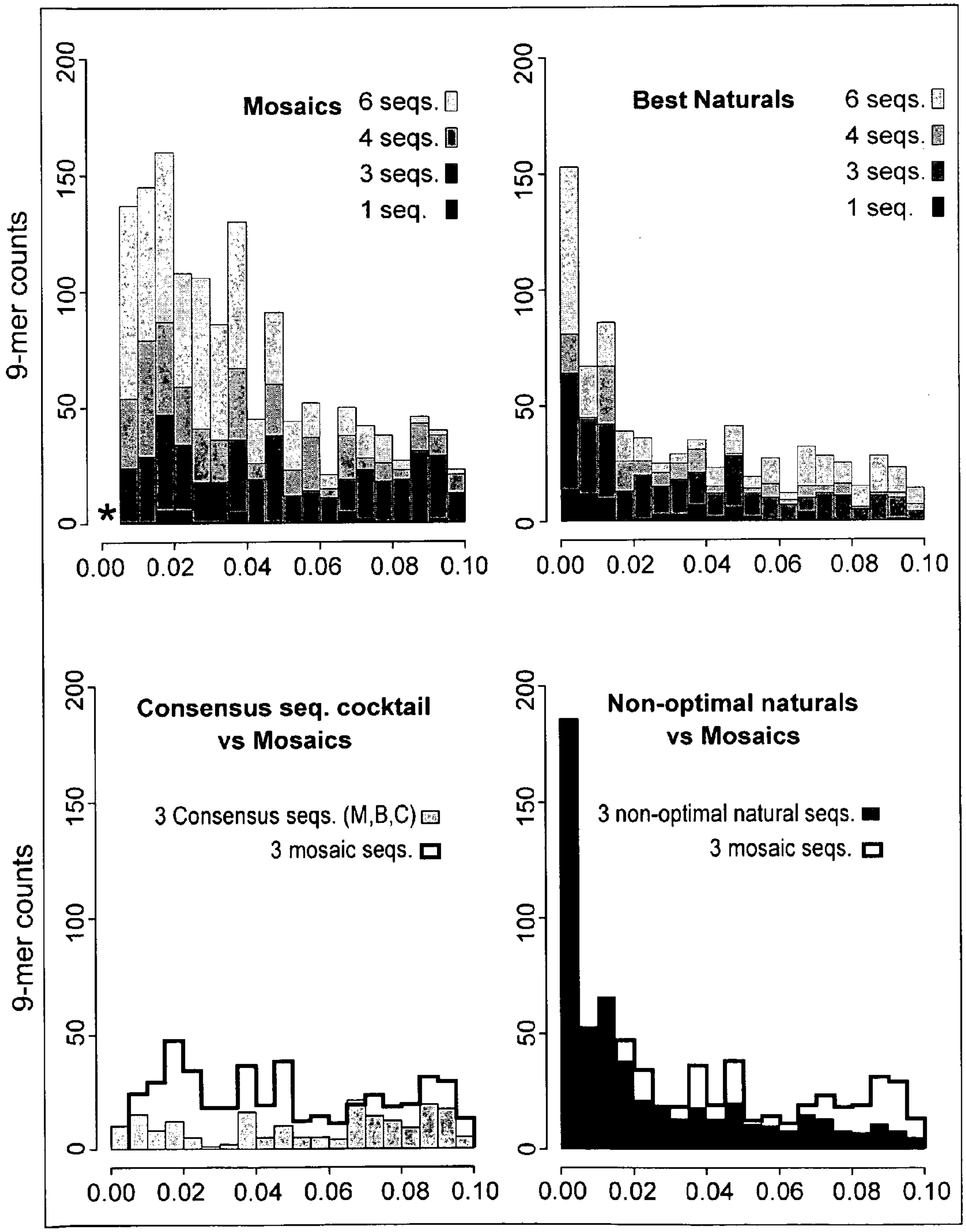
Figures 8A, 8B, 8C, 8D:
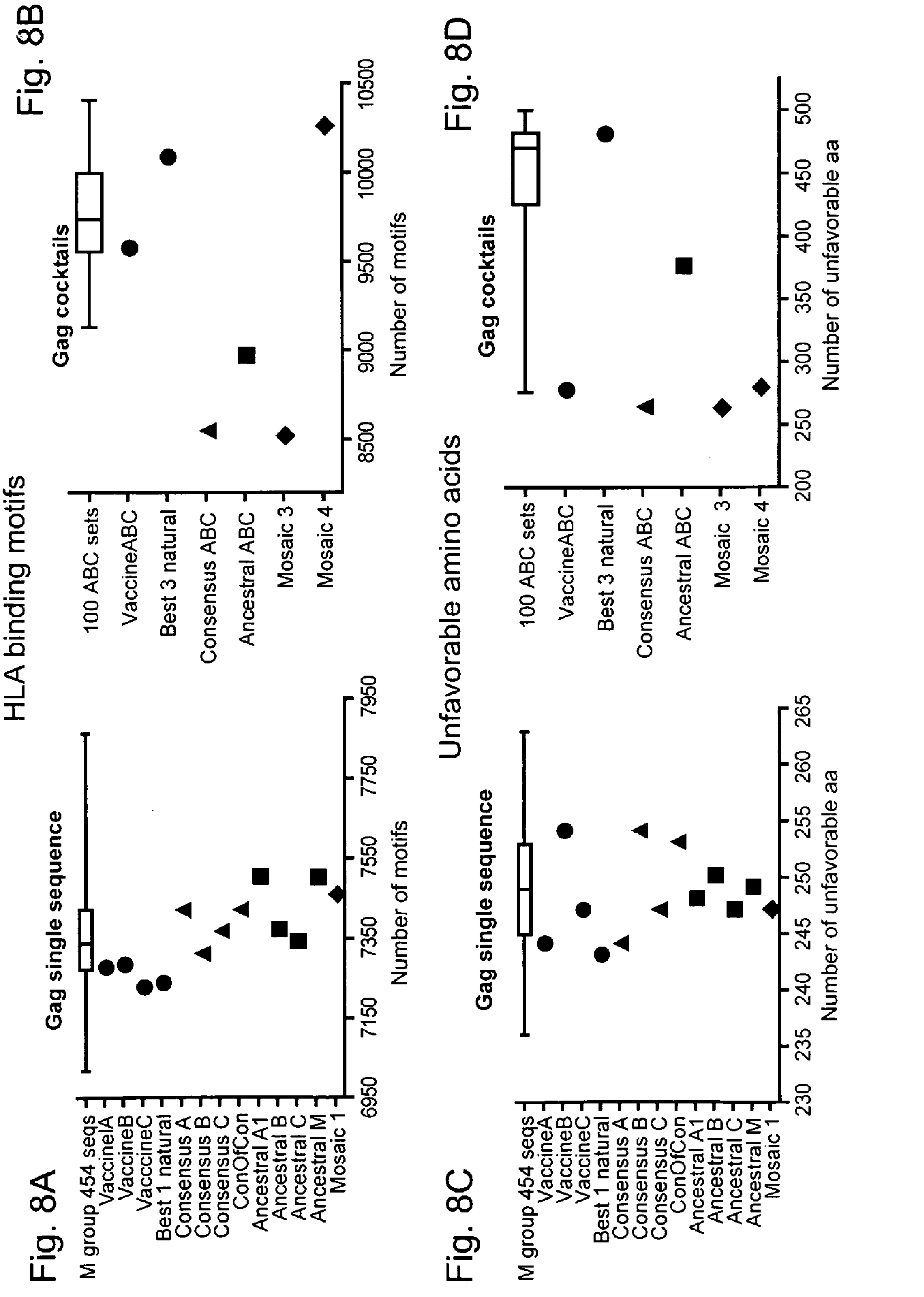
FIGS. 8A-8D. HLA binding potential of vaccine candidates.

Since coverage is increased by adding progressively rarer 9-mers, and rare epitopes may be problematic (e.g., by inducing vaccine-specific immunodominant responses), an investigation was made of the frequency distribution of 9-mers in the vaccine constructs relative to the natural sequences from which they were generated. Most additional epitopes in a k=6 cocktail compared to a k=4 cocktail are low-frequency (<0.1, FIG. 7). Despite enhancing coverage, these epitopes are relatively rare, and thus responses they induce might draw away from vaccine responses to more common, thus more useful, epitopes. Natural-sequence cocktails actually have fewer occurrences of moderately low-frequency epitopes than mosaics, which accrue some lower frequency 9-mers as coverage is optimized. On the other hand, the mosaics exclude unique or very rare 9-mers, while natural strains generally contain 9-mers present in no other sequence. For example, natural M group Gag sequences had a median of 35 (range 0-148) unique 9-mers per sequence. Retention of HLA-anchor motifs was also explored, and anchor motif frequencies were found to be comparable between four mosaics and three natural strains. Natural antigens did exhibit an increase in number of motifs per antigen, possibly due to inclusion of strain-specific motifs (FIG. 8).

The increase in ever-rarer epitopes with increasing k, coupled with concerns about vaccination-point dilution and reagent development costs, resulted in the initial production of mosaic protein sets limited to 4 sequences (k=4), spanning Gag and the central region of Nef optimized for subtype B; subtype C, and the M group (these sequences are included in FIG. 9; mosaic sets for Env and Pol are set forth in FIG. 10). Synthesis of various four-sequence Gag-Nef mosaics and initial antigenicity studies are underway. In the initial mosaic vaccine, targeted are just Gag and the center of the Nef protein, which are conserved enough to provide excellent global population coverage, and have the desirable properties described above in terms of natural responses (Bansal et al, Aids 19:241-50 (2005)). Additionally, including B subtype p24 variants in Elispot peptide mixtures to detect natural CTL responses to infection significantly enhanced both the number and the magnitude of responses detected supporting the idea that including variants of even the most conserved proteins will be useful. Finally, cocktails of proteins in a polyvalent HIV-1 vaccine given to rhesus macaques did not interfere with the development of robust responses to each antigen (Seaman et al, J. Virol. 79:2956-63 (2005)), and antigen cocktails did not produce antagonistic responses in murine models (Singh et al, J. Immunol. 169:6779-86 (2002)), indicating that antigenic mixtures are appropriate for T-cell vaccines.

Even with mosaics, variable proteins like Env have limited coverage of 9-mers, although mosaics improve coverage relative to natural strains. For example three M group natural proteins, one each selected from the A, B, and C clades, and currently under study for vaccine design (Seaman et al, J. Virol. 79:2956-63 (2005)) perfectly match only 39% of the 9-mers in M group proteins, and 65% have at least 8/9 matches. In contrast, three M group Env mosaics match 47% of 9-mers perfectly, and 70% have at least an 8/9 match. The code written to design polyvalent mosaic antigens is available, and could readily be applied to any input set of variable proteins, optimized for any desired number of antigens. The code also allows selection of optimal combinations of k natural strains, enabling rational selection of natural antigens for polyvalent vaccines. Included in Table 1 are the best natural strains for Gag and Nef population coverage of current database alignments.

TABLE 1

Natural sequence cocktails having the best available 9-mer coverage for different genes, subtype sets, and numbers of sequences Gag, B-subtype, 1 natural sequence B.US.86.AD87__AF004394
Gag, B-subtype, 3 natural sequences B.US.86.AD87__AF004394
B.US.97.Ac__06__AY247251
B.US.88.WR27__AF286365
Gag, B-subtype, 4 natural sequences B.US.86.AD87__AF004394
B.US.97.Ac__06__AY247251

TABLE 1-continued

Natural sequence cocktails having the best available 9-mer coverage for different genes, subtype sets, and numbers of sequences B.US.__.R3__PDC1__AY206652
B.US.88.WR27__AF286365
Gag, B-subtype, 6 natural sequences B.CN.__.CNHN24__AY180905
B.US.86.AD87__AF004394
B.US.97.Ac__06__AY247251
B.US.__.P2__AY206654
B.US.__.R3__PDC1__AY206652
B.US.88.WR27__AF286365
Gag, C-subtype, 1 natural sequence C.IN.__.70177__AF533131
Gag, C-subtype, 3 natural sequences C.ZA.97.97ZA012
C.ZA.x.04ZASK161B1
C.IN.-.70177__AF533131
Gag, C-subtype, 4 natural sequences C.ZA.97.97ZA012
C.ZA.x.04ZASK142B1
C.ZA.x.04ZASK161B1
C.IN.__.70177__AF533131
Gag, C-subtype, 6 natural sequences C.ZA.97.97ZA012
C.ZA.x.04ZASK142B1
C.ZA.x.04ZASK161B1
C.BW.99.99BWMC168__AF443087
C.IN.__.70177__AF533131
C.IN.__.MYA1__AF533139
Gag, M-group, 1 natural sequence C.IN.__.70177__AF533131
Gag, M-group, 3 natural sequences B.US.90.US2__AY173953
C.IN.-.70177__AF533131
15__01B.TH.99.99TH__R2399__AF530576
Gag, M-group, 4 natural sequences B.US.90.US2__AY173953
C.IN.__.70177__AF533131
C.IN.93.93IN999__AF067154
15__01B.TH.99.99TH__R2399__AF530576
Gag, M-group, 6 natural sequences C.ZA.x.04ZASK138B1
B.US.90.US2__AY173953
B.US.__.WT1__PDC1__AY206656
C.IN.__.70177__AF533131
C.IN.93.93IN999__AF067154
15__01B.TH.99.99TH__R2399__AF530576
Nef (central region), B-subtype, 1 natural sequence B.GB.94.028jh__94__1__NP__AF129346
Nef (central region), B-subtype, 3 natural sequences B.GB.94.028jh__94__1__NP__AF129346
B.KR.96.96KCS4__AY121471
B.FR.83.HXB2__K03455
Nef (central region), B-subtype, 4 natural sequences B.GB.94.028jh__94__1__NP__AF129346
B.KR.96.96KCS4__AY121471
B.US.90.E90NEF__U43108
B.FR.83.HXB2__K03455
Nef (central region), B-subtype, 6 natural sequences B.GB.94.028jh__94__1__NP__AF129346
B.KR.02.02HYJ3__AY121454
B.KR.96.96KCS4__AY121471
B.CN.__.RL42__U71182
B.US.90.E90NEF__U43108
B.FR.83.HXB2__K03455

TABLE 1-continued

| Natural sequence cocktails having the best available 9-mer coverage for different genes, subtype sets, and numbers of sequences |
|---|
| Nef (central region), C-subtype, 1 natural sequence |
| C.ZA.04.04ZASK139B1 |
| Nef (central region), C-subtype, 3 natural sequences |
| C.ZA.04.04ZASK180B1<br>C.ZA.04.04ZASK139B1<br>C.ZA._.ZASW15_AF397568 |
| Nef (central region), C-subtype, 4 natural sequences |
| C.ZA.97.ZA97004_AF529682<br>C.ZA.04.04ZASK180B1<br>C.ZA.04.04ZASK139B1<br>C.ZA._.ZASW15_AF397568 |
| Nef (central region), C-subtype, 6 natural sequences |
| C.ZA.97.ZA97004_AF529682<br>C.ZA.00.1192M3M<br>C.ZA.04.04ZASK180B1<br>C.ZA.04.04ZASK139B1<br>C.04ZASK184B1<br>C.ZA._.ZASW15_AF397568 |
| Nef (central region), M-group, 1 natural sequence |
| B.GB.94.028jh_94_1_NP_AF129346 |
| Nef (central region), M-group, 3 natural sequences |
| 02_AG.CM._.98CM1390_AY265107<br>C.ZA.03.03ZASK020B2<br>B.GB.94.028jh_94_1_NP_AF129346 |
| Nef (central region), M-group, 4 natural sequences |
| 02_AG.CM._.98CM1390_AY265107<br>01A1.MM.99.mCSW105_AB097872<br>C.ZA.03.03ZASK020B2<br>B.GB.94.028jh_94_1_NP_AF129346 |
| Nef (central region), M-group, 6 natural sequences |
| 02_AG.CM._.98CM1390_AY265107<br>01A1.MM.99.mCSW105_AB097872<br>C.ZA.03.03ZASK020B2<br>C.03ZASK111B1<br>B.GB.94.028jh_94_1_NP_AF129346<br>B.KR.01.01CWS2_AF462757 |

Summarizing, the above-described study focuses on the design of T-cell vaccine components to counter HIV diversity at the moment of infection, and to block viral escape routes and thereby minimize disease progression in infected individuals. The polyvalent mosaic protein strategy developed here for HIV-1 vaccine design could be applied to any variable protein, to other pathogens, and to other immunological problems. For example, incorporating a minimal number of variant peptides into T-cell response assays could markedly increase sensitivity without excessive cost: a set of k mosaic proteins provides the maximum coverage possible for k antigens.

A centralized (consensus or ancestral) gene and protein strategy has been proposed previously to address HIV diversity (Gaschen et al, Science 296:2354-2360 (2002)). Proof-of-concept for the use of artificial genes as immunogens has been demonstrated by the induction of both T and B cell responses to wild-type HIV-1 strains by group M consensus immunogens (Gaschen et al, Science 296:2354-2360 (2002), Gao et al, J. Virol. 79:1154-63 (2005), Doria-Rose et al, J. Virol. 79:11214-24 (2005), Weaver et al, J. Virol., in press)). The mosaic protein design improves on consensus or natural immunogen design by co-optimizing reagents for a polyclonal vaccine, excluding rare CD8+ T-cell epitopes, and incorporating variants that, by virtue of their frequency at the population level, are likely to be involved in escape pathways.

The mosaic antigens maximize the number of epitope-length variants that are present in a small, practical number of vaccine antigens. The decision was made to use multiple antigens that resemble native proteins, rather than linking sets of concatenated epitopes in a poly-epitope pseudo-protein (Hanke et al, Vaccine 16:426-35 (1998)), reasoning that in vivo processing of native-like vaccine antigens will more closely resemble processing in natural infection, and will also allow expanded coverage of overlapping epitopes. T-cell mosaic antigens would be best employed in the context of a strong polyvalent immune response; improvements in other areas of vaccine design and a combination of the best strategies, incorporating mosaic antigens to cover diversity, may ultimately enable an effective cross-reactive vaccine-induced immune response against HIV-1.

EXAMPLE 2

Group M consensus envelope and trivalent mosaic envelopes (both of which were designed by in silico modeling and are predicted to be superior than wildtype envelopes) will be compared to a monovalent wild-type envelope and trivalent wild-type transmitted envelopes in a 4 arm immunogenicity clinical trial. The mosaic antigens have been designed based on the current Los Alamos database, a set that includes more full length envelopes sampled globally from more than 2000 individuals with a large set of sequences of transmitted viruses primarily from the CHAVI database.

The selection of the natural strains to be used for the comparison is based on the following criteria: For the monovalent natural antigen, use will be made of the single transmitted virus that is the best choice in terms of providing coverage of potential T cell epitopes in the global database. The database is biased towards B clade envelopes, so the single best acute Env is a B clade representative. One A, one B and one C subtype transmitted virus sequence is proposed for inclusion in the trivalent set, to compensate for the biases in sampling inherent in the global sequence collection, and to better reflect the circulating pandemic strains. The A and C natural sequences are those that optimally complement the best B clade sequence to provide potential epitope coverage of the database. Vaccine antigens have been selected from among available SGA sequenced acute samples, each representing a transmitted virus. Therefore, this study, although primarily a T cell study, will also provide important additional data regarding the ability of transmitted envelope vaccines to elicit neutralizing antibodies.

For a mosaic/consensus human trial, the following 4 arm trial is proposed, 20 people per group, with a negative control:

1) Con S (a well studied consensus of the consensus of each clade, based on the 2002 database; Con S has been extensively tested in animal models, and has theoretical coverage roughly comparable to a single mosaic.)
2) A 3 mosaic M group antigen set designed to, in combination, provide optimal global coverage of 9 amino acid long stretches in the database. Such 9-mers represent potential epitope coverage of the database. Unnatural 9-mers are excluded in mosaics, and rare variants minimized.
3) The optimal single best natural protein selected from sequences sampled from acutely infected patients with SGA sequences available; these sequences should correspond to viable, transmitted sequences. As in (2), this sequence will be selected to be the one that provides optimal 9-mer coverage of the database. The B clade currently dominates sampling for the sequence database, so the sequence with the best database coverage will be a B clade sequence.

4) The best natural strains from acute infection SGA sequences that in combination provide the best global coverage. (Note: the B and C dominate the M group sampling hence the code naturally selects one of each as the two best. Thus, the third complementary sequence was forced to be selected from an acute SGA A clade set, to counter this bias and better reflect the global epidemic).

5) Negative control buffer/saline

The current M group alignment in the HIV database was combined with all of the newer CHAVI sequences—this includes a total of 2020 sequences:

728 B clade

599 C clade 693 that are all other clades, circulating recombinant forms, and unique recombinants. This was used for the M group vaccine design.

This sampling is obviously skewed toward the B and C clade. As will be shown subsequently, the coverage of "potential epitopes" (9-mers) in other clades is still excellent.

The Sequences

M Consensus

```
>ConS (SEQ ID NO: 219)
MRVRGIQRNCQHLWRWGTLILGMLMICSAAENLWVTVYYGVPVWKEANT

TLFCASDAKAYDTEVHNVWATHACVPTDPNPQEIVLENVTENFNMWKNN

MVEQMHEDIISLWDQSLKPCVKLTPLCVTLNCTNVNVTNTTNNTEEKGE

IKNCSFNITTEIRDKKQKVYALFYRLDVVPIDDNNNNSSNYRLINCNTS

AITQACPKVSFEPIPIHYCAPAGFAILKCNDKKFNGTGPCKNVSTVQCT

HGIKPVVSTQLLLNGSLAEEEIIIRSENITNNAKTIIVQLNESVEINCT

RPNNNTRKSIRIGPGQAFYATGDIIGDIRQAHCNISGTKWNKTLQQVAK

KLREHFNNKTIIFKPSSGGDLEITTHSFNCRGEFFYCNTSGLFNSTWIG

NGTKNNNNTNDTITLPCRIKQIINMWQGVGQAMYAPPIEGKITCKSNIT

GLLLTRDGGNNNTNETEIFRPGGGDMRDNWRSELYKYKVVKIEPLGVAP

TKAKRRVVEREKRAVGIGAVFLGFLGAAGSTMGAASITLTVQARQLLSG

IVQQQSNLLRAIEAQQHLLQLTVWGIKQLQARVLAVERYLKDQQLLGIW

GCSGKLICTTTVPWNSSWSNKSQDEIWDNMTWMEWEREINNYTDIIYSL

IEESQNQQEKNEQELLALDKWASLWNWFDITNWLWYIKIFIMIVGGLIG

LRIVFAVLSIVNRVRQGYSPLSFQTLIPNPRGPDRPEGIEEEGGEQDRD

RSIRLVNGFLALAWDDLRSLCLFSYHRLRDFILIAARTVELLGRKGLRR

GWEALKYLWNLLQYWGQELKNSAISLLDTTAIAVAEGTDRVIEVVQRAC

RAILNIPRRIRQGLERALL

3 mosaics
>M_mos_3_1 (SEQ ID NO: 177)
MRVKGIRKNYQHLWRWGTMLLGMLMICSAAEQLWVTVYYGVPVWRDAET

TLFCASDAKAYEREVHNVWATHACVPTDPNPQEIVLENVTEEFNMWKNN

MVDQMHEDIISLWDESLKPCVKLTPLCVTLNCTDVNVTKTNSTSWGMME

KGEIKNCSFNMTTELRDKKQKVYALFYKLDIVPLEENDTISNSTYRLIN

CNTSAITQACPKVTFEPIPIHYCTPAGFAILKCNDKKFNGTGPCKNVST
```

-continued

```
VQCTHGIRPVVTTQLLLNGSLAEEEIIIRSENLTNNAKTIIVQLNESVV

INCTRPNNNTRKSIRIGPGQTFYATGDIIGNIRQAHCNISREKWINTTR

DVRKKLQEHFNKTIIFNSSSGGDLEITTHSFNCRGEFFYCNTSKLFNSV

WGNSSNVTKVNGTKVKETITLPCKIKQIINMWQEVGRAMYAPPIAGNIT

CKSNITGLLLVRDGGNVTNNTEIFRPGGGNMKDNWRSELYKYKVVEIKP

LGIAPTKAKRRVVEREKRAVGLGAVFLGFLGAAGSTMGAASMTLTVQAR

QLLSGIVQQQSNLLRAIEAQQHMLQLTVWGIKQLQARILAVERYLRDQQ

LLGIWGCSGKLICTTNVPWNSSWSNKSLDEIWNNMTWMQWEKEIDNYTS

LIYTLIEESQNQQEKNEQDLLALDKWANLWNWFDISNWLWYIRIFIMIV

GGLIGLRIVFAVLSIVNRVRKGYSPLSFQTLTPNPRGPDRLGRIEEEGG

EQDKDRSIRLVNGFLALAWDDLRNLCLFSYHRLRDLLLIVTRIVELLGR

RGWEALKYLWNLLQYWIQELKNSAVSLLNATAIAVAEGTDRVIEVVQRA

CRAILHIPRRIRQGLERALL

>M_mos_3_2 (SEQ ID NO: 178; SEQ ID NO: 220)
MRVKETQMNWPNLWKWGTLILGLVIICSASDNLWVTVYYGVPVWKEATT

TLFCASDAKAYDTEVHNVWATYACVPTDPNPQEVVLGNVTENFNMWKNN

MVEQMHEDIISLWDQSLKPCVRLTPLCVTLNCSNANTTNTNSTEEIKNC

SFNITTSIRDKVQKEYALFYKLDVVPIDNDNTSYRLISCNTSVITQACP

KVSFEPIPIHYCAPAGFAILKCKDKKFNGTGPCTNVSTVQCTHGIRPVV

STQLLLNGSLAEEEVVIRSENFTNNAKTIIVHLNKSVEINCTRPNNNTR

KSIHIGPGRAFYATGEIIGDIRQAHCNISRAKWNNTLKQIVKKLKEQFN

KTIIFNQSSGGDPEITTHSFNCGGEFFYCNTSGLFNSTWNSTATQESNN

TELNGNITLPCRIKQIVNMWQEVGKAMYAPPIRGQIRCSSNITGLILTR

DGGNNNSTNETFRPGGGDMRDNWRSELYKYKVVKIEPLGVAPTKAKRRV

VQREKRAVGTIGAMFLGFLGAAGSTMGAASLTLTVQARLLLSGIVQQQN

NLLRAIEAQQHLLQLTVWGIKQLQARVLAVERYLKDQQLLGIWGCSGKL

ICTTTVPWNTSWSNKSLNEIWDNMTWMEWEREIDNYTGLIYTLLEESQN

QQEKNEQELLELDKWASLWNWFDITKWLWYIKIFIMIVGGLVGLRIVFT

VLSIVNRVRQGYSPLSFQTHLPAPRGPDRPEGIEEEGGERDRDRSGRLV

DGFLAIIWVDLRSLCLFSYHQLRDFILIAARTVELLGHSSLKGLRRGWE

ALKYWWNLLQYWSQELKNSAISLLNTTAIVVAEGTDRIIEVLQRAGRAI

LHIPTRIRQGLERLLL

>M_mos_3_3 (SEQ ID NO: 179)
MRVRGIQRNWPQWWIWGILGFWMLMICNVVGNLWVTVYYGVPVWKEAKT

TLFCASDAKAYEKEVHNVWATHACVPTDPSPQEVVLENVTENFNMWKND

MVDQMHEDVISLWDQSLKPCVKLTHLCVTLNCTNATNTNYNNSTNVTSS

MIGEMKNCSFNITTEIRDKSRKEYALFYRLDIVPLNEQNSSEYRLINCN

TSTITQACPKVSFDPIPIHYCAPAGYAILKCNNKTFNGTGPCNNVSTVQ

CTHGIKPVVSTQLLLNGSLAEGEIIIRSENLTDNAKTIIVHLNESVEIV

CTRPNNNTRKSVRIGPGQAFYATGDIIGDIRQAHCNLSRTQWNNTLKQI

VTKLREQFGNKTIVFNQSSGGDPEIVMHSFNCGGEFFYCNTTQLFNSTW
```

-continued

ENSNITQPLTLNRTKGPNDTITLPCRIKQIINMWQGVGRAMYAPPIEGL

IKCSSNITGLLLTRDGGNNSETKTTETFRPGGGNMRDNWRNELYKYKVV

QIEPLGVAPTRAKRRVVEREKRAVGIGAVFLGFLGTAGSTMGAASITLT

VQARQVLSGIVQQQSNLLKAIEAQQHLLKLTVWGIKQLQTRVLAIERYL

KDQQLLGLWGCSGKLICTTAVPWNSSWSNKSQTDIWDNMTWMQWDREIS

NYTDTIYRLLEDSQNQQEKNEKDLLALDSWKNLWNWFDITNWLWYIKIF

IIIVGGLIGLRIIFAVLSIVNRCRQGYSPLSLQTLIPNPRGPDRLGGIE

EEGGEQDRDRSIRLVSGFLALAWDDLRSLCLFSYHRLRDFILIVARAVE

LLGRSSLRGLQRGWEALKYLGSLVQYWGLELKKSAISLLDTIAIAVAEG

TDRIIEVIQRICRAIRNIPRRIRQGFEAALL

Single optimal natural sequence selected from available acute SGA sequences:

>B.acute.Con.1059 (SEQ ID NO: 221)
MRVTEIRKNYLWRWGIMLLGMLMICSAAEQLWVTVYYGVPVWKEATTTL

FCASDAKAYTAEAHNVWATHACVPTDPNPQEVVLENVTENFNMWKNNMV

EQMHEDIISLWDQSLKPCVKLTPLCVTLNCTDLANNTNLANNTNSSISS

WEKMEKGEIKNCSFNITTVIKDKIQKNYALFNRLDIVPIDDDDTNVTNN

ASYRLISCNTSVITQACPKISFEPIPIHYCAPAGFAILKCNDKKFNGTG

PCTNVSTVQCTHGIKPVVSTQLLLNGSLAEEEVVIRSENFTDNVKTIIV

QLNESVIINCTRPNNNTRKSITFGPGRAFYTTGDIIGDIRKAYCNISST

QWNNTLRQIARRLREQFKDKTIVFNSSSGGDPEIVMHSFNCGGEFFYCN

TTQLFNSTWNGNDTGEFNNTGKNITYITLPCRIKQIINMWQEVGKAMYA

PPIAGQIRCSSNITGILLTRDGGNSSEDKEIFRPEGGNMRDNWRSELYK

YKVVKIEPLGVAPTKAKRRVVQREKRAVGIGAVFLGFLGAAGSTMGAAS

MTLTVQARLLLSGIVQQQNNLLRAIEAQQHLLQLTVWGIKQLQARVLAV

ERYLKDQQLLGIWGCSGKLICTTAVPWNASWSNRSLDNIWNNMTWMEWD

REINNYTNLIYNLIEESQNQQEKNEQELLELDKWASLWNWFDITKWLWY

IKIFIMIVGGLVGLRIVFVILSIVNRVRQGYSPLSFQTHLPTPRGLDRH

EGTEEEGGERDRDRSGRLVDGFLTLIWIDLRSLCLFSYHRLRDLLLIVT

RIVELLGRRGWEILKYWWNLLQYWSQELKNSAVSLLNATAIAVAEGTDR

IIEIVQRIFRAILHIPTRIRQGLERALL 3 optimal natural selected from available acute samples, SGA sequences:

>B.acute.Con.1059 (SEQ ID NO: 221)
MRVTEIRKNYLWRWGIMLLGMLMICSAAEQLWVTVYYGVPVWKEATTTL

FCASDAKAYTAEAHNVWATHACVPTDPNPQEVVLENVTENFNMWKNNMV

EQMHEDIISLWDQSLKPCVKLTPLCVTLNCTDLANNTNLANNTNSSISS

WEKMEKGEIKNCSFNITTVIKDKIQKNYALFNRLDIVPIDDDDTNVTNN

ASYRLISCNTSVITQACPKISFEPIPIHYCAPAGFAILKCNDKKFNGTG

PCTNVSTVQCTHGIKPVVSTQLLLNGSLAEEEVVIRSENFTDNVKTIIV

-continued

QLNESVIINCTRPNNNTRKSITFGPGRAFYTTGDIIGDIRKAYCNISST

QWNNTLRQIARRLREQFKDKTIVFNSSSGGDPEIVMHSFNCGGEFFYCN

TTQLFNSTWNGNDTGEFNNTGKNITYITLPCRIKQIINMWQEVGKAMYA

PPIAGQIRCSSNITGILLTRDGGNSSEDKEIFRPEGGNMRDNWRSELYK

YKVVKIEPLGVAPTKAKRRVVQREKRAVGIGAVFLGFLGAAGSTMGAAS

MTLTVQARLLLSGIVQQQNNLLRAIEAQQHLLQLTVWGIKQLQARVLAV

ERYLKDQQLLGIWGCSGKLICTTAVPWNASWSNRSLDNIWNNMTWMEWD

REINNYTNLIYNLIEESQNQQEKNEQELLELDKWASLWNWFDITKWLWY

IKIFIMIVGGLVGLRIVFVILSIVNRVRQGYSPLSFQTHLPTPRGLDRH

EGTEEEGGERDRDRSGRLVDGFLTLIWIDLRSLCLFSYHRLRDLLLIVT

RIVELLGRRGWEILKYWWNLLQYWSQELKNSAVSLLNATAIAVAEGTDR

IIEIVQRIFRAILHIPTRIRQGLERALL

>C.acute.Con.0393 (SEQ ID NO: 222)
MRVRGILRNYQQWWIWGILGFWMLMICSVGGNLWVTVYYGVPVWREAKT

TLFCASDAKAYEREVHNVWATHACVPTDPNPQELFLENVTENFNMWKND

MVDQMHEDIISLWDQSLKPCVKLTPLCVTLNCSNANITRNSTDGNTTRN

STATPSDTINGEIKNCSFNITTELKDKKKKEYALFYRLDIVPLNEENSN

FNEYRLINCNTSAVTQACPKVSFDPIPIHYCAPAGYAILKCNNKTFNGT

GPCNNVSTVQCTHGIKPVVSTQLLLNGSLAEEEIIIRSENLTNNAKTII

VHLKEPVEIVCTRPNNNTRKSMRIGPGQTFYATDIIGDIRQASCNIDEK

TWNNTLNKVGEKLQEHFPNKTLNFAPSSGGDLEITTHSFNCRGEFFYCN

TSKLFYKTEFNSTTNSTITLQCRIKQIINMWQGVGRAMYAPPIEGNITC

KSNITGLLLTRDGGTNDSMTETFRPGGGDMRDNWRSELYKYKVVEIKPL

GVAPTEAKRRVVEREKRALTLGALFLGFLGTAGSTMGAASITLTVQARQ

LLSGIVQQQSNLLKAIEAQQHLLQLTVWGIKQLQTRVLAIERYLQDQQL

LGLWGCSGKLICTTAVPWNSSWSNKSQGEIWGNMTWMQWDREISNYTNT

IYRLLEDSQIQQEKNEKDLLALDSWKNLWSWFSITNWLWYIKIFIMIVG

GLIGLRIIFAVLSIVNRVRQGYSPLPFQTLIPNPRGPDRLGRIEEEGGE

QDRDRSIRLVNGFLAIAWDDLRSLCLFSYHRLRDFILIAARAAELLGRS

SLRGLQRGWEALKYLGSLVQYWGLELKKSAISLLDTVAITVAEGTDRII

EVVQRICRAICNIPRRIRQGFEAALQ

Coverage Comparison of the Four Vaccine Antigens.

Mosaics and naturals are optimized for the first red bar on the left for each vaccine (the total). The "total" represents all sequences, database +CHAVI. The "B" is the subset that are B clade, "C" the subset that are C clade, and "N" the remaining M group sequences that are not B or C (all other clades and recombinants). As B is most common, the single best natural is of course a B, and B thus has the best coverage for Nat.1. Con S, as expected, provides much more even coverage for all clades, and provides better coverage for all the groups except B clade. (Note: in a Con S Macaque study, the natural B was not selected to be optimal, and Con S had better coverage even within B clade than the B vaccine strain that had been used; this was reflected in the number of detected responses to heterogeneous B's. A difference here is that the natural B was selected to be the natural B clade sequence from acute infection that provides optimal coverage). Nat.3 gives good broad coverage, Mos.3 better. (See FIG. 11.)

The mosaics will minimize rare 9-mers but in Env they cannot be excluded or it is not possible to span certain really variable regions to make intact proteins. For all other HIV proteins tested, it was possible to exclude 9-mers that were found at 3 times or less. Still, the 3 best natural Envs contain more than twice the number of rare 9-mer variants relative to the 3 Env mosaics.

Figure 12:
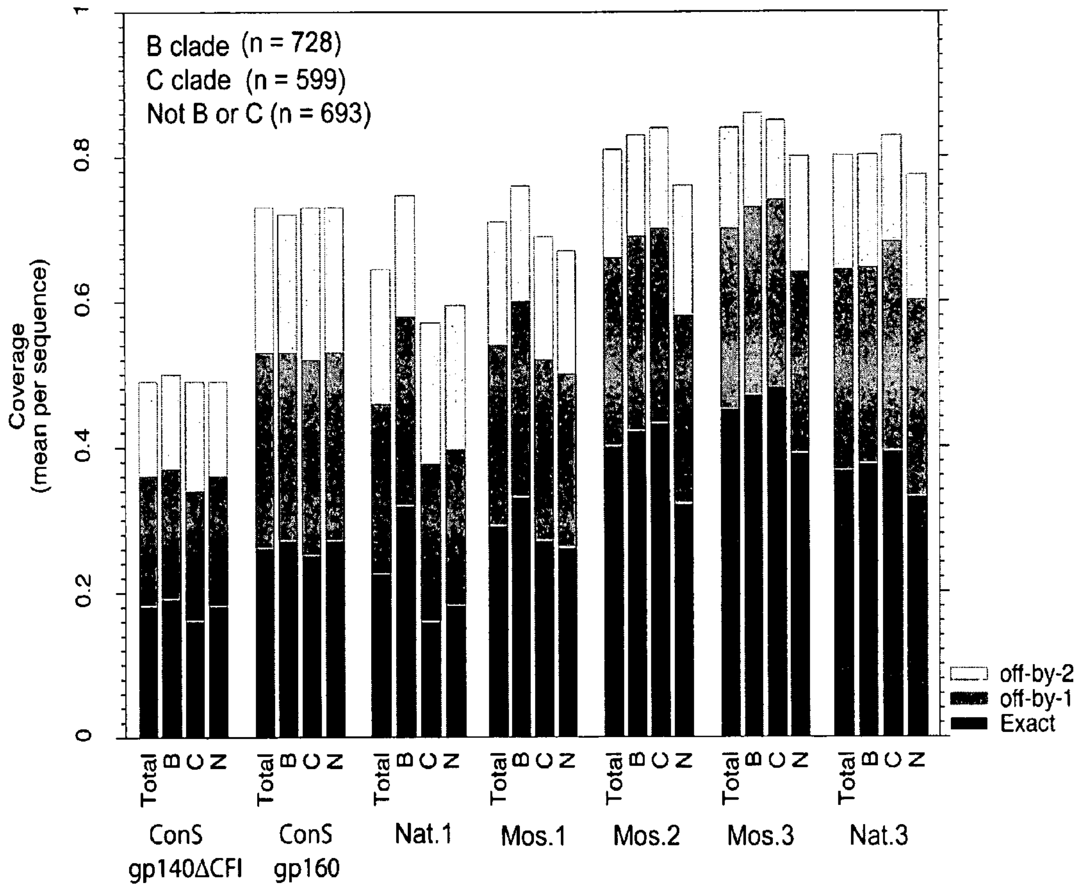
FIG. 12. Additional summaries of coverage.

FIG. 12 includes additional summaries of coverage; ConS gp160 contains quite a few conserved 9-mers that are missed in gp140DCFI, as one would expect. ConS provides slightly less coverage than a single mosaic, but it is already known that ConS works very well in macaques so serves as a good positive control. 1, 2, and 3 mosaics give increasingly better coverage, and Nat.3 is not as good as Mos.3.

Figure 13:
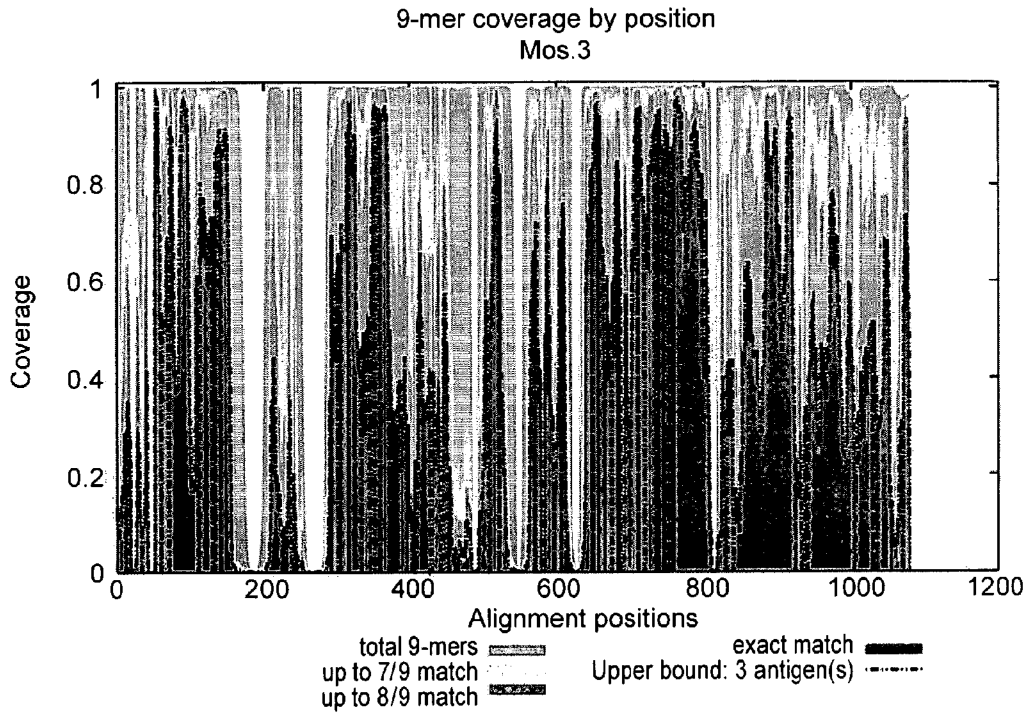
FIG. 13. 9-mer coverage by position (Mos.3 vaccine cocktail).

FIG. 13 is alignment dependent, and based on the database alignment (the tow plots above this are alignment independent). Each position represents the 9-mer it initiates as one moves across the protein. The upper bound (black dashed lined) is the sum of the frequencies of the three most common 9-mers starting from each position; it represents the maximal limit that could be achieved for coverage with 3 proteins, and this is not quite achievable in practice because there can be conflicts in a given position for overlapping 9-mers, although the 3 mosaic combination very nearly achieves it. The reason the "total 9-mers" shown in grey varies is because of insertions and deletions in the alignment.

Figures 14A, 14B, 14C, 14D:
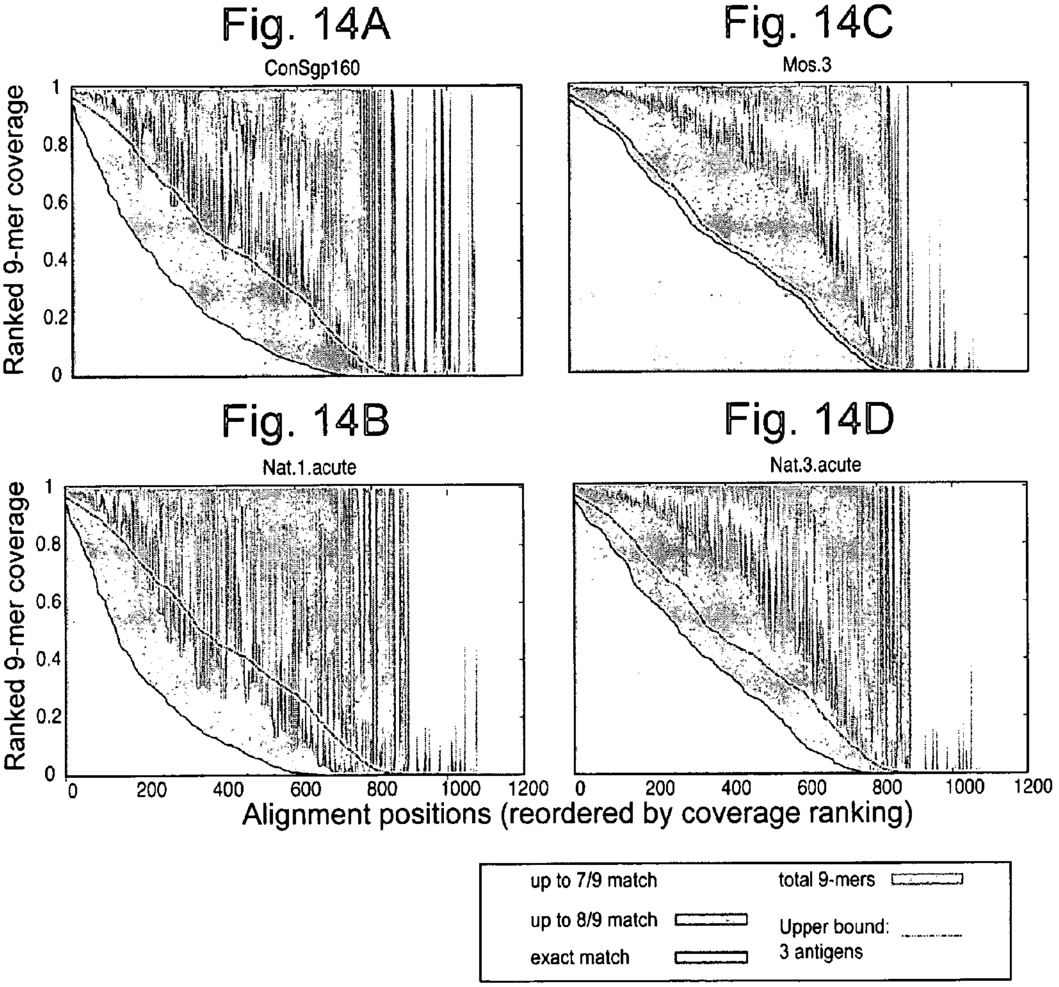
FIGS. 14A-14D. Plots resorted by frequency of 9-mer matches for each vaccine proposed for use.

Only the Mos.3 vaccine cocktail is shown in FIG. 13. However, all four vaccines resorted by coverage is shown in FIG. 14, where those positions that start the 9-mers that are best covered by the vaccine are moved to the left. The exact match line is left in all four plots for a reference point. Not only does Mos.3 (red) approach the maximum, but the orange and yellow near-matches that have potential for cross-reactivity are also improved in this vaccine cocktail as compared to the others.

The plots shown in FIG. 15 map every amino acid in every sequence in the full database alignment. A row of pixels is a sequence, a column is an alignment position. White patches are insertions to maintain the alignment. All 9-mers that encompass an amino acid are considered. If every 9-mer that spans the amino acid has a perfect match in the vaccine cocktail, the pixel is yellow, so yellow is good. If one is off, light orange, two off, darker orange . . . through no spanning 9-mer matches represented by black. Note: lots of yellow for 3 mosaics, relative to the other vaccines. There is a big patch of the most yellow for the B clade in Nat.1 as the single best natural is a B clade. Note, all those dark bits: in these regions the sequences in the database are different than any 9-mer in the vaccine, so cross-reactivity would be several limited.

Optimization Using 9-Mers.

Figure 16:
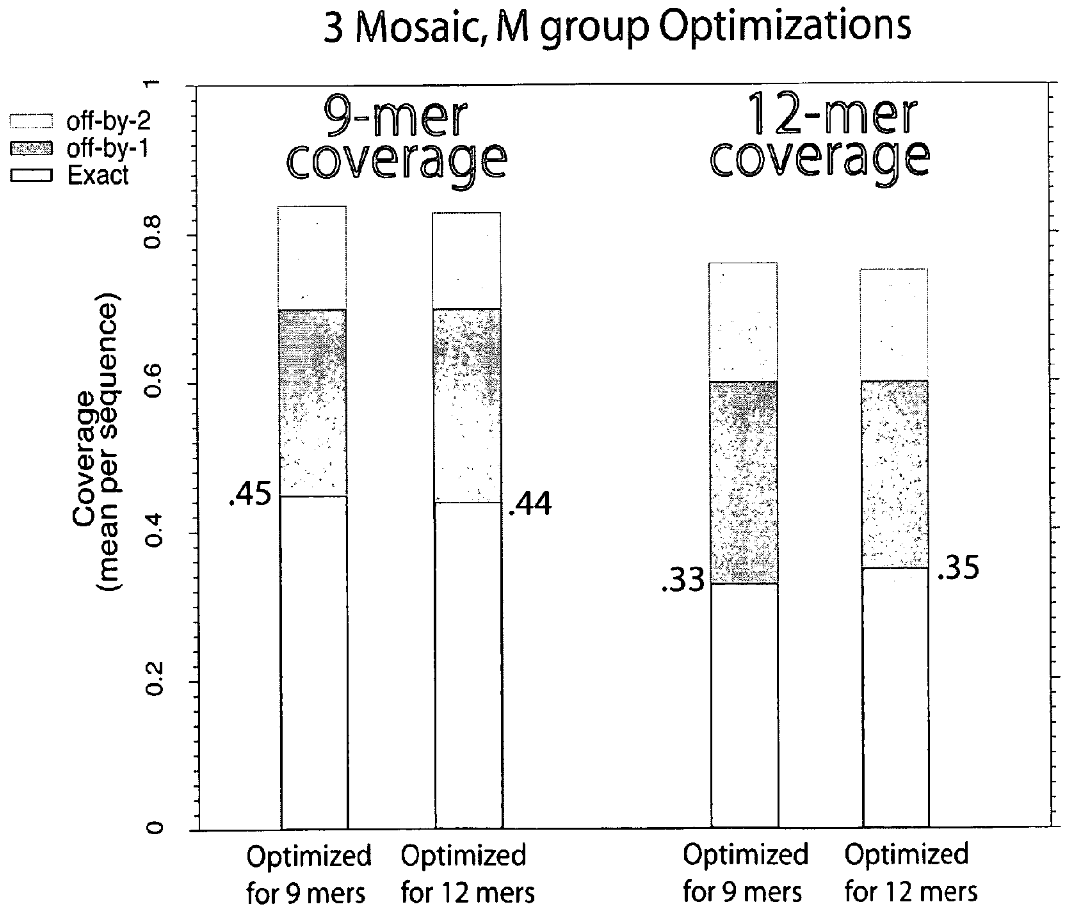
FIG. 16. 3 Mosaic, M group Optimizations.

9-mers were selected because that is the most common size of an optimal CD8+ T cell epitope. They range from 8-12, and optimal CD4+ T cell epitopes can be even be larger or smaller. As it turns out, coverage of 9-mers is best when optimized for 9-mer coverage, but if optimization on a different size yields very little decrease in coverage for 9-mers. The same goes for all lengths, 8-12, the peak coverage is for the size selected but the coverage is excellent for other lengths, as the solutions are related. 9-versus 12-mers are shown in FIG. 16, 12 being the most extreme value one might reasonably consider. The coverage is nearly identical for 9-mers optimized for 9 or 12, or for 12-mers optimized for 9 or 12; it is 1-2% higher for the length selected for optimization. Naturally, 12-mers have fewer identities than 9-mers in general, because they are longer so it is harder to find a prefect match. A more comprehensive study was made of this for HIV proteins showing that the loss was consistently larger for 12-mers when optimized on 9 rather than vice versa, and that, in other proteins, this difference could be up to 4-5%. Thus, for Env the selection of 9-mers is less of a problem. Given all of the above, 9-mers were selected since this is the most common optimal CTL epitope length, and since optimal coverage of 9-mers provides approaching optimal coverage of other lengths.

Options for the 3 Best Natural Strains: Acute Transmission Cases, SGA Sequences.

Use of all database sequences as a source for natural strains for vaccine cocktails was first explored, and then a comparison was made of that with selecting from a restricted group of just acute SGA sequences, essentially transmitted viruses. Essentially comparable coverage of the full database could be achieved by restricting to acute infection sequences. As these have other obvious advantages, they will be used for the natural sequences.

First, the exploration of coverage using the full database as a source for a natural cocktail. As noted above, the current M group Env one-seq-per-person data set is dominated by B clade infections, closely followed by C clade. Thus, the single best optimal natural selected by the vaccine design program to cover 9-mers in the (database +CHAVI) data set is a B. If one picks from among any sequence in the database, YU-2 comes up as the best single sequence. To get better representation of other clades, the best B was fixed, and then the next best sequence was added to complement YU-2, which is (logically) a C clade sequence, DU467. Those two were then fixed, and the third complement of the antigen was selected. (If the first two are not fixed, and the program is allowed to choose the third, it logically found a B/C recombinant, it has to be forced to select an A. It is believed that forcing the ABC set would improve global coverage, and partly counteract the B & C clade sampling bias among sequences.)

The optimal naturals from the database tend to harken back to older sequences; this is not surprising, as the older sequences tend to be more central in phylogenetic trees, and thus more similar other circulating strains. For this study, however, it is preferred to use more contemporary Envelope proteins sampled during acute infection and sequenced using SGA, as these sequences accurately reflect the transmitted virus. Given that constraint, it is still desired to optimize for 9-mer coverage, so that the cocktail of natural sequences is given the best chance for success in the comparison with mosaics. It turns out when this was done there was an extremely minor loss of coverage when comparing the trivalent cocktail selected from among acute SGA sequences to the trivalent antigen selected from the entire database, (in both cases optimizing for coverage the full database). Thus, by restricting the antigen cocktails to transmitted virus, coverage is not compromized. This alternative has several advantages. Most importantly, it enables a determination of the cross-reactive potential of antibodies generated from acute infection viruses used for the natural cocktail relative to consensus or mosaics as a secondary endpoint of interest, without compromising the primary endpoint focusing on a comparison of T-cell response breadth of coverage. A large set of B (113) and C (40) clade acute samples sequenced from CHAVI study is available, giving a large dataset from which to select an optimum combination. For the selection of the complementary sequence from the A clade, to complete the B and C in the trivalent vaccine. Several acute sequences were available.

Analysis of gp160 was undertaken that included the 8 subtype A gp160s, and also a subregion analysis was done with all 15 in V1-V4, to get an indication of whether or not more sequencing was required. Fortunately, one of the available full length sequences made an excellent complement to the B and C acutes, essentially as good as any of the others. This comparison indicated there was no particular need to do more sequencing at this time. It is believed that this is appropriate since with such a limited A baseline to select from, because the A sequence only needs to complement the choice of B and C clade strains, and many Bs and Cs were available from which to choose. Two of the patients from which the Nat.3 cocktail is derived are below. Nat.1 is just the first one.

Figure 18:
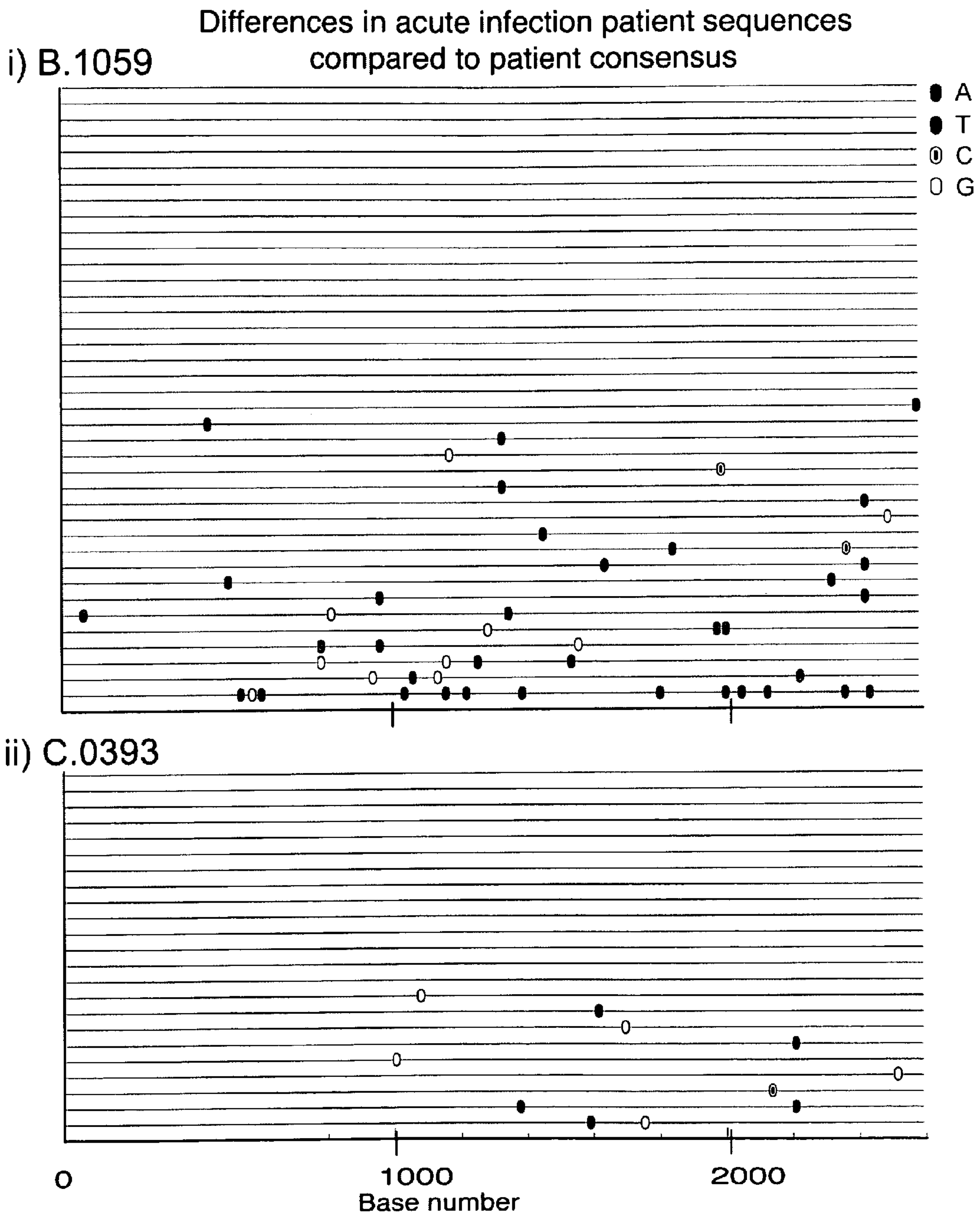
FIG. 18. Differences in acute infection patient sequences compared to patient consensus.

B Patient 1059
Patient Sex=M
RiskFactor=PPD
Sample country=USA
Sample city=Long Beach, Calif.
Patient cohort=CA-UCSF
Patient health status=Acute
Viral Load=2,800,000
Infection country=USA
Sample date=03/26/98
C Patient 0393
Fiebig Stage=4
Infection country=Malawi
Sample date=17-Jul-2003
Viral Load=12,048,485
Patient sex=F
CD4count=618 (measured 13 days after sequenced sample)
Patient age=23
STD=GUD,PID FIGS. 17 and 18 illustrate the minimal loss of coverage in selecting from acute SGA sequences, and a highlighter plot of each of the 3 patients env sequences, that shows that the consensus of each patient is equivalent to the most common strains, and thus an excellent estimate of the actual transmitted virus.

Why M Group and Not Clade Specific Coverage?

Figure 19:
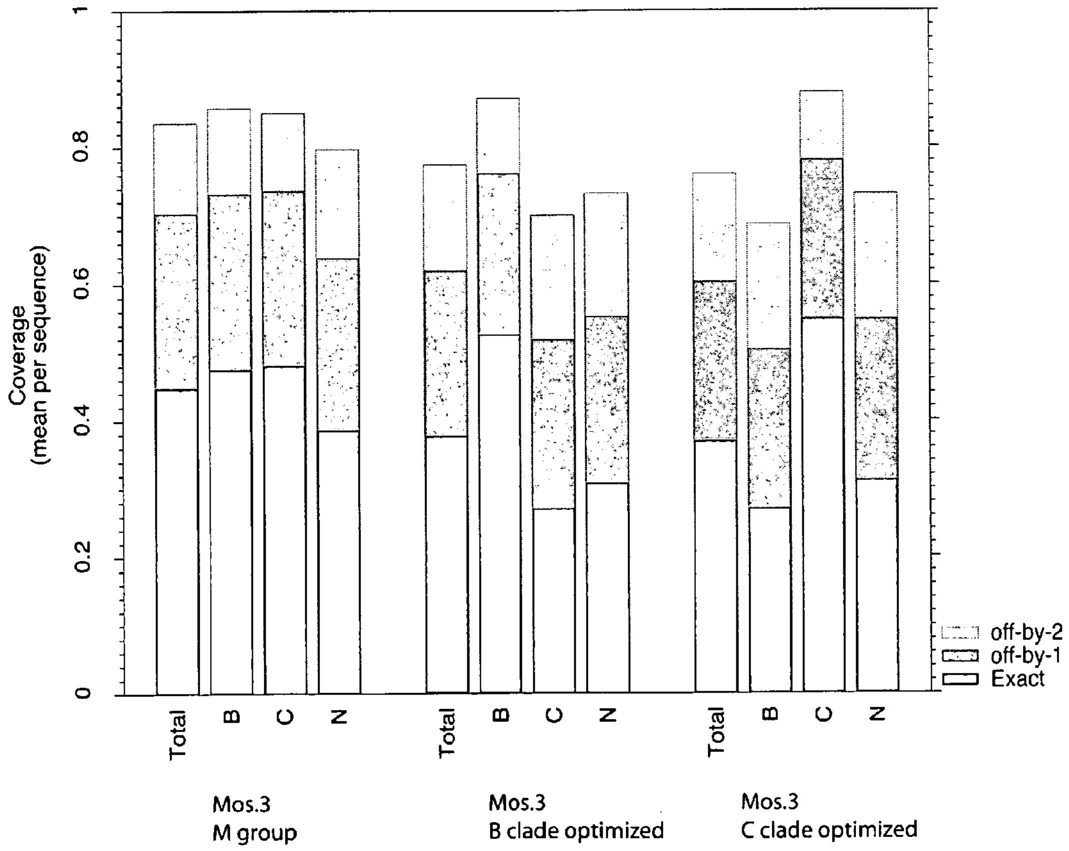
FIG. 19. The compromise and benefit in terms of coverage for Env M group versus subtype-specific design.

It is believed that it is important to strive for a global HIV vaccine, if at all possible, with exploratory methods such as these since many nations have multiclade epidemics, and people travel. While intra-clade coverage can definitely be gained by a within-clade optimized vaccine, the result of such a strategy would be dramatic loss of inter-clade coverage. The hope is that a multivalent mosaic could provide enough breadth to counter viruses of virtually any clades or recombinants. The compromise and benefit in terms of coverage for Env M group versus subtype-specific design is shown in FIG. 19.

Why Env?

Figure 20:
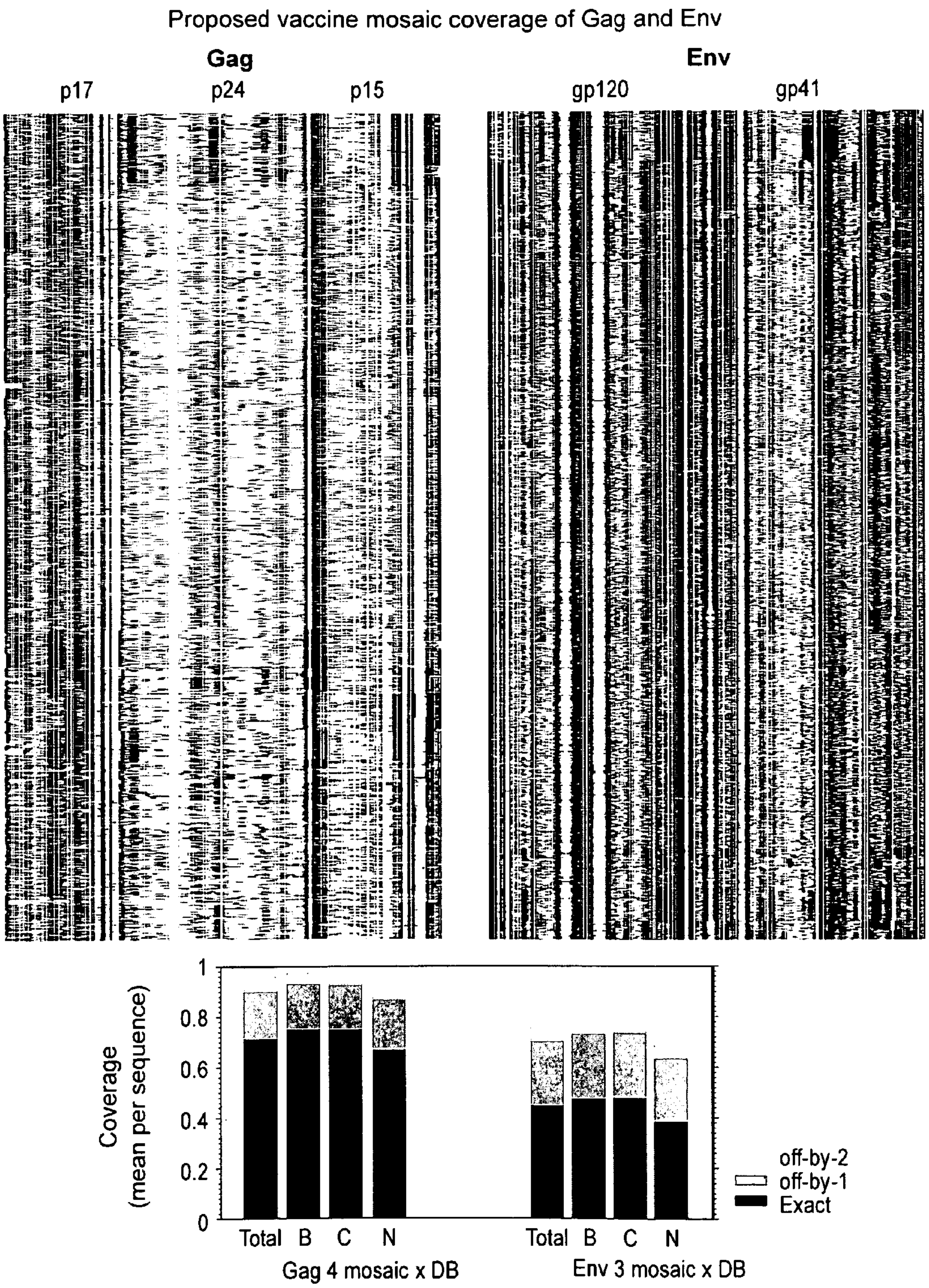
FIG. 20. Proposed vaccine mosaic coverage of Gag and Env.

This proof of concept study is well positioned to see differences in breadth of responses using Env as the test antigen. This is partly because of the theoretical considerations described herein (ENV has twice many conserved 9 mers in the mosaics relative to the best natural strain, and only half as many rare variants) and partly because of the prior animal studies. Env studies with a consensus versus natural in macaques showed a highly significant increase in breadth of responses: 3-4 fold more epitopes per Env protein were s recognized (Santra et al, in press, PNAS). Env mosaics have shown an even more profound advantage in a mouse study (up to 10-fold over comparable numbers of natural antigens, manuscript in preparation in collaboration with the VRC). Based on this prior work, it makes sense to start with a small human trial testing the breadth of responses to Env. Ultimately, the hope is to apply the proof of concept gained with Env to a more conserved protein like a Gag where it may be possible to confer broadest protection. Gag gives outstanding coverage of the full M group. Tests of Gag and Nef are ongoing in macaque, using a 4 mosaic vaccine cocktail approach (see Example 3). A coverage comparison of macaque 4 mosaic Gag vaccine and proposed human Env 3 mosaic vaccine against the current database is in FIG. 20. There is more theoretical potential for cross-reactivity with the Gag vaccine, but more progress has been made with Env in the animal models to date, so Env has the best foundation to justify moving forward. The three mosaic Env sequences described above and the sequences used in Example 3 are shown in FIG. 21.

DNA

The DNAs to be used will be in the form of the full gp160 Env. The gp160 would be in the PCMVR plasmid (Gary Nabel) and will be the identical plasmid used in all VRC DNA immunization trials. Dose is anticipated to be 4 mg. The following DNA constructs will be used:

DNA optimal Wildtype Env transmitted/founder env (WT Env)
DNA group M consensus Env (ConS Env)
DNA Trivalent optimal wildtype transmitted/founder Env (WT Tri Env)
DNA Trivalent Mosaic Env

NYVAC

NYVAC (vP866) is a recombinant poxvirus vector which has an 18 gene deletion versus wild-type virus. The NYVAC vector will be licensed from Sanofi-Pasteur and manufactured by a third party contractor and will be propagated on a CEF cell substrate. The Env construct expressed in NYVAC will be gp140C (entire Env with transmembrane and cytoplasmic domain deleted and gp41/gp120 cleavage site mutated) or will be a full gp160. The choice of construct design will depend on the ability to make the NYVAC with gp160 forms vs gp140. The dose of NYVAC is anticipated to be ~1×10ˆ7 TCID50. The following NYVAC constructs will be used:

NYVAC WT Env
NYVAC ConS Env
NYVAC Trivalent Native Env
NYVAC Trivalent Mosaic Env Vaccinations will be given by intramuscular injection.

TABLE

Protocol Schema

| Group | Number | Dose | Injection schedule in weeks 0 | 4 | 20 | 24 |
|---|---|---|---|---|---|---|
| 1 | 20 | | DNA WT | DNA WT | NYVAC WT | NYVAC WT |
| | 4 | | Env | Env | EnvA | EnvA |
| | | | Placebo | Placebo | Placebo | Placebo |
| 2 | 20 | | DNA ConS | DNA ConS | | |
| | 4 | | Env | Env | NYVAC ConS | NYVAC ConS |
| | | | Placebo | Placebo | Placebo | Placebo |

TABLE-continued

| Protocol Schema | | | | | | |
|---|---|---|---|---|---|---|
| | | | Injection schedule in weeks | | | |
| Group | Number | Dose | 0 | 4 | 20 | 24 |
| 3 | 20 | | DNA | DNA | NYVAC | NYVAC |
| | 4 | | Trivalent | Trivalent | Trivalent | Trivalent |
| | | | Native Env | Native Env | Native Env | Native Env |
| | | | Placebo | Placebo | Placebo | Placebo |
| 4 | 20 | | DNA | DNA | NYVAC | NYVAC |
| | 4 | | Trivalent | Trivalent | Trivalent | Trivalent |
| | | | Mosaic Env | Mosaic Env | Mosaic Env | Mosaic Env |
| | | | Placebo | Placebo | Placebo | Placebo |
| Total | 96 (80/16) | | | | | |

Participants:
Healthy, HIV-1—Uninfected Volunteers Aged 18 to 50 Years:
80 vaccinees
16 control recipients
96 total participants
Design:
Randomized, placebo-controlled, double-blind trial
Duration Per Participant:
Approximately 12 months
Estimated Total Study Duration:
Approximately 18 months

EXAMPLE 3

Construction of the plasmid DNA vaccines and recombinant vaccinia (rVV). Mosaic gag and nef genes, group M consensus gag and nef genes were generated by converting amino acid sequences of said Gag and Nef, group M consensus Gag and Nef CON-S to nucleotide sequences using a strategy for optimal gene expression. For use as a DNA vaccine, mosaic gag and nef genes, group M consensus gag and nef genes were subcloned into WLV0001-AM DNA vaccine vector. Endotoxin-free plasmid DNA preparation were produced by Puresyn, Inc. (Malvern, Pa.) for the immunization of rhesus monkeys. For boosting recombinant vaccinia viruses expressing the individual mosaic gag and nef genes, group M consensus gag and nef genes were generated. The methods used were as previously described (Liao et al, Virology 353:268-282 (2006); Earl, BioTechniques 23:1094-1097 (1997)).

Experimental groups and vaccination schedule. Three groups of rhesus monkeys were immunized with either 10 mg of the empty DNA vector plasmid (group 1, 6 monkeys), or 5 mg each of group M gag and nef plasmid DNA (group 2, 12 monkeys) or 1.25 mg each of 4 mosaic gag and 4 nef plasmid DNA (group 3, 12 monkeys) intramuscularly at Day 0 and Day 30. The monkeys will be boosted with the corresponding rVV expressing the initial immunizing immunogen (10^9 pfu/monkey) 5 month post-immunization with the 2nd DNA immunization.

Myristoylation of Gag and Nef has a potential down regulation effect on immune responses and thus the myristoylation of Gag and Nef has been mutated in the sequences used in this study.

* * *

All documents and other information sources cited above are hereby incorporated in their entirety by reference.

SEQUENCE LISTING

The patent contains a lengthy “Sequence Listing” section. A copy of the “Sequence Listing” is available in electronic form from the USPTO web site (http://seqdata.uspto.gov/?pageRequest=docDetail&DocID=US09044445B2). An electronic copy of the “Sequence Listing” will also be available from the USPTO upon request and payment of the fee set forth in 37 CFR 1.19(b)(3).

What is claimed is:

1. A nucleic acid encoding any one of the mosaic Gag polypeptide Gag M4.1-4Dmyr selected from the group consisting of SEQ ID NOs: 173-176.

2. A vector comprising the nucleic acid according to claim 1.

3. The vector according to claim 2, wherein said vector is a viral vector.

4. A composition comprising at least one nucleic acid according to claim 1 and a carrier.

5. A method of inducing an immune response in a mammal comprising administering to said mammal of at least one nucleic acid according to claim 1 operably linked to a promoter capable of directing expression of the polypeptide, in an amount sufficient to effect said induction.

6. The nucleic acid according to claim 1, wherein the polypeptide comprises the amino acid sequence of SEQ ID NO: 173.

7. The nucleic acid according to claim 1, wherein the polypeptide comprises the amino acid sequence of SEQ ID NO: 174.

8. The nucleic acid according to claim 1, wherein the polypeptide comprises the amino acid sequence of SEQ ID NO: 175.

9. The nucleic acid according to claim 1, wherein the polypeptide comprises the amino acid sequence of SEQ ID NO: 176.

10. The vector according to claim 2, wherein the nucleic acid is present in the vector operably linked to a promoter.

11. The vector according to claim 2, wherein the vector is an adenoviral vector, an adeno-associated virus vector, a pox virus vector, an enteric virus vector, a Venezuelean Equine Encephalitis Virus vector, a Semliki Forest Virus vector or a Tobacco Mosaic Virus vector.

12. The composition according to claim 4 comprising nucleic acids encoding the four mosaic Gag polypeptide Gag M4.1-4Dmyr of SEQ ID NOs: 173-176.

13. The composition according to claim 4, further comprising an adjuvant.

14. The composition according to claim 12, further comprising an adjuvant.

15. A method of inducing an immune response in a mammal comprising administering to said mammal nucleic acids according to the composition of claim 12, wherein each nucleic acid is operably linked to a promoter capable of directing expression of the polypeptide, in an amount sufficient to effect said induction.

16. The method according to claim 15, wherein each nucleic acid is present in a vector.

17. The method according to claim 16, wherein the vector is a viral vector.

18. The method according to claim 16, wherein the vector is an adenoviral vector, an adeno-associated virus vector, a pox virus vector, an enteric virus vector, a Venezuelean Equine Encephalitis Virus vector, a Semliki Forest Virus vector or a Tobacco Mosaic Virus vector.

* * * * *